United States Patent [19]
Kalish et al.

[11] Patent Number: 5,824,688
[45] Date of Patent: Oct. 20, 1998

[54] HIV PROTEASE INHIBITORS

[75] Inventors: Vincent J. Kalish; Siegfried Heinz Reich, both of San Diego; John H. Tatlock, Poway, all of Calif.; Michael J. Rodriguez, Indianapolis, Ind.

[73] Assignee: Agouron Pharmaceuticals, Inc.

[21] Appl. No.: 473,363

[22] Filed: Jun. 7, 1995

Related U.S. Application Data

[60] Division of Ser. No. 190,764, Feb. 2, 1994, Pat. No. 5,484,926, which is a continuation-in-part of Ser. No. 133,543, Oct. 7, 1993, abandoned, and a continuation-in-part of Ser. No. 133,696, Oct. 7, 1993, abandoned, and a continuation-in-part of Ser. No. 137,254, Oct. 18, 1993, abandoned, which is a continuation-in-part of Ser. No. 995,621, Dec. 22, 1992, abandoned.

[51] Int. Cl.$^6$ .................... A61K 31/47; A61K 31/425; A61K 31/40; A61K 31/38
[52] U.S. Cl. .................... 514/307; 514/311; 514/314; 514/354; 514/365; 514/419; 514/448; 546/146; 546/156; 546/314; 548/200; 548/492; 549/72
[58] Field of Search .................... 514/307, 311, 514/314, 354, 365, 419, 448; 546/146, 156, 314; 548/200, 492; 549/72

[56] References Cited

U.S. PATENT DOCUMENTS

| | | | |
|---|---|---|---|
| 5,063,208 | 11/1991 | Rosenberg et al. | 514/19 |
| 5,142,056 | 8/1992 | Kempe et al. | 546/265 |
| 5,157,041 | 10/1992 | Handa et al. | 514/314 |
| 5,196,438 | 3/1993 | Martin et al. | 514/311 |
| 5,204,471 | 4/1993 | Negele et al. | 546/144 |
| 5,235,039 | 8/1993 | Heath, Jr. et al. | 530/328 |

FOREIGN PATENT DOCUMENTS

| | | |
|---|---|---|
| 2075666 | 2/1993 | Canada . |
| 0337714 | 10/1989 | European Pat. Off. . |
| 0346847A2 | 12/1989 | European Pat. Off. . |
| 0356223A2 | 2/1990 | European Pat. Off. . |
| 0361341A2 | 4/1990 | European Pat. Off. . |
| 0402646 | 12/1990 | European Pat. Off. . |
| 0432694A2 | 6/1991 | European Pat. Off. . |
| 0432695A2 | 6/1991 | European Pat. Off. . |
| 0434365A2 | 6/1991 | European Pat. Off. . |
| 0490667 | 6/1992 | European Pat. Off. . |
| 0498680A1 | 8/1992 | European Pat. Off. . |
| 0526009A1 | 2/1993 | European Pat. Off. . |
| 0533000A1 | 3/1993 | European Pat. Off. . |
| 0539192A1 | 4/1993 | European Pat. Off. . |
| 0560268A1 | 9/1993 | European Pat. Off. . |
| WO 91/08221 | 6/1991 | WIPO . |
| WO 93/04043 | 3/1993 | WIPO . |
| WO 93/13066 | 7/1993 | WIPO . |
| WO 93/23379 | 11/1993 | WIPO . |
| WO 94/04492 | 3/1994 | WIPO . |
| WO 94/05639 | 3/1994 | WIPO . |

OTHER PUBLICATIONS

Tam et al., J. Med. Chem., 35(7):1318–1320 (1992).
Huff, J. Med. Chem., 34(8):2305–2314 (1991).
Ghosh et al., J. Med. Chem., 36(2):292–294 (1993).
Ghosh et al., J. Med. Chem., 36(16):2300–2310 (1993).
Thompson et al., J. Am. Chem. Soc., 115(2):801–802 (1993).
Rich et al., J. Med. Chem., 34(3):1222–1225 (1991).
Thaisvivongs et al., J. Med. Chem., 34:2344–2356 (1991).
Ghosh et al., J. Med. Chem., 36:924–927 (1993).
Chong et al., J. Med. Chem., 36:2575–2577 (1993).
Vava Pradad et al., Peptides, Chemistry and Biology, Proceedings of the Twelfth American Peptide Symposium, Jun. 16–21, pp. 721–722(1991).
Rich, et al., Chem. Abstracts, 114(15) Abstract No. 143998g (1991).
Houpis et al., Tetrahedron Letters, 34(16):2593–2596 (1993).
Roberts, N.A. et al., Science, 248:358–361 (1990).
Gilbert et al., J. Chem. Soc. Perkin Trans., 2:475–479 (1993).
Young et al., J. Med. Chem., 35:1702–1709 (1992).
Lyle et al., J. Med. Chem., 34:1228–1230 (1991).

*Primary Examiner*—Alan L. Rotman
*Assistant Examiner*—D. Margaret M. Mach
*Attorney, Agent, or Firm*—Finnegan, Henderson, Farabow, Garrett & Dunner, L.L.P.

[57] ABSTRACT

HIV protease inhibitors, obtainable by chemical synthesis, inhibit or block the biological activity of the HIV protease enzyme, causing the replication of the HIV virus to terminate. These compounds, as well as pharmaceutical compositions that contain these compounds and optionally other anti-viral agents as active ingredients, are suitable for treating patients or hosts infected with the HIV virus, which is known to cause AIDS.

15 Claims, No Drawings

HIV PROTEASE INHIBITORS

CROSS-REFERENCE TO RELATED APPLICATIONS

This application is a division of U.S. patent application Ser. No. 08/190,764, filed on Feb. 2, 1994 now U.S. Pat. No. 5,484,926, which is a continuation-in-part of each of U.S. patent application Ser. Nos. (i) 08/133,543 and (ii) 08/133,696, both filed on Oct. 7, 1993 and both abandoned, and a CIP of Ser. No. 08/137,254, filed Oct. 18, 1993, now abandoned, which is a CIP of Ser. No. 07/995,621, filed Dec. 22, 1992, now abandoned. The disclosures of the two parent applications, Ser. Nos. 08/133,543 and 08/133,696 (including the specification and claims as originally filed), are specifically incorporated by reference herein, except for the "Background of the Invention" section of the specification of each application, with the caveat that the definitions of preferences, terms, variables, labels and the like used in each application are applicable only to the corresponding disclosure from that application.

In particular, since each of the above-identified applications incorporated by reference was prepared separately, the original applications may use in some instances the same term, label or variable to mean something different. For example, the variable "X" is used in each application, but each application has its own distinct definition of the substituent or moiety represented by this variable. It will be apparent to those skilled in the art that the terms, labels and variables in each application incorporated by reference are limited solely to the disclosure from that application, and may be replaced by other suitable terms, labels and variables or the like representing the particular substituents and moieties. Of course, those skilled in the art will realize that any suitable set of terms, labels and variables may be used to generically or more specifically represent the subject matter disclosed in the present application, including terms, labels, variables, and the like universally applicable to the incorporated disclosures of the above-identified applications and the following disclosure.

BACKGROUND OF THE INVENTION

This invention relates to a novel series of chemical compounds useful as HIV protease inhibitors and to the use of such compounds as antiviral agents.

Acquired Immune Deficiency Syndrome (AIDS) is a relatively newly recognized disease or condition. AIDS causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, *Karposis sarcoma*, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

In accordance with this invention, there is provided a novel class of chemical compounds that can inhibit and/or block the activity of the HIV protease, which halts the proliferation of HIV virus, pharmaceutical compositions containing these compounds, and the use of the compounds as inhibitors of the HIV protease.

SUMMARY OF THE INVENTION

The present invention relates to compounds falling within formula (1) below, and pharmaceutically acceptable salts thereof, that inhibit the protease encoded by human immunodeficiency virus (HIV) type 1 (HIV-1) or type 2 (HIV-2). These compounds are useful in the treatment of infection by HIV and the treatment of the acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Compounds of the present invention can also be used as prodrugs. Methods of treating AIDS, methods of treating HIV infection and methods of inhibiting HIV protease are disclosed.

The compounds of the present invention are of the formula (1):

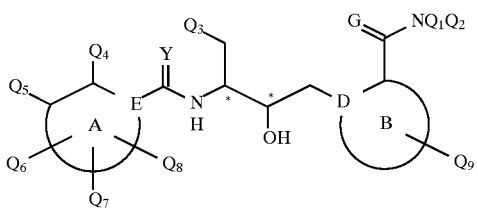

wherein:
- $Q_1$ and $Q_2$ are independently selected from hydrogen and substituted and unsubstituted alkyl and aryl, and $Q_1$ and $Q_2$ may form a ring with G,
- $Q_3$ is selected from mercapto and substituted and unsubstituted alkoxyl, aryloxyl, thioether, amino, alkyl, cycloalkyl, saturated and partially saturated heterocycle, and aryl,
- $Q_4$–$Q_8$ are independently selected from hydrogen, hydroxyl, mercapto, nitro, halogen, —O—J, wherein J is a substituted or unsubstituted hydrolyzable group, and substituted and unsubstituted alkoxyl, aryloxyl, thioether, acyl, sulfinyl, sulfonyl, amino, alkyl, cycloalkyl, saturated and partially saturated heterocycle and aryl, and further wherein any one of $Q_4$–$Q_8$ may be a member of a spiro ring and any two of $Q_4$–$Q_8$ may together be members or a ring,
- Y and G are independently selected from oxygen, —NH, —N-alkyl, sulfur, selenium, and two hydrogen atoms,
- D is carbon or nitrogen,
- E is carbon or nitrogen,
- $Q_9$ is selected from hydrogen, halogen, hydroxyl, mercapto, and substituted and unsubstituted alkoxyl, aryloxyl, thioether, amino, alkyl, and aryl, wherein $Q_9$ may form part of a ring,
- A is a carbocycle or heterocycle, which is optionally further substituted,
- and B is a carbocycle or heterocycle, which is optionally further substituted,
- or a pharmaceutically acceptable salt thereof.

The invention also relates to compounds of formula (1), wherein all variables are the same as those defined above for formula (1) with the exception of D, which is carbon or nitrogen, and is singly bonded to each of the adjacent ring atoms.

The invention more particularly relates to preferred compounds of formula (1) wherein:
- at least one of $Q_1$ and $Q_2$ is substituted or unsubstituted alkyl and the other is as defined above,
- $Q_3$ is selected from thioether and aryl,
- $Q_4$–$Q_8$ are independently selected from hydrogen, hydroxyl, halogen, —O—J, wherein J is a substituted or unsubstituted hydrolyzable group, and substituted and unsubstituted acyl, alkoxyl, amino and alkyl, and further wherein any one or more of $Q_4$–$Q_8$ may form part or a ring,
- Y and G are each oxygen,
- D is nitrogen,
- E is carbon or nitrogen,
- $Q_9$ is hydrogen,
- A is a carbocycle or heterocycle that is an aromatic or partially saturated, 5–7 membered mono-ring, which is optionally further substituted,
- and B is a heterocycle that is a saturated or partially saturated, 8–12 membered poly-ring, which is optionally further substituted, or a pharmaceutically acceptable salt thereof.

The invention even more particularly relates to compounds of the formula (1) wherein:
- one of $Q_1$ and $Q_2$ is substituted or unsubstituted alkyl, preferably t-butyl, and the other is hydrogen,
- $Q_3$ is selected from thioaryl and aryl, preferably thiophenyl and phenyl,
- $Q_4$ is alkyl, preferably methyl,
- $Q_5$ is hydroxyl or —O—J, wherein J is a hydrolyzable group, or substituted or unsubstituted alkoxyl or amino,
- $Q_6$–$Q_8$ are independently selected from hydrogen, hydroxyl, halogen, 13 O—J, wherein J is a substituted or unsubstituted hydrolyzable group, and substituted and unsubstituted alkoxyl, acyl, amino and alkyl, and further wherein any one or more of $Q_6$–$Q_8$ may form part of a ring,
- Y and G are each oxygen,
- D is nitrogen,
- E is carbon,
- $Q_9$ is hydrogen,
- A is a carbocycle that is an aromatic, 5–6 membered monocyclic ring, preferably phenyl, which is optionally further substituted,
- and B is a heterocycle that is a saturated, 6–14 membered monocyclic or polycyclic ring, which is optionally further substituted, preferably of the formula

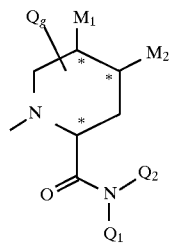

wherein $M_1$ and $M_2$ are independently selected from hydrogen, mercapto, hydroxyl, and substituted and unsubstituted thioether, alkyl, alkoxyl, aryloxyl, amino, five membered heterocycle and carbocycle, sulfinyl, sulfonyl, and acyl, and wherein $M_1$ and $M_2$ optionally form a ring having up to 10 members, wherein preferably $M_1$ and $M_2$ independently have from zero to eight non-hydrogen atoms;

or a pharmaceutically acceptable salt thereof.

Preferred compounds of the formula (1) include those wherein:
- one of $Q_1$ and $Q_2$ is tertiary alkyl, preferably t-butyl, and the other is hydrogen,
- $Q_3$ is thiophenyl, phenyl, naphthyl, or thionaphthyl,
- $Q_4$ is methyl,
- $Q_5$ is hydroxyl, amino, or —O—J, wherein J is a substituted or unsubstituted hydrolyzable group,
- $Q_6$–$Q_8$ are independently selected from hydrogen, hydroxyl, halogen, —O—J, wherein J is a substituted or unsubstituted hydrolyzable group, and substituted and unsubstituted alkoxyl, acyl, amino and alkyl, and further wherein any one or more of $Q_6$–$Q_8$ may form part of a ring,
- Y and G are each oxygen,
- D is nitrogen,
- E is carbon, $Q_9$ is hydrogen, A is phenyl, which is optionally further substituted, and B is a heterocycle that is a saturated, 9–10 membered bi-ring, preferably decahydroisoquinolinyl or octahydrothieno[3,2,-c]pyridinyl, or a pharmaceutically acceptable salt thereof.

According to certain embodiments, the portion of formula (1):

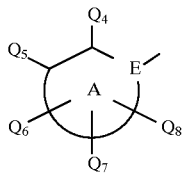

is designated as Z or $Z^1$, and/or the portion of formula (1):

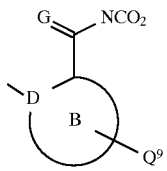

is designated as X or $X^1$.

According to certain of those embodiments, the compounds have the formula 1(A):

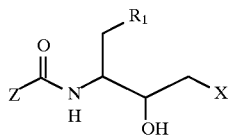

wherein:

Z is a group having the structure:

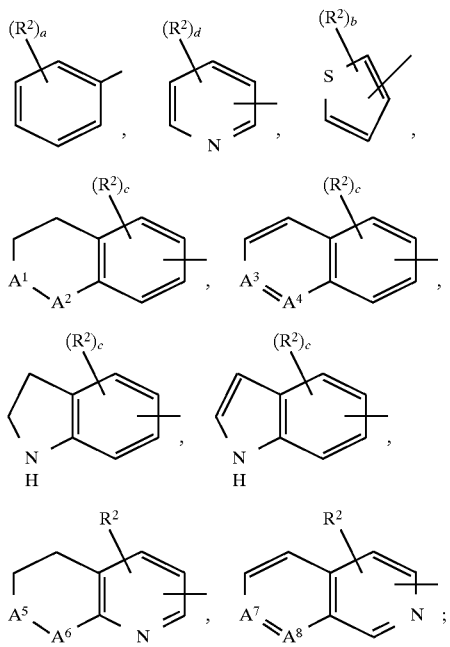

where:

a is 1, 2, 3, 4, or 5;

b is 1, or 2;

c is 1, or 2;

d is 1, 2, 3, or 4;

each $R^2$ is independently hydrogen, hydroxy, thiol, halo, amino, $C_1$–$C_4$ alkylamino, di($C_1$–$C_4$)alkylamino, nitro, carboxy, $C_1$–$C_6$ alkyl, $C_1$–$C_6$ alkoxy, $C_1$–$C_6$ alkylthio, halo($C_1$–$C_4$)alkyl, hydroxy($C_1$–$C_4$)alkyl, $C_1$–$C_6$ alkylthio($C_1$–$C_6$)alkyl, $C_1$–$C_4$ alkoxycarbonyl, carbamoyl, N—($C_1$–$C_4$) alkylcarbamoyl, $C_1$–$C_4$ alkylsulfonyl, N,N-di($C_1$–$C_4$)alkylcarbamoyl, or $C_1$–$C_4$ alkylsulfonylamino;

$A^1$ and $A^2$ are independently —$CH_2$— or —N($R^8$)—;

$A^3$ and $A^4$ are independently —CH— or —N—;

$A^5$ and $A^6$ are independently —$CH_2$— or —N($R^9$)—;

$A^7$ and $A^8$ are independently —CH— or —N—;

$R^8$ is hydrogen or $C_1$–$C_4$ alkyl;

$R^9$ is hydrogen or $C_1$–$C_4$ alkyl;

$R^1$ is aryl, or —S-aryl;

X is a group having the structure:

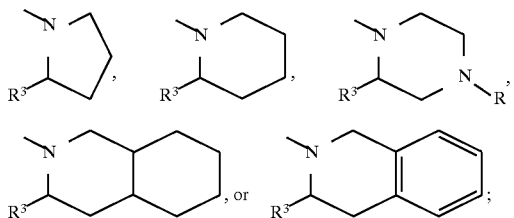

where:

R is hydrogen, $C_1$–$C_4$ alkyl, or —$CH_2$-pyridyl;

$R^3$ is a group having the structure:

1) —C(O)—$NR^4R^4$,

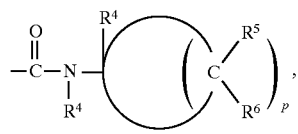

or

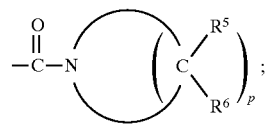

p is 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$ alkoxy, or hydroxy ($C_1$–$C_4$)alkyl; with the provisos that:

(1) one of $A^1$ and $A^2$ must be —N($R^8$)—;

(2) $A^1$ and $A^2$ cannot both be —N($R^8$)—;

(3) $A^3$ and $A^4$ cannot both be —N—;

(4) one of $A^5$ and $A^6$ must be —N($R^9$)—;

(5) $A^5$ and $A^6$ cannot both be —N($R^9$)—;

(6) $A^7$ and $A^8$ cannot both be —N—; or a pharmaceutically acceptable salt thereof.

Also, according to certain of those embodiments, the compounds have the formula 1(B):

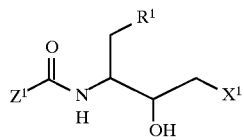

wherein:

R¹ is aryl, or —S-aryl;

X¹ is a group having the formula:

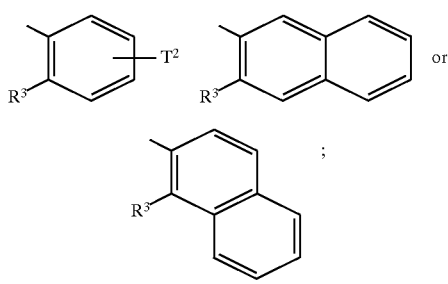

R² is hydrogen, halo, or $C_1$–$C_4$ alkyl;

R₃ is a group having the structure:
1) —C(O)—NR⁴R⁴,
2)

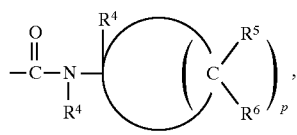

or

3)

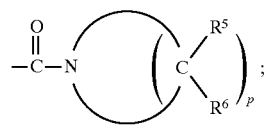

p is 4 or 5;

R⁴ at each occurrence is independently hydrogen, $C_1$–$C_6$ alkyl or hydroxy ($C_1$–$C_4$) alkyl; and R⁵ and R⁶ are independently selected from hydrogen, hydroxy, $C_1$–$C_6$ alkyl, $C_1$–$C_6$ alkoxy, or hydroxy ($C_1$–$C_4$) alkyl;

Z¹ is a group having the structure:

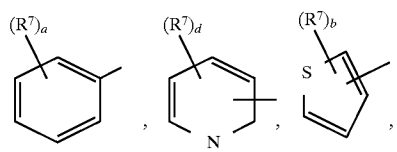

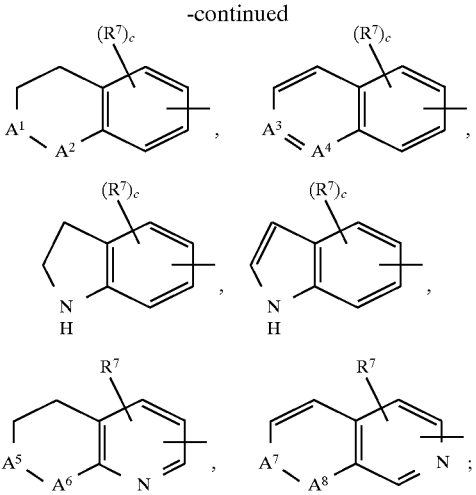

where:

a is 1, 2, 3, 4, or 5;

b is 1, or 2;

c is 1, or 2;

d is 1, 2, 3, or 4 each R⁷ is independently hydrogen, hydroxy, thiol, halo, amino, $C_1$–$C_4$ alkylamino, di($C_1$–$C_4$)alkylamino, nitro, carboxy, $C_1$–$C_6$ alkyl, $C_1$–$C_6$ alkoxy, $C_1$–$C_4$ alkylthio, halo($C_1$–$C_4$)alkyl, hydroxy($C_1$–$C_4$)alkyl, $C_1$–$C_4$ alkylthio($C_1$–$C_4$)alkyl, $C_1$–$C_4$ alkoxycarbonyl, carbamoyl, N-($C_1$–$C_4$)alkylcarbamoyl, $C_1$–$C_4$ alkylsulfonyl, N,N-di($C_1$–$C_4$)alkylcarbamoyl, or $C_1$–$C_4$ alkylsulfonylamino;

A¹ and A² are independently —CH₂— or —N(R⁸)—;

A³ and A⁴ are independently —CH— or —N—;

A⁵ and A⁶ are independently —CH₂— or —N(R⁹)—;

A⁷ and A⁸ are independently —CH— or —N—;

R⁸ is hydrogen or $C_1$–$C_4$ alkyl;

R⁹ is hydrogen or $C_1$–$C_4$ alkyl;

T² is hydrogen, or $C_1$–$C_4$ alkyl; with the provisos that:
(1) one of A¹ and A² must be —N(R⁸)—;
(2) A¹ and A² cannot both be —N(R⁸)—;
(3) A³ and A⁴ cannot both be —N—;
(4) one of A⁵ and A⁶ must be —N(R⁹)—;
(5) A⁵ and A⁶ cannot both be —N(R⁹)—;
(6) A⁷ and A⁸ cannot both be —N—; or a pharmaceutically acceptable salt thereof.

Preferred species of the formula (1) are: [3S-(3R*,4aR*,8aR*,2'S*,3'S*)]-2-[2'-hydroxy-3'-phenylthiomethyl-4'-aza-5'-oxo-5'-(2"-methyl-3"-hydroxyphenyl)pentyl]decahydroisoquinoline-3-N-t-butylcarboxamide and its pharmaceutically acceptable salts, especially methanesulfonic acid salt, and its prodrug analogs, wherein the 3" hydroxy is converted to —O—J, as defined above, especially the dihydrogen phosphate hydrochloride salt; and [6S-(6R*,3aS*,7aR*,2'S*,3'S*)]-2-[2'-hydroxy-3'-phenylthiomethyl-4'aza-5'-oxo-5'-(2"-methyl-3"-hydroxyphenyl)pentyl]-octahydro-thieno[3,2-c]pyridine-6-N-t-butylcarboxamide and its pharmaceutically acceptable salts, especially methanesulfonic acid salt, and its prodrug analogs, wherein the 3" hydroxy is converted to —O—J, as defined above.

The present invention further provides pharmaceutical formulations comprising an effective amount of a compound of formula (1) or a pharmaceutically acceptable salt thereof, in combination with a pharmaceutically acceptable carrier, such as a diluent or excipient.

The present invention further provides a method of treating AIDS comprising administering to a host or patient, such as a primate, an effective amount of a compound of the present invention.

The present invention further provides a method of inhibiting HIV replication comprising administering to an HIV infected cell, a cell susceptible to HIV infection or a host or patient, such as a primate, an effective amount of a compound of the present invention.

DETAILED DESCRIPTION OF THE INVENTION

The present invention provides new compounds falling within formula (1), as described above, that are useful for treating HIV infection and/or AIDS.

Compounds of the formula (1) may be prodrugs. For example, compounds wherein at least one of $Q_4$–$Q_8$ is —O—J, as defined above, may be used as prodrugs, which can serve to improve the pharmaceutical properties of the compounds, such as pharmacokinetic properties, for example, improved bioavailability or solubility. The preparation of the prodrugs may be carried out by reacting a compound of the formula (1), wherein at least one of $Q_4$–$Q_8$ is —O—H, with, for example, an activated amino acyl, phosphoryl or hemisuccinyl derivative.

All temperatures stated herein are in degrees Celsius (°C.). All units of measurement employed herein are in weight units except for liquids which are in volume units.

The term "alkyl" as used herein refers to straight or branched chain groups, preferably, having one to eight, more preferably having one to six, and most preferably having from one to four carbon atoms. The term "$C_1$–$C_6$ alkyl" represents a straight or branched alkyl chain having from one to six carbon atoms. Exemplary $C_1$–$C_6$ alkyl groups include methyl, ethyl, n-propyl, isopropyl, butyl, isobutyl, sec-butyl, t-butyl, pentyl, neo-pentyl, hexyl, isohexyl, and the like. The term "$C_1$–$C_6$ alkyl" includes within its definition the term "$C_1$–$C_4$ alkyl".

The term "cycloalkyl" represents a saturated or partially saturated, mono- or poly-carbocyclic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "alkoxyl" represents —O-alkyl. An example of an alkoxyl is a $C_1$–$C_6$ alkoxyl, which represents a straight or branched alkyl chain having from one to six carbon atoms attached to an oxygen atom. Exemplary $C_1$–$C_6$ alkoxyl groups include methoxyl, ethoxyl, propoxyl, isopropoxyl, butoxyl, sec-butoxyl, t-butoxyl, pentoxyl, hexoxyl, and the like. $C_1$–$C_6$ alkoxyl includes within its definition a $C_1$–$C_4$ alkoxyl.

The term "aryl" as used herein refers to a carbocyclic or heterocyclic, aromatic, 5–14 membered monocyclic or polycyclic ring. Exemplary aryls include phenyl, naphthyl, anthryl, phenanthryl, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "aryloxyl" represents —O-aryl.

The term "hydrolyzable group" is a group, which when bonded to an oxygen, forms an ester, which can be hydrolyzed in vivo to a hydroxyl group. Exemplary hydrolyzable groups, which are optionally substituted, include acyl function, sulfonate function and phosphate function. For example, such hydrolyzable groups include blocked or unblocked amino acid residue, a hemisuccinate residue, and a nicotinate residue.

The term "halogen" represents chlorine, fluorine, bromine or iodine. The term "halo" represents chloro, fluoro, bromo or iodo.

The term "carbocycle" represents an aromatic or a saturated or a partially saturated 5–14 membered monocyclic or polycyclic ring, such as a 5- to 7-membered monocyclic or 7- to 10-membered bicyclic ring, wherein all the ring members are carbon atoms.

The term "heterocycle" represents an aromatic or a saturated or a partially saturated, 5–14 membered, monocyclic or polycyclic ring, such as a 5- to 7-membered monocyclic or 7- to 10-membered bicyclic ring, having from one to three heteroatoms selected from nitrogen, oxygen and sulfur, and wherein any nitrogen and sulfur heteroatoms may optionally be oxidized, and any nitrogen heteroatom may optionally be quaternized. The heterocyclic ring may be attached at any suitable heteroatom or carbon atom. Examples of such heterocycles include decahydroisoquinolinyl, octahydrothieno[3,2-c]pyridinyl, piperidinyl, piperazinyl, azepinyl, pyrrolyl, pyrrolidinyl, pyrazolyl, pyrazolidinyl, imidazolyl, isobenzofuranyl, furazanyl, imidazolinyl, imidazolidinyl, pyridyl, pyrazinyl, pyrimidinyl, pyridazinyl, oxazolyl, oxazolidinyl, isoxazolyl, thianthrenyl, triazinyl, isoxazolidinyl, morpholinyl, thiazolyl, thiazolidinyl, isothiazolyl, quinuclidinyl, isothiazolidinyl, indolyl, quinolinyl, chromenyl, xanthenyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, benzo[b]thienyl, naphtho[2,3-b] thienyl, thiamorpholinyl, thiamorpholinylsulfoxide, thiamorpholinylsulfone, oxadiazolyl, triazolyl, tetrahydroquinolinyl, tetrahydrisoquinolinyl, phenoxathienyl, indolizinyl, isoindolyl, indazolyl, purinyl, isoquinolyl, quinolyl, phthalazinyl, naphthyridinyl, quinoxyalinyl, quinzolinyl, tetrahydroquinolinyl, cinnolinyl, pteridinyl, carbazolyl, beta-carbolinyl, phenanthridinyl, acridinyly perimidinyly phenanthrolinyl, phenazinyl, isothiazolyl, phenothiazinyl, and phenoxazinyl.

The term "thioether" includes S-aryl, such as phenylthio and naphthylthio; S-heterocycle where the heterocycle is saturated or partially saturated; S—($C_5$–$C_7$)-cycloalkyl; and S-alkyl, such as $C_1$–$C_6$ alkylthio. In the thioether the -aryl, the -heterocycle, the -cycloalkyl and the -alkyl can optionally be substituted. An example of a thioether is "$C_1$–$C_6$ alkylthio", which represents a straight or branched alkyl chain having from one to six carbon atoms attached to a sulfur atom. Exemplary $C_1$–$C_6$ alkylthio groups include methylthio, ethylthio, propylthio, isopropylthio, butylthio, sec-butylthio, t-butylthio, pentylthio, hexylthio, and the like.

The term "mercapto" represents —SH.

The term "amino" represents —$NL_1L_2$, wherein $L_1$ and $L_2$ are preferably independently selected from oxygen, carbocycle, heterocycle, alkyl, sulfonyl and hydrogen; or NC(O)L$_3$, wherein L$_3$ is preferably alkyl, alkoxyl, hydrogen or —NL$_1$L$_2$. The aryl, alkyl and alkoxyl groups can optionally be substituted. An example of an amino is C$_1$–C$_4$ alkylamino, which represents a straight or branched alkyl chain having from one to four carbon atoms attached to an amino group. Exemplary C$_1$–C$_4$ alkylamino groups include methylamino, ethylamino, propylamino, isopropylamino, butylamino, sec-butylamino, and the like. Another example of an amino is di(C$_1$–C$_4$)alkylamino, which represents two straight or branched alkyl chains, each having from one to four carbon atoms attached to a common amino group. Exemplary di(C$_1$–C$_4$)alkylamino groups include dimethylamino, ethylmethylamino, methylpropylamino, ethylisopropylamino, butylmethylamino, sec-butylethylamino, and the like. An example of an amino is C$_1$–C$_4$ alkylsulfonylamino, which has a straight or branched alkyl chain having from one to four carbon atoms attached to a sulfonylamino moiety. Exemplary C$_1$–C$_4$ alkylsulfonylamino groups include methylsulfonylamino, ethylsulfonylamino, propylsulfonylamino, isopropylsulfonylamino, butylsulfonylamino, sec-butylsulfonylamino, t-butylsulfonylamino, and the like.

The term "acyl" represents L$_6$C(O)L$_4$, wherein L$_6$ is a single bond, —O or —N, and further wherein L$_4$ is preferably alkyl, amino, hydroxyl, alkoxyl or hydrogen. The alkyl and alkoxyl groups can optionally be substituted. An exemplary acyl is a C$_1$–C$_4$ alkoxycarbonyl, which is a straight or branched alkoxyl chain having from one to four carbon atoms attached to a carbonyl moiety. Exemplary C$_1$–C$_4$ alkoxycarbonyl groups include methoxycarbonyl, ethoxycarbonyl, propoxycarbonyl, isopropoxycarbonyl, butoxycarbonyl, and the like. Another exemplary acyl is a carboxy wherein L$_6$ is a single bond and L$_4$ is alkoxyl, hydrogen, or hydroxyl. A further exemplary acyl is N—(C$_1$–C$_4$)alkylcarbamoyl (L$_6$ is a single bond and L$_4$ is an amino), which is a straight or branched alkyl chain having from one to four carbon atoms attached to the nitrogen atom of a carbamoyl moiety. Exemplary N—(C$_1$–C$_4$) alkylcarbamoyl groups include N-methylcarbamoyl, N-ethylcarbamoyl, N-propylcarbamoyl, N-isopropylcarbamoyl, N-butylcarbamoyl, and N-t-butylcarbamoyl, and the like. Yet another exemplary acyl is N,N-di(C$_1$–C$_4$)alkylcarbamoyl, which has two straight or branched alkyl chains, each having from one to four carbon atoms attached to the nitrogen atom of a carbamoyl moiety. Exemplary N,N-di(C$_1$–C$_4$)alkylcarbamoyl groups include N,N-dimethylcarbamoyl, N,N-ethylmethylcarbamoyl, N,N-methylpropylcarbamoyl, N,N-ethylisopropylcarbamoyl, N,N-butylmethylcarbamoyl, N,N-sec-butylethylcarbamoyl, and the like.

The term "sulfinyl" represents —SO—L$_5$, wherein L$_5$ is preferably alkyl, amino, aryl, cycloalkyl or heterocycle. The alkyl, aryl, cycloalkyl and heterocycle can all optionally be substituted.

The term "sulfonyl" represents —SO$_2$—L$_5$, wherein L$_5$ is preferably alkyl, aryl, cycloalkyl, heterocycle or amino. The alkyl, aryl, cycloalkyl and heterocycle can all optionally be substituted. An example of a sulfonyl is a C$_1$–C$_4$ alkylsulfonyl, which is a straight or branched alkyl chain having from one to four carbon atoms attached to a sulfonyl moiety. Exemplary C$_1$–C$_4$ alkylsulfonyl groups include methylsulfonyl, ethylsulfonyl, propylsulfonyl, isopropylsulfonyl, butylsulfonyl, sec-butylsulfonyl, t-butylsulfonyl and the like.

As indicated above, many of the groups are optionally substituted. Examples of substituents for alkyl and aryl include mercapto, thioether, nitro (NO$_2$), amino, aryloxyl, halogen, hydroxyl, alkoxyl, and acyl, as well as aryl, cycloalkyl and saturated and partially saturated heterocycles. Examples of substituents for heterocycle and cycloalkyl include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino(C$_1$–C$_4$)alkoxy carbonyl, pyridyl (C$_1$–C$_4$)alkoxycarbonyl, halo (C$_1$–C$_4$)alkyl, C$_1$–C$_4$ alkyl, C$_1$–C$_4$ alkoxy, carboxy, C$_1$–C$_4$ alkoxycarbonyl, carbamoyl, N—(C$_1$–C$_4$)alkylcarbamoyl, amino, C$_1$–C$_4$ alkylamino, di(C$_1$–C$_4$)alkylamino or a group of the formula —(CH$_2$)$_a$—R$^7$ where a is 1, 2, 3 or 4; and R$^7$ is hydroxy, C$_1$–C$_4$ alkoxy, carboxy, C$_1$–C$_4$ alkoxycarbonyl, amino, carbamoyl, C$_1$–C$_4$ alkylamino or di(C$_1$–C$_4$)alkylamino.

Another substituted alkyl is halo(C$_1$–C$_4$)alkyl, which represents a straight or branched alkyl chain having from one to four carbon atoms with 1–3 halogen atoms attached to it. Exemplary halo(C$_1$–C$_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

Another substituted alkyl is hydroxy(C$_1$–C$_4$)alkyl, which represents a straight or branched alkyl chain having from one to four carbon atoms with a hydroxy group attached to it. Exemplary hydroxy(C$_1$–C$_4$)alkyl groups include hydroxymethyl, 2-hydroxyethyl, 3-hydroxypropyl, 2-hydroxyisopropyl, 4-hydroxybutyl and the like.

Yet another substituted alkyl is C$_1$–C$_4$ alkylthio(C$_1$–C$_4$) alkyl, which is a straight or branched C$_1$–C$_4$ alkyl group with a C$_1$–C$_4$ alkylthio group attached to it. Exemplary C$_1$–C$_4$ alkylthio(C$_1$–C$_4$)alkyl groups include methylthiomethyl, ethylthiomethyl, propylthiopropyl, sec-butylthiomethyl, and the like.

Yet another exemplary substituted alkyl is heterocycle (C$_1$–C$_4$)alkyl, which is a straight or branched alkyl chain having from one to four carbon atoms with a heterocycle attached to it. Exemplary heterocycle(C$_1$–C$_4$)alkyls include pyrrolylmethyl, quinolinylmethyl, 1-indolylethyl, 2-furylethyl, 3-thien-2-ylpropyl, 1-imidazolylisopropyl, 4-thiazolylbutyl and the like.

Yet another substituted alkyl is aryl(C$_1$–C$_4$)alkyl, which is a straight or branched alkyl chain having from one to four carbon atoms with an aryl group attached to it. Exemplary aryl(C$_1$–C$_4$)alkyl groups include phenylmethyl, 2-phenylethyl, 3-naphthyl-propyl, 1-naphthylisopropyl, 4-phenylbutyl and the like.

The heterocycle can, for example, be substituted with 1, 2 or 3 substituents independently selected from halo, halo (C$_1$–C$_4$)alkyl, C$_1$–C$_4$ alkyl, C$_1$–C$_4$ alkoxy, carboxy, C$_1$–C$_4$ alkoxycarbonyl, carbamoyl, N—(C$_1$–C$_4$)alkylcarbamoyl, amino, C$_1$–C$_4$alkylamino, di(C$_1$–C$_4$)alkylamino or a group having the structure —(CH$_2$)$_a$—R$^7$ where a is 1, 2, 3 or 4 and R$^7$ is hydroxy, C$_1$–C$_4$ alkoxy, carboxy, C$_1$–C$_4$ alkoxycarbonyl, amino, carbamoyl, C$_1$–C$_4$ alkylamino or di(C$_1$–C$_4$)alkylamino.

Examples of substituted heterocycles include 3-N-t-butyl carboxamide decahydroisoquinolinyl, 6-N-t-butyl carboxamide octahydro-thieno[3,2-c]pyridinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethylnaphthyl, 2-methyl-1,2,3,4- tetrahydroisoquinolinyl, N-methyl-quinolin-2-yl, 2-t-butoxycarbonyl-1,2,3,4-isoquinolin-7-yl and the like.

Exemplary heterocyclic ring systems represented by A or B include (1) 5-membered monocyclic ring groups such as thienyl, pyrrolyl, imidazolyl, pyrazolyl, furyl, isothiazolyl, furazanyl, isoxazolyl, thiazolyl and the like; (2) 6-membered monocyclic groups such as pyridyl, pyrazinyl, pyrimidinyl, pyridazinly, triazinyl and the like; and (3) polycyclic heterocyclic rings groups, such as decahydroisoquinolinyl, octahydro-thieno[3,2-c]pyridinyl, benzo[b]thienyl, naphtho[2,3-b]thianthrenyl, isobenzofuranyl, chromenyl, xanthenyl, and fully or partially saturated analogs thereof.

A cycloalkyl may be optionally substituted with 1, 2 or 3 substituents independently selected from halo, halo($C_1$–$C_4$) alkyl, $C_1$–$C_4$ alkyl, $C_1$–$C_4$ alkoxy, carboxy, $C_1$–$C_4$ alkoxycarbonyl, carbamoyl, N—($C_1$–$C_4$)alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Exemplary substituted cycloalkyl groups include 3-methylcyclopentyl, 4-ethoxycyclohexyl, 5-carboxycyclo-heptyl, 6-chlorocyclohexyl and the like.

Exemplary substituted hydrolyzable groups include N-benzyl glycyl, N-Cbz-L-valyl, and N-methyl nicotinate.

Exemplary compounds of formula (1) include those compounds of formula I in each of the incorporated applications Ser. Nos. 08/137,254, 08/133,696, and 08/133,543 that fall within the scope of formula (1) as defined herein.

The compounds of the present invention have at least two asymmetric centers denoted by an asterisk in the formula (1) below:

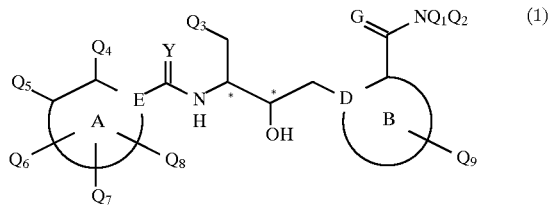

As a consequence of these asymmetric centers, the compounds of the present invention can occur in any of the possible stereoisomeric forms, and can be used in mixtures of stereoisomers, which can be optically active or racemic, or can be used alone as essentially pure stereisomers, i.e., at least 95% pure. All asymmetric forms, individual stereoisomers and combinations thereof, are within the scope of the present invention.

The individual stereoisomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

Preferably, the compounds of the present invention are substantially pure, i.e, over 50% pure. More preferably, the compounds are at least 75% pure. Even more preferably, the compounds are more than 90% pure. Even more preferably, the compounds are at least 95% pure, more preferably, at least 97% pure, and most preferably at least 99% pure.

As mentioned above, the invention includes the pharmaceutically acceptable salts of the compounds defined by formula (1). A compound of this invention may possess a sufficiently acidic, a sufficiently basic, or both functional groups, and accordingly react with any of a number of inorganic or organic bases, and inorganic and organic acids, to form a pharmaceutically acceptable salt.

The term "pharmaceutically acceptable salt", as used herein, refers to salts of the compounds of the above formula which are substantially non-toxic to living organisms. Exemplary pharmaceutically acceptable salts include those salts prepared by reaction of the compounds of the present invention with a mineral or organic acid or an inorganic base. The reactants are generally combined in a mutual solvent such as diethylether or benzene, for acid addition salts, or water or alcohols for base addition salts. The salts normally precipitate out of solution within about one hour to about ten days and can be isolated by filtration or other conventional methods. Such salts are known as acid addition and base addition salts.

Acids that may be employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methane-sulfonate, propanesulfonate, naphthalene-1sulfonate, napththalene-2-sulfonate, mandelate and the like.

Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic and organic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Certain compounds are those compounds of formula 1(A) above wherein:

Z is a group having the structure:

[structures: phenyl with (R²)ₐ; quinoline with (R²)c; tetrahydroquinoline with (R²)c; naphthalene with (R²)c; tetrahydroquinoline with R²]

R² is hydrogen, hydroxy, C₁–C₄ alkyl, halo, amino, nitro, or trifluoromethyl;
a is 1, 2, or 3;
c is 1; and
R is —C(O)NR⁴R⁴;
or a pharmaceutically acceptable salt thereof.
Of these compounds, more preferred are those compounds where:
Z is

[structure: phenyl with (R²)ₐ]

R² is hydrogen, methyl, ethyl, propyl, chloro, fluoro, hydroxy, or amino;
X is

[two structures: decahydroisoquinoline with R³; piperazine-type with R³ and R]

R is —CH₂-pyridyl;
R¹ is phenyl or —S-phenyl; and
R³ is —C(O)NH(R⁴);
or a pharmaceutically acceptable salt thereof.
Of these compounds, especially preferred are those compounds where:
Z is

[structure: phenyl with R²ᵃ, R²ᵇ, R²c]

R²ᵃ is methyl, ethyl, or propyl;

R²ᵇ is hydrogen, hydroxy, or amino;
R²c is hydrogen, hydroxy, or amino;
X is

[structure: decahydroisoquinoline with R³]

and

R³ is —C(O)NH(t-butyl);
or a pharmaceutically acceptable salt thereof.
Certain other preferred compounds are those compounds of formula 1(B) wherein:
X¹ is

[structure: phenyl with R³ and T²]

T² is hydrogen or methyl;
Z¹ is a group having the structure:

[structures: phenyl with (R⁷)ₐ; quinoline with (R⁷)c; tetrahydroquinoline with (R⁷)c; tetrahydroquinoline with R⁷]

R⁷ is hydrogen, C₁–C₄ alkyl, halo, nitro, amino, hydroxy;
a is 1, 2, or 3;
c is 1;
or a pharmaceutically acceptable salt thereof.
Of these compounds, more preferred are those compounds where:
Z¹ is

[structure: phenyl with (R⁷)ₐ]

R⁷ is hydrogen, methyl, ethyl, hydroxy, amino, chloro;
R¹ is —S-phenyl, or —S-naphth-2-yl; and
R³ is —C(O)NR⁴R⁴;
or a pharmaceutically acceptable salt thereof.
Of these compounds, especially preferred are those compounds where:

$Z^1$ is

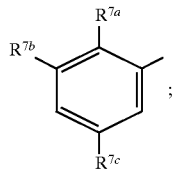

$R^{7a}$ is hydrogen, methyl, ethyl, chloro, bromo, or fluoro;
$R^{7b}$ is hydrogen, hydroxy, chloro, or amino;
$R^{7c}$ is hydrogen, hydroxy, or amino;
$R^3$ is —C(O)NH(t-butyl);
or a pharmaceutically acceptable salt thereof.

Preferred compounds are:

2-[2'-hydroxy-3'-phenylthiomethyl-4'-aza-5'-oxo-5'-(2"-methyl-3"-hydroxyphenyl)pentyl]decahydroisoquinoline-3-N-t-butylcarboxamide:

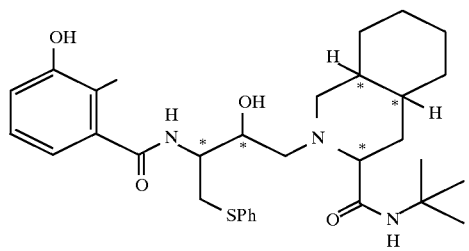

2-[2'-hydroxy-3'-phenylthiomethyl-4'-aza-5'-oxo-5'-(2"-methyl-3"-hydroxyphenyl)pentyl]decahydroisoquinoline-3-N-t-butylcarboxamide methanesulfonic acid salt:

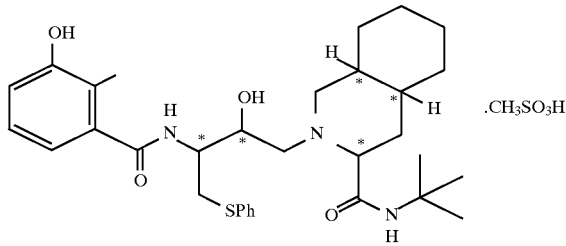

2-[2'-hydroxy-3'-phenylthiomethyl-4'-aza-5'-oxo-5'-(2"-methyl-3"-hydroxyphenyl)pentyl]decahydroisoquinoline-3-N-t-butylcarboxamide 3"-dihydrogen phosphate hydrochloride salt:

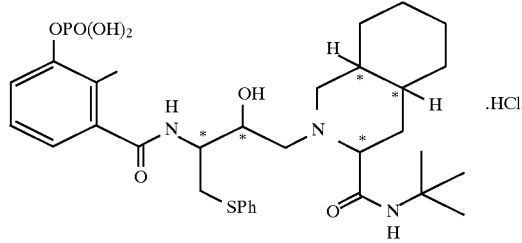

2-[2-hydroxy-3'-phenylthiomethyl-4'aza-5'-oxo-5'-(2"-methyl-3"-hydroxyphenyl)pentyl]-octahydro-thieno[3,2-c]pyridine-6-N-t-butylcarboxamide:

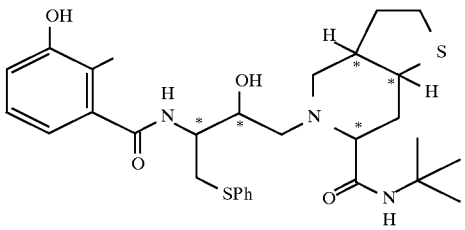

and
2-[2'-hydroxy-3'-phenylthiomethyl-4'aza-5'-oxo-5'-(2"-methyl-3"-hydroxyphenyl)pentyl]-octahydro-thieno[3,2-c]pyridine-6-N-t-butylcarboxamide methanesulfonic acid salt:

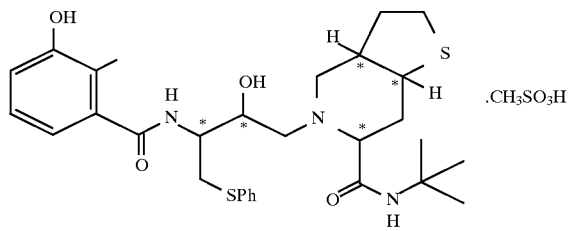

Each of the above five formulae has five asymmetric centers and thus defines a compound selected from the group of 32 individual stereoisomers and any mixture of two or more stereoisomers.

Preferred stereisomers of these compounds are:
[3S-(3R*,4aR*,8aR*,2'S*,3'S*)]-2-[2'-hydroxy-3'-phenylthiomethyl-4'-aza-5'-oxo-5'-(2"-methyl-3"-hydroxyphenyl)pentyl]decahydroisoquinoline-3-N-t-butylcarboxamide:

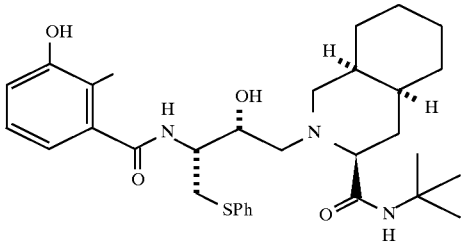

[3S-(3R*,4aR*,8aR*,2'S*,3'S*)]-2-[2-hydroxy-3'-phenylthiomethyl-4'-aza-5'-oxo-5'-(2"-methyl-3"-hydroxyphenyl)pentyl]decahydroisoquinoline-3-N-t-butylcarboxamide methanesulfonic acid salt:

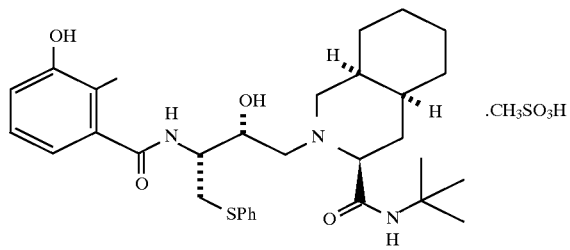

[3S-(3R*,4aR*,8aR*,2'S*,3'S*)]-2-[2'-hydroxy-3-phenylthiomethyl-4'-aza-5'-oxo-5'-(2"-methyl-3"-hydroxyphenyl)pentyl]decahydroisoquinoline-3-N-t-butylcarboxamide 3"-dihydrogen phosphate hydrochloride salt:

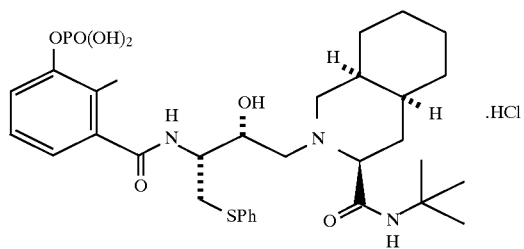

[6S-(6R*,3aS*,7aR*,2'S*,3'S*)]-2-[2'-hydroxy-3'-phenylthiomethyl-4'aza-5'-oxo-5'-(2"-methyl-3"-hydroxyphenyl)pentyl]-octahydrothieno[3,2-c]pyridine-6-N-t-butylcarboxamide:

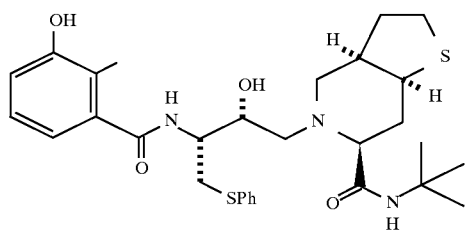

and

[6S-(6R*,3aS*,7aR*,2'S*,3'S*)]-2-[2'-hydroxy-3'-phenylthiomethyl-4'aza-5'-oxo-5'-(2"-methyl-3"-hydroxyphenyl)pentyl]-octahydrothieno[3,2-c]pyridine-6-N-t-butylcarboxamide methanesulfonic acid salt:

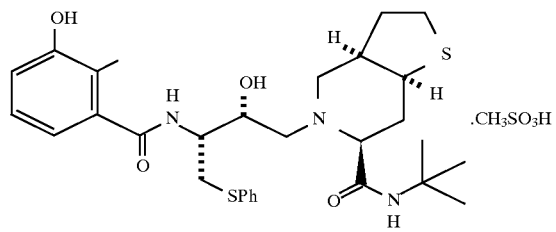

[3S-(3R*,4aR*,8aR*,2'S*,3'R*)]-2-[2'-hydroxy-3'-phenylmethyl-4'-aza-5'-oxo-5'-(2"-propyl-3"-hydroxyphenyl)pentyl]decahydroisoquinoline-3-N-t-butylcarboxamide;

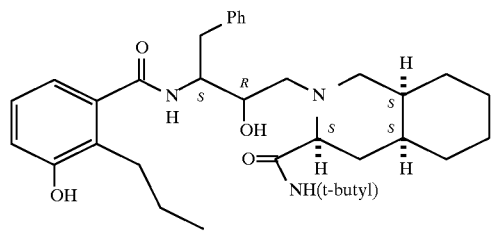

[2S-(2R*,2'S*,3'S*)]-1-[2'-hydroxy-3'-phenylthiomethyl-4'-aza-5'-oxo-5'-(3"-hydroxy-2"-methylphenyl)pentyl]-4-pyrid-3"-ylmethyl piperazine-2-N-t-butylcarboxamide;

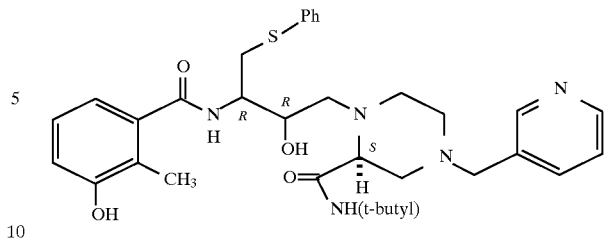

[3S-(3R*,4aR*,8aR*,2'S*,3'S*)]-2-[2'-hydroxy-3'-phenylthiomethyl-4'-aza-5'-oxo-5'-(1",2",3",4"-tetrahydroquinolin-5"-yl)pentyl[decahydroisoquinoline-3-N-t-butylcarboxamide;

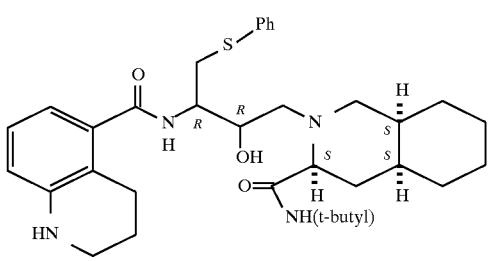

[3S-(3R*,4aR*,8aR*,2'S*,3'R*)]-2-[2'-hydroxy-3'-phenylmethyl-4'-aza-5'-oxo-5'-(2"-methyl-3"-hydroxyphenyl)pentyl]decahydroisoquinoline-3-N-t-butylcarboxamide;

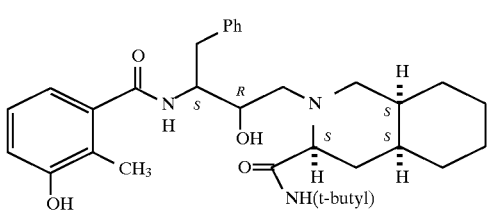

[3S-(3R*,4aR*,8aR*,2'S*,3'R*)]-2-[2'-hydroxy-3'-phenylmethyl-4'-aza-5'-oxo-5'-(2"-ethyl-3"-hydroxyphenyl)pentyl]decahydroisoquinoline-3-N-t-butylcarboxamide;

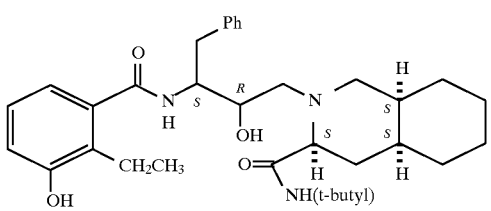

[2'R-(2'R*,3'S*)]-N-t-butyl-2-[2'-hydroxy-3-naphth-2-yl-ylthiomethyl-4'-aza-5'-oxo-5'-(1",2",3",4"-tetrahydroquinolin-5"-yl)pentyl]benzamide;

[2'R-(2'R*,3'S*)]-N-t-butyl-2-[2'-hydroxy-3'-naphth-2-ylthiomethyl-4'-aza-5'-oxo-5'-(2"-methyl-3"-hydroxyphenyl)pentyl]benzamide;

[2'R-(2'R*,3'S*)]-N-t-butyl-2-[2'-hydroxy-3'-naphth-2-ylthiomethyl-4'-aza-5'-oxo-5'-(2"-methyl-3",5"-diaminophenyl)pentyl]benzamide;

[2'R-(2'R*,3'S*)]-N-t-butyl-2-[2'-hydroxy-3'-naphth-2-ylthiomethyl-4'-aza-5'-oxo-5'-(2"-methyl-3"-hydroxyphenyl)pentyl]-1-naphthylamide; and

[2'R-(2'R*,3'S*)]-N-t-butyl-2-[2'-hydroxy-3'-naphth-2-ylthiomethyl-4'-aza-5'-oxo-5'-(2"-chloro-3"-aminophenyl)pentyl]-1-naphthylamide;

or a pharmaceutically acceptable salt of any of the foregoing most preferred compounds.

The compounds of formula 1 can be prepared according to the following Reaction I.

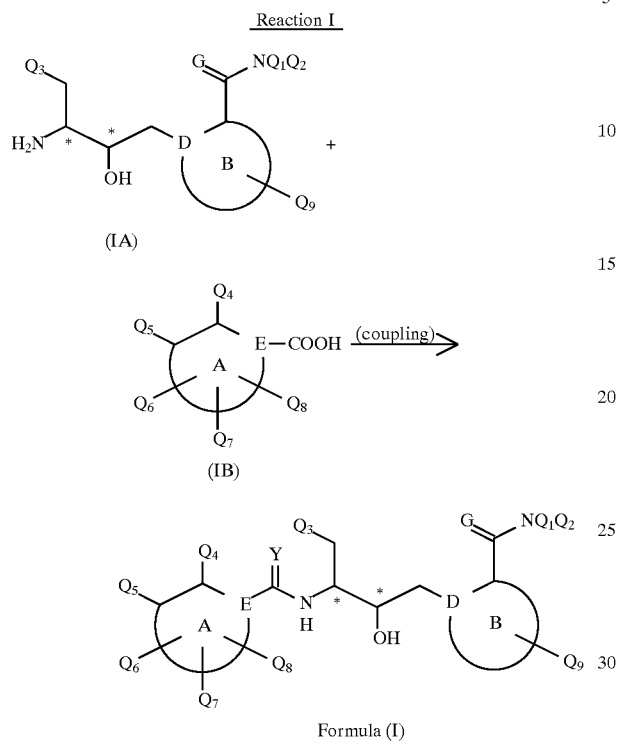

Formula (I)

where the variables are as defined for formula 1 above.

Reaction I is a standard coupling reaction commonly employed in the synthesis of amides which is carried out by reacting an appropriately substituted amine of formula IA, with an appropriately substituted carboxylic acid reactant of formula IB, in an aprotic solvent or mixture of solvents. The reaction is carried out in the presence or absence of a promoting agent, preferably in the presence of a promoting agent, and in the presence of a coupling reagent. Typical aprotic solvents for this reaction are tetrahydrofuran and dimethylformamide, or a mixture of such solvents. The reaction is carried out at a temperature from about −30° C. to about 25° C. The amine reactant is generally employed in equimolar proportions relative to the carboxylic acid reactant, in the presence of an equimolar quantity to a slight excess of the coupling reagent. Typical coupling reagents include the carbodiimides such as dicyclohexylcarbodiimide (DCC) and N,N'-diethylcarbodiimide; the imidazoles such as carbonyldiimidazole; as well as reagents such as bis(2-oxo-3-oxazolidinyl)phosphinic chloride (BOP-Cl) or N-ethoxycarbonyl-2-ethoxy-1,2-dihydroquinoline (EEDQ). A preferred coupling reagent for this reaction is DCC. A promoting agent is preferably included for this reaction; a preferred promoting agent is hydroxybenzotriazole hydrate (HOBT.H$_2$O).

Once the reaction is complete, the compound may be isolated, if desired, by procedures known in the art, for example, the compound may be crystallized and then collected by filtration, or the reaction solvent may be removed by extraction, evaporation or decantation. The compound may be further purified, if desired, by common techniques such as crystallization or chromatography over solid supports such as silica gel or alumina.

The starting compounds of formula IA may be prepared according to the procedures shown in Reaction Scheme A.

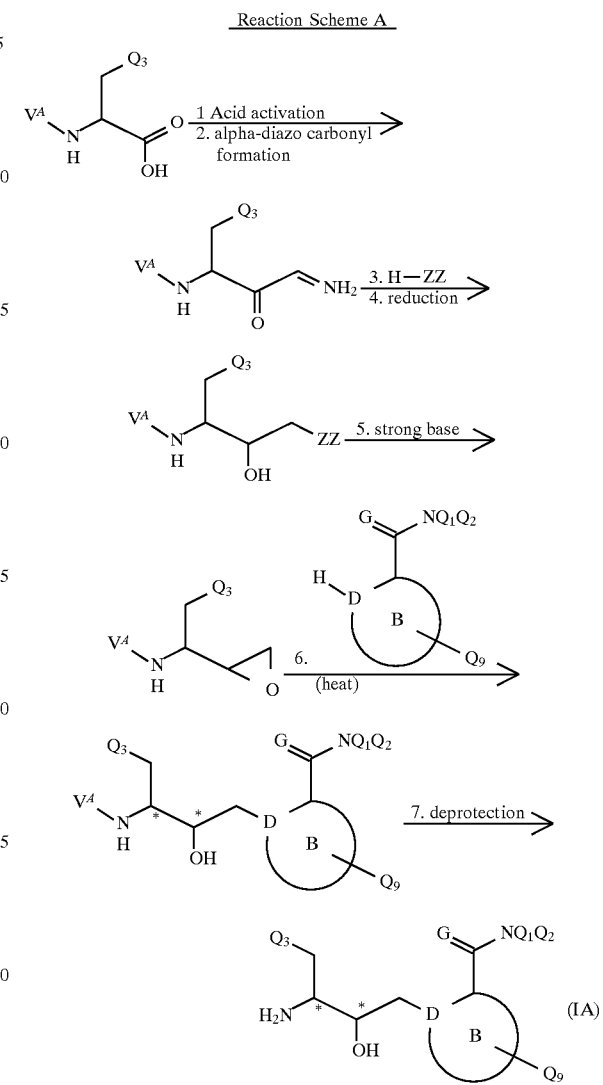

where:

$V^A$ is an amino-protecting group;

B, D, G, $Q_1$, $Q_2$, $Q_3$, and $Q_9$ are defined the same as they are defined above for formula (1); and ZZ is halo.

Reaction Scheme A, above, is accomplished by carrying out reactions 1–7 in sequential order. Once a reaction is complete, the intermediate compound may be isolated, if desired, by Procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction A.1 is carried out by converting an amino-protected carboxylic acid reactant having the structure:

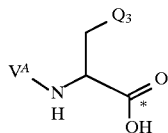

to the corresponding mixed anhydride under conditions known in the art. For example, the amino-protected carboxylic acid reactant may be reacted with a $C_1$–$C_6$ alkylchloroformate, such as isobutylchloroformate preferably in the presence of an acid scavenger. Preferred acid scavengers are the trialkylamines, preferably triethylamine. The reaction is typically carried out in an aprotic solvent such as ethyl acetate. Solvent choice is not critical so long as the solvent employed is inert to the ongoing reaction and the reactants are sufficiently solubilized to effect the desired reaction. The resulting mixed anhydride reactant is preferably used in Reaction A.2 without further isolation or purification.

Reaction A.2 is accomplished in two steps. First, a solution of sodium hydroxide, covered with a layer of an ether solvent, preferably diethyl ether, is reacted with a large excess of N-methyl-N-nitro-N-nitrosoguanidine to form a diazomethane reactant. The sodium hydroxide is preferably used as an aqueous solution having about four to six mol/liter of sodium hydroxide. Once this reaction is substantially complete, the organic layer is dried over a dessicant such as potassium hydroxide. This solution is then reacted with the mixed anhydride from Reaction A.1, above, to form the corresponding alpha-diazo carbonyl compound. The diazomethane reactant is preferably used in this reaction without isolation or purification. The reaction is typically carried out at a temperature of from about –50° C. to about –10° C., preferably about –20° C.

In Reaction A.3, the alpha-diazo carbonyl compound prepared in Reaction A.2 is reacted with an acid of the formula H-ZZ where ZZ is halo, in an aprotic solvent such as diethylether to form an alpha-halo carbonyl compound. A preferred acid reactant is hydrochloric acid which provides the corresponding alpha-chloro carbonyl compound. The reaction is typically carried out at a temperature from about –30° C. to about 0° C. Solvent choice is not critical so long as the solvent employed is inert to the ongoing reaction and the reactants are sufficiently solubilized to effect the desired reaction. The acid reactant is typically added in the form of an anhydrous gas in small increments until the reaction appears substantially complete. The reaction can be monitored by thin layer chromatography.

In Reaction A.4, the carbonyl moiety on the compound prepared in Reaction A.3 is reduced using standard conditions known in the art to form the corresponding alpha-chloro hydroxy compound. For example, the compound prepared in Reaction A.3 is combined with a reducing agent in a mixture of solvents. Typical reducing agents include sodium borohydride, lithium borohydride, zinc borohydride, diisobutylaluminum hydride, and sodium bis(2-methoxyethoxy) aluminum hydride. A preferred reducing agent is sodium borohydride. Typical solvent mixtures include a protic and aprotic mixture such as tetrahydrofuran/water. Solvent choice is not critical so long as the solvent employed is inert to the ongoing reaction, and the reactants are sufficiently solubilized to effect the desired reaction. The reaction is typically carried out at a temperature from about –10° C., preferably about 0° C.

In Reaction A.5, the alpha-chloro hydroxy compound prepared in Reaction A.4 is treated with a strong base to form the corresponding epoxide (which is used above in Reaction II.5) under standard conditions known in the art. For example, the alpha-chloro hydroxy compound may be reacted with a potassium hydroxide/ethanol mixture in an alcoholic solvent such as ethanol. The reaction is typically carried out at a temperature from about 0° C. to about the reflux temperature of the solvent. Preferably the reaction is carried out at room temperature.

In Reaction A.6, the epoxide prepared in Reaction A.5 is reacted with a heterocyclic reactant:

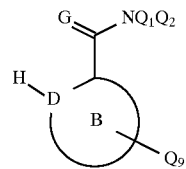

in an alcoholic solvent at a temperature of from about 20° C. to 100° C. Solvent choice is not critical so long as the solvent employed is inert to the ongoing reaction and the reactants are sufficiently solubilized to effect the desired reaction. Typical solvents for this reaction include the alcohols, preferably isopropanol or ethanol. The reaction is preferably carried out at a temperature of about 80° C.

Reaction A.7 is a standard amino deprotection reaction using procedures and methods known in the art to afford the corresponding amine which is used in Reaction I, above. This amine may be reacted without purification, but it is preferably purified first.

The compounds of formula IA, where $Q_3$ is —S-aryl, are prepared by first reacting amino-protected serine with triphenylphosphine and diethylazodicarboxylate (DEAD) in an aprotic solvent at a temperature of from about –80° C. to 0° C. to form the corresponding beta-lactone. The reaction is typically carried out in an ether, such as tetrahydrofuran at a temperature of from about –80° C. to –50° C. Next, the lactone ring is opened to provide a compound having the structure:

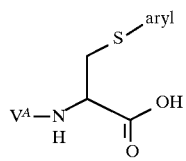

by reacting the lactone with an appropriately substituted thioanion having the structure, —S-aryl. The thioanion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran.

Alternatively, the compounds of formula IA, where $Q_3$ is —S-aryl, may be prepared using the procedures detailed in *Photaki*, JACS, 85, 1123 (1963), and Sasaki N. A. et al, Tetrahedron Letters, 28, 6069 (1987). For example, the compounds may be prepared by reacting doubly protected serine (carboxy-protected and amino-protected) with toluenesulfonyl chloride in the presence of dimethylaminopyridine (DMAP) and an acid scavenger such as pyridine in an aprotic solvent such as methylene chloride to form the corresponding toluenesulfonate which may then be reacted with an appropriately substituted thioanion having the structure, —S-aryl. The thioanion compound is preferably formed by reacting the corresponding thiol with a strong base as described above. The carboxy-protecting group may be removed from the resulting doubly protected arylthioalanine using conditions known in the art.

The heterocyclic reactants of the formula

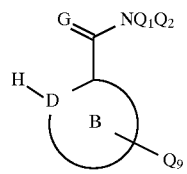

used in Reaction A.6, may be prepared using procedures and methods known in the art. For example, the heterocyclic reactants were typically prepared from the corresponding amino-protected amino acids by acid activation followed by treatment with an alkylamine. This reaction is typically carried out in the presence of an acid scavenger, such as N-methylmorpholine. Removal of the amino-protecting group using standard chemical deprotecting techniques then provides the desired heterocyclic reactants. Specifically, the [3S-(3R*,4aR*,8aR*)]-decahydroisoquinoline-3-N-t-butylcarboxamide was prepared using 2S-1,2,3,4-tetrahydro-3-isoquinolinecarboxylic acid by the following procedure:

1) amino-protection (t-Boc);
2) acid activation/reaction with t-butylamine;
3) catalytic hydrogenation;
4) amino-deprotection.

The piperazine reactants may be prepared by converting an appropriately substituted pyrazine compound to the corresponding piperazine compound using procedures known in the art, preferably using catalytic hydrogenation. For example, the hydrogenation may be accomplished by combining the pyrazine reactant with a catalyst under a hydrogen atmosphere in an aprotic solvent at a temperature from about 0° C. to about 60° C. Suitable catalysts include palladium-on-carbon, platinum metal, platinum oxide and the like. A preferred catalyst is platinum oxide. Typical solvents for this reaction include tetrahydrofuran, dimethylformamide or a mixture of tetrahydrofuran and dimethylformamide.

The nitrogen atom on the resultant piperazine reactant may be alkylated using procedures known in the art. For example, the piperazine reactant may be reacted with a halo($C_1$–$C_4$)alkyl, or halomethylpyridine, such as methyl iodide or chloromethylpyridine. Preferred halo substituents include chloro, bromo and iodo. The reaction is carried out at temperatures of from about 0° C. to 60° C. in a mutually inert solvent and in the presence of an acid scavenger. A preferred acid scavenger is potassium carbonate. Typical solvents include a mixture of a protic and aprotic solvents such as acetonitrile and water. Solvent choice is not critical so long as the solvent employed is inert to the ongoing reaction and the reactants are sufficiently solubilized to effect the desired reaction.

Alternatively, the alkylated piperazine reactant may be prepared using reductive amination. For example, the piperazine reactant prepared above may be reacted with an aldehyde (for example, 3-pyridine carboxylic aldehyde, ethanal, propanal) or a ketone in the presence of a reducing agent and an acid. The reaction is typically carried out in an alcoholic solvent such as methanol, ethanol or isopropanol. Typical reducing agents include sodium borohydride, lithium cyanoborohydride, sodium cyanoborohydride, and the like. A preferred reducing agent is sodium cyanoborohydride. Typical acids include any protic acid such as hydrochloric acid, sulfuric acid, methanesulfonic acid, or acetic acid. A preferred acid is acetic acid.

The intermediate reactant

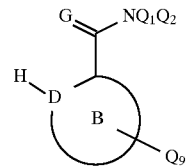

can also be prepared that has the formula 2:

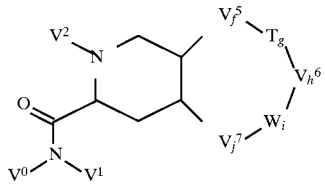

wherein:

$V^0$ and $V^1$ are independently hydrogen, $C_1$–$C_6$ alkyl, or hydroxy ($C_1$–$C_6$) alkyl;

$V^2$ is hydrogen, an amino-protecting group, or a group of the formula:

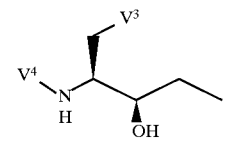

$V^3$ is —(CH$_2$)$_t$—$V^{3'}$;

t is 0, 1, 2, 3, or 4;

$V^{3'}$ is aryl, —O-aryl, or —S-aryl;

$V^4$ is hydrogen or an amino-protecting group; f, h and j are each independently 0, 1 or 2; g and i are each independently 0 or 1;

$V^5$ is —CH$_2$—, —CHV$^{5'}$—, or —CV$^{5'}$V$^{5'}$—;

$V^6$ is —CH$_2$—, —CHV$^{6'}$, —CV$^{6'}$V$^{6'}$13 ;

$V^7$ is —CH$_2$—, —CHV$^{7'}$, or —CV$^{7'}$V$^{7'}$—;

each of $V^{5'}$, $V^{6'}$, and $V^{7'}$ is independently selected from the group consisting of halo, hydroxy, $C_1$–$C_6$ alkyl, halo($C_1$–$C_6$)alkyl, hydroxy($C_1$–$C_6$)alkyl, $C_1$–$C_6$ alkoxy, $C_1$–$C_6$ alkylthio, amino, or cyano;

T and W are independently —S—, —S(O)—, —S(O)$_2$—, —O—, —NH—, or —(V$^9$)—; and $V^9$ is $C_1$–$C_6$ alkyl, aryl($C_1$–$C_6$)alkyl, aryl, or acyl; with the provisos that:

g and i cannot both be 0;

the sum of f, g, h, i and j must be 2, 3, 4, or 5;

if $V^5$ is —CV$^{5'}$V$^{5'}$—, then $V^6$ must be —CH$_2$— or —CHV$^{6'}$—; and $V^7$ must be —CH$_2$— or —CHV$^{7'}$—;

if $V^6$ is —CV$^{6'}$V$^{6'}$—, then $V^5$ must be —CH$_2$— or —CHV$^{5'}$—; and $V^7$ must be —CH$_2$— or —CHV$^{7'}$—;

if $V^7$ is —CV$^{7'}$V$^{7'}$—, then $V^5$ must be —CH$_2$— or —CHV$^{5'}$—; and $V^6$ must be —CH$_2$— or —CHV$^{6'}$—;

or a pharmaceutically acceptable salt thereof.

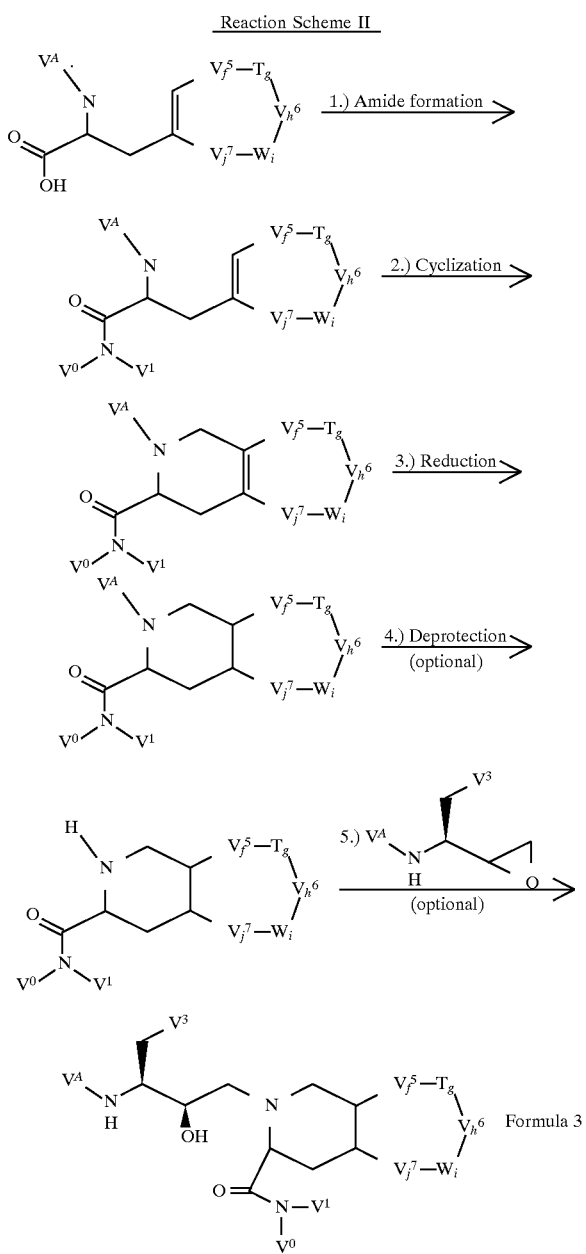

wherein $V^4$, $V^3$, $V^0$, $V^1$, $V^5$, T, $V^6$, W, $V^7$, f, g, h, i, j, are defined above for formula 2;

$V^A$ is an amino-protecting group; and

U on the bicyclic ring in reaction 1–3 above represents the presence of double bonds between, for example, $V_f$ and $V_h$, $V_f$ and $V_p$ or $V_j$ and $V_h$ and the like, where b, c, or d is O, respectively.

Reaction Scheme II, above, is accomplished by carrying out reactions 1–3 (or 1–5) in sequential order. Once a reaction is complete, the intermediate compound may be isolated, if desired, by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

Reaction II.1 is typically carried out by activating the carboxylic acid moiety using, for example, DCC or a mixed anhydride such as isobutyl, followed by reaction with a primary or secondary amine having the formula $NV^0V^1$ where $V^0$ and $V^1$ are as defined above for formula (2). The reaction is typically carried out in a nonpolar aprotic solvent or mixture of solvents in the presence or absence of an acid scavenger at a temperature of from about −20° C. to about 25° C. to afford the corresponding amide. Suitable solvents for this reaction include ethers and chlorinated hydrocarbons, preferably diethyl ether, chloroform, or methylene chloride. Preferably, this reaction is carried out in the presence of an acid scavenger such as a tertiary amine, preferably triethylamine. The amide afforded by this reaction may be isolated or further reacted as shown in Reaction II.2.

Reaction II.2 is typically carried out by reacting the compound obtained from Reaction II.1 using the procedures detailed in *Comprehensive Organic Synthesis*, "Heteroatom Manipulation", Barry M. Trost, ed., volume 6, pages 736–746, (1991). In general, an appropriately substituted monocyclic ring is reacted with an aldehyde, such as formaldehyde or trichloroacetaldehyde, in the presence of an acid. The acid may be used as a solvent. Typical acids include hydrochloric acid, hydrobromic acid, sulfuric acid, acetic acid, trifluoroacetic acid, and the like. A co-solvent may optionally be added to the reaction mixture. The co-solvent choice is not critical so long as the co-solvent employed is inert to the ongoing reaction, and the reactants are sufficiently solubilized to effect the desired reaction. Typical solvents for this reaction include halogenated solvents such as methylene chloride, trichloroethane, carbontetrachloride, and the like. Alternatively, the aldehyde may be produced in situ using for example, dimethoxymethane and a suitable acid.

In reaction II.3, the compound isolated from reaction II.2 is reduced to provide a saturated heterocyclic compound as depicted above. Catalytic hydrogenation is a preferred method of reduction. Typical catalysts include palladium catalysts, rhodium catalysts (for example rhodium on aluminum) and rhenium catalysts. Preferred catalysts include palladium-on-carbon. Suitable solvents for this reaction include the $C_1$–$C_4$ alcohols, tetrahydrofuran, acetic acid in alcohol, ethyl acetate and the like. A preferred solvent is ethanol. The reaction is typically carried out under an atmosphere of hydrogen from about 1000 to about 4000 psi at a temperature of from about 25° C. to about 150° C. Preferably, the reaction is carried out under an atmosphere of hydrogen from about 2000 to about 3000 psi at a temperature of from about 50° C. to 100° C. The catalyst is generally employed in a amount ranging from about equimolar proportions to about a twelve-fold excess (by weight) of the reactant, preferably in about a six- to ten-fold excess (by weight) of the catalyst relative to the substrate.

Reactions II.4 and II.5 may be used to prepare compounds of formula (3) which correspond to compounds of formula (2) where $V^2$ is

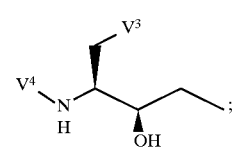

and $V^3$ and $V^4$ are as defined above for formula (2), including their definitions of $V^{3'}$ and t.

Reaction II.4 is a standard amino deprotection reaction using procedures and methods known in the art to afford the corresponding amine which is then used in Reaction II.5. Chemical deprotection procedures are preferred. For example, the compound isolated from II.3 may be deprotected using trimethylsilyliodide (TMSI) in an aprotic solvent or mixture of solvents at a temperature of from about 10° C. to 60° C., preferably at a temperature of from about 20° C. to 40° C. Typical solvents include methylene chloride, acetonitrile trichloroethane, and the like.

In Reaction II.5, the epoxide prepared in Reaction A.5, above, in which $Q_3$ of Reaction A.5 is replaced by $V^3$, is reacted with the compound isolated from Reaction II.4 in an alcoholic solvent at a temperature of from about 20° C. to 100° C. Solvent choice is not critical so long as the solvent employed is inert to the ongoing reaction, and the reactants are sufficiently solubilized to effect the desired reaction. Typical solvents for this reaction include the alcohols, preferably isopropanol or ethanol. The reaction is preferably carried out at a temperature of about 80° C.

The compound isolated from reaction II.5 may optionally be deprotected to provide a compound of formula (3) where $V^4$ is hydrogen.

The epoxide used in Reaction II.5 may be synthesized using Reaction Scheme A above.

The carboxylic acid reactant of formula (IB)

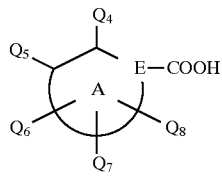

used in Reaction Scheme I, to the extent not commercially available, can be prepared using known procedures. More particularly, this reactant may be prepared by further substitution and/or oxidation of a commercially available aryl or heterocyclic compound. For example, aryl or heterocyclic compounds of the formula

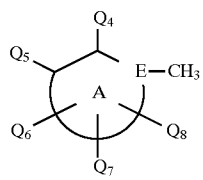

may be oxidized using procedures known in the art. Specifically, the compound of the formula

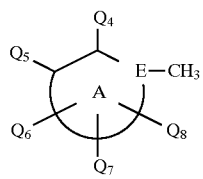

may be reacted with an oxidizing agent such as selenium dioxide or potassium permanganate at temperatures of from about 0° C. to 200° C. in a mutually inert solvent, such as water or diphenylether.

A second method for preparing compounds of the formula (IB) involves protecting an appropriately substituted carboxylated aryl or heterocyclic with a carboxy-protecting group, and then further substituting the aryl or heterocyclic group using procedures known in the art. The carboxy-protecting group may then be removed using procedures known in the art to provide the desired carboxylic acid reactant of formula (IB).

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxy-trityl, 4,4',4"-trimethoxytrityl, 2-phenylprop-2-yl, trimethylsilyl, t-butyldimethylsilyl, phenacyl, 2,2,2-trichloroethyl, b-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. A preferred method of protecting the carboxy group involves converting the carboxy moiety to an amide moiety and then hydrolyzing the amide back to provide the desired carboxy substituent. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

A preferred procedure for protecting the carboxy moiety involves the acid activation of the carboxy moiety, followed by the formation of an amide. For example, the carboxy moiety may be converted to an acyl halide, acyl anhydride, acyl imidazole and the like, preferably in the presence of an acid scavenger to form an activated carboxy moiety. A commercially available acid chloride is typically employed, obviating the need for further acid activation. Preferred acid scavengers are the trialkylamines, preferably triethylamine. The reaction is typically carried out in an aprotic solvent such as diethylether, methylene chloride or the like. A preferred solvent is methylene chloride. Solvent choice is not critical so long as the solvent employed is inert to the ongoing reaction and the reactants are sufficiently solubilized to effect the desired reaction. The activated carboxy moiety is then reacted with an amine, $R^{11}$—$NH_2$, for example aniline, in an aprotic solvent to provide an amide reactant

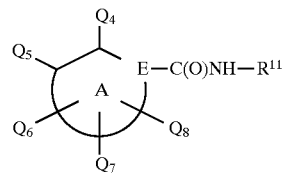

which may then be further substituted according to known procedures.

The amide reactant

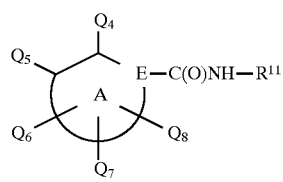

may be further substituted by ortho deprotonation of the heterocyclic or aryl group

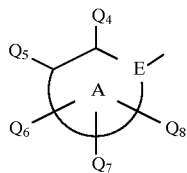

to provide the corresponding anion followed by reaction with a variety of reagents such as alkyl halides, or halogenating agents such as bromine. The amide reactant is generally deprotonated twice using two equivalents of a strong base such as n-butyl lithium or sec-butyl lithium relative to the amide reactant, optionally in the presence of a metal coordinating agent such as tetramethylethylenediamine (TMEDA). The reaction is typically carried out in an aprotic solvent, preferably an ether such as diethylether, tetrahydrofuran or the like at a temperature from about −78° C. to about 25° C.

The resultant compound may then be hydrolyzed using procedures known in the art to provide the desired, substituted carboxylic acid reactant of formula (IB). For example, a suitable hydrolysis involves exposing the amide reactant to a strong mineral acid, organic acid, or a mineral acid/organic mixture at a temperature from about 100° C. to about 160° C. Typical acids which may be used in this react on include hydrobromic acid, acetic acid, hydrochloric acid and the like. A sealed tube may optionally be employed to accelerate the reaction rate.

A third method for preparing the substituted carboxylic acid reactant of formula (IB) involves diazotization of an aniline, followed by a quenching of the resultant diazonium salt. Specifically, the amino moiety of the aniline reactant is converted to a diazonium salt by reaction with nitrous acid. Nitrous acid may be produced in situ by treating sodium nitrite with an aqueous solution of a strong acid such as hydrochloric acid, or sulfuric acid. This reaction is typically carried out at or below 5° C. The diazonium salt is then quenched by reaction with suitable reagent to provide the desired substituted aromatic system. Representative quenching reagents include water, cyanide, halide, aqueous sulfuric acid, and the like. Typically, the reaction will be heated to facilitate the desired reaction.

There are a variety of reactions that are known in the art which may be used to produce the desired substitutions on the aryl or heterocyclic rings. For example, there are a variety of aromatic electrophilic and nucleophilic substitution reactions outlined in chapters 11 and 13 of March, J., "Advanced Organic Chemistry," 3rd edition, Wiley, 1985.

In addition, the compounds of the formula (IB) may be prepared by carboxylating an appropriately substituted aryl of heterocyclic compound. The carboxylation may be accomplished using a number of different reagents. For example, the aryl or heterocyclic reagent may be reacted with phosgene, oxalyl chloride, urea hydrochloride, or N,N-diethylcarbamoyl chloride in the presence of Friedel-Crafts catalysts. A variation of this method involves reacting the aryl or heterocyclic reagent with an alkyl thiolchloroformate (RSCOCl), or a carbamoyl chloride ($H_2$NCOCl) to provide an amide and a thiol ester, respectively. The amide and thiol ester may then be hydrolyzed to provide the desired carboxy group. March, at 491.

Examples of Friedel-Crafts catalysts include the Lewis acids, such as aluminum bromide ($AlBr_3$), aluminum chloride ($AlCl_3$), iron (III) chloride ($FeCl_3$), boron trichloride ($BCl_3$), boron trifluoride ($BF_3$), and the like. See also, March, J., "Advanced Organic Chemistry," 3rd edition, Wiley, 1985; Olah, "Friedel-Crafts and Related Reactions," Interscience, New York, 1963–1965; and Olah, "Friedel-Crafts Chemistry," Wiley, New York, 1973.

Additionally, the quinoline carboxylic acid reactants may be prepared by reacting an appropriately substituted aniline with glycerol using the Skraup reaction disclosed in Bradford, L. et al., J. Chem. Soc., 1947, p 437. For example, 3-amino benzoic acid may be reacted with glycerol in the presence of an oxidizing agent such as m-nitro benzene sulfonic acid or sodium m-nitro benzene sulfonate in a 60–75% aqueous solution of sulfuric acid to provide the desired carboxy-substituted quinoline. The reaction is typically carried out at a temperature from about 35° C. to reflux temperature for one to six hours, preferably from about 50° C. to reflux temperature for two to four hours.

The resultant reactants may then be reduced or hydrogenated using procedures known in the art. See e.g., March, at 700. A preferred procedure involves catalytic hydrogenation, or example by combining the quinoline carboxylic acid reactant with hydrogen gas in the presence of a catalyst. A preferred catalyst is palladium-on-carbon. Typical solvents suitable for use in this reaction include any organic solvent such as ethyl acetate. Solvent choice is not critical so long as the solvent employed is inert to the ongoing reaction. The reaction is generally substantially complete after about 1 to 24 hours when conducted at a temperature in the range of from about 25° C. to about 100° C.

According to other embodiments, the compounds of formula IA, in which $Q_3$ is replaced by $R^1$, can be prepared according to the following Reaction Scheme B.

Reaction Scheme B

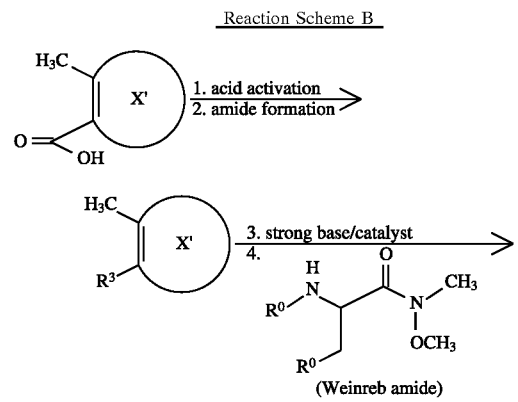

(Weinreb amide)

-continued
Reaction Scheme B

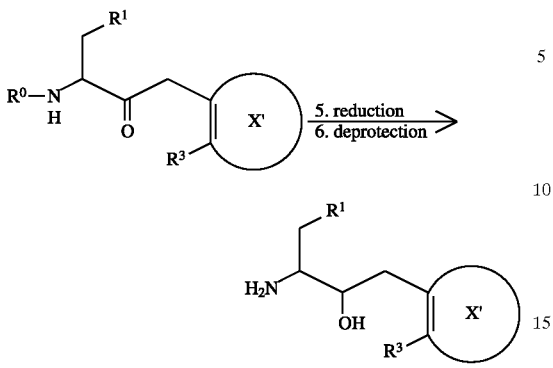

where:

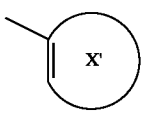

is a group having the formula:

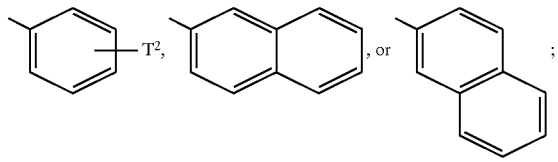

where:

$R^b$ is an amino-protecting group; and $R^1$, and $R^3$ are as defined above for formula 1(B)

Reaction Scheme B, above, is accomplished by carrying out reactions 1–6 in sequential order. Once a reaction is complete, the intermediate compound may be isolated, if desired by procedures known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

In Reaction B.1, the reaction is typically carried out by activating, that is, converting, a suitably substituted aryl or unsaturated heterocycle carboxylic acid to the corresponding acyl chloride or acyl bromide by reaction with thionyl chloride, thionyl bromide, phosphorous trichloride, phosphorous tribromide, phosphorous pentabromide or phosphorous pentachloride according to procedures and under conditions known in the art. Suitable aryl, heterocycle or unsaturated heterocycle carboxylic acid compounds are commercially available or prepared by standard procedures known in the art.

In Reaction B.2, the acyl chloride or acyl bromide, prepared in Reaction B.1, is reacted with ammonia or a primary or secondary amine having the formula $H—NR^4R^4$,

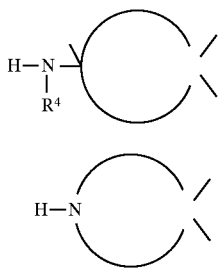

where $R^4$, $R^5$, $R^6$ and p are as defined above for formula 1(B), in a nonpolar aprotic solvent or mixture of solvents in the presence or absence of an acid scavenger to afford the corresponding amide. The reaction is typically carried out at a temperature of from about −20° C. to about 25° C. Typical solvents for this reaction include ethers and chlorinated hydrocarbons, preferably diethylether, chloroform or methylene chloride. Preferably, this reaction is carried out in the presence of an acid scavenger such as a tertiary amine, preferably triethylamine.

In Reaction B.3, the amide prepared in Reaction B.2, is reacted with a strong base in the presence of a solubilizing agent to afford the corresponding anion which is then reacted in Reaction B.4 with a Weinreb amide to afford a ketone. Reaction B.3 is carried out in an aprotic solvent at a temperature of from about −78° C. to about 0° C. Typical bases used in Reaction B.3 include lithium amide bases and alkyl lithium bases, preferably $C_1$–$C_4$ alkyl lithium bases and lithium di($C_1$–$C_4$)alkylamide bases. Typical solubilizing agents for Reaction 3 are tetramethyl($C_1$–$C_4$) alkylenediamines, preferably tetramethylethylenediamine. Reaction B.4 is carried out in an aprotic solvent at a temperature from about −80° C. to about −40° C. Typical solvents for Reactions B.3 and B.4 include ethers, preferably tetrahydrofuran. In Reaction B.4, the anion is generally employed in an amount ranging from about equimolar proportions to about a three molar excess of the anion, preferably in about a two molar excess of the anion relative to the Weinreb amide reactant.

In Reaction B.5, the ketone prepared in Reaction B.3, is reduced to the corresponding alcohol using a suitable reducing agent. The reaction is carried out in a protic solvent at a temperature of from about −25° C. to about 25° C. Typical reducing agents for this reaction include sodium borohydride, lithium borohydride, diisobutylaluminum hydride, and sodium bis(2-methoxyethoxy)aluminum hydride. A preferred reducing agent is sodium borohydride. Typical protic solvents for this reaction include alcohols, preferably ethanol.

Reaction B.6 is a standard amino deprotection reaction using procedures and methods known in the art to afford the corresponding amine which is used in Reaction I above. This amine may be reacted without purification, but it is preferably purified first.

The Weinreb amide used as a reactant in Reaction B.4 is prepared by reacting an amino-protected amino acid with N-methoxy-N-methyl-amine in the presence of a promoting agent, an acid scavenger, and a coupling agent. The reaction is carried out in an aprotic solvent or mixture of solvents at a temperature of from about −25° C. to 25° C. A preferred promoting agent for this reaction is HOBT.$H_2O$. Preferred acid scavengers are the tertiary alkylamines, preferably triethylamine or N-methyl-morpholine. A preferred coupling reagent is ethyl dimethylaminopropylcarbodiimide hydrochloride. The Weinreb amide afforded by this reaction is preferably isolated prior to its use in Reaction B.4.

The compounds of formula IA, where $R^1$ replaces $Q_3$ and where $R^1$ is —S-aryl, are prepared in Scheme B by first reacting amino-protected serine with triphenylphosphine and diethylazodicarboxylate (DEAD) in an aprotic solvent at a temperature of from about −80° C. to 0° C. to form the corresponding beta-lactone. The reaction is typically carried out in an ether, such as tetrahydrofuran at a temperature of from about −80° C. to −50° C. Next, the lactone ring is opened to provide a compound having the structure:

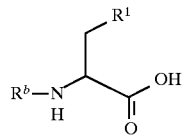

by reacting the lactone with an appropriately substituted thioanion having the structure, —S-aryl. The thioanion compound is preferably formed by reacting the corresponding thiol with a strong base, such as sodium hydride or potassium hydride. This reaction is typically carried out in an aprotic solvent at a temperature from about 0° C. to about 40° C. and under an inert atmosphere, such as nitrogen. Typical solvents for this reaction include ethers, preferably tetrahydrofuran. The desired amide reactant is then formed by reacting the resulting carboxylic acid reactant with N-methoxy-N-methyl-amine in the presence of a promoting agent, an acid scavenger and a coupling agent substantially as described above.

Alternatively, the compounds of formula (IA), where $R^1$ replaces $Q_3$ and where $R^1$ is —S-aryl, may be prepared in Scheme B using the procedures detailed in Photaki, JACS, 85, 1123 (1963), and Sasaki, N. A. et al., Tetrahedron Letters, 28, 6069 (1987). For example, the compounds may be prepared by reacting doubly protected serine (carboxy-protected and amino-protected) with toluenesulfonyl chloride in the presence of dimethylaminopyridine (DMAP) and an acid scavenger such as pyridine in an aprotic solvent such as methylene chloride to form the corresponding toluenesulfonate compound which may then be reacted with an appropriately substituted thioanion having the structure, —S-aryl. The thioanion compound is preferably formed by reacting the corresponding thiol with a strong base as described above. The carboxy-protecting group may then be removed from the resulting doubly protected arylthioalanine using conditions known in the art.

According to certain embodiments, an intermediate for making compounds of the present invention is prepared as follows. The intermediate has the formula 4:

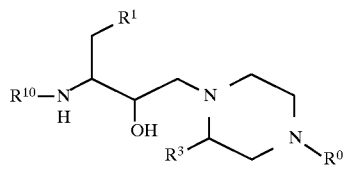

wherein:

$R^1$ is aryl, or —S-aryl;

$R^{10}$ is hydrogen or an amino-protecting group;

$R^0$ is $C_1$–$C_4$ alkyl or —$CH_2$-pyridyl;

$R^3$ is a group having the structure:

1) —C(O)—NR$^4$R$^4$

2)

$$-\overset{\overset{O}{\|}}{C}-\underset{R^4}{N}\diagup$$

3)

$$-\overset{\overset{O}{\|}}{C}-N\left(\diagup\overset{R^5}{\underset{R^6}{C}}\right)_p ;$$

$p$ is 4 or 5;

$R^4$ at each occurrence is independently hydrogen, $C_1$–$C_6$ alkyl or hydroxy($C_1$–$C_4$)alkyl; and $R^5$ and $R^6$ are independently selected from hydrogen, hydroxy, $C_1$–$C_6$ alkyl, $C_1$–$C_6$alkoxy, or hydroxy($C_1$–$C_4$)alkyl; or a pharmaceutically acceptable salt thereof; comprising:

(a) reducing a compound of the formula

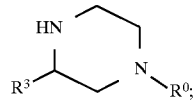

to provide a piperazine compound;

(b) alkylating the piperazine compound to provide a compound of the formula $$\text{HN}\diagdown\diagup\text{N}\diagdown_{R^0}$$
$$R^3$$

and then (c) reacting the piperazine compound of step (b) with an epoxide of the formula $$R^b-\underset{H}{N}-\diagup\overset{R^1}{\diagdown}\diagup\text{O}$$

where $R^b$ is an amino protecting group; in an alcoholic solvent at a temperature of from about 20° C. to 100° C. to form a compound of formula II wherein R10 is an amino-protecting group; and d) optionally removing the amino-protecting group to form a compound of formula 4 wherein $R^{10}$ is hydrogen.

The following Preparations and Examples illustrate aspects of the invention. These examples are for illustrative purposes and are not intended to limit the scope of the invention.

Abbreviations for the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are, respectively, m.p., NMR, EIMS, MS(FD), MS(FAB), IR, UV, Analysis, HPLC, and TLC. In addition, the absorption maxima listed for the IR spectra are those of interest, not all maxima observed.

In conjunction with the NMR spectra, the following abbreviations are used: singlet (s), doublet (d), doublet of doublets (dd), triplet (t), quartet (q), multiplet (m), doublet of multiplets (dm), broad singlet (br.s), broad doublet (br.s), broad triplet (br.t), and broad multiplet (br.m). J indicates the coupling constant in Hertz (Hz). Unless otherwise noted, NMR data refer to the free base of the subject compound.

The NMR spectra were obtained on a Bruker Corp. 270 MHz instrument or on a General Electric QE-300 300 MHz instrument. The chemical shifts are expressed in delta values (ppm downfield from tetramethylsilane). MS(FD) spectra were taken on a Varian-MAT 731 Spectrometer using carbon dendrite emitters. EIMS spectra were obtained on a CEC 21-110 instrument from Consolidated Electrodynamics Corporation. MS(FAB) spectra were obtained on a VG ZAB-3 Spectrometer. IR spectra were obtained on a Perkin-Elmer 281 instrument. UV spectra were obtained on a Cary 118 instrument. TLC was carried out on E. Merck silica gel plates. Melting points are uncorrected.

Preparation 1

A. [3S-(3R*,4aR*,8aR*,2'S*,3'R*)]-2-[3'-N-(Benzyloxycarbonyl)amino-2'-hydroxy-4'-phenyl]butyl decahydroisoquinoline-3-N-t-butylcarboxamide A solution of [1'S-(1'R*,1R*)]-1-[1'-N-(benzyloxycarbonyl)amino-2'-(phenyl)ethyl]oxirane and [3S-(3R*,4aR*,8aR*)]-decahydroisoquinoline-3-N-t-butylcarboxamide in absolute ethanol was heated at 80° C. overnight. The reaction mixture was reduced to dryness under reduced pressure to provide a residue. This residue was purified using flash chromatography (gradient eluent of 10–50% ethyl acetate in methylene chloride) to provide 6.47 g of an off-white foam.

Yield: 75%.

$^1$H NMR (CDCl$_3$): δ1.29 (s, 9H), 1.25–2.05 (m, 2H), 2.20–2.35 (m, 2H), 2.55–2.70 (m, 11H), 2.85–3.10 (m, 3H), 3.24 (br.s, 1H), 3.82 (br.s, 1H), 3.98 (br.s, 1H), 4.99 (br.s, 2H), 5.16–5.18 (m, 1H), 5.80 (br.s, 1H), 7.05–7.38 (m, 10H).

IR (CHCl$_3$): 3600–3100 (br.), 3031, 2929, 1714, 1673, 1512, 1455, 1368, 1232, 1199, 1047 cm$^{-1}$.

MS(FD): m/e 536 (M$^+$).

B. [3S-(3R*,4aR*,8aR*,2'S*,3'R*)]-2-[3'-Amino-2'-hydroxy-4'-phenyl]butyl decahydroisoquinoline-3-N-t-butylcarboxamide A rapidly stirring suspension of 6.37 g (11.91 mmol) of the subtitled compound of Preparation 1A and 1.2 g of 10% palladium-on-carbon in 200 mL of absolute ethanol was placed under an atmosphere of hydrogen. After approximately 48 hours, the reaction mixture was filtered through celite and reduced to dryness under reduced pressure to provide 5.09 g of the desired subtitled compound. This compound was used without further purification.

$^1$H NMR (CDCl$_3$): δ1.33 (s, 9H), 1.40–1.95 (m, 10H), 2.25–2.48 (m, 2H), 2.59–2.75 (m, 3H), 2.80–3.40 (m, 7H), 3.75–3.90 (m, 1H), 6.19 (br.s, 7H), 7.18–7.35 (m, 5H).

IR (CHCl$_3$): 3600–3100 (br.), 2929, 2865, 1671, 1515, 1455, 1367, 1245, 1047 cm$^{-1}$.

MS(FD): m/e 402 (M$^+$, 100).

Preparation 2

A. 2R-N(Benzyloxycarbonyl)amino-3-naphth-2-ylthio propanoic acid

To a solution of 1.28 g (8.00 mmol) of naphthalene-2-thiol in 30 mL of tetrahydrofuran, was slowly added 1.77 g (8.16 g) of 60% sodium hydride, under nitrogen. After stirring for approximately 15 minutes, a solution of N(benzyloxycarbonyl)serine-β-lactone in 20 mL of tetrahydrofuran was slowly added. The reaction mixture was allowed to react at room temperature for approximately one hour, and then was concentrated under reduced pressure to provide a residue. This residue was dissolved in ethyl acetate and washed sequentially with 0.5N sodium bisulfate and a saturated brine solution. The resulting layers were separated and the organic layer was dried over sodium sulfate, filtered, and then concentrated under reduced pressure to provide a residue. This residue was purified using flash chromatography to provide 2.08 g of a pale yellow solid.

Yield: 68%.

$^1$H NMR (CDCl$_3$): δ3.42–3.61 (br.m, 2H), 5.53–5.76 (br.s, 1H), 4.85–5.08 (br.m, 2H), 5.54–5.76 (br.s, 1H), 7.06–7.97 (m, 12H).

[α]$_D$–55.72° (c 1.0, MeOH).

IR (KBr): 3348, 3048, 1746, 1715, 1674, 1560, 1550, 1269, 1200, 1060 cm$^{-1}$.

MS(FD): m/e 381 (M$^+$), 381 (100).

Analysis for C$_{20}$H$_{19}$NO$_4$S: Calcd: C, 66.12; H, 5.02; N, 3.67; Found: C, 66.22; H, 5.04; N, 3.86.

B. 3R-1-Diazo-2-oxo-3-N-(benzyloxycarbonyl)amino-4-(naphth-2-ylthio) butane

To a cold (–30° C.) solution of 15.38 g (40.3 mmol) of the subtitled compound of Preparation 2A in 230 mL of ethyl acetate, was slowly added 5.62 mL (40.3 mmol) of triethylamine, under nitrogen via syringe. To the resulting solution was then added 7.84 mL (60.5 mmol) of isobutyl chloroformate, via syringe. In a separate flask, 10 g of N(methyl)-N(nitro)-N(nitroso)-guanidine was carefully added to a bilayer mixture of 170 mL of diethylether and 170 mL of a 5N sodium hydroxide solution, resulting in a large evolution of gas. When this reaction was substantially complete, the organic layer was decanted from the aqueous layer onto potassium hydroxide and dried. This diazomethane formation and addition was repeated using identical quantities of diethylether and sodium hydroxide and 30 g of N(methyl)-N(nitro)-N(nitroso)-guanidine. The resultant diazomethane reactant was then added to the mixed anhydride solution prepared above and the reaction mixture was allowed to react cold (–30° C.) for approximately 20 minutes. When the reaction was substantially complete, as indicated by TLC, nitrogen was bubbled through the solution using a fire polished Pasteur pipet to remove any excess diazomethane and then the solution was concentrated under reduced pressure to provide a residue. This residue was purified using flash chromatography (eluent of 10% ethyl acetate in methylene chloride) to provide 13.62 g of a yellow oil.

Yield: 83%.

$^1$H NMR (CDCl$_3$): δ3.32–3.46 (m, 2H), 4.40–4.67 (m, 1H), 5.00–5.09 (m, 2H), 5.44 (s, 1H), 5.76 (d, J=7.8 Hz, 1H), 7.25–7.86 (m, 12H).

C. 3R-1-Chloro-2-oxo-3-N-(benzyloxycarbonyl)amino-4-(naphth-2-ylthio) butane

A short burst (about 2 seconds) of anhydrous hydrochloric acid (gas) was passed through a cold (–20° C.) solution of 13.62 g (33.59 mmol) of the subtitled compound of Preparation 2B in 230 mL of diethylether, resulting in the evolution of a gas. This procedure was repeated taking care not to add excess hydrochloric acid. When the reaction was substantially complete, as indicated by TLC, the solution was concentrated under reduced pressure to provide a residue. This residue was purified using flash chromatography (eluent of 10% ethyl acetate in methylene chloride) to provide 12.05 g of a pale tan solid.

Yield: 87%.

$^1$H NMR (CDCl$_3$): δ3.41 (dd, J=12,6 Hz, 1H), 3.53 (dd, J=12,6 Hz, 1H), 4.18 (AB q, J=41.9 Hz, J=15.9 Hz, 2H), 4.77 (dd, J=9, 3 Hz, 1H), 5.04 (AB q, J=12 Hz, J=10.4 Hz, 2H), 5.59 (d, J=7 Hz, 1H), 7.24–7.85 (m, 12H).

[α]$_D$ –80.00° (c 1.0, MeOH).

IR (CHCl$_3$): 3426, 3031, 3012, 1717, 1502, 1340, 1230, 1228, 1045 cm$^{-1}$.

MS(FD): m/e 413 (M$^+$), 413 (100).

Analysis for C$_{22}$H$_{20}$NO$_3$SCl: Calcd: C, 63.84; H, 4.87; N, 3.38; Found: C, 64.12; H, 4.95; N, 3.54.

D. [3R-(3R*,4S*)]-1-Chloro-2-hydroxy-3-N-(benzyloxycarbonyl)amino-4-(naphth-2-ylthio) butane To a cold (0° C.) solution of 530 mg (1.28 mmol) of the subtitled compound of Preparation 2C, in 10 mL of tetrahydrofuran and 1 mL of water, was added 73 mg (1.92 mmol) of sodium borohydride. When the reaction was substantially complete as indicated by TLC, the solution was adjusted to pH 3 using 10 mL of an aqueous saturated ammonium chloride solution and 500 μL of a 5N hydrochloric acid solution. The resultant solution was extracted twice with methylene chloride and the combined organic layers were washed with water, dried over sodium sulfate, filtered and then concentrated under reduced pressure to provide a residue. This residue was purified using radial chromatography (eluent of methylene chloride) to provide 212 mg of a tan solid.

Yield: 40%.

$^1$H NMR (CDCl$_3$): δ3.40 (s, 2H), 3.61–3.71 (m, 2H) 3.97–3.99 (m, 2H), 4.99 (s, 2H), 5.16 (br.s, 1H), 7.21–7.83 (complex, 12H).

MS(FD): m/e 415 (M$^+$), 415 (100).

[α]$_D$ –47.67° (c 0.86, MeOH).

IR (CHCl$_3$): 3630, 3412, 3011, 1720, 1502, 1236, 1044 cm$^{-1}$.

Analysis for C$_{22}$H$_{22}$NO$_3$ClS: Calcd: C, 63.53; H, 5.33; N. 3.37; Found: C, 63.72; H, 5.60; N, 3.64.

E. [1'R-(1'R*,1S*)]-1-[(1'-N-(Benzyloxycarbonyl) amino-2'-(naphth-2-ylthio)ethyl] oxirane A solution of 31 mg (0.55 mmol) of potassium hydroxide in 1 mL of ethanol was added to a solution of 190 mg (0.46 mmol) of the subtitled compound of Preparation 2D, in 6 mL of a 1:2 ethanol/ethyl acetate solution. When the reaction was substantially complete, as indicated by TLC, the reaction mixture was poured into a water/methylene chloride mixture. The resulting layers were separated, and the organic layer was washed with water, dried over sodium sulfate, filtered and then concentrated under reduced pressure to provide a residue. This residue was purified using radial chromatography (eluent of 10% ethyl acetate in methylene chloride) to provide 172 mg of a light tan solid.

Yield: 99%.

$^1$H NMR (CDCl$_3$): δ2.76 (br.s, 2H) 3.01 (br.s, 1H), 3.31 (d, J=5 Hz, 2H), 3.77 (br.s, 1H), 5.05 (s, 2H), 5.22 (d, J=6 Hz, 1H), 7.25–7.85 (complex, 12H).

[α]$_D$ –125.42° (c 0.59, MeOH).

MS(FD): m/e 379 (M$^+$), 379 (100).

IR (CHCl$_3$) 3640, 3022, 2976, 1720, 1502, 1235, 1045 cm$^{-1}$.

Analysis for C$_{22}$H$_{21}$NO$_3$S: Calcd: C, 69.63; H, 5.58; N, 3.69; Found: C, 69.41; H, 5.53; N, 3.64.

F. [2S-(2R*,2'R*,3'S*)]-1-[2'-Hydroxy-3'-(N-benzyloxycarbonyl)amino-4'-(naphth-2-ylthio)butyl] piperidine-2-N-(t-butyl)carboxamide A solution of 0.51 g (1.34 mmol) of the subtitled compound of Preparation 2E and 0.26 g (1.41 mmol) of the subtitled compound of Preparation 4C in 25 mL of isopropanol was heated to 55° C. for approximately forty eight hours. The resultant reaction mixture was cooled and then concentrated under reduced pressure to provide a crude material. This material was purified using radial chromatography (4 mm plate; eluent of 10% acetone in methylene chloride) to provide 104 mg of a white foam.

Yield: 14%.

$^1$H NMR (CDCl$_3$): δ1.29 (s, 9H), 1.44–1.82 (m, 6H), 2.19 (m, 1H), 2.40 (m, 1H), 2.68 (m, 2H), 3.09 (m, 1H), 3.46 (m, 2H), 4.00 (m, 2H), 5.01 (s, 2H), 5.73 (d, 1H), 6.01 (br.s, 1H), 7.23–7.34 (m, 5H), 7.45 (m, 3H), 7.72–7.83 (m, 4H).

MS(FD): m/e 563 (M$^+$, 100).

G. [2S-(2R*,2'S*,3'S*)]-1-[2'-Hydroxy-3'-amino-4'-(naphth-2-ylthio)butyl]piperidine-2-N-(t-butyl) carboxamide A solution containing 1.05 g (0.18 mmol) of the subtitled compound of Preparation 2F in 10 mL of 30% hydrobromic acid in acetic acid was reacted for approximately one hour. The resultant reaction mixture was concentrated, azeotroped three times with toluene, redissolved in methanol containing 4.5 mL each of diethylamine and ammonium hydroxide and then concentrated under reduced pressure to provide a residue. This residue was purified using radial chromatography (1 mm plate; eluent of 3% methanol in methylene chloride containing 1% acetic acid) to provide 64 mg of a white foam.

Yield: 80%.

$^1$H NMR (CDCl$_3$): δ1.29 (s, 9H), 1.52–1.73 (m, 6H), 1.84 (m, 1H), 2.31–2.43 (m, 2H), 2.75–3.04 (m, 5H), 3.17 (m, 1H), 3.41 (m, 1H), 3.71 (m, 1H), 6.22 (br.s, 1H), 7.47 (m, 3H), 7.73–7.82 (m, 4H).

MS(FD): m/e 430 (M$^+$, 100).

Preparation 3

A. 2S-N-(Benzyloxycarbonyl)-2-pyrrolidinecarboxylate pentafluorophenyl ester

To a cold (0° C.) solution of 30 g (0.12 mol) of 2S-N (benzyloxycarbonyl)-2-pyrrolidinecarboxylic acid and 25.8 g (0.14 mol) of pentafluorophenol in 450 mL of tetrahydrofuran, was added 27.7 g (0.14 mol) of 1-(3-dimethylaminopropyl)-3-ethylcarbodiimide (EDC) in one portion, followed by 150 mL of methylene chloride. The resultant reaction mixture was warmed to room temperature and reacted for approximately four hours. When the reaction was substantially complete, as indicated by TLC, the reaction mixture was concentrated under reduced pressure to provide a residue. This residue was dissolved in 500 mL of ethyl acetate and washed sequentially with water, potassium carbonate, 1N hydrochloric acid and brine, dried over sodium sulfate, filtered and then reduced to dryness under reduced pressure to provide a solid. This solid was redissolved in hexane and washed with potassium carbonate, dried over sodium sulfate, filtered and reduced to dryness under reduced pressure to provide 45.95 g of the desired subtitled compound.

Yield: 92%.

$^1$H NMR (CDCl$_3$): δ1.95–2.15 (m, 2H), 2.20–2.35 (m, 1H), 2.35–2.50 (m, 1H), 3.50–3.75 (m, 2H), 4.65–4.75 (m, 1H), 5.02–5.30 (m, 2H), 7.20–7.45 (m, 5H).

B. 2S-N-(Benzyloxycarbonyl)pyrrolidine-2-N(t-butyl) carboxamide

To a cold (0° C.) solution of 45.90 g (0.111 mmol) of the subtitled compound of Preparation 3A in 100 mL of anhydrous methylene chloride, was slowly added 100 mL (0.952 mmol) of t-butylamine. The reaction mixture was warmed to room temperature and reacted for approximately one hour and then diluted with 1000 mL of methylene chloride and then washed sequentially with 1N potassium carbonate, 1N hydrochloric acid, 1N potassium carbonate, and brine, dried over sodium sulfate, and then plug filtered using 50% ethyl acetate in hexane to provide 37.74 g of the desired compound which was used without further purification.

$^1$H NMR (CDCl$_3$): δ0.95–1.50 (m, 9H), 1.70–2.40 (m, 4H) 3.30–3.60 (m, 2H), 4.10–4.30 (m, 1H), 4.95–5.35 (m, 2H), 5.65 (br.s, 0.5H), 6.55 (br.s, 1H), 7.20–7.50 (m, 5.5H).

C. 2S-Pyrrolidine-2-N-(t-Butyl)carboxamide

The subtitled compound of Preparation 3B (2.71 g, 8.9 mmol) was deprotected substantially as detailed in Preparation 1B, using 500 mg of 10% palladium-on-carbon and hydrogen gas (1 atmosphere) in 200 mL of ethanol.

Yield: 1.53 g (100%).

$^1$H NMR (CDCl$_3$): δ1.35 (s, 9H), 1.60–1.75 (m, 2H), 1.76–1.90 (m, 1H), 2.00–2.15 (m, 1H), 2.58 (br.s, 1H), 2.80–3.05 (m, 2H), 3.55–3.65 (m, 1H), 7.45 (br.s, 1H).

D. [2S-(2R*,2'S*,3'R*)]-1-[3'-N(Benzyloxycarbonyl)-amino-2'-hydroxy-4'-phenylbutyl]pyrrolidine-2-N-(t-butyl)carboxamide A solution containing 122 mg (0.72 mmol) of the subtitled compound of Preparation 3C and 200 mg (0.68 mmol) of [1S-(1R*,1'R*)]-1- [(1'-N-(benzyloxycarbonyl)amino-2'-phenyl)ethyl]oxirane in 10 mL of methanol was stirred overnight. When the reaction was substantially complete, as indicated by TLC, the reaction mixture was concentrated under reduced pressure. The desired compound was purified using column chromatography (gradient eluent of 2–4% methanol in methylene chloride) to provide 232.2 mg of a clear amorphous solid.

Yield: 55%.

[α]$_D$–56.97° (c=0.27, MeOH).

$^1$H NMR (CDCl$_3$): δ1.33 (s, 9H), 1.55–1.95 (m, 4H), 2.05–2.25 (m, 1H), 2.40–2.55 (m, 1H), 2.65–2.75 (m, 2H), 2.80–3.00 (m, 3H), 3.15–3.30 (m, 1H), 3.65–3.75 (m, 1H), 3.85–3.95 (m, 1H), 4.86 (br.d, J=1.1 Hz, 1H), 5.03 (s, 2H), 6.95 (m, 1H), 7.15–7.40 (m, 10H).

IR (CHCl$_3$): 3700–3100 (br.), 3434, 3031, 2976, 1720, 1664, 1604, 1512, 1455, 1394, 1367, 1343, 1233, 1156, 1107, 1063, 1028, 911 cm$^{-1}$.

MS(FD): m/e 468 (M$^+$, 100)

E. [2S-(2R*,2'S*,3'R*)]-1-[3'-Amino-2'-hydroxy-4'phenylbutyl]pyrrolidine-2-N-t-butylcarboxamide The subtitled compound of Preparation 3D (222 mg, 0.47 mmol) was deprotected substantially as detailed in Preparation 1B, using 67 mg of 10% palladium-on-carbon and hydrogen gas (1 atmosphere) in 15 mL of ethanol. The desired compound was purified using column chromatography (eluent of 10% isopropanol in methylene chloride containing 0.75% ammonium hydroxide) to provide 80 mg of an off-white solid.

Yield: 51%.

[α]$_D$–55.26° (c=0.23, MeOH).

$^1$H NMR (CDCl$_3$): δ0.80–3.70 (m, 25H), 6.90–7.40 (m, 6H).

IR (CHCl$_3$): 3692, 3600–3200 (br.), 2975, 1657, 1603, 1522, 1497, 1479, 1455, 1393, 1366, 1232, 1198, 1137, 1049, 882 cm $^{-1}$.

MS(FD): m/e 334 (M$^+$, 100).

Preparation 4

A. 2S-N-(t-Butoxycarbonyl) piperidine-2-carboxylic acid

A solution of 1.64 g of sodium carbonate in 15 ml of water was added to a cold (0° C.) solution of 2.0 g (15.5 mol) of 2S-piperidinecarboxylic acid in 50 mL of dioxane. After approximately ten minutes, 3.7 g (17.0 mol) of di-t-butyl dicarbonate was added to the mixture. The resultant reaction mixture was reacted for approximately six hours, concentrated to one fourth of the original volume and then acidified to pH 2 using 1M sodiumhydrogen sulfate and ethyl acetate. The resulting layers were separated, and the organic layers were washed with a saturated brine solution, dried over sodium sulfate, filtered and then reduced to dryness under reduced pressure to provide 2.67 g of a white crystalline solid.

Yield: 75%.

[α]$_D$–55.26° (c=0.23, MeOH). $^1$H NMR (CDCl$_3$): δ1.20–1.80 (m, 15H), 2.15–2.30 (m, 1H), 2.85–3.10 (m, 1H), 3.90–4.10 (m, 2H), 4.70–5.00 (m, 1H).

IR (CHCl$_3$): 3700–1800 (br.), 3025, 3018, 3011, 2980, 2947, 2865, 1716, 1685, 1449, 1394, 1368, 1280, 1252, 1162, 1147, 1129 cm$^{-1}$.

MS(FD): m/e 229 (M$^+$, 100).

Analysis for C$_{27}$H$_{37}$N$_3$O$_4$: Calcd: C, 57.63; H, 8.35; N, 6.11; Found: C, 57.90; H, 8.35; N, 6.19.

3. 2S-N-(t-Butoxycarbonyl) piperidine-2-carboxylate, pentafluorophenylester

To a cold (0° C.) solution of 2.53 g (11.03 mol) of the subtitled compound of Preparation 4A and 2.34 g (12.7 mol) of pentafluorobenzoic acid in 50 mL of tetrahydrofuran, was added 2.42 g (12.7 mol) of EDC. The resultant reaction mixture was warmed to room temperature and reacted for approximately two hours. The mixture was then concentrated under reduced pressure to provide a solid. This solid was redissolved in methylene chloride and washed sequentially with potassium carbonate and brine, dried over sodium sulfate, filtered and then reduced to dryness under reduced pressure to provide 3.85 g of a clear oil which solidified on standing.

Yield: 88%.

$^1$H NMR (CDCl$_3$): δ1.20–1.90 (m, 15H), 2.30–2.40 (m, 1H), 2.90–3.15 (m, 1H), 3.90–4.15 (m, 1H), 5.05–5.35 (m, 1H).

C. 2S-N-(t-Butoxycarbonyl) piperidine-2-N-t-butylcarboxamide

To a cold (0° C.) solution of 3.8 g (9.6 mmol) of the subtitled compound of Preparation 4B in 200 mL of methylene chloride, was slowly added 2.53 mL (24.0 mmol) of t-butylamine. The reaction mixture was reacted for approximately four hours and then concentrated under reduced pressure to provide a residue. This residue was redissolved in methylene chloride and then washed sequentially with 1M potassium carbonate and brine, dried over sodium sulfate, filtered and then purified using column chromatography (gradient eluent of 10–20% ethyl acetate in hexane) to provide 2.52 g of a white solid.

Yield: 92%.

[α]$_D$–41.47° (c=0.506, MeOH). $^1$H NMR (CDCl$_3$): δ1.10–1.70 (m, 15H), 2.20–2.35 (m, 1H), 2.65–2.82 (m, 1H), 3.90–4.10 (m, 1H), 4.62 (br.s, 1H).

IR (CHCl$_3$): 3600–3300 (br.), 2978, 2945, 2869, 1677, 1512, 1455, 1413, 1394, 1367, 1317, 1280, 1255, 1162, 1144, 1127, 1078, 1042, 868 cm$^{-1}$.

MS(FD): m/e 284 (M$^+$, 100).

Analysis for C$_{15}$H$_{28}$N$_2$O$_3$: Calcd: C, 63.35; H, 9.92; N, 9.85; Found: C, 63.10; H, 9.66; N, 9.92.

D. 2S-Piperidine-2-N-t-butylcarboxamide

A solution containing 1.0 g (3.5 mol) of the subtitled compound of Preparation 4C and 3.5 mL of trifluoroacetic acid in 25 mL of methylene chloride was stirred at room temperature for approximately two hours. The reaction mixture was concentrated and azeotroped once with toluene. The resultant reaction mixture was then partitioned between methylene chloride and sodium bicarbonate. The resulting layers were separated and the organic layer was dried over sodium sulfate, filtered and reduced to dryness under reduced pressure to provide 641 mg of the subtitled compound.

Yield: 99%.

[α]$_D$ −22.45° (c=0.95, MeOH).

$^1$H NMR ¯(CDCl$_3$): δ1.20–1.50 (m, 12H), 1.51–1.62 (m, 1H), 1.64 (s, 1H), 1.75–1.88 (m, 1H), 1.90–2.00 (m, 1H), 2.60–2.72 (m, 1H), 2.98–3.10 (m, 2H), 6.63 (br.s, 1H).

IR (CHCl$_3$): 3363, 3002, 2969, 2940, 2860, 1738, 1660, 1522, 1480, 1455, 1398, 1367, 1324, 1295, 1230, 1129, 1110, 852 cm$^{-1}$.

MS(FD): m/e 184 (M$^+$, 100).

E. [2S-(2R*,2'S*,3'R*)]-N-[3'-(N-Benzyloxycarbonyl)amino-2'-hydroxy-4'-phenyl]butyl piperidine-2-N-t-butylcarboxamide A solution containing 195 mg (1.06 mmol) of the subtitled compound of Preparation 4D and 300 mg (1.01 mmol) of [1S-(1R*,1'R*)]-1-[(1'-N(benzyloxycarbonyl)amino-2'-phenyl)ethyl]oxirane in 10 mL of isopropanol was stirred at 55° C. for approximately forty eight hours. When the reaction was substantially complete, as indicated by TLC, the reaction mixture was concentrated under reduced pressure. The desired compound was purified using column chromatography (gradient eluent of 1–5% isopropanol in methylene chloride).

Yield: 395 mg (81%).

[α]$_D$ −55.64° (c=0.22, MeOH).

$^1$H NMR (CDCl$_3$): δ1.32 (s, 9H), 1.45–1.90 (m, 6H), 2.25–2.50 (m, 2H), 2.70–3.20 (m, 5H), 3.30–3.40 (m, 1H), 3.75–4.05 (m, 2H), 4.95–5.10 (m, 3H), 6.15 (br.s, 1H), 7.18–7.40 (m, 10H).

IR (CHCl$_3$): 3700–3100 (br.), 3623, 3021, 2976, 1668, 1603, 1511, 1456, 1313, 1047, 878 cm$^{-1}$.

MS(FD): m/e 482 (M$^+$, 100).

F. [2S-(2R*,2'S*,3'R*)]-N-[3'-Amino-2'-hydroxy-4'-phenyl]butyl piperidine-2-N-t-butylcarboxamide The subtitled compound of Preparation 4E (371 mg, 0.77 mmol) was deprotected substantially as detailed in Preparation 1B, using 110 mg of 10% palladium-on-carbon and hydrogen gas in 20 mL of ethanol to provide 260 mg of a white foam.

Yield: 97%.

[α]$_D$ −64.92° (c=0.39, MeOH).

$^1$H NMR (CDCl$_3$): δ1.35 (s, 9H), 1.45–1.90 (m, 6H), 2.25–2.35 (m, 1H), 2.50–2.90 (m, 5H), 3.00–3.40 (m, 3H), 3.85–3.98 (m, 1H), 6.29 (s, 1H), 7.15–7.38 (m, 5H).

IR (CHCl$_3$): 3693, 3650–3100 (br.), 2943, 2862, 1671, 1603, 1517, 1497, 1455, 1394, 1367, 1233, 1185, 1049, 887 cm$^{-1}$.

MS(FD): m/e 348 (M$^+$, 100).

Preparation 5

A. Pyrazine-2-N-(C-butyl)carboxamide

To a slurry of 50 g (0.403 mol) pyrazine-2-carboxylic acid in 600 mL of tetrahydrofuran and 100 mL of dimethylformamide, was added 65.9 g (0.407 mol) of carbonyldiimidazole. The resultant reaction mixture was reacted at 50° C. until gas evolution ceased. After the reaction mixture cooled, 73.5 g (1.00 mol) t-butylamine was slowly added. The reaction mixture was reacted for approximately thirty minutes, concentrated under reduced pressure, redissolved in 500 mL of methylene chloride and then washed sequentially with water, hydrochloric acid (pH 2), saturated sodium bicarbonate, water, 1M Potassium hydroxide, and brine, dried over sodium sulfate, and concentrated to provide 68.5 g of a white solid.

Yield: 95%.

$^1$H NMR (CDCl$_3$): δ1.51 (s, 9H), 7.73 (br.s, 1H) 8.49 (m, 1H), 8.72 (m, 1H), 9.38 (s, 1H).

B. (±)-Piperazine-2-N-(t-butyl)carboxamide

A mixture of 68.5 g (0.382 mol) of the subtitled compound of Preparation 5A, 70 g (0.308 mol) of platinum oxide in 186 mL of ethanol was heated overnight at 40° C. under a hydrogen atmosphere (60 psi). The resultant crude material was filtered and the filtrate was concentrated to provide 65 g of white solid.

Yield: 95%.

MS (FD): m/e 185 (M$^+$, 100).

C. (±)-4-(Pyrid-3'-ylmethyl)piperazine-2-N-(t-butyl)carboxamide

To a solution of 5.0 g (0.027 mol) of the subtitled compound of Preparation 5B in 160 mL of a 1:1 mixture of water and acetonitrile, was added 18.65 g (0.135 mol) of potassium carbonate. The resultant mixture was vigorously stirred during the addition of 4.43 g (0.027 mol) of 3-chloromethylpyridine hydrochloride and then allowed to react overnight. The resultant reaction mixture was concentrated under reduced pressure, slurried in a solution of 20% isopropanol in chloroform and washed sequentially with water and brine, cried over sodium sulfate, filtered and then concentrated to provide a residue. This residue was purified using flash chromatography (eluent of 5% methanol in methylene chloride containing 1% ammonium hydroxide) to provide 1.34 g of a clear yellow oil.

Yield: 18%.

$^1$H NMR (CDCl$_3$): δ1.10 (s, 9H), 1.89–2.01 (m, 2H), 2.35 (m, 1H), 2.57–2.74 (m, 4H), 3.09 (m, 1H), 3.27 (s, 2H), 6.71 (br.s, 1H), 7.03 (m, 1H) 7.44 (m, 1H) 8.26 (m, 2H).

IR (KBr): 3691, 3611, 3366, 2974, 1666, 1602, 1521, 1479, 1456, 1427, 1393, 1366, 1324, 1139, 1047, 839 cm$^{-1}$.

MS(FD): m/e 276 (M$^+$, 100).

D. [2S-(2R*,2'S*,3'R*)]-1-[2'-Hydroxy-3'-(N-benzyloxycarbonyl)amino-4'-phenylbutyl]-4-(pyrid-3"-ylmethyl) piperazine-2-N-(t-butyl)carboxamide A solution containing 0.377 g (1.27 mmol) of [1S-(1R*,1'R*)]-1-[(1'-N-Benzyloxycarbonyl)amino-2'-phenyl)ethyl]oxirane and 0.350 g (1.27 mmol) of the subtitled compound of Preparation 5C in 12 mL of isopropanol was reacted at 45° C. for approximately forty eight hours. The reaction mixture was cooled and then concentrated under reduced pressure to provide a crude material. This material was purified using radial chromatography (6 mm plate; gradient eluent of 5–10% isopropanol in methylene chloride) to provide 120 mg of isomer A and 68 mg of isomer B.

Yield: 26% overall.

Isomer A:

$^1$H NMR (CDCl$_3$): δ1.33 (s, 9H), 2.26–2.89 (m, 13H), 3.29 (m, 1H), 3.45 (s, 2H), 3.79–3.95 (m, 3H), 4.73 (br.s, 1H), 4.97 (br.s, 2H), 5.20 (m, 1H), 7.14–7.29 (m, 6H) 7.57 (m, 1H), 7.82 (br.s, 1H), 8.53 (m, 2H).

IR (KBr): 3692, 3434, 2970, 2829, 1714, 1661, 1604, 1579, 1512, 1455, 1427, 1393, 1365, 1231, 1149, 1029, 909 cm$^{-1}$.

MS(FD): m/e 573 (M$^+$, 100).

E. [2S-(2R*,2'S*,3'R*)]-1-[2'-Hydroxy-3'-amino-4'-phenyl]butyl-4-(pyrid-3"-ylmethyl) piperazine-2-N-(t-butyl)carboxamide A solution containing 0.062 g (0.11 mmol) of the subtitled compound of Preparation 5D (isomer A) was stirred for approximately ninety minutes in 1.5 mL of a solution of 30% hydrobromic acid in acetic acid. The resultant mixture was concentrated, azeotroped three times with toluene, redissolved in methanol containing 1 mL each of diethylamine and ammonium hydroxide and then concentrated under reduced pressure to provide a residue. This residue was purified using radial chromatography (2 mm plate; gradient eluent of 15–25% methanol in methylene chloride containing 1% ammonium hydroxide) to provide 13 mg of a white solid.

Yield: 28%.
¹H NMR (CDCl₃): δ1.33 (s, 9H), 2.36–3.21 (m, 15H), 3.47 (d, 2H), 3.75 (m, 1H), 7.19–7.30 (m, 6H) 7.57 (m, 2H), 8.52 (m, 2H).
MS(FD): m/e 440 (M⁺, 100).

Preparation 6
[2S-(2R*,2'S*,3'S*)]-1-[3'-N-(Benzyloxycarbonyl)amino-2'-hydroxy-4'-phenylthiobutyl]-4-[pyrid-3"-ylmethyl]piperazine-2-N-t-butylcarboxamide [isomer B]

A solution of 596 mg (1.81 mmol) of [1S-(1R*,1'S*)]-1-[1'-N-(benzyloxycarbonyl)amino-2'-(phenylthio)ethyl]oxirane and 500 mg (1.81 mmol) of the subtitled compound of Preparation 5C in 15 mL of isopropanol were heated at 43° C. for approximately forty-eight hours. The reaction was monitored using TLC (10% isopropanol in methylene chloride containing 1% ammonium hydroxide; Isomer A R$_f$=0.7; Isomer B R$_f$=0.6). When the reaction was substantially complete, the reaction mixture was concentrated under reduced pressure to provide a residue. This residue was purified using radial chromatography (6 mm plate; gradient eluent of 5–15% isopropanol in methylene chloride containing 1% ammonium hydroxide) to provide 200 mg of isomer A as a light tan foam and 119 mg of an off-white foam (isomer B).

Isomer A:
Yield: 18%.
¹H NMR (CDCl₃): δ1.31 (s, 9H), 2.25–2.62 (m, 7H), 2.78–2.95 (m, 2H), 2.98–3.08 (m, 1H), 3.10–3.25 (m, 2H), 3.40–3.55 (m, 2H), 3.72–3.85 (m, 1H), 3.90–4.00 (m, 1H), 3.05 (m, 2H), 7.01 (br.s, 1H), 7.10–7.40 (m, 11H), 7.62 (d, J=7.8 Hz, 1H), 8.49 (s, 2H).
MS(FD): m/e 606 (M⁺, 100).
Analysis for C₃₃H₄₃N₅O₄S: Calcd: C, 65.42; H, 7.15; N, 11.56; Found: C, 65.38; H, 7.27; N, 11.36.

Isomer B:
Yield: 11%.
¹H NMR (CDCl₃): δ1.33 (s, 9H), 2.25–2.85 (m, 8H), 3.20–3.32 (m, 3H), 3.47 (s, 2H), 3.78–3.95 (m, 2H), 5.06 (s, 2H), 5.30–5.38 (m, 1H), 7.10–7.42 (m, 12H), 7.55–7.85 (m, 2H), 8.50–8460 (m, 2H).
MS (FD): m/e 606 (M), 497 (100).
HR MS(FAB) for C₃₃H₄₄N₅O₄S: Calcd: 606.3114; Found: 606.3141.

B. [2S-(2R*,2'S*,3'S*)]-1-[2'-Hydroxy-3'-amino-4'-phenylthiobutyl]-4-[pyrid-3"-ylmethyl]piperazine-2-N-t-butylcarboxamide A solution of 110 mg (0.18 mmol) of isomer B from Preparation 6A in 5 mL of 30% hydrobromic acid in acetic acid was stirred at room temperature for approximately 1 hour. The reaction mixture was concentrated under reduced pressure to provide a residue. This residue was redissolved in 4 mL of ammonium hydroxide. The resultant solution was extracted four times with 10 mL portions of a 10% solution of isopropanol in chloroform. The combined organic layers were dried over sodium sulfate, filtered and concentrated under reduced pressure to provide a residue. This residue was purified using radial chromatography (2 mm plate; gradient eluent of 10–30%; methanol in methylene chloride containing 1% ammonium hydroxide) to provide 65 mg of a light yellow foam.
Yield: 72%.
¹H NMR (CDCl₃): δ1.25 (s, 9H), 2.25–2.78 (m, 7H), 3.00–3.32 (m, 4H), 3.47 (s, 2H), 3.60–3.75 (m, 1H), 4.18–4.35 (m, 1H), 6.90–7.65 (m, 9H), 8.40–8.60 (m, 2H).
MS(FD): m/e 473 (M⁺, 100).

Preparation 7
A. [3S-(3R*,4aR*,8aR*,2'S*,3'S*)]-2-[3'-N-(Benzyloxycarbonyl)amino-2'-hydroxy-4'-(naphth-2-ylthio)]butyl decahydroisoquinoline-3-N-(t-butyl)carboxamide A solution was prepared containing 165 mg (0.40 mmol) of the subtitled intermediate of Preparation 2E and 94 mg (0.43 mmol) of 3-(1-N(t-butyl)amino-1-oxomethyl)octahydro-(2H)-isoquinoline in 5 mL of ethanol. The resulting reaction mixture was allowed to react at 80° C. for approximately 19 hours. The solution was then cooled to room temperature and concentrated under reduced pressure to provide a residue. This residue was purified using radial chromatography (eluent of 10% ethyl acetate in methylene chloride) to provide 103 mg of an off-white foam.
Yield: 42%.
¹H NMR (CDCl₃): δ1.10–1.73 (m, 20H), 2.13–2.31 (m, 2H), 2.44–2.53 (m, 1H), 2.56–2.68 (m, 1H), 2.86–2.97 (m, 1H), 3.52 (br.s, 2H), 4.02 (br.s, 2H), 4.98 (s, 2H), 5.65 (s, 1H), 5.94 (s, 1H), 7.25–7.83 (complex, 13H).
MS (FD): m/e 629 (M⁺), 138 (100).
[α]$_D$–92.45° (c 1.06, MeOH).
IR (CHCl₃): 3429, 3010, 2929, 1713, 1670, 1514, 1455, 1047 cm⁻¹.
Analysis for C₃₅H₄₇N₃O₄S: Calcd: C, 69.98; H, 7.67; N, 6.80; Found: C, 69.86; H. 7.78; N, 6.58.

B. [3S-(3R*,4aR*,8aR*,2'S*,3'S*)]-2-[3'-amino-2'-hydroxy-4'-(naphth-2-ylthio)]butyl decahydroisoquinoline-3-N-(t-butyl)carboxamide A solution was prepared containing 50 mg (0.081 mmol) of the subtitled intermediate of Preparation 7A and 1 mL of a 38% aqueous hydrobromic acid solution in acetic acid. The resultant reaction mixture was allowed to react at room temperature for approximately 1 hour and then was concentrated under reduced pressure to provide a residue. This residue was slurried with toluene and then concentrated under reduced pressure to provide 61 mg of the desired subtitled intermediate. This compound was used crude without purification in Example 9.
¹H NMR (CDCl₃): δ1.14 (s, 1H), 1.17–2.07 (complex, 15H), 2.66–2.87 (m, 2H), 3.21–3.25 (m, 2H), 3.75 (d, J=12 Hz, 1H), 3.85 (d, J=6 Hz, 1H), 4.36–4.47 (m, 1H), 6.73 (s, 1H), 7.39–7.90 (complex, 7H).
MS (FD): 483 (M⁺), 483 (100).

Preparation 8
A. 2R-2-N(Benzyloxycarbonyl)amino-3-phenylthio propanoic acid

The desired subtitled intermediate was prepared substantially in accordance with the procedure detailed in Procedure 2A, using 13.1 mL (127 mmol) of thiophenol, 4.6 g (117 mmol) of a 60% sodium hydride solution and 25.6 g (116 mmol) of L-N(benzyloxycarbonyl)-serine β-lactone in 450 mL of tetrahydrofuran to provide a residue. This residue was purified using flash chromatography (gradient eluent of 0–2% acetic acid in a 4:1 methylene chloride/ethyl acetate mixture) to provide 27.9 g of a white solid.
Yield: 72%.
¹H NMR (CDCl₃): δ7.55–7.18 (m, 10H), 5.55 (d, J=7 Hz, 1H), 5.08 (s, 2H), 4.73–4.60 (m, 1H), 3.55–3.30 (m, 2H).
IR (KBr): 3304, 3035, 1687, 1532, 736 cm⁻¹.
MS(FD): m/e 332, 288, 271, 181.
Analysis for C₁₇H₁₇NO₄S: Calcd: C, 61.61; H, 5.17; N, 4.23; Found: C, 61.69; H, 5.22; N, 4.47.

B. 3S-1-Diazo-2-oxo-3-N-(benzyloxycarbonyl)amino-4-phenylthio butane

The desired subtitled compound was prepared substantially in accordance with the procedure detailed in Procedure 2B, using 12.1 g (37 mmol) of the subtitled compound of Preparation 8A, 5.09 mL (37 mmol) of triethylamine, 7.13 mL (55 mmol) isobutyl chloroformate, 146 mmol of a diazomethane solution to provide a residue. The diazomethane solution was prepared using 100 mL of diethylether, 150 mL of a 5N sodium hydroxide solution and 21 g (146 mmol) of N(methyl)-N(nitro)-N(nitroso)-guanidine as described in Preparation 2B. This residue was purified using flash chromatography (gradient eluent of 0–5%; ethyl acetate in methylene chloride) to provide a yellow oil.

Yield: 73.

$^1$H NMR (CDCl$_3$): δ7.50–7.19 (m, 10H), 5.62 (d, J=7 Hz, 1H), 5.47 (br.s, 1H), 5.11 (s, 2H), 4.50–4.32 (m, 1H), 3.33 (d, J=6 Hz, 1H).

IR (KBr): 3012, 2115, 1720, 1501, 1367, 1228 cm$^{-1}$.

MS (FD): m/e 356, 328, 242.

C. 3R-1-Chloro-2-oxo-3-N-(benzyloxycarbonyl)amino-4-phenylthio butane

The desired subtitled compound was prepared substantially in accordance with the procedure detailed in Procedure 2C, using 22.3 g (63 mmol) of the subtitled compound of Preparation 8B and small quantities of hydrochloric acid (gas) in 400 mL of diethylether to provide 21 g of a white solid. This solid was used without further purification.

$^1$H NMR (CDCl$_3$): δ7.50–7.15 (m, 10H), 5.56 (dd, J=2, 6.7 Hz, 1H), 5.11 (s, 2H), 4.78–4.67 (m, 1H), 4.20 (d, J=15.9 Hz, 1H), 4.12 (d, J=15.9 Hz, 1H), 3.48–3.23 (m, 2H).

IR (KBr): 3349, 1732, 1684, 1515, 1266 cm$^{-1}$.

MS (FD): m/e 363 (M$^+$).

Analysis for C$_{18}$H$_{18}$NO$_3$SCl: Calcd: C, 59.42; H, 4.99; N, 3.85; Found: C, 59.57; H, 5.09; N, 4.13.

D. [2S-(2R*,3S*)]-1-Chloro-2-hydroxy-3-N-(benzyoxycarbonyl)amino-4-phenylthio butane The desired subtitled compound was prepared substantially in accordance with the procedure detailed in Procedure 2D, using 21 g (58 mmol) of the subtitled compound of Preparation 8C, and 2.4 g (63 mmol) of sodium borohydride in 300 mL of tetrahydrofuran to provide a residue. This residue was purified using flash chromatography (gradient eluent of 0–2% methanol in methylene chloride) followed by flash chromatography (gradient eluent of 0–2% ethyl acetate in chloroform) and then recrystallized from methylene chloride at −78° C. to provide 8.3 g of the subtitled compound.

Yield: 39%.

$^1$H NMR (CDCl$_3$): d 7.47–7.19 (m, 10H), 5.22–5.03 (m, 1H), 5.09 (s, 2H), 4.01–3.89 (m, 2H), 3.75–3.58 (m, 2H), 3.32 (d, J=4 Hz, 2H).

IR (KBr): 3321, 2951, 1688, 1542, 1246, 738 cm$^{-1}$.

MS (FD): m/e 366 (M$^+$), 119.

Analysis for C$_{18}$H$_{20}$NO$_3$SCl: Calcd: C, 59.09; H, 5.51; N, 3.83; Found: C, 59.03; H, 5.50; N, 3.96.

E. [1'R-(1'R*,1S*)]-1-[(1'-N-(benzyoxycarbonyl)amino-2'-phenylthio)ethyl oxirane The desired subtitled compound was prepared substantially in accordance with the procedure detailed in Procedure 2E, using 8.3 g (23 mmol) of the subtitled compound of Preparation 8D, 1.4 g (25 mmol) of potassium hydroxide in 400 mL of ethanol to provide a residue. This residue was purified using flash chromatography (gradient eluent of 0–2% ethyl acetate in methylene chloride) to provide 6.4 g of a white solid.

Yield: 85%.

$^1$H NMR (CDCl$_3$): δ7.45–7.15 (m, 10H), 5.12 (s, 1H), 5.08 (s, 2H), 3.77–3.62 (m, 1H), 3.21 (d, J=6 Hz, 2H), 2.99 (m, 1H), 2.77 (m, 2H).

IR (KBr): 3303, 3067, 1694, 1538, 1257, 741 cm$^{-1}$.

MS (FD) m/e 329.

Analysis for C$_{32}$H$_{45}$N$_3$O$_4$S: Calcd: C, 65.63; H, 5.81; N, 4.25; Found: C, 65.48; H, 5.82; N, 4.29.

F. [3S-(3R*,4aR*,8aR*,2'S*,3'S*)]-2-[3'-N-(benzyloxycarbonyl)amino-2'-hydroxy-4'-(phenyl)thio]butyl decahydroisoquinoline-3-N-t-butyl carboxamide The desired subtitled compound was prepared substantially in accordance with the procedure detailed in Procedure 2F, using 6.3 g (19 mmol) of the subtitled compound of Preparation 8E, 5 g (21 mmol) of [3S-(3R*,4aR*,8aR*)]-decahydroisoquinoline-3-N-t-butylcarboxamide in 300 mL of ethanol to provide a residue. This residue was purified using flash chromatography (gradient eluent of 0–20% ethyl acetate in methylene chloride) to provide 4.3 g of a white solid.

Yield: 40%.

$^1$H NMR (CDCl$_3$): δ7.41–7.11 (m, 10H), 5.90 (d, J=5 Hz, 1H), 5.64 (s, 1H), 5.05 (d, J=4 Hz, 2H), 4.08–3.90 (m, 2H), 3.40 (d, j=6, 2H), 3.05 (s, 1H), 2.95–2.85 (m, 1H), 2.62–2.45 (m, 2H), 2.28–2.15 (m, 2H), 2.05–1.88 (m, 2H), 1.78–1.10 (m, 7H), 1.29 (s, 9H).

IR(KBr): 3330, 2925, 2862, 1706, 1661, 1520, 1454, 1246, 738, 694 cm$^{-1}$.

MS (FD): m/e 568 (M$^+$), 467.

Analysis for C$_{32}$H$_{45}$N$_3$O$_4$S: Calcd: C, 67.69; H, 7.99; N, 7.40; round: C, 67.64; H, 8.20; N, 7.45.

G. [3S-(3R*,4aR*,8aR*,2'S*,3'S*)]-2-[3'-amino-2'-hydroxy-4'-(phenyl)thio]butyl decahydroisoquinoline-3-N-t-butyl carboxamide The desired subtitled compound was prepared substantially in accordance with the procedure detailed in Procedure 2G using 1 g (1.8 mmol) of the subtitled compound of Preparation 8F and 40 mL of a 30% hydrobromic acid in acetic acid solution, with the exception that the crude material was dissolved in 30 mL of methanol. To the resulting solution, was added 2 mL of diethylamine and 2 mL of concentrated ammonium hydroxide and then the mixture was concentrated under reduced pressure to provide a residue. This residue was redissolved in water and ethyl acetate. The resulting layers were separated and the organic layer was washed sequentially with an aqueous sodium bicarbonate solution and brine, dried over sodium sulfate, filtered and then reduced to dryness under reduced pressure to provide a residue. This residue was purified using flash chromatography (gradient eluent of 0–10% methanol in chloroform (containing 3 drops of ammonium hydroxide per 1000 mL of chloroform) to provide 0.54 g of a white foam.

Yield: 71%. separate $^1$H NMR (CDCl$_3$): δ7.41–7.16 (m, 5H), 6.07 (s, 1H), 3.78–3.70 (m, 1H), 3.45–3.38 (m, 1H), 3.03–2.84 (m, 3H), 2.38–2.20 (m, 3H), 2.00–1.05 (m, 12H), 1.33 (s, 9H).

IR (KBr): 2924, 2862, 1660, 1517, 1454, 1439, 737, 691 cm$^{-1}$.

MS (FD): m/e 434 (M$^+$), 293.

Preparation 9

A. 3-Methoxy-N-phenylbenzamide

A solution of 13.4 mL (147 mmol) of aniline in 30.7 mL of triethylamine was slowly added to a solution containing 25.1 g (147 mmol) of 3-methoxybenzoyl chloride in methylene chloride. The resulting reaction mixture was reacted for approximately thirty minutes and then diluted with 1N sodium bicarbonate. The resultant layers were separated and the organic layer was washed sequentially with water, 1M sodium hydroxide and then brine, dried over sodium sulfate, filtered and then reduced to dryness under reduced pressure to provide 31.5 g of an off-white solid.

Yield: 95%.

B. 3-Methoxy-2-methyl-N-phenylbenzamide

To a cold (−70° C.) solution of 4.54 g (20 mmol) of the subtitled compound of Preparation 9A and 5.11 g (44 mmol) of TMEDA in 70 mL of anhydrous tetrahydrofuran, was added 26.9 mL of a 1.56M solution of n-butyl lithium in hexane. The resultant reaction mixture was warmed to −15°

C. and stirred for approximately 45 minutes to provide a yellow slurry. The slurry was then recooled to −70° C. and 2.89 g (20 mmol) of methyl iodide was added, resulting in the formation of a white precipitate. The reaction mixture was stirred overnight at room temperature, quenched with saturated ammonium chloride and diluted with diethylether. The resulting layers were separated and the organic phase washed sequentially with saturated ammonium chloride, water, saturated sodium bicarbonate and brine solutions. The organic extracts were then dried over sodium sulfate and concentrated to provide a white solid which was purified by recrystallization from a 2:1 ethyl acetate/hexane solution to provide 4.00 g of needles.

Yield: 99%.

$^1$H NMR (CDCl$_3$): δ2.36 (s, 3H), 3.88 (s, 3H), 3.89 (s, 1H), 6.90–7.70 (m, 8H).

IR (CHCl$_3$): 3424, 3013, 2963, 2943, 2840, 1678, 1597, 1585, 1519, 1463, 1438, 1383, 1321, 1264, 1240, 1178, 1083, 1069 cm$^{-1}$.

MS(FD): m/e 241 (M$^+$, 100).

Analysis for C$_{15}$H$_{15}$NO$_2$: Calcd: C, 74.67; H, 6.27; N, 5.80; Found: C, 74.65; H, 6.29; N, 5.82.

C. 3-Hydroxy-2-methylbenzoic acid

A mixture of 1.21 g (5.00 mmol) of the subtitled compound of Preparation 9B, 35 mL of 5N hydrochloric acid and 20 mL of a 30% solution of hydrobromic acid in acetic acid were heated at reflux for 24 hours. After cooling, the reaction mixture was diluted with 100 mL of ethyl acetate and 100 mL of water. The resulting layers were separated and the organic layer was washed once with water and then basified to pH 11 using 0.5N sodium hydroxide The resulting layers were separated and the aqueous layer reacidified to pH 1 using 5N hydrochloric acid. The desired compound was then extracted from this aqueous layer using ethyl acetate. The ethyl acetate extracts were then washed with brine, dried over sodium sulfate, filtered, and then concentrated to provide a residue which after two concentrations from hexane yielded 750 mg of a white solid.

Yield: 98%.

$^1$H NMR (DMSO-d$_6$): δ2.26 (s, 3H), 6.98 (d, J=8.03 Hz, 1H), 7.02 (t, J=7.69 Hz, 1H), 7.15 (d, J=7.37 Hz, 1H), 9.55 (br.s, 1H)

IR (CHCl$_3$): 3600–2100 (br.), 3602, 2983, 1696, 1588, 1462, 1406, 1338, 1279, 1174, 1154, 1075, 1038, 920, 892, 854, 816 cm$^{-1}$.

MS(FD): m/e 152 (M$^+$, 100).

Analysis for C$_8$H$_8$O$_3$: Calcd: C, 63.15; H, 5.30; Found: C, 63.18; H, 5.21.

Alternatively, the desired subtitled compound was prepared by adding 22.6 g (0.33 mol) of sodium nitrite in small portions to a cooled (−10° C.) solution of 45 g (0.30 mol) of 3-amino-2-methylbenzoic acid and 106 g (58 mL; 1.08 mol) of concentrated sulfuric acid in 400 mL of water, while maintaining the temperature below 7° C. The resultant reaction mixture was stirred for approximately 30 minutes at −10° C., poured into a solution of 240 mL of concentrated sulfuric acid in 1.2 L water, and then slowly heated to 80° C. (heavy gas evolution occurs between the temperatures of 40–60° C.). When the gas evolution stopped, the reaction mixture was cooled to room temperature and the subtitled compound was extracted five times with ethyl acetate (600 mL). The combined organic phases were combined with 500 mL of an aqueous saturated sodium carbonate solution. The resultant layers were separated and the aqueous layer was acidified to pH 2 with concentrated hydrochloric acid. The titled compound was then extracted using ethyl acetate (500 mL) and the combined organic phases were washed with brine, dried over sodium sulfate, filtered and then concentrated under reduced pressure to provide a crude material. This material was purified using two recrystallizations from a ethyl acetate/chloroform mixture to provide 23.2 g of a light orange powder.

Yield: 52%.

Preparation 10

A. 2-Ethyl-3-methoxy-N-phenylbenzamide

The subtitled compound was prepared substantially in accordance with the procedure detailed in Preparation 9B, using 13.5 mL (21 mmol) of 1.56M n-butyl lithium, 2.27 g (10.0 mmol) of the subtitled compound of Preparation 9A, 2.56 g (22.0 mmol) of TMEDA and 1.56 g (10.0 mmol) of ethyl iodide in 50 mL of anhydrous tetrahydrofuran. The resultant crude material was purified by recrystallization from a 3:1 solution of ethyl acetate/hexane to provide 1.57 g of needles.

Yield: 62%.

$^1$H NMR (CDCl$_3$): δ1.22 (t, J=7.4 Hz, 3H), 2.81 (q, J=7.4 Hz, 2H), 3.88 (s, 3H), 6.96 (d, J=8.2 Hz, 1H), 7.05 (d, J=7.6 Hz, 1H), 7.10–7.45 (m, 4H), 7.50 (s, 1H), 7.62 (d, J=7.95 Hz, 1H).

MS(FD): m/e 255 (M$^+$, 100).

Analysis for C$_{16}$H$_{17}$NO$_2$: Calcd: C, 75.27; H, 6.71; N, 5.49; Found: C, 75.39; H, 6.72; N, 5.43.

B. 2-Ethyl-3-hydroxybenzoic Acid

A solution containing 180 mg (0.71 mmol) of the subtitled compound of Preparation 10A, 3 mL of 5N hydrochloric acid and 3 mL of a 30% solution of hydrobromic acid/acetic acid were heated for 20 hours in a sealed tube at 155° C. After cooling, the reaction mixture was diluted with ethyl acetate and water. The resulting layers were separated and the organic layer was extracted once with water and then basified to pH 11 using 0.5N sodium hydroxide. The resulting layers were separated and the aqueous layer reacidified to pH 1 using 5N hydrochloric acid. The desired compound was then extracted from this aqueous layer using ethyl acetate. The ethyl acetate extracts were washed with brine, dried over sodium sulfate, filtered and then concentrated to provide 103 mg of a pale red solid.

Yield: 88%.

$^1$H NMR (acetone-d$_6$): δ1.16 (t, J=7.4 Hz, 3H), 2.98 (q, J=7.4 Hz, 2H), 7.00–7.15 (m, 2H), 7.32–7.36 (m, 1H), 8.48 (br.s, 1H).

MS(FD): m/e 166 (M$^+$, 100).

Preparation 11

A. 2-Fluoro-3-methoxy-N-phenylbenzamide

The desired subtitled compound was prepared substantially in accordance with the procedure detailed in Preparation 9B, by adding a solution of 3.15 g (10.0 mmol) of N-fluorobenzenesulfonimide in 5 mL of tetrahydrofuran to a solution containing 13.5 mL (21.0 mmol) of 1.56M n-butyl lithium, 2.27 g (10.0 mmol) of the subtitled compound of Preparation 9A and 2.56 g (22.0 mmol) of TMEDA in 50 mL of anhydrous tetrahydrofuran. The resultant crude material was recrystallized twice from a 2:1 solution of ethyl acetate/ hexane and then further purified using radial chromatography (6 mm, 0.5% ethyl acetate in methylene chloride) to provide 540 mg of an off-white solid.

Yield: 22%.

$^1$H NMR (CDCl$_3$): δ3.94 (s, 3H), 7.05–7.80 (m, 8H), 8.35–8.50 (m, 1H).

MS(FD): m/e 245 (M$^+$, 100).

B. 2-Fluoro-3-hydroxybenzoic Acid

The subtitled compound was prepared substantially in accordance with the procedure detailed in Preparation 9C, using a solution of 255 mg (1.02 mmol) of the subtitled compound of Preparation 11A, 3 mL of 5N hydrochloric acid and 5 mL of a 30% solution of hydrobromic acid in acetic acid to provide 134 mg of a white solid.

Yield: 86%.

$^1$H NMR (acetone-$d_6$): δ7.05–7.50 (m, 5H).

MS (FD): m/e 156 (M$^+$, 100).

Preparation 12

A. 4-N-(Phenyl)carbamoyl pyridine

A solution of 22.8 mL (250 mmol) of aniline in 104.5 mL (750 mmol) of triethylamine was slowly added to a solution of 44.5 g (250 mmol) of 4-chloroformyl pyridinium hydrochloride in 500 mL of chloroform. The resulting reaction mixture was stirred overnight and then refluxed for 2 hours. After cooling, the reaction mixture was diluted with 600 mL of water which resulted in the formation of a precipitate. After adding 200 mL of isopropanol to the mixture, the resultant layers were separated and the organic layer was washed sequentially with 0.1N sodium hydroxide, water and then brine, dried over sodium sulfate, filtered and then concentrated under reduced pressure at 70° C. to provide a white solid with a brown tinge. This solid was washed with 200 mL of ethyl acetate to provide 38.9 g of the desired subtitled compound.

Yield: 78%.

B. 4-N-(Phenyl)carbamoyl pyridine N-oxide

To a hot (85°–90° C.) solution of 19.8 g (100 mmol) of the subtitled compound of Preparation 12A in 60 mL of glacial acetic acid, was slowly added 51 mL of hydrogen peroxide behind a blast shield. The resultant reaction mixture was reacted for approximately four hours at 90° C., cooled to room temperature, diluted in about 60 mL of a mixture of isopropanol and chloroform and then basified to pH 12. The resultant layers were separated and the combined organic extracts were dried over sodium sulfate, filtered and concentrated under reduced pressure to provide a pale yellow solid. This solid was triturated with 250 mL of methylene chloride and reduced to dryness to provide 15.95 g of an off-white solid.

Yield: 75%.

C. 2-Chloro-4-N-(phenyl)carbamoyl pyridine

To a solution of 20.2 g (97.0 mmol) of phosphorus pentachloride in 27 mL (289 mmol) of phosphorous oxychloride, was added 14.4 g (67.2 mmol) of the subtitled compound of Preparation 12B. The resultant reaction mixture was slowly heated to 130° C. and reacted for approximately 40 minutes. The reaction mixture was cooled to room temperature and then concentrated under reduced pressure to provide a residue. This residue was redissolved in 80 mL of water and then diluted with 80 mL of aqueous potassium carbonate resulting in the formation of a yellow precipitate. The precipitate was isolated by filtration, dissolved in 250 mL of hot ethanol and then hot filtered to provide a dark yellow solution. This solution was concentrated under reduced pressure to approximately 160 mL and then hot filtered again before the addition of about 50–60 mL of water. The resultant solution was cooled and the desired compound was isolated by recrystallization to provide 8.0 g of pale yellow and white needles.

Yield: 51%.

D. 2-Methoxy-4-N-(phenyl)carbamoyl pyridine

To a slurry of 4.09 g (18.0 mmol) of the subtitled compound of Preparation 12C in 30 mL of methanol, was added 2.92 g (42.0 mmol) of sodium methoxide. The resultant reaction mixture was refluxed for approximately eighteen hours, cooled and concentrated under reduced pressure to provide a solid. This solid was washed with water and triturated with cold benzene to provide 1.8 g of a solid. Analysis of this solid indicated that the reaction was not complete, so an additional 10.01 g (144 mmol) of sodium methoxide was added to the solid in methanol. The resultant reaction mixture was refluxed in methanol for fifteen hours and worked up identically to provide 300 mg of a solid. This solid was purified using column chromatography (2 mm plate; eluent of 40% ethyl acetate in hexane) followed by recrystallization from hot hexane to provide 140 mg of the desired compound.

Yield: 3%.

E. 2-Methoxy-3-methyl-4-N-(phenyl)carbamoyl pyridine

The subtitled compound was prepared substantially in accordance with the procedure detailed in Preparation 9B, using 260 mg (1.17 mmol) of the subtitled compound of Preparation 12D, 404 μL (2.68 mmol) of TMEDA, 1.78 mL (2.68 mmol) of n-butyl lithium, and 329 μL (5.61 mmol) of methyl iodide in 2 mL of tetrahydrofuran. The crude material was purified using radial chromatography (2 mm plate; eluent of 40% ethyl acetate in hexane) followed by recrystallization from hot hexane to provide 140 mg of the desired subtitled compound.

F. 3-methyl-2-pyridone-4-carboxylic acid

A slurry of 150 mg (0.598 mmol) of the subtitled compound of Preparation 12E in 4 mL of 5N hydrochloric acid (aqueous) was refluxed for approximately five hours. After cooling, the reaction mixture was concentrated under reduced pressure to provide a yellow oil. This oil was dissolved in 15 mL of water and the resultant solution was adjusted to pH 8 using potassium hydroxide and then diluted with 10 mL of toluene. The resulting layers were separated and the aqueous layer was acidified to pH 3.5 using a 5N hydrochloric acid solution and then concentrated under reduced pressure to provide a yellow solid. This solid was slurried in 2 mL of hot ethanol and filtered through a cotton plug. The filtrate was then reduced to dryness under reduced pressure to provide 130 mg of a solid. This solid was washed with 5 mL of hot 10% acetic acid in ethyl acetate to provide 17 mg of a solid which was then crystallized in ethanol to provide 6.8 mg of the desired subtitled compound.

Yield: 6%.

Preparation 13

2,6-Dichloro-3-hydroxy benzoic acid

Chlorine gas (20 g; 282 mmol) was slowly bubbled through a cold (−70° C.) solution of 20 g (145 mmol) of 3-hydroxy benzoic acid in 100 mL of methanol, under nitrogen, resulting in a temperature increase to about −5° C. The reaction mixture was recooled and after approximately thirty minutes, the chlorine gas was flushed out with nitrogen. The reaction mixture was then warmed to room temperature and diluted with 100 mL of water. The desired titled compound was isolated by recrystallization to provide a white solid. This solid was purified by recrystallization from 90 mL of water followed by recrystallization from 250 mL of benzene containing 10 mL of acetone to provide 4.8 g of the desired titled compound.

Yield: 16%.

Preparation 14

2-Chloro-3-hydroxy benzoic acid

Chlorine gas (10.3 g; 147 mmol) was slowly bubbled through a cold solution of 20 g (145 mmol) of 3-hydroxy benzoic acid in 100 mL of methanol, under nitrogen, while maintaining the temperature below −60° C. After approximately thirty minutes, the chlorine gas was flushed out with nitrogen and the reaction mixture was allowed to warm to room temperature and diluted with 100 mL of water. The desired titled compound was isolated by recrystallization to provide a white solid. This solid was purified by recrystallization from 50 mL of water followed by recrystallization from 130 mL of benzene containing 10 mL of acetone to provide the desired titled compound.

Preparation 15

A. 2-Methyl-3-methoxy benzoate methyl ester

A slurry of 306 mg (2.00 mmol) of the subtitled compound of Preparation 9C, 1.06 mL (20.0 mmol) of methyl iodide and 1.38 g (10.0 mmol) of potassium carbonate in 8 mL of acetone was refluxed for approximately 3 hours. Since the reaction was not complete, an additional 2 mL (37.7 mmol) of methyl iodide, 2 g (14.5 mmol) of potassium carbonate and 10 mL of acetone were added to the reaction mixture. After refluxing the mixture for approximately sixteen hours, the mixture was filtered. The filtrate was then concentrated under reduced pressure to provide a residue. This residue was dissolved in ethyl acetate and washed with water and then reduced to dryness under reduced pressure to provide 188 mg of material which was 88% desired product.

B. 2-Methyl-3-methoxy benzoic acid

A solution of 116 mg (4.86 mmol) of lithium hydroxide in 1 mL of water was added to a solution of 175 mg (0.97 mmol) of the subtitled compound of Preparation 15A in 3 mL of tetrahydrofuran. The resultant reaction mixture was stirred rapidly. When the reaction was substantially complete, as indicated by TLC, the reaction mixture was concentrated under reduced pressure to provide a residue. This residue was redissolved with 10 mL of hexane, 25 mL of water and 3 mL of 1N sodium hydroxide. The resulting layers were separated and the aqueous layer was diluted with ethyl acetate and then acidified to pH 1 using 1M hydrochloric acid. The resulting layers were separated and the ethyl acetate layer was washed with brine, dried over sodium sulfate, filtered and reduced to dryness under reduced pressure to provide 73 of the desired subtitled compound.

Preparation 16

A. 2-Butyl-3-methoxy-N-phenylbenzamide

The desired subtitled compound was prepared substantially in accordance with the procedure detailed in Preparation 9B, using 11.95 mL of 1.51M of n-butyl lithium in hexanes (18.04 mmol), 1.95 g (8.95 mmol) of the subtitled compound of Preparation 9A, 2.19 g (18.89 mmol) of TMEDA and 1.60 g (9.45 mmol) butyl iodide in 30 mL of anhydrous tetrahydrofuran. The resultant crude material was purified using radial chromatography (4 mm plate; eluent of 15% ethyl acetate in hexane) to provide 83 mg of a clear, colorless oil.

Yield: 3.5%.

$^1$H NMR (CDCl$_3$): δ0.89 (t, J=7.27 Hz, 3H), 1.36 (m, 2H), 1.56 (m, 2H), 2.78 (m, 2H), 3.84 (s, 3H), 6.92 (d, J=7.98 Hz, 1H), 7.00 (d, J=7.36 Hz, 1H), 7.11–7.22 (m, 2H), 7.35 (t, 2H), 7.59 (m, 2H).

IR (CHCl$_3$): 3691, 3619, 3424, 3024, 3010, 2963, 2874, 1679, 1602, 1580, 1517, 1459, 1437, 1315, 1265, 1177, 1055, 877 cm$^{-1}$.

MS (FD): m/e 283 (M$^+$, 100).

A. 2-Butyl-3-hydroxybenzoic Acid

The desired subtitled compound was prepared substantially in accordance with the procedure detailed in Preparation 10B, using 80 mg (0.28 mmol) of the subtitled compound of Preparation 16A in 2 mL of 5N hydrochloric acid, and 2 mL of 30% hydrobromic acid in acetic acid to provide 44 mg of crude material which was used without further purification.

Yield: 60% (by $^1$H NMR).

1H NMR (CDCl$_3$): δ0.96 (t, J=8.09 Hz, 3H), 1.44 (m, 2H), 1.59 (m, 2H), 3.03 (m, 2H), 6.99 (d, J=8.03 Hz, 1H), 7.15 (t, J=7.77 Hz, 1H), 7.59 (d, J=6.85 Hz, 1H).

Preparation 17

A. 3-Methoxy-2-propyl-N-phenylbenzamide

The desired subtitled compound was prepared substantially in accordance with the procedure detailed in Preparation 9B, using 2.5 g (11.0 mmol) of the subtitled compound of Preparation 9A, 2.81 g (24.2 mmol) of TMEDA, 15.23 mL (23.13 mmol) of n-butyl lithium and 1.33 g (11.0 mmol) of allyl bromide in 30 mL of tetrahydrofuran to provide 2.4 g of crude material. This material was dissolved in 30 mL of absolute ethanol in the presence of 0.5 g of 10% palladium-on-carbon and the resulting mixture was reacted under a hydrogen atmosphere for approximately twelve hours. The mixture was then filtered over celite and the filtrate was concentrated under reduced pressure to provide an orange oil. This oil was purified using radial chromatography (6 mm plate; eluent of 10% ethyl acetate in hexane) to provide 438 mg of a white foam.

Yield: 15%.

$^1$H NMR (CDCl$_3$): δ0.94 (t, J=7.35 Hz, 3H) 1.62 (m, 2H) 2.75 (m, 2H), 3.84 (s, 3H), 6.92 (d, J=8.06 Hz, 1H), 7.00 (d, J=7.39 Hz, 1H), 7.16 (m, 2H), 7.34 (t, 2H), 7.59 (d, 2H), 7.69 (br.s, 1H).

B. 3-Hydroxy-2-propylbenzoic Acid

The desired subtitled compound was prepared substantially in accordance with the procedure detailed in Preparation 10B, using 438 mg (1.62 mmol) of the subtitled compound of Preparation 17A in 7 mL of 5N hydrochloric acid and 7 mL of 30% hydrobromic acid in acetic acid to provide a tan solid. This solid was purified by recrystallization from hot toluene to provide 84 mg of a tan solid.

Yield: 29%.

$^1$H NMR (CDCl$_3$): δ1.01 (t, J=7.33 Hz, 3H), 1.63 (m, 2H), 2.98 (m, 2H), 6.98 (d, J=7.97 Hz, 1H), 7.14 (t, J=7.86 Hz, 1H), 7.57 (d, J=7.25 Hz, 1H).

IR (KBr): 3383, 3047, 2962, 2872, 2641, 1698, 1458, 1412, 1341, 1296, 1278, 1223, 1174, 1086, 929, 815, 752 cm$^{-1}$.

MS (FD): m/e 180 (M$^+$, 100).

Preparation 18

A. 2-Isopropyl)-3-methoxybenzonitrile

To a mixture of 2.76 g (0.115 mol) of magnesium in 75 mL of diethylether, was slowly added 24.31 g (0.143 mol) isopropyl iodide. The resulting reaction mixture was allowed to react until all of the magnesium was consumed. Then, a solution of 15.0 g (0.92 mol) of 2,3-dimethoxy benzonitrile in 75 mL of diethylether was added over ninety minutes. The resulting reaction mixture was reacted overnight at room temperature and then refluxed for four hours. The resultant reaction mixture was then cooled to 0° C., and the top layer was decanted into saturated ammonium chloride and ice. The resultant layers were separated and the organic layer was washed sequentially with a dilute sodium hydroxide solution, water, and a dilute hydrochloric acid solution, dried over sodium sulfate, filtered and then concentrated to provide an orange oil. This oil was distilled under reduced pressure (5 inch vigreux column; 0.2 mm Hg) to provide 6.25 g of an orange oil.

Yield: 39%.

$^1$H NMR (CDCl$_3$): δ1.37 (d, J=6.47 Hz, 6H), 3.55 (m, 1H), 3.83 (s, 3H), 7.04 (d, J=7.79 Hz, 1H), 7.18 (m, 2H).

IR (CHCl3): 3690, 3617, 3019, 2968, 2939, 2841, 2228, 1577, 1470, 1457, 1440, 1387, 1363, 1265, 1100, 1070, 1045, 878 cm$^{-1}$.

MS(FD): m/e 175 (M$^+$, 100).

B. 3-Hydroxy-2-isopropyl benzoic acid

The desired subtitled compound was prepared substantially in accordance with the Procedure detailed in Preparation 10B, using 330 mg (1.88 mmol) of the subtitled compound of Preparation 18A in 2 mL of 5N hydrochloric acid and 30% hydrobromic acid in acetic acid. The crude product was purified using radial chromatography (2 mm plate; eluent of 3% methanol in methylene chloride containing 1% acetic acid) to provide 125 mg of a rose colored solid.

Yield: 37%.

$^1$H NMR (CDCl$_3$): δ1.40 (d, J=6.92 Hz, 6H), 3.62 (m, 1H), 6.83 (d, J=7.86 Hz, 1H), 7.06 (t, J=7.89 Hz, 1H), 7.24 (d, J=7.55 Hz, 1H).

IR (CHCl$_3$): 3599, 3025, 2965, 2876, 1695, 1603, 1584, 1466, 1454, 1404, 1360, 1275, 1234, 1166, 1148, 1086, 1057, 926 cm$^{-1}$.

MS(FD): m/e 180 (M$^+$, 100).

Analysis for C$_{10}$H$_{12}$O$_3$: Calcd: C, 66.65; H, 6.71; Found: C, 66.53; H, 6.84.

Preparation 19

3-methylisonicotinic acid

To a hot (155° C.) solution of 10.7 g (0.1 mol) of 3,4-lutidine in 100 mL diphenylether, was added 18 g (0.16 mol) selenium dioxide in portions. After about 20 minutes, the reaction was heated to 185° C. and allowed to react for approximately thirty minutes. After cooling, the reaction mixture was diluted with water and filtered. The filtrate was extracted with chloroform and the chloroform extracts were then concentrated under reduced pressure to provide 6.0 g of a pale brown solid.

Yield: 44%.

$^1$H NMR (CDCl$_3$): δ2.43 (s, 3H), 7.61 (d, J=4.98 Hz, 1H), 8.49 (d, J=4.99 Hz, 1H), 8.53 (s, 1H).

$^{13}$C NMR (CDCl$_3$): δ17.91, 123.21, 132.81, 138.15, 148.12, 152.71, 167.89 ppm.

IR (KBr): 3425, 2418, 1724, 1606, 1445, 1387, 1303, 1278, 1235, 1100, 1072, 850 cm$^{-1}$.

MS(FD): m/e 138 (M$^+$, 100).

Preparation 20

5-quinolinecarboxylic acid

To a solution containing 15 g (0.1 mol) of m-aminobenzoic acid, 27 g (0.13 mol) of m-nitrobenzene sulfonate and 25 g (0.4 mol) of glycerol, was added 125 g of 70% sulfuric acid. The resultant reaction mixture was refluxed for about 2.5 hours, diluted with 125 mL of water, basified to pH 9 using ammonium hydroxide, stirred overnight with 5 g of charcoal, and then filtered. The filtrate was then boiled with 5 g charcoal, filtered, and then cooled to 50° C., acidified to pH 5 with glacial acetic acid (15 mL), and filtered to provide a brown solid. This solid was boiled in 300 mL of water containing 10 mL of acetic acid and hot filtered to provide crude material. This material was purified using recrystallization from boiling acetic acid to provide 6.1 g of a pale brown solid.

Yield: 32%.

$^1$H NMR (CDCl$_3$): δ7.62 (m, 1H), 7.81 (t, J=7.82 Hz, 1H), 8.20 (m, 2H), 8.93 (d, J=3.79 Hz, 1H), 9.24 (d, J=8.58 Hz, 1H).

IR (Kr): 2772, 2431, 1906, 1708, 1610, 1589, 1507, 1363, 1323, 1269, 1235, 1211, 1141, 1076, 1034, 999, 866, 807 cm$^{-1}$.

MS(FD): m/e 173 (M$^+$, 100).

Preparation 21

1,2,3,4-tetrahydro-5-quinolinecarboxylic acid

A solution containing 1.03 g (5.95 mmol) of the titled compound of Preparation 20, 1.87 g (29.77 mmol) of ammonium formate in 100 mL of ethanol was purged with nitrogen for 10 minutes. To this solution was added 0.5 g of palladium black and the resultant reaction mixture was heated to 65° C. After approximately three hours, the reaction mixture was filtered; the resultant filtrate was concentrated under reduced pressure to provide a residue. This residue was partitioned between water (pH 4) and a solution of 10% isopropanol in chloroform. The resulting layers were separated, and the organic layer was washed with water (pH=4), dried over sodium sulfate, filtered, and concentrated to provide crude material. This material was purified using radial chromatography (2 mm plate; gradient eluent of 5–10% methanol in methylene chloride containing 1% acetic acid) to provide 87 mg of a tan solid.

Yield: 8%.

$^1$H NMR (CDCl$_3$): δ1.04 (m, 2H), 2.16 (t, 2H), 2.40 (m, 2H), 5.81 (d, J=8.05 Hz, 1H), 6.09 (t, J=7.78 Hz, 1H), 6.23 (d, J=7.96 Hz, 1H).

IR(Kr): 3296, 2965, 2929, 1691, 1597, 1474, 1461, 1443, 1350, 1305, 1279, 1236, 1184, 1159, 1106, 1073, 1022, 827 cm$^{-1}$.

MS(FD): m/e 177 (M$^+$, 100).

Analysis for C$_{10}$H$_{11}$NO$_2$: Calcd: C, 67.78; H, 6.26; N, 7.90; Found: C, 67.96; H, 6.10; N, 7.88.

Preparation 22

A. 3-Amino-2-methyl benzoate methyl ester

A solution of 10 g (66.2 mmol) of 3-amino-2-methyl benzoic acid and 20 g of p-toluenesulfonic acid monohydrate in 400 mL of methanol was refluxed overnight and then diluted with a mixture of ethyl acetate and 1M potassium carbonate. The resulting layers were cooled and then separated. The organic layer was then washed sequentially with 1M potassium carbonate, and brine, dried over sodium sulfate, filtered and then concentrated to provide 9.23 g or an orange oil.

Yield: 85%.

$^1$H NMR (CDCl$_3$): δ2.34 (s, 3H), 3.73 (br.s, 2H), 3.88 (s, 3H), 6.81 (d, J=7.96 Hz, 1H), 7.05 (t, J=7.78 Hz, 1H), 7.19–7.30 (m, 1H).

IR (CHCl$_3$): 3406, 3027, 3012, 2978, 2953, 1718, 1621, 1467, 1435, 1315, 1301, 1265, 1196, 1159, 1108, 1066, 1045, 810 cm$^{-1}$.

MS(FD): m/e 165 (M$^+$, 100).

B. 3-N-(Methylsulfonyl)amino-2-methyl benzoate methyl ester

To a cold (0° C.) solution of 1.07 g (6.48 mmol) of the subtitled compound of Preparation 22A in 50 mL of anhydrous methylene chloride, was added 1.18 g (6.80 mmol) of methylsulfonic anhydride. The resultant reaction mixture was reacted overnight at room temperature and then diluted with 100 mL of methylene chloride, washed twice with a sodium bicarbonate solution, dried over sodium sulfate, filtered, concentrated, redissolved in hexane and then concentrated again to provide a residue. This residue was then triturated three times in hexane and then reduced to dryness under reduced pressure to provide 1.46 g of a pink solid. This solid was then recrystallized using 20 mL of a 30% hexane/50% ethyl acetate/20% methanol mixture.

Yield: 57%.

$^1$H NMR (DMSO-d$_6$): δ2.25–2.45 (m, 4.5H), 2.97 (s, 1.5H), 3.80 (s, 3H), 7.23–7.63 (m, 3H), 9.24 (s, 1H).

IR (KBr): 3900–2400 (br.), 3298, 1713, 1466, 1320, 1290, 1265, 1248, 1210, 1183, 1156, 1047, 971, 964, 752, 563, 519 cm$^{-1}$.

MS(FD): m/e 243 (M$^+$, 100).

Analysis for C$_{10}$H$_{13}$NO$_4$S: Calcd: C, 49.37; H, 5.39; N, 5.76; Found: C, 49.15; H, 5.54; N, 5.80.

C. 3-N-(Methylsulfonyl)amino-2-methyl benzoic acid

The desired subtitled compound was prepared substantially in accordance with the procedure detailed in Preparation 15B, using 400 mg (1.64 mmol) of the subtitled compound of Preparation 22B, and 118 mg (4.93 mmol) of lithium hydroxide in 20 mL of tetrahydrofuran and 8 mL of water, to provide 206 mg of a white solid.

Yield: 55%.

$^1$H NMR (DMSO-d$_6$): δ2.43 (s, 3H), 2.97 (s, 3H), 7.26 (t, J=7.87 Hz, 1H), 7.43 (d, J=7.79 Hz, 1H), 7.60 (d, J=7.17 Hz, 1H).

IR (KBr): 3800–2200 (br.), 3252, 1685, 1404, 1334, 1309, 1277, 1149, 982, 965, 914, 780, 763, 748, 632, 518, 498 cm$^{-1}$.

MS(FD): m/e 243 (M$^+$, 100).

Preparation 23

A. 3-methoxy-N-phenylbenzamide

A solution of 13.4 mL (147 mmol) of aniline in 30.7 mL of triethylamine was slowly added to a solution containing 25.1 g (147 mmol) of 3-methoxybenzoyl chloride in methylene chloride. The resulting reaction mixture was reacted for approximately thirty minutes and then diluted with 1N sodium bicarbonate. The resultant layers were separated and the organic layer was washed sequentially with water, 1M sodium hydroxide and then brine, dried over sodium sulfate, filtered and then reduced to dryness under reduced pressure to provide 31.6 g of an off-white solid.

Yield: 95%.

B. 3-Methoxy-2-methyl-N-phenylbenzamide

To a cold (–70° C.) solution of 4.54 g (20 mmol) of the subtitled compound of Preparation 23A and 5.11 g (44 mmol) of TMEDA in 70 mL of anhydrous tetrahydrofuran, was added 26.9 mL of a 1.56M solution of n-butyl lithium in hexane. The resultant reaction mixture was warmed to –15° C. and stirred for approximately 45 minutes to provide a yellow slurry. The slurry was then recooled to –70° C. and 2.89 g (20 mmol) of methyl iodide was added, resulting in the formation of a white precipitate. The reaction mixture was stirred overnight at room temperature, quenched with saturated ammonium chloride and diluted with diethylether. The resulting layers were separated and the organic phase washed sequentially with saturated ammonium chloride, water, saturated sodium bicarbonate and brine solutions. The organic extracts were then dried over sodium sulfate and concentrated to provide a white solid which was purified by recrystallization from a 2:1 ethyl acetate/hexane solution to provide 4.00 g of needles.

Yield: 99%.

$^1$H NMR (CDCl$_3$): δ2.36 (s, 3H), 3.88 (s, 3H), 3.39 (s, 1H), 6.90–7.70 (m, 8H).

IR (CHCl$_3$): 3424, 3013, 2963, 2943, 2840, 1678, 1597, 1585, 1519, 1463, 1438, 1383, 1321, 1264, 1240, 1178, 1083, 1069 cm$^{-1}$.

MS(FD): m/e 241 (M$^+$, 100).

Analysis for C$_{15}$H$_{15}$NO$_2$: Calcd: C, 74.67; H, 6.27; N, 5.80; Found: C, 74.65; H, 6.29; N, 5.82.

C. 2-Methyl-3-hydroxybenzoic acid

A mixture of 1.21 g (5.00 mmol) of the subtitled compound of Preparation 23B, 35 mL of 5N hydrochloric acid and 20 mL of a 30% solution of hydrobromic acid in acetic acid were heated at reflux for 24 hours. After cooling, the reaction mixture was diluted with 100 mL of ethyl acetate and 100 mL of water. The resulting layers were separated and the organic layer was washed once with water and then basified to pH 11 using 0.5N sodium hydroxide. The resulting layers were separated and the aqueous layer reacidified to pH 1 using 5N hydrochloric acid. The desired compound was then extracted from this aqueous layer using ethyl acetate. The ethyl acetate extracts were then washed with brine, dried over sodium sulfate, filtered, and then concentrated to provide a residue which after two concentrations from hexane yielded 750 mg of a white solid.

Yield: 98%.

$^1$H NMR (DMSO-d$_6$): δ2.26 (s, 3H), 6.98 (d, J=8.03 Hz, 1H), 7.02 (t, J=7.69 Hz, 1H), 7.15 (d, J=7.37 Hz, 1H), 9.55 (br.s, 1H).

IR (CHCl$_3$): 3600–2100 (br.), 3602, 2983, 1696, 1588, 1462, 1406, 1338, 1279, 1174, 1154, 1075, 1039, 920, 892, 854, 816 cm$^{-1}$.

MS(FD): m/e 152 (M$^+$, 100).

Analysis for C$_8$H$_8$O$_3$: Calcd: C, 63.15; H, 5.30; Found: C, 63.18; H, 5.21.

Alternative Preparation for 2-Methyl-3-hydroxybenzoic acid

To a cold (0° C.) suspension of 0.54 g (3.3 mmol) of 2-methyl-3-aminobenzoic acid in 5 mL of water containing 0.65 mL of concentrated sulfuric acid, was added 0.25 g (3.6 mmol) of solid sodium nitrite. After approximately 15 minutes the reaction mixture was poured into 20 mL of warm water containing 4 mL of concentrated sulfuric acid. The resultant reaction mixture was heated slowly to 90° C., resulting in gas evolution. After the gas evolution ceased, the solution was cooled to room temperature and extracted with ethyl acetate. The organic layers were combined, washed with 0.5N hydrochloric acid, dried and concentrated under reduced pressure. The crude residue was purified by rapid filtration through silica gel (eluent of 5% methanol in methylene chloride) to yield 350 mg of a white solid (m.p. 137°–138° C.).

Yield: 69%.

$^1$H NMR (CDCl$_3$): δ8.18 (br.s, 1H), 7.42 (d, J=7.7 Hz, 1H), 7.13 (t, J=7.9 Hz, 1H), 6.93 (d, J=7.9 Hz, 1H), 2.46 (s, 3H).

Analysis for C$_8$H$_8$O$_3$: Calcd: C, 63.15; H, 5.29; Found: C, 63.32; H, 5.36.

Preparation 24

A. N-(t-Butyl)-2-methylbenzamide

To a cold (0° C.) solution of 139.2 g (0.9 mol) of o-toluoyl chloride in 1200 mL of methylene chloride at 25° C., under nitrogen, was slowly added 180.0 g (1.8 mol) of triethylamine followed by the dropwise addition of a solution containing 73.14 g (1.0 mol) of t-butylamine in 200 mL of methylene chloride. The resulting reaction mixture was warmed to room temperature and allowed to react for 2.5 hours. The reaction mixture was then diluted with 1800 mL of water. The resulting organic and aqueous layers were separated, and the organic layer was washed sequentially with 2N sodium hydroxide, 1.0N hydrochloric acid and brine, dried over magnesium sulfate, filtered and then reduced to dryness under reduced pressure to provide 167.6 g of the desired subtitled compound as an off-white solid (mp 77°–78° C.).

Yield: 97%.

$^1$H NMR (CDCl$_3$): δ1.41 (s, 9H), 2.41 (s, 3H), 5.54 (br.s, 1H), 7.13–7.30 (m, 4H).

IR (CHCl$_3$): 3430, 3011, 2971, 2932, 1661, 1510, 1484, 1452, 1393, 1366, 1304, 1216, 876 cm$^{-1}$.

MS(FD): m/e 191 (M$^+$), 191 (100).

Analysis for C$_{12}$H$_{17}$NO: Calcd: C, 75.35; H, 8.76; N, 7.32; Found: C, 75.10; H, 9.11; N, 7.20.

B. S-N-t-Butyl-2-(3-(N-benzyloxycarbonyl)amino-2-oxo-4-phenylbutyl)benzamide

To a solution of 7.0 g (36.5 mmol) of the subtitled compound of Preparation 24A in 200 mL of anhydrous tetrahydrofuran, was added 12.1 mL (80.3 mmol) of N,N,N',N'-tetramethylethylenediamine (TMEDA) was added via syringe. The resulting solution was cooled to –78° C. and then 55.9 mL of sec-butyllithium was added dropwise via syringe while maintaining the temperature of the reaction under −60° C. The resulting reaction solution was then allowed to stir for approximately 1 hour at −78° C. before the addition of a solution containing 5.00 g (14.6 mmol) of S-N-methoxy-N-methyl-2-(N-benzyloxycarbonyl)amino-3-phenylpropanamide in 50 mL of anhydrous tetrahydrofuran was added via cannula while maintaining the reaction temperature below −65° C. The resulting reaction mixture was warmed to −20° C., quenched using 20 mL of saturated ammonium chloride and then diluted with 200 mL of diethylether. The organic and aqueous layers were separated and the organic layer was washed sequentially with water, 0.2N sodiumhydrogensulfate and brine, dried over sodium sulfate, filtered and then reduced to dryness under reduced pressure to provide a colorless oil. This oil was purified using flash chromatography (eluent of 25% ethyl acetate in methylene chloride) to provide 6.08 g of a colorless foam.

Yield: 88%.

$[\alpha]_D$−289.26° (c 0.12, MeOH).

$^1$H NMR (CDCl$_3$): δ1.38 (s, 9H), 2.99 (dd, J=15; 6 Hz, 1H) 3.24 (dd, J=15; 6 Hz, 1H), 3.89 (d, J=18 Hz, 1H), 4.16 (d, J=18 Hz, 1H), 4.72 (dd, J=15, 6 Hz, 1H), 5.00–5.09 (m, 2H), 5.56 (d, J=6 Hz, 1H), 5.93 (br.s, 1H), 7.03–7.40 (m, 14H).

IR (CHCl$_3$): 3431, 3027, 3012, 2973, 1713, 1658, 1511, 1454, 1383, 1366, 1307, 1231, 1046 cm$^{-1}$.

MS(FD) m/e 472 (M$^+$), 218 (100).

Analysis for C$_{29}$H$_{32}$N$_2$O$_4$: Calcd: C, 73.70; H, 6.82; N, 5.93; Found: C, 73.41; H, 6.98; N, 5.83.

C. [2R-(2R*,3S*)]-N-t-Butyl-2-(3-(N-benzyloxycarbonyl)amino-2-hydroxy-4-phenylbutyl)benzamide To a solution of 6.96 g (14.7 mmol) of the subtitled compound of Preparation 24B in 200 mL of absolute ethanol, under nitrogen, was added 2.78 g (73.5 mmol) of sodium borohydride. When the reaction was substantially complete, as indicated by thin layer chromatography (TLC), the reaction mixture was diluted with 200 mL of ethyl acetate and quenched by the dropwise addition of 20 mL of saturated ammonium chloride. The organic and aqueous layers were then separated and the organic layer was washed sequentially with 1N hydrochloric acid, saturated sodium bicarbonate solution and brine, dried over sodium sulfate, filtered and then reduced to dryness under reduced pressure to provide 6.4 g of a colorless oil. This oil was purified using flash chromatography (gradient eluent of 2–10% methylene chloride in ethyl acetate) to provide 5.12 g of the subtitled compound.

Yield: 74%.

$[\alpha]_D$−10.38° (c 0.10, MeOH).

$^1$H NMR (CDCl$_3$): δ1.40 (s, 9H), 2.79 (dd, J=12; 3 Hz, 1H), 2.90–2.98 (m, 2H), 3.04 (44, J=12, 3 Hz, 1H), 3.70–3.81 (m, 1H), 3.97 (m, 1H), 4.96–5.08 (m, 2H), 5.10 (d, J=9 Hz, 1H), 5.88 (d, J=6 Hz, 1H), 5.93 (s, 1H), 7.13–7.42 (m, 14H).

IR (CHCl$_3$): 3431, 3028, 3012, 2971, 1773, 1643, 1515, 1454, 1367, 1229, 1028 cm$^{-1}$.

MS(FD): m/e 475 (M$^+$), 475 (100).

Analysis for C$_{29}$H$_{34}$N$_2$O$_4$: Calcd: C, 73.39; H, 7.22; N, 5.99; Found: C, 73.12; H, 7.48; N, 5.62.

D. [2R-(2R*,3S*)]-N-t-Butyl-2-(3-amino-2-hydroxy-4-phenylbutyl) benzamide

A suspension was prepared containing 41.0 g (120 mmol) of the subtitled compound of Preparation 24C and 500 mg of 10% palladium-on-carbon in 150 mL of absolute ethanol. This suspension was shaken under 60 psi hydrogen in a Parr shaker apparatus. The 10% palladium-on-carbon catalyst was then removed by filtration. The resultant filtrate was reduced to dryness under reduced pressure to provide 31.1 g of a light yellow foam. This compound was used without further purification.

Yield: 96%.

$[\alpha]_D$−34.68° (c 1.0, MeOH).

$^1$H NMR (CDCl$_3$): δ1.46 (s, 9H), 2.71 (dd, J=13.7; 9.5 Hz, 1H), 2.84 (dd, J=13.3; 2.51 Hz, 1H), 2.95–3.06 (m, 2H), 3.23–3.29 (m, 1H), 3.84–3.90 (m, 1H), 6.23 (s, 1H), 7.19–7.37 (m, 12H).

IR (CHCl$_3$): 3440, 3382, 3007, 2970, 2934, 1643, 1516, 1454, 1367, 1213 cm$^{-1}$.

MS(FD): m/e 341 (M$^+$), 341 (100).

Preparation 25

A. 2R-2-N(t-Butoxycarbonyl)amino-3-naphth-2-ylthio propanoic acid

To a solution of 2.14 g (13.4 mmol) 2-naphthalene thiol in 40 mL of anhydrous tetrahydrofuran at room temperature, was added a suspension of 0.54 g (13.5 mmol) of sodium hydride in mineral oil. After approximately 15 minutes, a solution of 2.5 g (13.4 mmol) of S-N(t-butoxycarbonyl)-serine-β-lactone in 30 mL of tetrahydrofuran was added dropwise. The resultant reaction mixture was allowed to react for approximately one hour and then was concentrated under reduced pressure to provide a gummy solid. This solid was purified using flash chromatography (eluent of 1% methanol in ethyl acetate) to provide 4.35 g of a white solid.

Yield: 94%.

$^1$H NMR (CDCl$_3$): δ10.25 (s, 1H), 7.89 (s, 1H), 7.78 (m, 3H), 7.46 (m, 3H), 5.39 (d, 1H), 4.61 (m, 1H), 3.49 (m, 2H), 1.37 (s, 9H).

B. 2R-N(Methoxy)-N(methyl)[2-N(t-butoxycarbonyl)amino-3-naphth-2-ylthio propanamide To a cold (0° C.) solution containing 4.3 g (12.4 mmol) of the subtitled intermediate of Preparation 25A, 1.58 g (16.15 mmol) of N,O-dimethylhydroxylamine hydrochloride, 2.18 g (16.15 mmol) of 1-hydroxybenzotriazole hydrate (HOBT.H$_2$O), 2.24 mL (16.15 mmol) of triethylamine and 2.73 mL (24.86 mmol) N-methylmorpholine in 100 mL of methylene chloride, was added 2.62 g (13.67 mmol) of 1-(3-dimethylaminopropyl)-3-ethylcarbodiimide hydrochloride (EDC). The resulting reaction mixture was allowed to react at room temperature overnight. The reaction mixture was diluted with 100 mL of hexane, washed sequentially with 200 mL of a saturated sodium bicarbonate solution and 200 mL of brine. The resulting layers were separated and the organic layer was dried over sodium sulfate, filtered and then concentrated under reduced pressure to provide a clear yellow oil.

$^1$H NMR (CDCl$_3$): δ7.90 (s, 1H), 7.80 (m, 3H), 7.49 (m, 3H), 5.41 (d, 1H), 4.92 (m, 1H), 3.59 (s, 3H), 3.18–3.46 (m, 2H), 3.05 (s, 3H), 1.42 (s, 9H).

MS (FD): m/e 391 (M$^+$), 390 (100).

C. 3R-N(t-Butyl)-2-[2'-oxo-3'-N(t-butoxycarbonyl)amino-4'-naphth-2-ylthio]butyl benzamide To a cold (−78° C.) solution containing 8.60 g (45 mmol) of the subtitled compound of Preparation 24A, and 14.2 mL (95 mmol) of TMEDA in 100 mL of anhydrous tetrahydrofuran and under an inert atmosphere, was slowly added 111 mL (95 mmol) of a 0.85M solution of sec-butyllithium in hexanes, via syringe. The internal temperature of the reaction vessel was monitored during the addition of the sec-butyllithium to ensure that the temperature did not exceed −57° C. After allowing the resultant reaction mixture to react for approximately one hour at −78° C., a solution of 7.90 g (20 mmol) of the subtitled intermediate of Preparation 2B in 80 mL of tetrahydrofuran was added dropwise. When the addition was complete, the reaction was warmed to −20° C. and then was quenched by the addition of a saturated ammonium chloride solution. The resulting mixture was then diluted with 600 mL of diethylether. The resulting layers were separated and the organic layer was washed sequentially with a 1M sodium bisulfate solution and a brine solution, dried over sodium sulfate, filtered and then concentrated under reduced pressure to provide a yellow oil. This oil was purified using flash chromatography (gradient eluent of 10–50% ethyl acetate in hexane) to provide 8.5 g of the desired subtitled intermediate.

Yield: (82%).

$^1$H NMR (CDCl$_3$): δ7.90 (s, 1H), 7.79 (t, 3H), 7.48 (m, 3H), 7.40 (d, 1H), 7.29 (m, 2H), 7.05 (d, 1H), 5.94 (br.s, 1H), 5.65 (m, 1H), 4.65 (d, 1H), 4.24 (d, j=17 Hz, 1H), 3.86 (d, J=17 Hz, 1H), 3.66 (m, 1H), 3.40 (m, 1H), 1.42 (s, 9H), 1.39 (s, 9H).

MS (FD): m/e 521(M$^+$), 521(100).

D. [(2R-(2R*,3R*)]-N(t-Butyl)-2-(2'-hydroxy-3'-N(t-butoxycarbonyl)amino-4'-naphth-2-ylthio]butyl benzamide To a solution of 3.49 g (6.7 mmol) of the subtitled intermediate of Preparation 25C in 150 mL of absolute ethanol, was added 0.51 g (13 mmol)-of sodium borohydride and the resulting reaction mixture was allowed to react overnight at room temperature. The reaction was then cooled to 0° C., quenched with a saturated ammonium chloride solution and diluted with 550 mL of methylene chloride. The resulting layers were separated and the organic layer was washed sequentially with 1N hydrochloric acid, 2N sodium hydroxide and brine, dried over sodium sulfate, filtered and then concentrated under reduced pressure to provide a colorless foam. This foam was purified using flash chromatography (gradient eluent of 10–25% hexane in ethyl acetate) to provide 2.78 g of the desired subtitled intermediate.

Yield: 78%.

$^1$H NMR (CDCl$_3$): δ7.84 (s, 1H), 7.73 (m, 3H), 7.41 (m, 3H), 7.29 (t, 2H), 7.16 (t, 2H), 6.53 (s, 1H), 5.32 (d, 1H), 3.86 (m, 2H), 3.33 (m, 2H), 2.83 (m, 2H), 1.40 (s, 9H).

MS (FD): m/e 523 (M$^+$),522 (100).

Analysis for C$_{30}$H$_{38}$N$_2$O$_4$S: Calcd: C, 68.94; H, 7.33; N, 5.36; Found: C, 68.65; H, 7.34; N, 5.15.

E. [(2R-(2R*,3R*)]-N(t-Butyl)-2-[2'-hydroxy-3'amino-4'-naphth-2-ylthio]butyl benzamide To a cold (0° C.) solution of 2.89 g (5.53 mmol) of the subtitled intermediate of Preparation 25D in 100 mL of methylene chloride, was added 18 mL of trifluoroacetic acid. The resulting reaction mixture was allowed to react for approximately one hour. The reaction mixture was then concentrated under reduced pressure to provide a foam. This foam was slurried in toluene and then concentrated under reduced pressure to provide a foam which was purified using flash chromatography (eluent of 5% methanol in methylene chloride) to provide 1.71 g of a white foam.

Yield: 74%.

$^1$H NMR (CDCl$_3$): δ7.75–7.85 (m, 4H), 7.24–7.51 (m, 7H), 6.06 (s, 1H), 3.75 (m, 1H), 3.61 (m, 1H), 3.07 (m, 2H), 2.95 (m, 2H), 1.47 (s, 9H).

MS(FD): m/e 423(M$^+$), 422(100).

Preparation 26
A. N-t-Butyl-2-methyl-1-naphthylamide

The desired subtitled compound was prepared substantially in accordance with the procedure detailed in Preparation 24A. The crude material was purified by recrystallization from a hexane/ethyl acetate mixture to provide 20.99 g of colorless needles (mp 124°–126° C.).

Yield: 68%.

$^1$H NMR (CDCl$_3$): δ1.54 (s, 9H), 2.50 (s, 3H), 5.50–5.65 (br.s, 1H), 7.23–7.54 (m, 3H), 7.74 (d, J=10 Hz, 1H), 7.78 (d, J=10 Hz, 1H), 7.87 (d, J=10 Hz, 1H).

IR (CHCl$_3$): 3424, 3010, 2969, 1660, 1512, 1503, 1454, 1366, 1291, 1263, 1221 cm$^{-1}$.

MS(FD): m/e 241(M$^+$), 241(100).

Analysis for C$_{16}$H$_{19}$NO: Calcd: C, 79.63; H, 7.94; N, 5.80; Found: C, 79.90; H, 8.11; N, 5.76.

B. S-N-t-Butyl-2-(3-(N-benzyloxycarbonyl)amino-4phenyl-2-oxobutyl)-1-naphthylamide The desired subtitled compound was prepared substantially in accordance with the procedure detailed in Preparation 24A. The resultant residue was purified using flash chromatography (gradient eluent of 10–30% ethyl acetate in hexane) to provide 7.43 g of a colorless foam.

Yield: 86%.

[α]$_D$ −6.86° (c 0.10, MeOH).

$^1$H NMR (CDCl$_3$): δ1.45 (s, 9H), 3.03 (dd, J=15, 8 Hz, 1H), 3.18 (dd, J=15, 5 Hz, 1H), 3.91 (d, J=16 Hz, 1H), 4.04 (d, J=16 Hz, 1H), 4.70–4.80 (m, 1H), 4.94–5.06 (m, 2H), 5.41 (d, J=8 Hz, 1H), 6.12–6.20 (br.s, 1H), 7.10–7.38 (m, 11H), 7.42–7.58 (m, 2H), 7.76–7.85 (m, 2H), 7.93 (d, J=9 Hz, 1H).

IR (CHCl$_3$): 3420, 3029, 3012, 2970, 1713, 1658, 1505, 1455, 1367, 1232, 1045 cm$^{-1}$.

MS(FD): m/e 522(M$^+$), 522(100).

Analysis for C$_{33}$H$_{34}$N$_2$O$_4$: Calcd: C, 75.84; H, 6.56; N, 5.36; Found: C, 75.56; H, 6.74; N, 5.17.

C. [2R-(2R*,3S*)]-N-t-Butyl-2-(3-(N-benzyloxycarbonyl) amino-3-phenylmethyl-2-hydroxypropyl)-1-naphthylamide The desired subtitled compound was prepared substantially in accordance with the procedure detailed in Preparation 24C. The resultant material was purified using flash chromatography (gradient eluent of 2–10% ethyl acetate in methylene chloride) to provide 5.50 g of a colorless foam.

Yield: 74%.

[α]$_D$ +11.85° (c 0.20, MeOH).

$^1$H NMR (CDCl$_3$): δ1.54 (s, 9H), 2.85–3.15 (m, 4H), 3.85–3.95 (m, 1H), 4.00–4.13 (m, 2H), 4.90–5.34 (m, 3H), 5.85–5.95 (m, 1H), 7.05–7.60 (m, 15H), 7.81 (d, J=9 Hz, 2H), 7.91 (d, 9 Hz, 1H).

IR (CHCl$_3$) 3420, 3012, 2970, 1713, 1643, 1515, 1454, 1367, 1219, 1209, 1028 cm$^{-1}$.

MS (FD): m/e 524(M$^+$), 524(100).

Analysis for C$_{33}$H$_{36}$N$_2$O$_4$: Calcd: C, 75.55; H, 5.92; N, 5.34; Found: C, 75.41; H, 7.16; N, 5.14.

D. [2R-(2R*,3S*)]-N-t-Butyl-2-(3-amino-2-hydroxypropyl) -1-naphthylamide

The desired subtitled compound was prepared substantially in accordance with the procedure detailed in Preparation 24D. The crude filtrate was concentrated to provide 1.30 g of a colorless foam which was used without any further purification.

Yield: 92%.

Preparation 27
A. 2-Iodo-4-hydroxymethyl toluene

To a solution of 5.0 g (19.1 mmol) of 2-iodo-3-methyl benzoic acid in 50 mL of anhydrous tetrahydrofuran, was slowly added 22 mL of a 1M borane solution in tetrahydrofuran. The resultant reaction mixture was reacted for approximately ninety minutes and then was quenched with ethanol resulting in the evolution of hydrogen gas. The mixture was diluted with ethyl acetate. The resulting layers were separated and the organic layer was washed sequentially with sodium bicarbonate and brine, dried over sodium sulfate, filtered and crystallized from a hexane/ethyl acetate mixture to provide 120 mg of the desired subtitled compound.

B. 2-Methyl-5-hydroxymethyl benzoic acid

A mixture of 142 mg (5.92 mmol) of lithium hydroxide and 249 mg (1.48 mmol) of the subtitled compound of Preparation 27A in a 3:1 tetrahydrofuran/water mixture were reacted for approximately twenty four hours. When the reaction was complete, as indicated by TLC, the reaction mixture was concentrated under reduced pressure and acidified by the addition of 1N hydrochloric acid. The mixture was diluted with ethyl acetate and the resulting layers were separated. The organic layer was washed with brine, dried over sodium sulfate, filtered and reduced to dryness to provide 70 mg of the desired subtitled compound.

Preparation 28

2-Methyl-3-methylamino benzoic acid

To a solution of 500 mg (2.5 mmol) of 2-methyl-3-amino benzoate methyl ester in 5 mL of dimethylformamide, was added 387 mg (2.7 mmol) of methyl iodide and 700 mg (5.4 mmol) of diisopropylethylamine. The resultant reaction mixture was heated to 70° C. for approximately two hours and then poured into 10 mL of 1N potassium hydroxide. After about sixteen hours, the mixture was acidified to pH 6 by the addition of 2N hydrochloric acid. The desired titled compound was extracted into ethyl acetate, dried and reduced to dryness under reduced pressure to provide 343 mg of a white solid (m.p. 165°–167° C.).

Yield: 84%.

$^1$H NMR (CDCl$_3$): δ12.52 (br.s, 1H), 7.38 (d, J=7.8 Hz, 1H) 7.25 (t, J=7.9 Hz, 1H), 6.93 (d, J=7.8 Hz, 1H), 2.92 (s, 3H), 2.21 (s, 3H).

Analysis for C$_9$H$_{11}$NO$_2$: Calcd: C, 65.44; H, 6.71; N, 8.48; Found: C, 65.62; H, 6.84; N, 8.26.

Preparation 29

A. 2-Methyl-5-amino benzoic acid

The desired titled compound was prepared by reducing 2methyl-5-nitrobenzoic acid using a tin/hydrochloric acid mixture (m.p. 142°–144° C.).

Yield: 75%

$^1$H NMR (DMSO-d$_6$): δ12.67 (br.s, 1H), 7.23 (s, 1H), 7.04 (d, J=8.2 Hz, 1H), 6.82 (d, J=7.9 Hz, 1H), 3.25 (s, 2H), 2.40 (s, 3H).

Analysis for C$_8$H$_9$NO$_2$: Calcd: C, 63.57; H, 6.00; N, 9.27; Found: C, 63.81; H, 6.24; N, 9.06.

B. 2-Methyl-5-hydroxybenzoic acid

The desired subtitled compound was prepared substantially in accordance with the procedure detailed in Alternate Preparation 23C, using the subtitled compound of Preparation 29A.

Yield: 65% (m.p. 136°–139° C.).

$^1$NMR (DMSO): δ12.77 (br.s, 1H), 9.46 (br. s, 1H), 7.26 (s, 1H), 7.12 (d, J=8.3 Hz, 1H), 6.85 (d, J=8.1 Hz, 1H), 2.41 (s, 3H).

Analysis for C$_8$H$_8$O$_3$: Calcd: C, 63.15; H, 5.29; Found: C, 63.27; H, 5.22.

Preparation 30

A. 5-Cyanoisoquinoline

To a cold (0° C.) solution of 10.0 g (61.4 mmol) of 5aminoisoquinoline in 288 mL of 1.5N hydrochloric acid, was added 15 mL of 5.2M sodium nitrite in water. After approximately 5 minutes, a cool saturated solution of sodium bicarbonate was added to the reaction mixture until the reaction solution tested negative using the iodide and starch paper test. The resultant solution was poured into a cold (0°–5° C.) biphasic mixture containing 300 ml of toluene and 150 mL of an aqueous solution containing 8.4 g (177 mmol) of sodium cyanide and 7.6 g (85 mmol) of copper cyanide. The resultant reaction mixture was warmed to room temperature, reacted for approximately 1 hour, and then diluted with a mixture of ethyl acetate and water. The resulting layers were separated, and the organic phase was dried over sodium sulfate, filtered, and then reduced to dryness under reduced pressure to provide 5.9 g of a yellow solid.

Yield: 56%.

$^1$H NMR (CDCl$_3$): δ9.38 (s, 1H), 8.76 (d, J=5.89 Hz, 1H), 8.25 (d, J=8.29 Hz, 1H), 8.13 (d, J=8.30 Hz, 1H), 8.03 (d, J=8.59 Hz, 1H), 7.71 (t, J=7.78 Hz, 1H);

IR (KBr): 3433, 3090, 3026, 2924, 2226, 1618, 1574, 1495, 1433, 1373, 1277, 1225, 1034, 829, 766, 714.

B. 5-Carboxyisoquinoline

A solution of 6.5 g (42 mmol) of the subtitled compound of Preparation 30A in 55 mL of concentrated hydrochloric acid was heated to 155° C. in a sealed tube for 5.5 hours and then was cooled to room temperature, and then reduced to dryness to provide a solid. This solid was redissolved in 300 mL of water, and he resultant solution was adjusted to pH 6 using a dilute ammonium hydroxide solution, resulting in the precipitation of a brown solid. This solid was isolated using filtration, azeotroped with benzene, and then dried at 130° C. under reduced pressure for approximately 3 hours to provide 5.7 g of a fine dark tan powder (m.p. 270°–272° C.).

Yield: 78%.

$^1$H NMR (DMSO): δ13.4 (br.s, 1H), 8.69 (d, 1H, J=6.00 Hz), 8.58 (d, 1H, J=4.6 Hz), 8.40 (d, 1H, J=7.37 Hz), 8.36 (d, 1H, J=8.12 Hz), 7.74 (t, 1H, J=7.76);

IR (KBr): 3460, 3014, 2930, 2851, 2777, 2405, 1912, 1711, 1622, 1574, 1493, 1427, 1375, 1264, 1211, 1152, 1044.

C. 5-Carboxyisoquinoline pentafluorophenylester

To a cold (0° C.) solution of 1.53 g (7.39 mmol) of 1,3-dicyclohexylcarbodiimide (DCC) in 60 mL of ethyl acetate, was added 1.28 g (7.39 mmol) of the subtitled compound of Preparation 30B, and 4.08 g (22.17 mmol) of pentafluorophenol in 30 mL of ethyl acetate. The resultant reaction mixture was reacted for approximately 6 hours at 0° C. and then filtered through celite. The resultant filtrate was washed sequentially with 1N sodium hydroxide, water, and brine, and then concentrated under reduced pressure to provide a white solid. This solid was purified using column chromatography (silica; eluent of 33% ethyl acetate in hexanes) to provide 1.80 g of the desired subtitled compound. (m.p. 142°–144° C.)

Yield 72%.

$^1$H NMR (CDCl$_3$): δ9.38 (s, 1H), 8.74 (m, 3H), 8.34 (d, J=8.1 Hz, 1H), 7.78 (t, J=7.7 Hz, 1H);

IR (KBr): 3422, 3021, 2089, 1752, 1622, 1522, 1215, 758.

Analysis for C$_{16}$H$_6$NO$_2$F$_5$·0.3CH$_2$Cl$_2$: Calcd: C, 57.30; H, 2.17; N, 4.03. Found: C, 57.40; H, 2.10; N, 4.33.

Preparation 31

5-Carboxyquinoline pentafluorophenylester

The desired subtitled compound was prepared substantially in accordance with the procedure detailed in Preparation 30C, using 0.236 g (1.36 mmol) of 5-carboxyquinoline, 0.746 g (4.05 mmol) of pentafluorophenol, and 0.571 g (2.76 mmol) of DCC in 25 mL of ethyl acetate, with the exception that the reaction mixture was allowed to react for 48 hours. The resultant crude material was purified using column chromatography to provide 0.40 g of a white solid.

Yield 87%.

$^1$H NMR (CDCl$_3$): δ9.33 (d, J=8.54 Hz, 1H), 9.03 (dd, J=4.16, 1.28 Hz, 1H), 8.63 (d, J=7.25 Hz, 1H), 8.47 (d, J=8.53 Hz, 1H); 7.87 (t, J=7.96 Hz, 1H), 7.61 (dd, J=8.76, 4.18 Hz, 1H);

IR (KBr): 3472, 2667, 2461, 1749, 1520, 1319, 1259, 1182, 1145, 1105, 1005, 947, 812.

Preparation 32
1H-indoline-4-carboxylic acid

To a cold (10° C.) solution containing 100 mg (0.62 mmol) of indole-4-carboxylic acid in 5 mL of acetic acid, was added 390 mg (6.2 mmol) of solid sodium cyanoborohydride. The resultant mixture was reacted at room temperature for approximately 16 hours and then diluted with water. The desired compound was extracted from this solution using methylene chloride and the organic extracts were then dried over sodium sulfate and filtered. The crude material was purified using column chromatography (silica; eluent of 1% methanol in methylene chloride) to provide 12 mg of the titled compound. (m.p. 97°–98° C.).

Yield: 12%.

$^1$H NMR (CDCl$_3$): δ7.48 (d, J=8.8 Hz, 1H), 7.34 (t, J=8.6 Hz, 1H), 6.88 (d, J=8.8 Hz, 1H), 3.59 (m, 4H).

Analysis for C$_9$H$_9$NO$_2$: Calcd: C, 66.25; H, 5.56; N, 8.58. Found: C, 66.36; H, 5.82; N, 8.42.

Preparation 33

A. 2.3-Dimethoxy-6-chlorotoluene

To a mixture of 25 g (0.16 mmol) of 1-methyl-2,3-dimethoxybenzene in 25 mL of acetic acid, was slowly added 26.4 g (0.33 mmol) of 1-chloromethylmethylether. The resultant reaction mixture was reacted overnight at 30° C. and then diluted with cold water, resulting in the formation of a precipitate. This precipitate was purified by recrystallization from hot hexanes and then reduced to dryness under reduced pressure to provide 20.3 g of a white solid (m.p. 69°–70° C.).

Yield: 62%.

$^1$H NMR (CDCl$_3$): δ7.01 (d, J=6.1 Hz, 1H), 6.75 (d, 4.62 (s, 2H), 3.85 (s, 3H), 3.76 (s, 3H), 2.37 (s, 3H).

Analysis for C$_{10}$H$_{13}$O$_2$Cl: Calcd: C, 59.93; H, 6.54; Found: C, 59.87; H, 6.43.

B. 2-Methyl-3,4-dimethoxybenzoic acid

To a mixture of 3.0 g (15 mmol) of the subtitled compound of Preparation 33A in 150 mL of water, was added 3.2 g (20 mmol) of solid potassium permangenate and 3.0 g (36 mmol) of sodium carbonate. The resultant reaction mixture was then heated to 80° C. and allowed to react for approximately 24 hours. After cooling, the reaction mixture was filtered and diluted with ethyl acetate. The resultant layers were then separated and the aqueous layer was acidified using 2N hydrochloric acid which resulted in the formation of a precipitate. This precipitate was isolated using filtration and washed with cold hexane to provide 1.7 g of a white solid (m.p. 179°–180° C.).

Yield: 58%.

$^1$H NMR (DMSO-d$_6$): δ12.49 (br.s, 1H), 7.71 (br.s, 1H), 6.99 (br.s, 1H), 3.89 (s, 3H), 3.77 (s, 3H), 2.45 (s, 3H).

Analysis for C$_{10}$H$_{12}$O$_4$: Calcd: C, 61.28; H, 6.17; Found: C, 61.36; H, 6.24.

C. 2-Methyl-3,4-dihydroxybenzoic acid

To a cold (0° C.) mixture of 250 mL (1.3 mmol) of the subtitled compound of Preparation 33B in 5 mL of methylene chloride, was added 6.4 mL of a 6.4 mmol/1.0 m solution of boron tribromide in methylene chloride. The resultant reaction mixture was reacted for approximately 90 minutes and then diluted with 25 mL of 2N hydrochloric acid. The desired compound was extracted using ethyl acetate, and the organic extracts were dried over sodium sulfate, filtered, and concentrated to provide 197 mg of a tan solid (m.p. 200°–201° C.).

Yield: 92%.

$^1$H NMR (DMSO): δ12.14 (br.s, 1H), 9.96 (br.s, 1H,), 8.34 (br.s, 1H), 7.27 (d, J=7.0 Hz, 1H), 6.67 (d, J=6.7 Hz, 1H), 2.37 (s, 3H).

Analysis for C$_8$H$_8$O$_4$: Calcd: C, 57.14; H, 4.80; Found: C, 57.34; H, 4.76.

EXAMPLE 1

[3S-(3R*,4aR*,8aR*,2'S*,3'R*)]-2-[2'-Hydroxy-3'-phenylmethyl-4'-aza-5'-oxo-5'-(2"-fluoro-3"hydroxyphenyl)pentyl]decahydroisoquinoline-3-N-t-butylcarboxamide To a cold (−10° C.) solution containing 80 mg (0.20 mmol) of the subtitled compound of Preparation 1B, 31 mg (0.20 mmol) of Preparation 11B and 27 mg (0.20 mmol) of 1-hydroxybenzotriazole hydrate (HOBT.H$_2$O) in 3 mL of anhydrous tetrahydrofuran, was added 41 mg (0.20 mmol) of 1,3-dicyclohexylcarbodiimide (DCC). The reaction mixture was stirred for 36 hours at room temperature and then concentrated under reduced pressure. The resultant residue was redissolved in ethyl acetate, filtered through celite, washed sequentially with saturated sodium bicarbonate and brine, dried over sodium sulfate, filtered and concentrated. The crude product was purified using radial chromatography (1 mm plate; gradient eluent of 2–5% methanol in methylene chloride) to provide 79 mg of a white foam.

Yield: 73%.

[α]$_{D-90.80}$° (c=0.333, MeOH).

$^1$H NMR (CDCl$_3$): δ1.24 (s, 9H), 1.16–2.05 (m, 14H), 2.20–2.40 (m, 2H), 2.55–2.70 (m, 2H), 2.90–3.04 (m, 2H), 3.10–3.25 (m, 1H), 4.03 (br.s, 1H), 4.51 (br.s, 1H), 6.01 (s, 1H), 6.90–7.35 (m, 9H).

IR (CHCl$_3$): 3580, 3550–3100 (br.), 2929, 2865, 1662, 1596, 1521, 1472, 1455, 1394, 1368, 1293, 1157, 1047, 879, 839 cm$^{-1}$.

MS(FD): m/e 540 (M$^+$, 100).

HR MS(FAB): m/e for C$_{31}$H$_{43}$N$_3$O$_6$F: Calcd: 540. 3238; Found: 540.3228.

EXAMPLE 2

[3S-(3R*,4aR*,8aR*,2'S*,3'R*)]-2-[2'-Hydroxy-3'-phenylmethyl-4'-aza-5'-oxo-5'-(2"-chloro-pyrid-3"-yl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 31 mg (0.20 mmol) of 2-chloronicotinic acid, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 0–5% methanol in methylene chloride) to provide 58 mg of an off-white foam.

Yield: 54%.

[α]$_D$−70.64° (c=0.224, MeOH).

$^1$H NMR (CDCl$_3$): δ1.16 (s, 9H), 1.17–2.10 (m, 12H), 2.25–2.37 (m, 2H), 2.52–2.70 (m, 2H), 2.97–3.06 (m, 2H), 3.44–3.53 (m, 2H), 4.05 (br.s, 1H), 4.60–4.70 (m, 1H), 5.64 (s, 1H), 7.18–7.38 (m, 7H), 7.60–7.63 (m, 1H), 8.38–8.40 (m, 1H).

IR (CHCl$_3$): 3618, 3428, 3650–3100 (br.), 2929, 1667, 1583, 1515, 1455, 1401, 1368, 1247, 1071, 1046, 377 cm$^{-1}$.

MS(FD): m/e 541 (M$^+$), 440 (100).

Analysis for C$_{30}$H$_{41}$N$_4$O$_3$Cl: Calcd: C, 66.59; H, 7.64; N, 10.35; Cl, 6.55; Found: C, 66.60; H, 7.58; N, 10.17; Cl, 6.84.

EXAMPLE 3

[3S-(3R*,4aR*,8aR*,2'S*,3'R*)]-2-[2'-Hydroxy-3'-phenylmethyl-4'-aza-5'-oxo-5'-(2"-ethyl-3"-hydroxyphenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 35 mg (0.21 mmol) of the subtitled compound of Preparation 10B, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 3–5% methanol in methylene chloride) to provide 71 mg of an off-white foam.

Yield: 65%.

[α]$_D$: −76.29° (c=0.291, MeOH).

$^1$H NMR (CDCl$_3$): δ1.03 (t, J=7.42 Hz, 3H), 1.21 (s, 9H), 1.22–2.10 (m, 11H), 2.24–2.35 (m, 2H), 2.44–2.70 (m, 4H), 2.96–3.05 (m, 2H), 3.26–3.40 (m, 1H), 3.96–4.23 (m, 2H), 4.53 (br.s, 1H), 5.80 (s, 1H), 6.30–6.56 (m, 3H), 6.77 (d, J=7.77 Hz, 1H), 6.88 (t, J=7.75 Hz, 1H), 7.19–7.39 (m, 5H).

IR (CHCl$_3$): 3700–3100 (br.), 3429, 3327, 3011, 2971, 2930, 2867, 1662, 1604, 1585, 1514, 1455, 1394, 1368, 1278, 1155, 1087, 1046, 910 cm$^{-1}$.

MS(FD): m/e 550 (M$^+$, 100).

HR MS(FAB): m/e for C$_{33}$H$_{48}$N$_3$O$_4$: Calcd: 550.3645; Found: 550.3664.

EXAMPLE 4

[2S-(2R*,2'S*,3'R*)]-1-[2'-Hydroxy-3'-phenylmethyl-4'-aza-5'-oxo-5'-(2"-methyl-3"-hydroxyphenyl)pentyl]pyrrolidine-2-N-t-butylcarboxamide The titled compound was prepared substantially in accordance with the procedure detailed in Example 1, using 55 mg (0.16 mmol) of the subtitled compound of Preparation 3E, 25 mg (0.16 mmol) of the subtitled compound of Preparation 9B, 33 mg (0.16 mmol) of DCC and 22 mg (0.16 mmol) of HOBT.H$_2$O in 2 mL of anhydrous tetrahydrofuran. The crude product was purified using radial chromatography (1 mm plate; gradient eluent of 4–8% methanol in methylene chloride) to provide 52 mg of a white solid.

Yield: 69%.

[α]$_D$: −72.15° (c=0.211, MeOH).

$^1$H NMR (CD$_3$OD): δ1.33 (s, 9H), 1.70–1.90 (m, 4H), 2.06–2.20 (m, 1H), 2.45–3.30 (m, 8H), 3.60–3.70 (m, 1H), 4.25–4.38 (m, 1H), 6.48 (d, J=8.8 Hz, 1H), 6.74 (d, J=7.7 Hz, 1H), 6.93 (t, J=7.7 Hz, 1H), 7.15–7.32 (m, 5H).

IR (CHCl$_3$): 3600–2700 (br.), 3450, 3255, 2968, 2928, 1653, 1632, 1588, 1513, 1454, 1364, 1291, 1233, 1064, 884, 836 cm$^{-1}$.

MS(FD): m/e 468 (M$^+$, 100).

Analysis for C$_{27}$H$_{37}$N$_3$O$_4$: Calcd: C, 69.35; H, 7.98; N, 8.99. Found: C, 69.54; H, 8.10; N, 9.19.

EXAMPLE 5

[3S-(3R*,4aR*,8aR*,2'S*,3'R*)]-2-[2'-Hydroxy-3'-phenylmethyl-4'-aza-5'-oxo-5'-(pyrid-3"-yl-N-oxidyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 28 mg (0.20 mmol) of nicotinic acid N-oxide, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 5–10% methanol in methylene chloride) to provide 81 mg of a white foam.

Yield: 76%.

[α]$_D$: −104.39° (c=0.213, MeOH)

$^1$H NMR (DMSO-d$_6$): δ1.19 (s, 9H), 1.19–2.10 (m, 14H), 2.50–2.60 (m, 1H), 2.65–2.79 (m, 1H), 2.95–3.10 (m, 2H), 3.83 (br.s, 1H), 4.22–14.32 (m, 1H), 4.87 (d, J=5.5 Hz, 1H), 7.06–7.11 (m, 1H), 7.17–7.22 (m, 2H), 7.33–7.44 (m, 3H), 7.57 (d, J=8.0 Hz, 1H), 8.26 (d, J=6.4 Hz, 1H), 8.44–8.48 (m, 2H).

IR (CHCl$_3$): 3600–3100 (br.), 3428, 2930, 2864, 1669, 1603, 1515, 1479, 1455, 1432, 1394, 1368, 1300, 1279, 1245, 1135, 1083, 1046, 1017 cm$^{-1}$.

MS(FD): m/e 522 (M$^+$, 100).

EXAMPLE 6

[2S-(2R*,2'S*,3'R*)]-1-[2'-Hydroxy-3'-phenylmethyl-4'-aza-5'-oxo-5'-(2"-methyl-3"-hydroxyphenyl)pentyl]piperidine-2-N-t-butylcarboxamide The titled compound was prepared substantially in accordance with the procedure detailed in Example 1, using 100 mg (0.29 mmol) of the subtitled compound of Preparation 4F, 44 mg (0.29 mmol) of the subtitled compound of Preparation 9B, 59 mg (0.29 mmol) of DCC and 39 mg (0.29 mmol) of HOBT.H$_2$O in 5 mL of anhydrous tetrahydrofuran. The crude product was purified using radial chromatography (1 mm plate; gradient eluent of 1.5–7% methanol in methylene chloride) to provide 57 mg of an off-white foam.

Yield: 41%.

[α]$_D$: −58.90° (c=0.163, MeOH).

$^1$H NMR (CD$_3$OD): δ1.29 (s, 9H), 1.50–2.20 (m, 10H), 2.60–2.75 (m, 4H), 3.10–3.35 (m, 4H), 3.85–4.02 (m, 2H), 4.10–4.35 (m, 2H), 4.85 (s, 1H), 3.85–4.02 (m, 2H), 4.10–4.35 (m, 2H), 4.85 (s, 1H), 6.55 (d, J=7.29 Hz, 1H), 6.75 (d, J=7.83 Hz, 1H), 6.90–6.96 (m, 1H), 7.15–7.35 (m, 5H).

IR (CDCl$_3$): 3601, 3600–3100 (br), 3428, 3340, 3008, 2941, 2861, 1661, 1601, 1587, 1514, 1455, 1394, 1367, 1284, 1156, 1086, 1047, 832 cm$^{-1}$.

MS(FD): m/e 482 (M$^+$, 100).

Analysis for C$_{28}$H$_{39}$N$_3$O$_4$: Calcd: C, 69.83; H, 8.16; N, 8.72. Found: C, 69.84; H, 8.46; N, 8.50.

EXAMPLE 7

[3S-(3R*,4aR*,8aR*,2'S*,3'R*)]-2-[2'-Hydroxy-3'-phenylmethyl-4'-aza-5'-aza-5'-oxo-5'-(2"-methyl-3"-fluorophenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 31 mg (0.20 mmol) of 3-fluoro-2-methylbenzoic acid, 41 mg (0.20 mmol) of DCC and 27 mg (0.20 mmol) of HOBT.H$_2$O in 3 mL of anhydrous tetrahydrofuran. The crude product was purified using radial chromatography (1 mm plate; gradient eluent of 1.5–3% methanol in methylene chloride) to provide 40 mg of a white foam.

Yield: 37%.

[α]$_D$: −80.10° (c=0.132, MeOH).

$^1$H NMR (CDCl$_3$): δ1.13 (s, 9H), 1.13–2.10 (m, 16H), 2.20–2.35 (m, 2H), 2.50–2.70 (m, 2H), 2.95–3.05 (m, 2H), 3.53–3.58 (m, 1H), 3.98 (s, 1H), 4.03–4.10 (m, 1H), 5.68 (s, 1H), 6.83–7.07 (m, 3H), 7.10–7.40 (m, 5H).

IR (CHCl$_3$): 3650–3150 (br), 3429, 3030, 3008, 2930, 2863, 1672, 1608, 1514, 1455, 1394, 1368, 1277, 1046, 910, 830 cm$^{-1}$.

MS(FD): m/e 538 (M$^+$, 100).

HR MS(FAB): m/e for C$_{32}$H$_{45}$N$_3$O$_3$F: Calcd: 538.3445; Found: 538.3469.

EXAMPLE 8

[3S-(3R*,4aR*,8aR*,2'S*,3'R*)]-2-[2'-Hydroxy-3'-phenylmethyl-4'-aza-5'-oxo-5'-(2"-chloro-3",5"-dihydroxyphenyl)pentyl]decahydroisoquinoline-3-N-t-butylcarboxamide The titled compound was prepared substantially in accordance with the procedure detailed in Example 1, using 100 mg (0.25 mmol) of the subtitled compound of Preparation 1B, 47 mg (0.25 mmol) of 2-chloro-3,5-dihydroxy benzoic acid, 51 mg (0.25 mmol) of DCC and 34 mg (0.25 mmol) of HOBT.H$_2$O in 2 mL of anhydrous tetrahydrofuran. The crude product was purified using radial chromatography (2 mm plate; gradient eluent of 2–10% methanol in methylene chloride) to provide 47 mg of a white solid.

Yield: 33%.

[α]$_D$: −53.79° (c=0.097, MeOH).

$^1$H NMR (CDCl$_3$): δ0.5–3.10 (m, 32H), 3.70–4.60 (m, 2H), 6.00–7.50 (m, 8H).

IR (CHCl$_3$): 3700–3100 (br.), 2930, 2865, 1658, 1604, 1521, 1455, 1368, 1246, 1156, 1047, 1014, 856 cm$^{-1}$.

MS(FD): 572 (M$^+$, 100).

Analysis for C$_{31}$H$_{42}$N$_3$O$_5$Cl: Calcd: C, 65.08; H, 7.40; N, 7.34. Found: C, 65.30; H, 7.35; N, 7.43.

EXAMPLE 9

[3S-(3R*,4aR*,8aR*,2'S*,3'R*)]-2-[2'-Hydroxy-3'-phenylmethyl-4'-aza-5'-oxo-5'-(2"-methyl-3",5"-diaminophenyl)pentyl]decahydroisoquinoline-3-N-t-butylcarboxamide The titled compound was prepared substantially in accordance with the procedure detailed in Example 1, using 100 mg (0.25 mmol) of the subtitled compound of Preparation 1B, 41 mg (0.25 mmol) of 3,5-diamino-2-methyl benzoic acid, 51 mg (0.25 mmol) of DCC and 34 mg (0.25 mmol) of HOBT.H$_2$O in 2 mL of anhydrous tetrahydrofuran and 0.5 mL of dimethylformamide. The crude product was purified using radial chromatography (1 mm plate; gradient eluent of 1–10% methanol in methylene chloride) to provide 30 mg of a light orange foam.

Yield: 22%

[α]$_D$−89.27° (c=0.137, MeOH).

$^1$H NMR (CDCl$_3$): δ1.21 (s, 9H), 1.30–2.02 (m, 16H), 2.19–2.35 (m, 2H), 2.48–2.70 (m, 2H), 2.90–3.07 (m, 2H), 3.10–3.23 (m, 1H), 3.50 (br.s, 4H), 3.94 (br.s, 1H), 4.40–4.50 (m, 1H), 5.70 (s, 1H), 5.89–5.95 (m, 2H), 6.30 (d, J=8.4 Hz, 1H), 7.15–7.33 (m, 5H).

IR (CHCl$_3$): 3600–3100 (br), 3029, 3005, 2928, 2865, 1664, 1621, 1513, 1455, 1392, 1367, 1276, 1244, 1171, 1047, 841 cm$^{-1}$.

MS(FD): m/e 550 (M$^+$, 100).

HR MS(FAB): m/e for C$_{32}$H$_{48}$N$_5$O$_3$: Calcd: 550.3757; Found: 550.3762.

EXAMPLE 10

[3S-(3R*,4aR*,8aR*,2'S*,3'R*)]-2-[2'-Hydroxy-3'-phenylmethyl-4'-aza-5'-oxo-5'-(2"-methyl-3",5"-dinitrophenyl)pentyl]decahydroisoquinoline-3-N-t-butylcarboxamide The titled compound was prepared substantially in accordance with the procedure detailed in Example 1, using 100 mg (0.25 mmol) of the subtitled compound of Preparation 1B, 56 mg (0.25 mmol) of 3,5-dinitro-2-methyl benzoic acid, 51 mg (0.25 mmol) of DCC and 34 mg (0.25 mmol) of HOBT.H$_2$O in 3 mL of anhydrous tetrahydrofuran. The crude product was purified using radial chromatography (1 mm plate; gradient eluent of 0–3% methanol in methylene chloride) to provide 61 mg of an off-white foam.

Yield: 41%.

[α]$_D$−105.96° (c=0.302, MeOH).

$^1$H NMR (CDCl$_3$): δ1.02 (s, 9H), 1.02–2.60 (m, 20H), 2.90–3.06 (m, 2H), 3.21 (br.s, 1H), 3.60–3.75 (m, 1H), 4.05–4.20 (m, 1H), 4.65–4.80 (m, 1H), 5.47 (s, 1H), 7.20–7.50 (m, 5H), 8.00–8.20 (m, 2H), 8.56 (s, 1H).

IR (CHCl$_3$): 3621, 3500–3100 (br), 3428, 3024, 2977, 2931, 1665, 1615, 1539, 1455, 1347, 1278, 1245, 1047, 878 cm$^{-1}$.

MS(FD): m/e 610 (M$^+$, 100).

HR MS(FAB): m/e for C$_{32}$H$_{44}$N$_5$O$_7$: Calcd: 610.3241; Found: 610.3240.

EXAMPLE 11

[3S-(3R*,4aR*,8aR*,2'S*,3'R*)]-2-[2'-Hydroxy-3'-phenylmethyl-4'-aza-5'-oxo-5'-(2"-chloro-3"-hydroxyphenyl)pentyl]decahydroisoquinoline-3-N-t-butylcarboxamide The titled compound was prepared substantially in accordance with the procedure detailed in Example 1, using 116 mg (0.29 mmol) of the subtitled compound of Preparation 1B, 50 mg (0.29 mmol) of the titled compound of Preparation 14, 60 mg (0.29 mmol) of DCC and 39 mg (0.29 mmol) of HOBT.H$_2$O in 4 mL of anhydrous tetrahydrofuran. The crude product was purified using radial chromatography (1 mm plate; gradient eluent of 2.5–5% methanol in methylene chloride) to provide 83 mg of a white solid.

Yield: 51%.

[α]$_D$−74.29° (c=0.140, MeOH).

$^1$H NMR (CDCl$_3$): δ1.19 (s, 9H), 1.19–2.80 (m, 16H), 2.90–3.15 (m, 2H), 3.35 (br.s, 1H), 4.06 (br.s, 1H), 4.56 (br.s, 1H), 5.85 (br.s, 1H), 6.60–6.70 (m, 1H), 6.90–7.35 (m, 8H).

IR (CHCl$_3$): 3621, 3600–3100 (br), 3429, 2977, 2929, 1671, 1584, 1515, 1445, 1394, 1368, 1292, 1182, 1046, 878, 823 cm$^{-1}$.

MS(FD): m/e 556 (M$^+$, 100).

Analysis for C$_{31}$H$_{42}$N$_3$O$_4$Cl: Calcd: C, 66.95; H, 7.61; N, 7.56. Found: C, 66.76; H, 7.72; N, 7.69.

EXAMPLE 12

[3S-(3R*,4aR*,8aR*,2'S*,3'R*)]-2-[2'-Hydroxy-3'-phenylmethyl-4'-aza-5'-oxo-5'-(2"-methyl-3"-hydroxyphenyl)pentyl]decahydroisoquinoline-3-N-t-butylcarboxamide The titled compound was prepared substantially in accordance with the procedure detailed in Example 1, using 261 mg (0.65 mmol) of the subtitled compound of Preparation 1B, 100 mg (0.65 mmol) of the subtitled compound of Preparation 9B, 134 mg (0.65 mmol) of DCC and 88 mg (0.65 mmol) of HOBT.H$_2$O in 6 mL of anhydrous tetrahydrofuran and 0.2 mL of anhydrous dimethylformamide. The crude product was purified using radial chromatography (2 mm plate; gradient eluent of 1–5 methanol in methylene chloride) to provide 304 mg of a white solid.

Yield: 87%.

[α]$_D$ –75.00° (c=0.200, MeOH).

$^1$H NMR (CDCl$_3$): δ1.18 (s, 9H), 1.19–2.05 (m, 18H), 2.20–2.35 (m, 2H), 2.50–2.70 (m, 2H), 2.90–3.05 (m, 2H), 3.22–3.35 (m, 1H), 3.96–4.05 (m, 1H), 4.45–4.55 (m, 1H), 5.77 (s, 1H), 6.53 (d, J=7.4 Hz, 2H), 6.75 (d, J=7.8 Hz, 1H), 6.85–6.90 (m, 1H), 7.15–7.35 (m, 6H).

IR (CHCl$_3$): 3606, 3600–3100 (br.), 3429, 3011, 2929, 2865, 1663, 1604, 1587, 1514, 1455, 1367, 1277, 1200, 1156, 1046, 910 cm$^{-1}$.

MS(FD): m/e 537 (M$^+$, 100).

HR MS(FAB): m/e for C$_{32}$H$_{46}$N$_3$O$_4$: Calcd: 536.3488; Found: 536.3488.

EXAMPLE 13

[3S-(3R*,4aR*,8aR*,2'S*,3'R*)]-2-[2'-Hydroxy-3'-phenylmethyl-4'-aza-5'-oxo-5'S-(2"-methyl-3"-methoxyphenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 33 mg (0.20 mmol) of the subtitled compound of Preparation 15B, 41 mg (0.20 mmol) of DCC and 27 mg (0.20 mmol) of HOBT.H$_2$O in 2 mL of anhydrous tetrahydrofuran. The crude product was purified using radial chromatography (2 mm plate; eluent of 2.5% methanol in methylene chloride) to provide 93 mg of a white foam.

Yield: 84%.

$^1$H NMR (CDCl$_3$): δ1.17 (s, 9H), 1.17–2.05 (m, 12H), 2.05 (s, 3H), 2.25–2.38 (m, 2H), 2.50–2.75 (m, 2H), 2.95–3.10 (m, 2H), 3.35–3.50 (m, 1H), 3.79 (s, 3H), 3.98–4.15 (m, 2H), 4.59–4.65 (m, 1H), 5.72 (s, 1H), 6.47 (br.d, J=8.21 Hz, 1H), 6.63 (d, J=7.7 Hz, 1H), 6.82 (d, J=8.12 Hz, 1H), 7.08 (t, J=7.0 Hz, 1H), 7.15–7.45 (m, 5H).

Analysis for C$_{33}$H$_{47}$N$_3$O$_4$: Calcd: C, 72.10; H, 8.62; N, 7.64. Found: C, 71.84; H, 8.49: N, 7.67.

EXAMPLE 14

[3S-(3R*,4aR*,8aR*,2'S*,3'R*)]-2-[2'-Hydroxy-3'-phenylmethyl-4'-aza-5'-oxo-5'-(2",3"-dichlorophenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 38 mg (0.20 mmol) of 2,3-dichloro benzoic acid, 41 mg (0.20 mmol) of DCC and 27 mg (0.20 mmol) of HOBT.H$_2$O in 3 mL of anhydrous tetrahydrofuran. The crude product was purified using radial chromatography (2 mm plate; gradient eluent of 2.5–5% methanol in methylene chloride) to provide 95 mg of a white foam.

Yield: 84%.

$^1$H NMR (CDCl$_3$): 1.16 (s, 9H), 1.17–2.05 (m, 12H) 2.20–2.38 (m, 2H), 2.50–2.75 (m, 2H), 2.95–3.10 (m, 2H), 3.40–3.55 (m, 1H), 3.69 (s, 1H), 4.00–4.10 (m, 1H), 4.58–4.72 (m, 1H), 5.77 (s, 1H), 6.98–7.47 (m, 9H).

MS(FD): m/e 574 (M$^+$), 473(100).

EXAMPLE 15

[3S-(3R*,4aR*,8aR*,2'S*,3'R*)]-2-[2'-Hydroxy-3'-phenylmethyl-4'-aza-5'-oxo-5'-(2"-trifluoromethylphenyl)pentyl]decahydroisoquinoline-3-N-t-butylcarboxamide The titled compound was prepared substantially in accordance with the procedure detailed in Example 1, using 80 mg (0.20 mmol) of the subtitled compound of Preparation 1B, 38 mg (0.20 mmol) of 2-trifluoromethyl benzoic acid, 41 mg (0.20 mmol) of DCC and 27 mg (0.20 mmol) of HOBT.H$_2$0 in 3 mL of anhydrous tetrahydrofuran. The crude product was purified using radial chromatography (2 mm plate; gradient eluent of 2.5–5% methanol in methylene chloride) to provide 72 mg of a white foam.

Yield: 63%.

$^1$H NMR (CDCl$_3$): δ1.10 (s, 9H), 1.16–2.05 (m, 14H), 2.15–2.35 (m, 2H), 2.45–2.70 (m, 2H), 2.92–3.05 (m, 2H), 3.38–3.55 (m, 1H), 3.70 (br.s, 1H), 3.98–4.10 (m, 1H), 4.58–4.70 (m, 1H), 5.90 (s, 1H), 7.00–7.65 (m, 10H).

MS(FD): m/e 573 (M$^+$, 100).

Analysis for C$_{32}$H$_{42}$N$_3$O$_3$F$_3$: Calcd: C, 67.00; H, 7.38; N, 7.32. Found: C, 67.11; H, 7.09; N, 7.10.

EXAMPLE 16

[3S-(3R*,4aR*,8aR*,2'S*,3'R*)]-2-[2'-Hydroxy-3'-phenylmethyl-4'-aza-5'-oxo-5'-(2"-oxo-3"-methyl-pyrid-4"-yl)pentyl]decahydroisoquinoline-3-N-t-butylcarboxamide The titled compound was prepared substantially in accordance with the procedure detailed in Example 1, using 14.7 mg (0.037 mmol) of the subtitled compound of Preparation 1B, 5.6 mg (0.037 mmol) of the subtitled compound of Preparation 12F, 7.6 mg (0.037 mmol) of DCC and 4.9 mg (0.037 mmol) of HOBT.H$_2$O in 1.3 mL of anhydrous dimethylformamide. The crude product was purified using radial chromatography (1 mm plate; eluent of 10% methanol in methylene chloride) to provide 6.5 mg of a white solid.

Yield: 34%.

$^1$H NMR (CDCl$_3$): δ1.00–3.40 (m, 32H), 4.00–4.70 (m, 3H), 5.90–6.10 (m, 1H), 6.90–7.40 (m, 8H).

MS(FD): m/e 537 (M$^+$, 100).

EXAMPLE 17

[3S-(3R*,4aR*,8aR*,2'S*,3'R*)]-2-[2'-Hydroxy-3'-phenylmethyl-4'-aza-5'-oxo-5'-(2",6"-dichloro-3"-hydroxyphenyl)pentyl]decahydroisoquinoline-3-N-t-butylcarboxamide The titled compound was prepared substantially in accordance with the procedure detailed in Example 1, using 48 mg (0.12 mmol) of the subtitled compound of Preparation 1B, 25 mg (0.12 mmol) of the subtitled compound of Preparation 13, 2.5 mg (0.12 mmol) of DCC and 16 mg (0.12 mmol) of HOBT.H$_2$O in 2 mL of anhydrous tetrahydrofuran. The crude product was purified using radial chromatography (1 mm plate; gradient eluent of 2–5% methanol in methylene chloride) to provide 14 mg of the desired titled compound.

$^1$H NMR (CDCl$_3$): δ0.9–2.15 (m, 23H), 2.22–2.85 (m, 4H), 2.95–3.10 (m, 2H), 3.30–3.58 (m, 1H), 3.98–4.12 (m, 1H), 4.56–4.75 (m, 1H), 5.60–5.82 (m, 1H), 6.60–6.79 (m, 1H), 6.90–7.40 (m, 6H).

IR (CHCl$_3$): 3010, 2937, 1644, 1606, 1605, 1497, 1474, 1454, 1433, 1417, 1341, 1313, 1274, 1252, 1161, 1093, 1074, 1027, 991 cm$^{-1}$.

MS(FD): m/e 590 (M$^+$, 100).

EXAMPLE 18

[3S-(3R*,4aR*,8aR*,2'S*,3'R*)]-2-[2'-Hydroxy-3'phenylmethyl-4'-aza-5'-oxo-5'-(2"-methyl-3"-aminophenyl)pentyl]decahydroisoquinoline-3-N-t-butylcarboxamide The titled compound was prepared substantially in accordance with the procedure detailed in Example 1, using 100 mg (0.25 mmol) of the subtitled compound of Preparation 1B, 38 mg (0.25 mmol) of 3-amino-2-methyl benzoic acid, 34 mg (0.25 mmol) of HOBT.H$_2$O, 52 mg (0.25 mmol) of DCC in 3 mL of anhydrous tetrahydrofuran, with the exception that the reaction was conducted in the presence of 76 mg (0.75 mmol) of triethylamine. The resultant material was purified using radial chromatography (2 mm plate; gradient eluent of 2–5% methanol in methylene chloride) to provide 78 mg of an off-white foam.

Yield: 58%.

$^1$H NMR (CDCl$_3$): δ1.19 (s, 9H), 1.20–2.08 (m, 15H), 2.20–2.35 (m, 2H), 2.50–2.70 (m, 2H), 2.92–3.05 (m, 2H), 3.28–3.38 (m, 1H), 3.61 (br.s, 1H), 3.93–4.20 (m, 2H), 4.45–4.58 (m, 1H), 5.80 (s, 1H), 6.44 (d, J=7.5 Hz, 2H), 6.63 (d, J=7.9 Hz, 1H), 6.90 (t, J=7.7 Hz, 1H), 7.17–7.36 (m, 6H).

MS(FD): m/e 535 (M$^+$, 100).

EXAMPLE 19

[2S-(2R*,2'S*,3'S*)]-1-[2'-Hydroxy-3'-phenylthiomethyl-4'-aza-5'-oxo-5'-(3"-hydroxy-2"-methylphenyl)pentyl]-4-pyrid-3"-ylmethyl piperazine-2-N-t-butylcarboxamide The titled compound was prepared substantially in accordance with the procedure detailed in Example 1, using 50 mg (0.11 mmol) of the subtitled compound of Preparation 6B, 16 mg (0.11 mmol) of the subtitled compound of Preparation 9C, 14 mg (0.11 mmol) of HOBT.H$_2$O and 22 mg (0.11 mmol) of DCC in 2 mL of anhydrous tetrahydrofuran. The resultant material was purified using radial chromatography (1 mm plate; gradient eluent of 5–10% methanol in methylene chloride) to provide 35 mg of an off-white foam.

Yield: 55%.

$^1$H NMR (CDCl$_3$): δ1.29 (s, 9H), 2.18 (s, 3H), 2.23–2.33 (m, 1H), 2.45–2.85 (m, 7H), 3.20–3.35 (m, 3H), 3.45 (s, 1H), 4.00–4.10 (m, 1H), 4.25–4.35 (m, 1H), 5.00–5.40 (br.s, 1H), 6.61 (d, J=7.6 Hz, 1H), 6.76–6.80 (m, 2H), 6.92 (t, J=7.7 Hz, 1H), 7.12–7.43 (m, 7H), 7.57–7.62 (m, 1H), 7.78 (br.s, 1H), 8.48–8.58 (m, 2H).

MS (FD): m/e 606 (M$^+$, 100).

EXAMPLE 20

[3S-(3R*,4aR*,8aR*,2'S*,3'R*)]-2-[2'-Hydroxy-3'-phenylmethyl-4'-aza-5'-oxo-5'-(2"-isopropyl-3"-hydroxyphenyl)pentyl]decahydroisoquinoline-3-N-t-butylcarboxamide The titled compound was prepared substantially in accordance with the procedure detailed in Example 1, using 55 mg (0.137 mmol) of the subtitled compound of Preparation 1B, 24.7 mg (0.137 mmol) of the subtitled compound of Preparation 18B, 28.25 mg (0.137 mmol) of DCC, and 18.5 mg (0.137 mmol) of HOBT.H$_2$O in 8 mL of tetrahydrofuran. The resultant crude material was purified using radial chromatography (1 mm plate; eluent of 30 methanol in methylene chloride) to provide 46 mg of a white foam.

Yield: 60%.

[α]$_D$ –84.61 (c=2.60, MeOH,).

$^1$H NMR (CDCl$_3$): δ1.19 (d, J=3.7 Hz, 3H), 1.21 (d, J=3.75 Hz, 3H), 1.23 (s, 9H), 1.27–1.51 (m, 7H), 1.61–2.00 (m, 6H), 2.26–2.35 (m, 2H), 2.56–2.65 (m, 2H), 2.91–3.03 (m, 3H), 3.19–3.27 (m, 1H), 3.96 (m, 1H), 4.51 (m, 1H), 5.82 (br.s, 1H:), 5.93 (br.s, 1H), 6.23 (d, J=8.53 Hz, 1H), 6.46 (d, J=7.15 Hz, 1H), 6.66 (d, J=7.17 Hz, 1H), 6.86 (t, J=7.74 Hz, 1H), 7.21–7.31 (m, 5H).

IR (CDCl$_3$): 3427, 3322, 3028, 3008, 2930, 2868, 1660, 1603, 1582, 1513, 1455, 1393, 1366, 1304, 1278, 1245, 1088, 1059 cm$^{-1}$.

MS(FD): m/e 564 (M$^+$, 100).

Analysis for C$_{34}$H$_{49}$N$_3$O$_4$: Calcd: C, 72.43; H, 8.76; N, 7.45; Found: C, 72.13; H, 8.85; N, 7.30.

EXAMPLE 21

[3S-(3R*,4aR*,8aR*,2'S*,3'R*)]-2-[2'-Hydroxy-3'-phenylmethyl-4'-aza-5'-oxo-5'-(2"-butyl-3"-hydroxyphenyl)pentyl]decahydroisoquinoline-3-N-t-butylcarboxamide The titled compound was prepared substantially in accordance with the procedure detailed in Example 1, using 91 mg (0.227 mmol) of the subtitled compound of Preparation 1B, 44 mg (0.227 mmol) of the subtitled compound of Preparation 16B, 46.7 mg (0.227 mmol) DCC, and 30.6 mg (0.227 mmol) of HOBT.H$_2$O in 10 mL of tetrahydrofuran. The resultant crude material was purified using radial chromatography (1 mm plate; gradient eluent of 4–7% methanol in methylene chloride) to provide 72 mg of a white foam.

Yield: 55%.

[α]$_D$ –77.36 (c=0.36, MeOH).

$^1$H NMR (CDCl$_3$): δ0.84 (t, J=7.2 Hz, 3H), 1.20 (s, 9H), 1.29–2.00 (m, 18H), 2.27 (m, 2H), 2.48–2.69 (m, 4H), 2.99 (m, 2H), 3.29 (m, 1H), 3.99 (m, 1H), 4.49 (m, 1H), 5.85 (s, 1H), 6.45 (m, 2H), 6.75 (d, J=7.19 Hz, 1H), 6.86 (t, J=7.67 Hz, 1H), 7.21–7.31 (m, 5H).

IR (KBr): 3303 (br.), 3087, 3029, 2927, 2862, 1647, 1583, 1520, 1455, 1366, 1281, 1209, 1108, 735, 698 cm$^{-1}$.

MS(FD): m/e 578 (M$^+$, 100).

HR MS(FAB): m/e for C$_{35}$H$_{51}$N$_3$O$_4$: Calcd: 578.3958; Found: 578.3962.

EXAMPLE 22

[3S-(3R*,4aR*,8aR*,2'S*,3'R*)]-2-[2'-Hydroxy-3'-phenylmethyl-4'-aza-5'-oxo-5'-(2"-propyl-3"-hydroxyphenyl)pentyl]decahydroisoquinoline-3-N-t-butylcarboxamide The titled compound was prepared substantially in accordance with the procedure detailed in Example 1, using 67 mg (0.167 mmol) of the subtitled compound of Preparation 1B, 30 mg (0.167 mmol) of the subtitled compound of Preparation 17B, 34 mg (0.167 mmol) of DCC, and 23 mg (0.167 mmol) of HOBT.H$_2$O in 4 mL of tetrahydrofuran. The resultant crude material was purified using radial chromatography (1 mm plate; eluent of 3% methanol in methylene chloride) to provide 75 mg of a white foam.

Yield: 80%.

[α]$_D$ –43.75 (c=0.160, MeOH).

$^1$H NMR (CDCl$_3$): δ0.87 (t, 3H), 1.18 (s, 9H), 1.21–2.04 (m, 15H), 2.24–2.33 (m, 2H), 2.49–2.58 (m, 3H), 2.66 (m, 1H), 2.98 (m, 2H), 3.37 (m, 1H), 3.99 (m, 1H), 4.52 (m, 1H), 5.07 (m, 1H), 5.70 (s, 1H), 6.43 (d, J =8.32 Hz, 1H), 6.56 (d, J=7.32 Hz, 1H), 6.76 (d, J=7.12 Hz, 1H), 6.95 (t, J=7.78 Hz, 1H), 7.20–7.33 (m, 5H).

IR (KBr): 3287 (br.), 3086, 2932, 2868, 1681, 1558, 1456, 1368, 1334, 1291, 1261, 1218, 1169, 1101, 1042, 776, 734, 552 cm$^{-1}$.

MS(FD): m/e 564 (M$^+$, 100).

HR MS(FAB): m/e for C$_{34}$H$_{50}$N$_3$O$_4$: Calcd: 564.3801; Found: 564.3789.

EXAMPLE 23

[3S-(3R*,4aR*,8aR*,2'S*,3'S*)]-2-[2'-Hydroxy-3'-phenylthiomethyl-4'-aza-5'-oxo-5'-(2"-methyl-3"-hydroxyphenyl)pentyl]decahydroisoquinoline-3-N-t-butylcarboxamide The titled compound was prepared substantially in accordance with the procedure detailed in Example 1, using 70 mg (0.16 mmol) of the subtitled compound of Preparation 8G, 24.6 mg (0.16 mmol) of the subtitled compound of Preparation 9C, 33 mg (0.16 mmol) of DCC, and 22 mg (0.16 mmol) of HOBT.H$_2$O in 4 mL of tetrahydrofuran. The resultant crude material was purified using radial chromatography (1 mm plate; eluent of 3% methanol in methylene chloride) to provide 54 mg of a white foam.

Yield: 60%.

[α]$_D$–119.23 (c=0.26, MeOH).

$^1$H NMR (CDCl$_3$): δ1.09 (s, 9H), 1.12–1.79 (m, 12H), 1.93–2.02 (m, 2H), 2.17–2.30 (m, 2H), 2.31 (s, 3H), 2.43–2.61 (m, 2H), 2.91 (m, 1H), 3.42 (m, 1H), 3.78 (m, 1H), 4.07 (m, 1H), 4.47 (m, 1H), 5.37 (m, 1H), 5.51 (br.s, 1H), 6.84 (m, 1H), 7.06 (m, 2H), 7.17–7.32 (m, 4H), 7.45 (m, 2H).

IR (KBr): 3297, 2925, 2862, 1627, 1586, 1530, 1482, 1466, 1439, 1366, 1287, 1221, 1156, 1119, 1026, 801, 735, 689 cm$^{-1}$.

MS(FD): m/e 568 (M$^+$, 100).

HR MS(FAB) for C$_{32}$H$_{46}$N$_3$O$_4$S: Calcd: 568.3209; Found: 568.3182.

EXAMPLE 24

[3S-(3R*,4aR*,8aR*,2'S*,3'S*)]-2-[2'-Hydroxy-3'-(naphth-2-ylthiomethyl)-4'-aza-5'-oxo-5'-(2"-methyl-3"-hydroxyphenyl)pentyl]decahydroisoquinoline-3-N-t-butylcarboxamide The titled compound was prepared substantially in accordance with the procedure detailed in Example 1, using 70 mg (0.145 mmol) of the subtitled compound of Preparation 7B, 22 mg (0.145 mmol) of the subtitled compound of Preparation 9C, 29 mg (0.145 mmol) of DCC, and 19 mg (0.145 mmol) of HOBT.H$_2$O in 4 mL of tetrahydrofuran. The resultant crude material was purified using flash chromatography (gradient eluent of 5–15% acetone in methylene chloride) to provide 65 mg of a white solid.

Yield: 73%.

[α]$_D$–112.00 (c=0.25, MeOH).

$^1$H NMR (CDCl$_3$): δ1.10 (s, 9H), 1.15–1.80 (m, 12H), 1.93–2.06 (m, 1H), 2.17–2.28 (m, 2H), 2.29 (s, 3H), 2.42–2.61 (m, 2H), 2.94 (d, 1H), 3.51 (m, 1H), 3.83–3.92 (m, 1H), 4.10 (m, 1H), 5.36 (br.s, 1H), 5.53 (br.s, 1H), 6.79 (m, 1H), 6.93 (m, 2H), 7.21 (d, J=8.83 Hz, 1H), 7.40–7.53 (m, 3H), 7.73 (m, 3H), 7.90 (s, 1H).

IR (KBr): 3427, 3311 (br), 2929, 2864, 1703, 1661, 1587, 1514, 1456, 1393, 1366, 1276, 1200, 1177, 1146, 1119, 1070, 1042 cm$^{-1}$.

MS(FD): m/e 618 (M$^+$, 100).

Analysis for C$_{34}$H$_{49}$N$_3$O$_4$: Calcd: C, 69.98; H, 7.67; N, 6.80. Found: C, 69.92; H, 7.72; N, 6.75.

EXAMPLE 25

[2S-(2R*,2'S*,3'S*)]-1-[2'-Hydroxy-3'-(naphth-2-ylthiomethyl)-4'-aza-5'-oxo-5'-(2"-methyl-3"-hydroxyphenyl)pentyl]piperidine-2-N-t-butylcarboxamide The titled compound was prepared substantially in accordance with the Procedure detailed in Example 1, using 28 mg (0.065 mmol of the subtitled compound of Preparation 2G, 10 mg (0.065 mmol) of the subtitled compound of preparation 9C, 13.5 mg (0.065 mmol) of DCC, and 9 mg (0.065 mmol) HOBT.H$_2$O in 2 mL of tetrahydrofuran. The resultant crude material was purified using radial chromatography (1 mm place; eluent of 2% methanol in methylene chloride) to provide 23 mg of a white foam.

Yield: 63. [α]$_D$–233.33 (c=0.09, MeOH).

$^1$H NMR (CDCl$_3$): δ1.17 (s, 9H), 1.26 (m, 1H), 1.56–1.73 (m, 6H), 2.19–2.23 (m, 2H), 2.25 (s, 3H), 2.42 (m, 1H), 2.62–2.73 (m, 2H), 3.11–3.19 (m, 1H), 3.50–3.72 (m, 2H), 4.10 (m, 1H), 4.45 (m, 1H), 5.89 (s, 1H), 6.77–6.87 (m, 3H), 7.00 (d, J=8.65 Hz, 1H), 7.43–7.51 (m, 3H), 7.72–7.80 (m, 3H), 7.88 (s, 1H).

IR (KBr): 3329, 2934, 2857, 1646, 1586, 1522, 1457, 1364, 1284, 1223, 1133, 1072, 944, 835, 811, 744, 474 cm$^{-1}$.

MS(FD): m/e 564 (M$^+$, 100).

HR MS(FAB) for C$_{32}$H$_{42}$N$_3$O$_4$S: Calcd: 564.2896; Found: 564.2916.

EXAMPLE 26

[2S-(2R*,2'S*,3'R*)]-1-[2'-Hydroxy-3'-phenylmethyl-4'-aza-5'-oxo-5'-(2"-methyl-3"-hydroxyphenyl)pentyl]-4-(pyrid-3'''-ylmethyl)piperazine-2-N-t-butylcarboxamide The titled compound was prepared substantially in accordance with the procedure detailed in Example 1, using 65 mg (0.148 mmol) of the subtitled compound of Preparation 5E, 22.5 mg (0.148 mmol) of the subtitled compound of Preparation 9C, 30.5 mg (0.148 mmol) of DCC, and 20 mg (0.148 mmol) of HOBT.H$_2$O in 5 mL of tetrahydrofuran. The resultant crude material was purified using radial chromatography (1 mm plate; eluent of 3% methanol in methylene chloride) to provide 64 mg of a white foam.

Yield: 75%.

$^1$H NMR (CDCl$_3$): δ1.33 (s, 9H), 1.86 (s, 3H), 2.30 (m, 1H), 2.49–2.98 (m, 11H), 3.33 (m, 1H), 3.46 (m, 1H), 4.02 (m, 1H), 4.46 (m, 1H), 6.29 (d, J=9.16 Hz, 1H), 6.46 (d, J=7.23 Hz, 1H), 6.73 (d, J=7.79 Hz, 1H), 6.83 (t, J=7.84 Hz, 1H), 7.17–7.31 (m, 7H), 7.60 (m, 1H), 7.95 (br.s, 1H), 8.50–8.55 (m, 2H).

MS(FD): m/e 574 (M$^+$, 100).

HR MS(FAB): m/e for C$_{33}$H$_{44}$N$_5$O$_4$: Calcd: 574.3393; Found: 574.3373.

EXAMPLE 27

[3S-(3R*,4aR*,8aR*,2'S*,3'R*)]-2-[2'-Hydroxy-3'-phenylmethyl-4'-aza-5'-oxo-5'-(2"-methyl-3"-hydroxyphenyl)pentyl]decahydroisoquinoline-3-N-t-butylcarboxamide monomesylate salt To a cold (0° C.) solution of 35.1 mg (0.064 mmol) of the titled compound of Example 3 in 2 mL of anhydrous methylene chloride, was added dropwise 134 μL (0.067 mmol) of a 0.5M solution of methanesulfonic acid in methylene chloride. The resulting reaction was reduced to dryness under reduced pressure (0.2–0.1 Torr) to provide 38 mg (crude) of a light yellow foam.

Yield: 90%.

$^1$H NMR (CD$_3$OD): δ0.91 (t, J=7.39, 3H), 1.29 (s, 9H), 1.30–3.20 (m, 21H), 4.00–4.40 (m, 2H), 6.47 (d, J=7.30 Hz, 1H), 6.73 (d, J=7.78 Hz, 1H), 6.91 (t, J=7.78 Hz, 1H), 7.15–7.32 (m, 5H).

EXAMPLE 28

[3S-(3R*,4aR*,8aR*,2'S*,3'R*)]-2-[2'-Hydroxy-3'-phenylmethyl-4'-aza-5'-oxo-5'-(2"-methyl-3"-hydroxyphenyl)pentyl]decahydroisoquinoline-3-N-t-butylcarboxamide monomesylate salt The titled compound was prepared substantially in accordance with the procedure detailed in Example 27, using 125 mg (0.23 mmol) of the titled compound of Example 13 in 5 mL of anhydrous methylene chloride, and 240 μL (0.24 of a 1.0M solution of methanesulfonic acid in methylene chloride to provide 163 mg (crude) of an off-white foam.

Yield: 95%

$^1$H NMR (CD$_3$OD): δ1.12 (s, 9H), 1.10–2.20 (m, 16H), 2.60–2.75 (m, 4H), 3.10–3.50 (m, 6H), 3.60–3.70 (m, 1H), 3.90–4.30 (m, 3H), 6.53 (d, J=7.35 Hz, 1H), (t, J=7.87 Hz, 1H), 6.89 (t, J=7.82 Hz, 1H).

EXAMPLE 29

[3S-(3R*,4aR*,8aR*,2'S*,3'S*)]-2-[2'-Hydroxy-3'-phenylthiomethyl-4'-aza-5'-oxo-5'-(2"-methylphenyl)pentyl]decahydroisoquinoline-3-N-t-butylcarboxamide The titled compound was prepared substantially in accordance with the procedure detailed in Example 1, using 15 mg (0.034 mmol) of the subtitled compound of Preparation 8G, 4.7 mg (0.034 mmol) of o-toluic acid, 7.13 mg (0.034 mmol) of DCC, and 4.7 mg (0.034 mmol) of HOBT.H$_2$O in 2.5 mL of tetrahydrofuran. The resultant material was purified using radial chromatography (1 mm plate; eluent 10% acetone in methylene chloride) to provide 16 mg of a white foam.

Yield: 84%.

[α]$_D$ –80.00 (c=0.15).

$^1$NMR (CDCl$_3$): δ1.04 (s, 9H), 1.08–1.80 (m, 11H), 1.93 (m, 3H), 2.22 (m, 4H), 2.44 (m, 1H), 2.49 (s, 3H), 2.58 (m, 1H), 2.94 (m, 1H), 3.47 (m, 1H) 3.84 (m, 1H) 4.03 (m, 1H), 4.50 (m, 1H), 5.45 (br.s, 1H), 7.12–7.32 (m, 7H), 7.45 (m, 2H), 7.51 (a, J=7.51 Hz, 1H).

IR (KBr): 3327, 2928, 2852, 1627, 1574, 1535, 1481, 1364, 1311, 1275, 1225, 1088, 737 cm$^{-1}$.

HR MS(FAB) for C$_{32}$H$_{46}$N$_3$O$_3$S: Calcd: 552.3260; Found: 552.3272.

EXAMPLE 30

[3S-(3R*,4aR*,8aR*,2'S*,3'S*)]-2-[2'-Hydroxy-3'-phenylthiomethyl-4'-aza-5'-oxo-5'-[3"-methyl-pyrid-4"-yl]pentyl]decahydroisoquinoline-3-N-t-butylcarboxamide The titled compound was prepared substantially in accordance with the procedure detailed in Example 1, using 15 mg (0.034 mmol) of the subtitled compound of Preparation 8G, 6.69 mg (0.048 mmol) of the titled compound of Preparation 19, 7.13 mg (0.034 mmol) of DCC, and 4.7 mg (0.034 mmol) of HOBT.H$_2$O in 1.5 mL of tetrahydrofuran and 1 mL of dimethylformamide. The resultant material was purified using radial chromatography (1 mm plate; gradient eluent of 3–55 methanol in methylene chloride) to provide 10 mg of a white foam.

Yield: 52%.

[α]$_D$ –95.65 (c=0.115)

$^1$H NMR (CDCl$_3$): δ1.00 (s, 9H), 1.20–1.77 (m, 12H), 1.99 (m, 1H), 2.17 (m, 2H), 2.44 (m, 5H), 2.92 (m, 1H), 3.41 (m, 1H), 3.84 (m, 1H), 4.13 (m, 1H), 4.56 (m, 1H), 5.39 (s, 1H), 7.20–7.46 (m, 6H), 7.75 (d, J=8.94 Hz, 1H), 8.46 (m, 2H).

IR (KBr): 3307, 2925, 2860, 1653, 1542, 1481, 1439, 1391, 1365, 1281, 1224, 1058, 1041, 738, 691, 669 cm$^{-1}$.

HR MS(FAB) for C$_{31}$H$_{45}$N$_4$O$_3$S: Calcd: 553.3212; Found: 553.3222.

EXAMPLE 31

[3S-(3R*,4aR*,8aR*,2'S*,3'S*)]-2-[2'-Hydroxy-3'-phenylthiomethyl-4'-aza-5'-oxo-5'-(quinolin-5"-yl)pentyl]decahydroisoquinoline-3-N-t-butylcarboxamide The titled compound was prepared substantially in accordance with the procedure detailed in Example 1, using 15 mg (0.034 mmol) of the subtitled compound of Preparation 8G, 6.0 mg (0.034 mmol) of the titled compound of Preparation 20, 7.13 mg (0.034 mmol) of DCC, and 4.7 mg (0.034 mmol) HOBT.H$_2$O in 2 mL of tetrahydrofuran. The resultant material was purified using radial chromatography (1 mm plate; gradient eluent of 3–5% methanol in methylene chloride) to provide 15 mg of a white foam.

Yield: 74%.

[α]$_D$ –99.50° (c=0.201).

$^1$H NMR (CDCl$_3$): δ0.74 (s, 9H), 1.15–1.79 (m, 12H), 1.97 (m, 1H), 2.17 (m, 2H), 2.36 (m, 1H), 2.54 (m, 1H), 2.90 (m, 1H), 3.45 (m, 1H), 3.99 (m, 1H), 4.16 (m, 1H), 4.62 (m, 1H), 5.29 (s, 1H), 7.18–7.32 (m, 3H), 7.40–7.50 (m, 3H), 7.70 (m, 1H), 7.89 (m, 2H.), 8.17 (m, 1H), 8.91 (m, 2H).

IR (KBr): 3299, 2923, 2862, 1644, 1546, 1481, 1439, 1390, 1327, 1279, 1222, 1207, 1037, 810, 735, 689 cm$^{-1}$.

HR MS(FAB) for C$_{34}$H$_{45}$N$_4$O$_3$S: Calcd: 589.3212; Found: 589.3237.

EXAMPLE 32

[3S-(3R*,4aR*,8aR*,2'S*,3'S*)]-2-[2'-Hydroxy-3'-phenylthiomethyl-4'-aza-5'-oxo-5'-(1",2",3",4"-tetrahydroquinolin-5"-yl)pentyl]decahydroisoquinoline-3-N-t-butylcarboxamide The titled compound was prepared substantially in accordance with the procedure detailed in Example 1, using 18 mg (0.04 mmol) of the subtitled compound of Preparation 8G, 7.38 mg (0.04 mmol) of the titled compound of Preparation 21, 8.56 mg (0.04 mmol) of DCC, and 5.61 mg (0.04 mmol) of HOBT.H$_2$O in 2 mL of tetrahydrofuran. The resultant material was purified using radial chromatography (1 mm plate; gradient eluent of 3–5% methanol in methylene chloride) to provide 12 mg of a white foam.

Yield: 50%.

[α]$_D$ –98.59 (c=0.142).

$^1$H NMR (CDCl$_3$): δ1.13 (s, 9H), 1.14–2.04 (m, 15H), 2.19 (m, 2H), 2.45 (m, 1H), 2.57 (m, 1H), 2.75 (m, 1H), 2.90–3.09 (m, 2H), 3.26 (m, 2H), 3.44 (m, 2H), 3.75 (m, 1H), 4.01–4.14 (m, 2H), 4.42 (m, 1H), 5.56 (s, 1H,) 6.49 (d, J=7.96 Hz, 1H), 6.80 (d, J=7.40 Hz, 1H), 6.93 (t, J=7.72 Hz, 1H), 7.08 (d, J=8.39 Hz, 1H), 7.18 (m, 1H), 7.27 (m, 2H), 7.42 (d, 2H).

IR (KBr): 3327, 2928, 2852, 1629, 1590, 1519, 1481, 1449, 1364, 1310, 1275, 1229, 1087, 738, 690 cm$^{-1}$.

HR MS(FAB) for C$_{34}$H$_{49}$N$_4$O$_3$S: Calcd: 593.3525; Found: 593.3552.

EXAMPLE 33

[2S-(2R*,2'S*,3'S*)]-1-[2'-Hydroxy-3'-phenylthiomethyl-4'-aza-5'-oxo-5'-(1",2",3",4"-tetrahydroquinolin-5"-yl)pentyl]-4-(pyrid-3'"-ylmethyl)piperazine-2-N-t-butylcarboxamide To a cooled (–10° C.) solution containing 45 mg (0.10 mmol) of the subtitled compound of Preparation 6B, 18 mg (0.10 mmol) of 1,2,3,4-tetrahydroquinoline-5-carboxylic acid, 30 mg (0.30 mmol) of triethylamine, and 14 mg (0.10 mmol) of HOBT.H$_2$O in 2 mL of anhydrous tetrahydrofuran, was added 22 mg (0.11 mmol) of DCC. The resultant reaction mixture was stirred for approximately 24 hours at room temperature and then concentrated under reduced pressure to provide a residue. This residue was redissolved in ethyl acetate, and filtered through celite. The filtrate was then extracted sequentially with saturated sodium bicarbonate (twice), brine, dried over sodium sulfate, filtered and concentrated under reduced pressure. The crude material was purified using radial chromatography (1 mm plate; gradient eluent of 2.5–5% methanol in methylene chloride) to provide 33 mg of an off-white foam.

Yield: 62%.

$^1$H NMR (CDCl$_3$): δ1.29 (s, 9H), 1.79–1.97 (m, 2H), 2.26–3.00 (m, 11H), 3.20–3.50 (m, 9H), 3.95–4.05 (m, 1H), 4.23–4.35 (m, 1H), 6.43–6.62 (m, 2H), 6.89 (t, J=7.8 Hz, 1H), 7.12–7.35 (m, 6H), 7.41 (d, J=7.7 Hz, 2H), 7.57–7.70 (m, 2H), 8.50–8.58 (m, 2H).

MS(FD): m/e 631 (M$^+$, 100).

EXAMPLE 34

[2S-(2R*,2'S*,3'S*)]-1-[2-Hydroxy-3'-phenylthiomethyl-4'-aza-5'-oxo-5'-(quinolin-5''-yl) pentyl]-4-(pyrid-3'''-ylmethyl)piperazine-2-N-t-butylcarboxamide The titled compound was isolated from Example 33 Yield: 13 mg of an off-white foam.

$^1$H NMR (CDCl$_3$): δ1.18 (s, 9H), 2.27–2.90 (m, 9H), 3.17–3.60 (m, 5H), 4.07–4.19 (m, 1H), 4.40–4.55 (m, 1H), 4.75–4.95 (m, 1H), 6.90–7.68 (m, 11H), 8.16 (d, J=8.1 Hz, 1H), 8.48–8.60 (m, 2H), 8.80 (d, J=8.4 Hz, 1H), 8.89–8.97 (m, 1H).

MS(FD): m/e 527 (M$^+$, 100).

EXAMPLE 35

[2S-(2R*,2'S*,3'S*)]-1-[2'-Hydroxy-3'-phenylthiomethyl-4'-aza-5'-oxo-5'-[3''-methyl-pyrid-4''-yl)pentyl]-4-(pyrid-3'''-ylmethyl)piperazine-2-N-t-butylcarboxamide The titled compound was prepared substantially in accordance with the procedure detailed in Example 1, using 20.3 mg (0.148 mmol) of the titled compound of Preparation 19, 70 mg (0.148 mmol) or the subtitled compound of Preparation 19, 31 mg (0.148 mmol) of DCC, and 20 mg (0.148 mmol) of HOBT.H$_2$O in tetrahydrofuran containing 62 mL of triethylamine. The resultant material was purified using radial chromatography (2 mm plate; gradient eluent of 2.5–15% methanol in methylene chloride) to provide 48 mg of a white foam.

Yield: 55%.

$^1$H NMR (CDCl$_3$): δ1.23 (s, 9H), 2.30–2.90 (m, 12H), 3.16–3.50 (m, 5H), 4.02–4.10 (m, 1H), 4.30–4.42.41 (m, 1H), 4.85 (br.s, 1H), 6.90–7.60 (m, 10H), 8.38–8.57 (m, 3H).

MS(FAB): m/e 591.4 (M$^+$, 100).

EXAMPLE 36

[3S-(3R*,4aR*,8aR*,2'S*,3'S*)]-2-[2'-Hydroxy-3'-phenylmethyl-4'-aza-5'-oxo-5'-[2''-methyl-3''-N-(methylsulfonyl)aminophenyl)]pentyl] decahydroisoquinoline-3-N-t-butylcarboxamide The titled compound was prepared substantially in accordance with the procedure detailed in Example 1, using 70 mg (0.17 mmol) of the subtitled compound of Preparation 1B, 40 mg (0.17 mmol) of the titled compound of Preparation 22, 35 mg (0.17 mmol) of DCC, and 23 mg (0.17 mmol) of HOBT.H$_2$O in 2 mL of anhydrous tetrahydrofuran. The resultant material was purified using radial chromatography (2 mm plate; gradient eluent of 1–5% methanol in methylene chloride) to provide 72 mg of an off-white solid.

Yield: 69%.

$^1$H NMR (CDCl$_3$): δ1.14 (s, 9H), 1.19–2.38 (m, 19H), 2.50–2.70 (m, 2H), 2.92–3.06 (m, 4H), 3.43–3.55 (m, 1H), 4.01–4.10 (m, 1H), 4.58–4.70 (m, 1H), 5.66 (s, 1H), 6.37 (br.s, 1H), 6.82–6.93 (m, 2H), 7.10–7.39 (m, 6H), 7.48 (d, J=8.16 Hz, 1H).

IR (KBr): 3691, 3600–3300 (br.), 2929, 2866, 1672, 1603, 1513, 1455, 1393, 1368, 1327, 1277, 1154, 1047, 972, 909, 877 cm$^{-1}$.

MS(FD): m/e (M$^+$, 100).

EXAMPLE 37

[3S-(3R*,4aR*,8aR*,2'S*,3'S*)]-2-[2'-Hydroxy-3'-phenylmethyl-4'-aza-5'-oxo-5'-[(1'',2'',3'',4'',-tetrahydroquinolin-5''-yl)]pentyl] decahydroisoquinoline-3-N-t-butylcarboxamide The titled compound was prepared substantially in accordance with the procedure detailed in Example 1, using 18.5 mg (0.046 mmol) of the subtitled compound of Preparation 1B, 8.14 mg (0.046 mmol) of the titled compound of Preparation 20, 9.48 mg (0.046 mmol) of DCC, and 6.21 mg (0.046 mmol) of HOBT.H$_2$O in 2 mL of anhydrous tetrahydrofuran. The resultant material was purified using radial chromatography (1 mm plate; gradient eluent of 2–5% methanol in methylene chloride) to provide 11 mg of a foam.

Yield: 43%.

$^1$H NMR (CDCl$_3$): δ1.20 (s, 9H), 1.25–2.02 (m, 15H), 2.28 (m, 2H), 2.46–2.70 (m, 4H), 2.99 (m, 2H), 3.21 (m, 1H), 3.35 (m, 1H), 3.98 (m, 1H), 4.49 (m, 1H), 5.75 (br.s, 1H), 6.38 (m, 3H), 6.83 (t, 1H), 7.21–7.33 (m, 5H).

EXAMPLE 38

[3S-(3R*,4aR*,8aR*,2'S*,3'S*)]-2-[2'-Hydroxy-3'-phenylthiomethyl-4'-aza-5'-oxo-5'-[6''-methyl-(1'',2'',3'',4''-tetrahydroquinolin-5''-yl)]pentyl] decahydroisoquinoline-3-N-t-butylcarboxamide The titled compound was prepared substantially in accordance with the procedure detailed in Example 1, using 15 mg (0.035 mmol) of the subtitled compound of Preparation 8G, 6.5 mg (0.035 mmol) of 6-methyl-1,2,3,4-tetrahydro-5-quinoline carboxylic acid, 7.15 mg (0.035 mmol) of DCC, and 4.7 mg (0.035 mmol) of HOBT.H$_2$O in 2 mL of tetrahydrofuran and 1 mL of dimethylformamide. The resultant material was purified using radial chromatography (1 mm plate; gradient eluent of 3–5% methanol in methylene chloride) to provide 12.5 mg of a white solid.

Yield: 60%.

HR MS(FAB) for C$_{35}$H$_{47}$N$_4$O$_3$S: Calcd: 603.3369; Found: 603.3384.

EXAMPLE 39

[3S-(3R*,4aR*,8aR*,2'S*,3'S*)]-2-[2'-Hydroxy-3'-phenylthiomethyl-4'-aza-5'-oxo-5'-[2'',6''-dimethyl-3''-hydroxyphenyl]pentyl]decahydroisoquinoline-3-N-t-butylcarboxamide The titled compound was prepared substantially in accordance with the procedure detailed in Example 1, using 20 mg (0.046 mmol) of the subtitled compound of Preparation 8G, 11.53 mg (0.0694 mmol) of 2,6-dimethyl-3-hydroxy benzoic acid, 9.54 mg (0.046 mmol) of DCC, and 6.25 mg (0.046 mmol) of HOBT.$H_2O$ in 3 mL of tetrahydrofuran. The resultant material was purified using radial chromatography (1 mm plate; eluent of 4% methanol in methylene chloride) to provide 14 mg of a white solid.

Yield: 52%.

HR MS(FAB) for $C_{33}H_{48}N_3O_4S$: Calcd: 582.3375; Found: 582.3373.

EXAMPLE 40

[2R'-(2R'*,3'S*)]-N-t-Butyl-2-(2'-hydroxy-3'-phenylmethyl-4'-aza-5'-oxo-5'-(2"-methyl-3"-hydroxyphenyl)pentyl]benzamide The titled compound was prepared substantially in accordance with the procedure detailed in Example 40, using 100 mg (0.29 mmol) of the subtitled compound from Preparation 24D, 44 mg (0.29 mmol) of the subtitled compound of Preparation 23C, 60 mg (0.29 mmol) of DCC and 39 mg (0.29 mmol) of 1-hydroxybenzotriazole hydrate (HOBT.$H_2O$) in 4 mL of anhydrous tetrahydrofuran. The crude product was purified using radial chromatography (2 mm plate; gradient eluent of 2–5% methanol in methylene chloride) to provide 58 mg of a white powder.

Yield: 42%.

$[\alpha]_D$ 2.34° (c=3.4, MeOH).

$^1$H NMR ($CD_3OD$): δ1.47 (s, 9H), 1.88 (s, 3H), 2.70–2.80 (m, 1H), 2.95–3.10 (m, 3H), 3.25–3.30 (m, 1H), 3.85–3.95 (m, 1H), 4.35–4.45 (m, 1H), 4.34 (s, 1H), 6.55–6.58 (m, 1H), 5.74 (d, J=8.0 Hz, 1H), 6.94 (t, J=7.8 Hz, 1H), 7.15–7.45 (m, 11H).

IR ($CHCl_3$): 3580, 3550–3100 (br), 2929, 2865, 1662, 1596, 1521, 1472, 1455, 1394, 1368, 1293, 1157, 1047, 879, 839 cm$^{-1}$.

MS(FD): 475 (M$^+$, 100).

HR MS(FAB): m/e for $C_{29}H_{35}N_2O_4$: Calcd: 475.2597; Found: 475.2610.

EXAMPLE 41

[2'R-(2'R*,3'S*)]-N-t-Butyl-2-[2'-hydroxy-3'-phenylmethyl-4'-aza-5'-oxo-5'-(2"-methyl-5"-hydroxymethylphenyl)pentyl]benzamide The titled compound was prepared substantially in accordance with the procedure detailed in Example 40, using 95 mg (0.28 mmol) of the subtitled compound of Preparation 24D, 65 mg (0.28 mmol) of the subtitled compound of Preparation 27B, 58 mg (0.28 mmol) of DCC and 38 mg (0.28 mmol) of HOBT.$H_2O$ in 2 mL of tetrahydrofuran containing 0.2 mL of dimethylformamide. The crude product was purified using radial chromatography (2 mm plate; eluent of 4% methanol in methylene chloride) to provide 64.6 mg of the desired titled compound.

Yield: 47%

$[\alpha]_D$ –0.003 (c=1.02, MeOH).

$^1$H NMR ($CDCl_3$): δ1.44 (s, 9H), 1.98 (s, 3H), 2.70–2.85 (m, 1H), 3.00–3.12 (m, 2H), 3.25–3.35 (m, 1H), 3.85–3.97 (m, 1H), 4.00–4.10 (m, 2H), 4.35–4.46 (m, 1H), 4.50 (s, 2H), 6.98–7.43 (m, 11H), 8.06–8.18 (m, 1H)

MS(FD): m/e (M$^+$+1, 490).

Analysis for $C_{30}H_{36}N_2O_4$: Calcd: C, 73.74; H, 7.43; N, 5.52; Found: C, 74.00; H, 7.49; N, 5.68.

EXAMPLE 42

[2'R-(2'R*,3'S*)]-N-t-Butyl-2-[2'-hydroxy-3'-naphth-2-ylthiomethyl-4'-aza-5'-oxo-5'-(2"-methyl-3"-aminophenyl)pentyl]benzamide To a cold (0° C.) solution of 50 mg (0.12 mmol) of the subtitled compound of Preparation 25E in 2.0 mL of dimethylformamide, was added 22 mg (0.14 mmol) of 2-methyl-3-aminobenzoic acid, 16 mg (0.12 mmol) of HOBT, 22 mg (0.12 mmol) of EDC and 0.081 mL (0.58 mmol) of triethylamine. The resulting reaction mixture was stirred at 0° C. for approximately one hour and then sixteen hours at room temperature. The mixture was then quenched with water and extracted with ethyl acetate. The resulting layers were separated and the organic layer was dried, filtered and concentrated under reduced pressure to provide a crude residue. This residue was purified using flash chromatography (eluent of 3% methanol in methylene chloride) to provide 52 mg of a white solid (mp 105°–106° C.).

Yield: 80%.

$^1$H NMR ($CDCl_3$): δ7.89 (s, 1H), 7.75 (m, 3H), 7.40 (m, 7H), 6.86 (t, J=9.0 Hz, 1H), 6.12 (s, 1H), 5.93 (s, 1H), 4.51 (m, 1H), 4.02 (m, 1H), 3.68 (br.s, 2H), 3.51 (m, 3H), 3.12 (s, 2H), 3.04 (dd, J=13.4, 10.1 Hz, 1H), 2.92 (dd, J=13.4, 3.3 Hz, 1H), 2.23 (s, 3H), 1.50 (s, 9H).

IR (KBr): 3304, 3068, 1633, 1516, 1321, 1221, 1076, 746 cm$^{-1}$.

Analysis for $C_{33}H_{37}N_3O_3S$: Calcd: C, 71.32; H, 6.71; N, 7.56; Found: C, 71.54; H, 6.83; N, 7.32.

EXAMPLE 43

[2'R-(2'R*,3'S*)]-N-t-Butyl-2-[2'-hydroxy-3'-naphth-2-ylthiomethyl-4'-aza-5'-oxo-5'-(2"-methyl-3"-N(methyl)aminophenyl)pentyl]benzamide The titled compound was prepared substantially in accordance with the procedure detailed in Example 42, using 100 mg (0.23 mmol) of the subtitled compound of Preparation 25E in 2.0 mL of dimethylformamide, 42 mg (0.26 mmol) of the titled compound of Preparation 28, 32 mg (0.23 mmol) of HOBT, 45 mg (0.23 mmol) of EDC and 0.16 mL (1.20 mmol) of triethylamine. The crude residue was purified using flash chromatography (eluent of 2% methanol in methylene chloride) to provide 102 mg of a white solid (mp 111°–113° C.).

Yield: 76%.

$^1$H NMR ($CDCl_3$): δ7.89 (s, 1H), 7.75 (m, 2H), 7.52–7.21 (m, 9H), 7.00 (t, J=7.9 Hz, 1H), 6.62 (t, J=7.4 Hz, 1H), 6.41 (d, J=9.1 Hz, 1H), 6.09 (d, J=5.8 Hz, 1H), 5.91 (s, 1H), 4.48 (m, 1H), 4.01 (m, 1H), 3.69 (s, 1H), 3.50 (m, 2H), 3.01 (m, 2H), 2.85 (s, 3H), 2.15 (s, 3H), 1.45 (s, 9H).

Analysis for $C_{34}H_{39}N_3O_3S$: Calcd: C, 71.67; H, 6.89; N, 7.37; Found: C, 71.92; H, 6.74; N, 7.42.

EXAMPLE 44

[2'R-(2'R*,3'S*)]-N-t-Butyl-2-[2'-hydroxy-3'-naphth-2-ylthiomethyl-4'-aza-5'-oxo-5'-(2"-chloro-3"-aminophenyl)pentyl]benzamide The titled compound was prepared substantially in accordance with the procedure detailed in Example 42, using 100 mg (0.23 mmol) of the subtitled compound of Preparation 25E in 2.0 mL of dimethylformamide, 48 mg (0.28 mmol) of 2-chloro-3-aminobenzoic acid, 32 mg (0.23 mmol) of HOBT, 45 mg (0.23 mmol) of EDC and 0.16 mL (1.20

EXAMPLE 45

[2'R-(2'R*,3'S*)]-N-t-Butyl-2-[2'-hydroxy-3'-naphth-2-ylthiomethyl-4'-aza-5'-oxo-5'-(2"-bromo-3"-aminophenyl)pentyl]benzamide The titled compound was prepared substantially in accordance with the procedure detailed in Example 42, using 100 mg (0.23 mmol) of subtitled compound of Preparation 25E in 2.0 mL of dimethylformamide, 61 mg (0.28 mmol) of 2-bromo-3-aminobenzoic acid, 32 mg (0.23 mmol) of HOBT, 45 mg (0.23 mmol) of EDC and 0.16 mL (1.20 mmol) of triethylamine. The crude residue was purified using flash chromatography (eluent of 2% methanol in methylene chloride) to provide 102 mg of a white solid (mp 110°–112° C.).

Yield: 71%.

$^1$H NMR (CDCl$_3$): δ7.88 (s, 1H), 7.78 (m, 2H), 7.60–7.25 (m, 9H), 6.95 (t, J=7.8 Hz, 1H), 6.78 (m, 1H), 6.52 (d, J=7.9 Hz, 1H), 6.1 (d, J=6.1 Hz, 1H), 5.90 (s, 1H), 4.52 (m, 1H), 4.21 (s, 2H), 4.15 (m, 1H), 3.50 (m, 2H), 3.00 (m, 3H), 1.49 (s, 9H).

Analysis for C$_{32}$H$_{34}$BrN$_3$O$_3$S: Calcd: C, 61.93; H, 5.52; N, 6.77; Found: C, 61.82; H, 5.83; N, 6.63.

EXAMPLE 46

[2'R-(2'R*,3'S*)]-N-t-Butyl-2-[2'-hydroxy-3'-naphth-2-ylthiomethyl-4'-aza-5'-oxo-5'-(2"-methyl-3"-hydroxyphenyl)pentyl]benzamide The titled compound was prepared substantially in accordance with the procedure detailed in Example 42, using 75 mg (0.18 mmol) of subtitled compound of Preparation 25E in 2.0 mL of dimethylformamide, 32 mg (0.21 mmol) of the subtitled compound of Preparation 23C, 24 mg (0.18 mmol) of HOBT, 34 mg (0.18 mmol) of EDC and 0.12 mL (0.88 mmol) of triethylamine. The crude residue was purified using flash chromatography (eluent of 1% methanol in methylene chloride) to provide 52 mg of a white solid (mp 119°–120° C.)

Yield: 53%.

IR (KBr): 3297, 1636, 1518, 1284, 1221, 1073, 746 cm$^{-1}$.

$^1$H NMR (CDCl$_3$): δ7.90 (s, 1H), 7.76 (m, 3H), 7.48 (m, 6H), 6.79 (m, 4H), 6.52 (d, J=9.2 Hz, 1H), 6.23 (s, 1H), 5.92 (s, 1H), 4.50 (m, 1H), 4.02 (m, 1H), 3.49 (m, 3H), 3.03 (dd, J=13.4, 10.2 Hz, 1H), 2.97 (dd, J=13.4, 3.4 Hz, 1H) 2.25 (s, 3H), 1.49 (s, 9H).

Analysis for C$_{33}$H$_{36}$N$_2$O$_4$S: Calcd: C, 71.19; H, 6.52; N, 5.03; Found: C, 70.95; H, 6.59; N, 4.87.

EXAMPLE 47

[2'R-(2'R*,3'S*)]-N-t-Butyl-2-[2'-hydroxy-3'-naphth-2-ylthiomethyl-4'-aza-5'-oxo-5'-(2"-methyl-5"-aminophenyl)pentyl]benzamide The titled compound was prepared substantially in accordance with the procedure detailed in Example 42, using 100 mg (0.23 mmol) of subtitled compound of Preparation 25E in 2.0 mL of dimethylformamide, 44 mg (0.28 mmol) of the titled compound of Preparation 29, 32 mg (0.23 mmol) of HOBT, 45 mg (0.23 mmol) of EDC and 0.16 mL (1.20 mmol) of triethylamine. The crude residue was purified using flash chromatography (eluent of 2% methanol in methylene chloride) to provide 101 mg of a white solid (mp 106°–107° C.).

Yield: 79%.

$^1$H NMR (CDCl$_3$): δ7.89 (s, 1H), 7.76 (m, 3H), 7.40–7.25 (m, 7H), 6.85 (t, J=9.0 Hz, 1H), 6.62 (d, J=7.7 Hz, 1H), 6.43 (d, J=9.0 Hz, 1H), 6.08 (d, J=5.8 Hz, 1Hz), 5.89 (s, 1H), 4.51 (m, 1H), 4.02 (m, 1H), 3.70 (br. s, 2H), 3.50 (m, 3H), 3.04 (dd, J=13.3, 10.1 Hz, 1H), 2.92 (dd, J=13.3, 3.2 Hz, 1H), 2.21 (s, 3H), 1.50 (s, 9H).

Analysis for C$_{33}$H$_{37}$N$_3$O$_3$S: Calcd: C, 71.32; H, 6.71; N, 7.56; Found: C, 71.64; H, 6.93; N, 7.45.

EXAMPLE 48

[2'R-(2'R*,3'S*)]-N-t-Butyl-2-[2'-hydroxy-3'-naphth-2-ylthiomethyl-4'-aza-5'-oxo-5'-(2"-methyl-3"-hydroxyphenyl)pentyl]-1-naphthylamide The titled compound was prepared substantially in accordance with the procedure detailed in Example 42, using 100 mg (0.21 mmol) of subtitled compound of Preparation 26D in 2.0 mL of dimethylformamide, 35 mg (0.23 mmol) of the subtitled compound of Preparation 23C, 29 mg (0.21 mmol) of HOBT, 40 mg (0.21 mmol) of EDC and 0.15 mL (1.10 mmol) of triethylamine. The crude residue was purified using flash chromatography (eluent of 1.5% methanol in methylene chloride) to provide 106 mg of a white solid (mp 115°–117° C.).

Yield: 82%.

$^1$H NMR (CDCl$_3$): δ7.90 (s, 1H), 7.76 (m, 2H), 7.53–7.24 (m, 11H), 6.B5 (t, J=7.6 Hz, 1H), 6.73 (m, 1H), 6.63 (d, J=5.7 Hz, 1H), 6.51 (d, J=9.2 Hz, 1H), 6.10 (, 1H), 5.90 (s, 1H), 4.50 (m, 1H), 4.09 (m, 1H), 3.48 (m, 2H), 3.10 (dd, J=12.9, 9.7 Hz, 1H), 2.88 (dd, J=12.9, 3.2 Hz, 1H), 2.13 (s, 3H), 1.46 (s, 9H).

Analysis for C$_{37}$H$_{38}$N$_2$O$_4$S: Calcd: C, 73.24; H, 6.31; N, 4.62; Found: C, 73.46; H, 6.70; N, 4.35.

EXAMPLE 49

[2'R-(2'R*,3'S*)]-N-t-Butyl-2-[2'-hydroxy-3'-naphth-2-ylthiomethyl-4'-aza-5'-oxo-5'-(2"-chloro-3"-aminophenyl)pentyl]-1-naphthylamide The titled compound was prepared substantially in accordance with the procedure detailed in Example 42, using 100 mg (0.21 mmol) of subtitled compound of Preparation 26D in 2.0 mL of dimethylformamide, 39 mg (0.23 mmol) of 2-chloro-3-aminobenzoic acid, (29 mg (0.21 mmol) of HOBT, 40 mg (0.21 mmol) of EDC, and 0.15 mL (1.10 mmol) of triethylamine. The crude residue was purified using flash chromatography (eluent of 1.5% methanol in methylene chloride) to provide 97 mg of a white solid (mp 110°–112° C.).

Yield: 74%.

$^1$H NMR (CDCl$_3$): δ7.90 (s, 1H), 7.81 (m, 4H), 7.75–7.21 (m, 9H), 6.95 (t, J=7.8 Hz, 1H), 6.75 (m, 1H), 6.51 (d, J=8.2 Hz, 1H), 6.12 (d, J=5.9 Hz, 1H), 5.95 (s, 1H), 4.50 (m, 1H), 4.21 (s, 2H), 4.15 (m, 1H), 3.51 (m, 2H), 3.00 (m, 3H), 1.49 (s, 9H).

Analysis for C$_{36}$H$_{36}$ClN$_3$O$_3$S: Calcd: C, 69.05; H, 5.79; N, 6.71; Found: C, 69.21; H, 5.85; N, 6.54.

EXAMPLE 50

[2'R-(2'R*,3'S*)]-N-t-Butyl-2-[2'-hydroxy-3'-naphth-2-ylthiomethyl-4'-aza-5'-oxo-5'-(3"-aminophenyl)pentyl]benzamide The titled compound was prepared substantially in accordance with the procedure detailed in Example 42, using 100 mg (0.23 mmol) of subtitled compound of Preparation 25E in 2.0 mL of dimethylformamide, 38 mg (0.28 mmol) of 3-aminobenzoic acid, 32 mg (0.23 mmol) of HOBT, 45 mg (0.23 mmol) of EDC, and 0.16 mL (1.20 mmol) of triethylamine. The crude residue was purified using flash chromatography (eluent of 2% methanol in methylene chloride) to provide 90 mg of a white solid (mp 101°–102° C.).

Yield: 72%.

$^1$H NMR (CDCl$_3$): δ7.87 (s, 1H), 7.78 (m, 2H), 7.61–7.22 (m, 10H), 6.96 (t, J=7.7 Hz, 1H), 6.76 (m, 1H), 6.52 (d, J=7.8 Hz, 1H), 6.04 (d, J=6.1 Hz, 1H), 5.91 (s, 1H), 4.5 (m, 1H), 4.20 (s, 2H), 4.15 (m, 1H), 3.50 (m, 2H), 3.01 (m, 3H), 1.49 (s, 9H).

Analysis for C$_{32}$H$_{35}$N$_3$O$_3$S: Calcd: C, 70.95; H, 6.51; N, 7.76; Found: C, 71.21; H, 6.72; N, 7.72.

EXAMPLE 51

[2'R-(2'R*,3'S*)]-N-t-Butyl-2-[2'-hydroxy-3'-naphth-2-ylthiomethyl-4'-aza-5'-oxo-5'-(3"-hydroxyphenyl)pentyl]benzamide The titled compound was prepared substantially in accordance with the procedure detailed in Example 42, using 50 mg (0.12 mmol) of subtitled compound of Preparation 25E in 2.0 mL of dimethylformamide, 20 mg (0.14 mmol) of 3-hydroxybenzoic acid, 16 mg (0.12 mmol) of HOBT, 22 mg (0.12 mmol) of EDC, and 0.081 mL (0.58 mmol) of triethylamine. The crude residue was purified using flash chromatography (eluent of 50% ethyl acetate in hexane) to provide 36 mg of a white solid (mp 125°–128° C.).

Yield: 57%.

$^1$H NMR (CDCl$_3$): δ7.87 (s, 1H), 7.73 (m, 3H), 7.20–7.50 (m, 7H), 6.95–7.15 (m, 4H), 6.80 (m, 1H), 6.80 (m, 1H), 6.50 (s, 1H), 6.30 (m, 1H), 5.95 (s, 1H), 4.53 (m, 1H), 4.10 (m, 1H), 3.45 (m, 2H), 3.03 (dd, J=13.4, 10.5 Hz, 1H), 2.90 (dd, J=13.4, 3.5 Hz, 1H), 1.46 (s, 9H).

HR MS for C$_{32}$H$_{34}$N$_2$O$_4$S: Calcd: m/e 675.1294; Found: m/e 675.1311.

EXAMPLE 52

[2'R-(2'R*,3'S*)]-N-t-Butyl-2-[2'-hydroxy-3'-naphth-2-ylthiomethyl-4'-aza-5'-oxo-5'-(2"-methylphenyl)pentyl]benzamide The titled compound was prepared substantially in accordance with the procedure detailed in Example 42, using 50 mg (0.12 mmol) of subtitled compound of Preparation 25E in 2.0 mL of dimethylformamide, 19 mg (0.14 mmol) of 2-methylbenzoic acid, 16 mg (0.12 mmol) of HOBT, 22 mg (0.12 mmol) of EDC, and 0.081 mL (0.58 mmol) of triethylamine. The crude residue was purified using flash chromatography (eluent of 40% ethyl acetate in hexane) to provide 33 mg of a white solid (m.p. 85°–87° C.).

Yield: 52%.

$^1$H NMR (CDCl$_3$): δ7.89 (d, J=1.0 Hz, 1H), 7.76 (m, 3H), 7.15–7.52 (m, 11H), 7.02 (t, J=7.4 Hz, 1H), 6.48 (d, J=9.0 Hz, 1H), 6.08 (d, J=6.1 Hz, 1H), 5.89 (s, 1H), 4.53 (m, 1H), 4.02 (m, 1H), 3.48 (d, J=6.8 Hz, 2H), 3.00 (dd, J=13.4, 10.2 Hz, 1H), 2.92 (dd, J=13.4, 3.6 Hz, 1H), 2.46 (s, 3H), 1.45 (s, 9H).

HR MS for C$_{33}$H$_{36}$N$_2$O$_3$S: Calcd: m/e 673.1501; Found: m/e 673.1504.

EXAMPLE 53

[2'R-(2'R*,3'S*)]-N-t-Butyl-2-[2'-hydroxy-3'-naphth-2-ylthiomethyl-4'-aza-5'-oxo-5'-(2"-methyl-3",5"-diaminophenyl)pentyl]benzamide The titled compound was prepared substantially in accordance with the procedure detailed in Example 42, using 50 mg (0.12 mmol) of subtitled compound of Preparation 25E in 2.0 mL of dimethylformamide, 23 mg (0.14 mmol) of 2-methyl-3,5-diaminobenzoic acid, 16 mg (0.12 mmol) of HOBT, 22 mg (0.12 mmol) of EDC, and 0.081 mL (0.58 mmol) of triethylamine. The crude oil was purified by flash chromatography (eluent of 5% methanol in methylene chloride) to provide 28 mg of an off-white powder (m.p. 125°–128° C.).

Yield: 42%.

$^1$H NMR (CDCl$_3$): δ7.90 (d, J=1.2 Hz, 1H), 7.77 (m, 3H), 7.20–7.53 (m, 10H), 6.35 (d, J=9.3 Hz, 1H), 6.15 (br.m, 1H), 6.01 (d, J=2.1 Hz, 1H), 5.92 (s, 1H), 5.83 (d, J=2.1 Hz, 1H), 4.50 (m, 1H), 3.96 (m, 1H), 3.50 (m, 4H), 3.03 (dd, J=13.4, 10.2 Hz, 1H), 2.91 (dd, J=13.4, 3.5 Hz, 1H), 2.10 (s, 3H), 1.47 (s, 9H).

HR MS for C$_{33}$H$_{38}$N$_4$O$_3$S: Calcd: m/e 703.1719; Found: m/e 703.1733.

EXAMPLE 54

[2'R-(2'R*,3'S*)]-N-t-Butyl-2-[2'-hydroxy-3'-naphth-2-ylthiomethyl-4'-aza-5'-oxo-5'-(2",2"-dichlorophenyl)pentyl]benzamide The titled compound was prepared substantially in accordance with the procedure detailed in Example 42, using 75 mg (0.18 mmol) of subtitled compound of Preparation 25E in 1.0 mL of dimethylformamide, 40 mg (0.21 mmol) of 2,3-dichlorobenzoic acid, 24 mg (0.18 mmol) of HOBT, 34 mg (0.18 mmol) of EDC, and 0.12 mL (0.88 mmol) of triethylamine. The crude oil was purified using flash chromatography (gradient eluent of 25–50% ethyl acetate in hexane) to provide 75 mg of a white solid (m.p. 116°–119° C.).

Yield: 74.

$^1$H NMR (CDCl$_3$): δ7.90 (s, 1H), 7.75 (m, 3H), 7.20–7.52 (m, 9H), 7.13 (dd, J=7.9, 1.2 Hz, 1H), 7.00 (t, J=7.8 Hz, 1H), 6.64 (d, J=9.9 Hz, 1H), 5.88 (br.s, 1H), 4.52 (m, 1H), 4.03 (m, 1H), 3.50 (d, J=6.0 Hz, 2H), 3.00 (m, 2H), 1.44 (s, 9H).

Analysis for C$_{32}$H$_{32}$Cl$_2$N$_2$O$_3$S: Calcd: C, 64.53; H, 5.42; N, 4.70; Found: C, 64.54; H, 5.50; N, 4.73.

EXAMPLE 55

[2'R-(2'R*,3'S*)]-N-t-Butyl-2-[2'-hydroxy-3'-naphth-2-ylthiomethyl-4'-aza-5'-oxo-5'-(2"-chloro-5"-aminophenyl)pentyl]benzamide The titled compound was prepared substantially in accordance with the procedure detailed in Example 42, using 75 mg (0.18 mmol) of subtitled compound of Preparation 25E in 1.0 mL of dimethylformamide, 36 mg (0.21mmol) of the titled compound of Preparation 29, 24 mg (0.18 mmol) of HOBT, 34 mg (0.18 mmol) of EDC and 0.12 mL (0.88 mmol) of triethylamine. The crude oil was purified using flash chromatography (eluent of 50% ethyl acetate in hexane) to provide 90 mg of a white solid (m.p. 109°–110° C.).

Yield: 90%.

$^1$H NMR (CDCl$_3$): δ7.89 (s, 1H), 7.75 (m, 3H), 7.21–7.52 (m, 10H), 7.04 (d, J=8.3 Hz, 1H), 6.73 (m, 1H), 6.55 (m, 2H), 5.92 (br.s, 1H), 4.50 (m, 1H), 3.99 (m, 1H), 3.52 (d, J=5.6 Hz, 2H), 3.02 (m, 2H), 1.45 (s, 9H).

Analysis for C$_{32}$H$_{34}$ClN$_3$O$_3$S: Calcd: C, 66.71; H, 5.95; N, 7.29; Found: C, 66.94; H, 6.34; N, 6.92.

EXAMPLE 56

[2'R-(2'R*,3'S*)]-N-t-Butyl-2-[2'-hydroxy-3'-naphth-2-ylthiomethyl-4'-aza-5'-oxo-5'-(2"-chloro-3"-hydroxyphenyl)pentyl]benzamide The titled compound was prepared substantially in accordance with the procedure detailed in Example 42, using 75 mg (0.18 mmol) of subtitled compound of Preparation 25E in 1.0 mL of dimethylformamide, 36 mg (0.21 mmol) of the titled compound of Preparation 14, 24 mg (0.18 mmol) of HOST, 34 mg (0.18 mmol) of EDC, and 0.12 mL (0.88 mmol) of triethylamine. The crude oil was purified using flash chromatography (gradient eluent of 25–50% ethyl acetate in hexane) to provide 71 mg of a white solid (m.p. 104°–105° C.)

Yield: 71%

$^1$H NMR (CDCl$_3$): δ7.90 (d, J=1.0 Hz, 1H), 7.7 (m, 3H), 7.19–7.52 (m, 8H), 7.00 (m, 2H), 6.87 (m, 1H), 6.64 (d, J=9.1 Hz, 1H), 5.89 (s, 1H), 4.52 (m, 1H), 4.04 (m, 1H), 3.50 (d, J=6.1 Hz, 1H), 3.05 (dd, J=13.4, 10.2 Hz, 2H), 2.94 (dd, J=13.4, 3.6 Hz, 1H), 1.45 (s, 9H).

Analysis for C$_{32}$H$_{33}$ClN$_2$O$_4$S: Calcd: C, 66.59; H, 5.76; N, 4.85; Found: C, 66.64; H, 5.90; N, 4.93.

EXAMPLE 57

[2'R-(2'R*,3'S*)]-N-t-Butyl-2-[2'-hydroxy-3'-naphth-2-ylthiomethyl-4'-aza-5'-oxo-5'-(isoquinolin-5"-yl)pentyl]benzamide To a solution of 0.40 g (0.95 mmol) of the subtitled compound of Preparation 25E and 134μL (1.22 mmol) of N-methyl morpholine in 15 mL of tetrahydrofuran, was added 0.45 g (1.33 mmol) of the subtitled compound of Preparation 30C. The resultant reaction mixture was reacted for approximately 8 hours and then diluted with ethyl acetate. The resultant layers were separated and the organic layer was washed sequentially with water, and brine, and then concentrated to provide a crude material. This crude material was purified using flash chromatography (silica; eluent of 4% methanol in methylene chloride) to provide 0.53 g of a white solid (m.p. 109°–112° C.).

Yield: 97%.

$^1$H NMR (CDCl$_3$): δ9.19 (s, 1H), 8.50 (d, J=4.6 Hz, 1H), 8.23 (d, J=5.9 Hz, 1H), 7.92 (m, 2H), 7.76 (m, 3H), 7.56 (m, 3H), 7.43 (m, 3H), 7.32 (m, 2H), 7.24 (m, 1H), 6.88 (d, J=9.0 Hz, 1H), 6.05 (br.s, 1H), 5.93 (s, 1H), 4.64 (m, 1H), 4.12 (m, 1H) 3.51 (d, J=6.3 Hz, 2H), 3.01 (m, 2H), 1.40 (s, 9H).

IR (neat film): 3428, 3019, 2978, 1647, 1514, 1215, 758 cm$^{-1}$.

HR MS for C$_{35}$H$_{36}$N$_3$O$_3$S (MH$^+$): Calcd: 578.2477; Found: 578.2468.

Analysis for C$_{35}$H$_{35}$N$_3$O$_3$S.0.17 CH$_2$Cl$_2$: Calcd: C, 71.33; H, 6.02; N, 7.10; S, 5.41; Found: C, 71.35; H, 6.00; N, 7.09; S, 5.44.

EXAMPLE 58

[2'R-(2'R*,3'S*)]-N-t-Butyl-2-[2"-hydroxy-3'-naphth-2-ylthiomethyl-4'-aza-5'-oxo-5'-(1",2",3",4"-tetrahydroisoquinolin-5"-yl)pentyl]benzamide To a solution of 0.15 g (0.26 mmol) of the titled compound of Example 57 in 6 mL of acetic acid, was added 0.08 g (1.27 mmol) of sodium cyanoborohydride. The resultant reaction mixture was reacted for approximately 1 hour, and then was quenched by the addition of a saturated solution of sodium bicarbonate. The desired compound was then extracted using ethyl acetate and the organic extracts were washed sequentially with water, and brine, and then concentrated under reduced pressure to provide a foam. This foam was purified using flash chromatography (silica; eluent of 4% methanol in methylene chloride) to provide 0.10 of a white amorphous solid (m.p. 197°–199° C.).

Yield: 66%.

$^1$H NMR (CDCl$_3$): δ7.85 (s, 1H), 7.75 (m, 3H), 7.50–7.20 (m, 7H), 7.06 (m, 1H), 6.95 (m, 2H), 6.59 (d, J=9.1 Hz, 1H), 6.02 (s, 1H), 4.48 (br.s, 1H), 4.00 (br.s, 1H), 3.98 (s, 2H), 3.45 (m, 2H), 3.01 (s, 1H), 2.98 (d, J=6.0 Hz, 3H), 2.89 (m, 3H), 1.44 (s, 9H), OH not observed.

IR (neat film): 3418, 3281, 3019, 1632, 1516, 1215, 756;

HR MS for C$_{35}$ H$_{40}$N$_3$O$_3$S: Calcd: 582.2790; Found: 582.2792.

Analysis for C$_{35}$H$_{35}$N$_3$O$_3$S.0.17 CH$_2$Cl$_2$: Calcd: C, 70.85; H, 6.65; N, 7.05; S, 5.38; Found: C, 70.85; H, 6.74; N, 7.16; S, 5.42.

EXAMPLE 59

[2'R-(2'R*,3'S*)]-N-t-Butyl-2-[2'-hydroxy-3'-naphth-2-ylthiomethyl-4'-aza-5'-oxo-5'-[2-N(methyl)-1",2",3"4"-tetrahydroisoquinolin-5"-yl)pentyl]benzamide To a hot (60° C.) solution of 0.11 g (0.19 mmol) of the titled compound of Example 57 in 3 mL of tetrahydrofuran, was added 53 mg (1.40 mmol) of sodium borohydride and 75 μL of formic acid. After approximately 1 hour, the reaction mixture was quenched by the addition of a saturated sodium bicarbonate solution. The desired compound was then extracted using ethyl acetate and the organic extracts were washed sequentially with water, and brine, and then concentrated to provide a foam. This foam was purified using flash chromatography (silica; eluent of 5% methanol in methylene chloride) to provide 0.05 g of a white amorphous solid (m.p. 110°–113° C.).

Yield: 44%.

$^1$H NMR (CDCl$_3$): δ7.86 (s, 1H), 7.75 (m, 3H), 7.50–7.20 (m, 7H), 7.00 (m, 3H), 6.46 (d, J=9.0 Hz, 1H), 6.13 (d, J=5.0 Hz, 1H), 5.96 (s, 1H), 4.45 (m, 1H), 3.97 (m, 1H), 3.54 (s, 2H), 3.46 (m, 2H), 3.20–2.90 (m, 4H), 2.60 (t, J=5.9 Hz, 2H), 2.40 (s, 3H), 1.44 (s, 9H).

IR (neat film): 3432, 3019, 2976, 1645, 1516, 1215, 756 cm$^{-1}$.

HRMS for C$_{36}$H$_{42}$N$_3$O$_3$S (MH$^+$): Calcd: 596.2947; Found: 596.2939.

Analysis for C$_{36}$H$_{41}$N$_3$O$_3$S.0.32 CH$_2$Cl$_2$: Calcd: C, 70.02; H, 6.74; N, 6.75; S, 5.15; Found: C, 70.03; H, 6.74; N, 6.81; S, 5.24.

EXAMPLE 60

[2'R-(2'R*,3'S*)]-N-t-Butyl-2-[2'-hydroxy-3'-phenylmethyl-4"-aza-5"-oxo-5'-(1",2",3",4"-tetrahydroisoquinolin-5"-yl)pentyl]benzamide The titled compound was prepared substantially in accordance with the procedure detailed in Example 58.

$^1$H NMR (CDCl$_3$): δ7.42 (m, 10H), 7.00 (m, 3H), 6.28 (d, J=9.4 Hz, 1H), 5.95 (s, 1H), 4.60 (m, 1H), 3.95 (bs, 3H), 2.80–3.20 (m, 7H), 2.62 (m, 1H), 1.47 (s, 9H).

Analysis for $C_{31}H_{37}N_3O_3$·MeOH: Calcd: C, 72.29; H, 7.77; N, 7.90; Found: C, 72.61; H, 7.58; N, 7.61.

EXAMPLE 61

[2'R-(2'R*,3'S*)]-N-t-Butyl-2-[2'-hydroxy-3'-naphth-2-ylthiomethyl-4'-aza-5'-oxo-5'-(naphth-1"-yl)pentyl]benzamide To a cold (0° C.) solution of 100 mg (0.23 mmol) of the subtitled compound of Preparation 25E in 2.0 mL of dimethylformamide, was added 45 mg (0.26 mmol) of naphthalene-1-carboxylic acid, 32 mg (0.23 mmol) of HOST, 45 mg (0.23 mmol) of EDC and 0.16 mL (1.20 mmol) of triethylamine. The resultant reaction mixture was reacted for approximately 1 hour at 0° C. and 16 hours at room temperature, then diluted with 10 mL of ethyl acetate. The resultant mixture was washed with water, dried over sodium sulfate, filtered and then concentrated under reduced pressure to provide a residue. This residue was purified using flash chromatography (eluent of 1% methanol in methylene chloride to provide 82 mg of a white solid (m.p. 92°–95° C.).

Yield: 63%.

$^1$H NMR (CDCl$_3$): δ8.35 (br.s, 1H), 7.95–7.68 (m, 7H), 7.62–7.30 (m, 10H), 6.71 (d, J=8.9 Hz, 1H), 6.10 (d, 6.2 Hz, 1H), 5.89 (s, 1H), 4.61 (m, 1H), 4.26 (m, 1H), 3.51 (d, J=8.9 Hz, 2H), 3.0 (m, 2H), 1.51 (s, 9H).

Analysis for $C_{36}H_{36}N_2O_3S$: Calcd: C, 74.97; H, 6.29; N, 4.86; Found: C, 75.13; H, 6.45; N, 4.49.

EXAMPLE 62

[2'R-(2'R*,3'S*)]-N-t-Butyl-2-[2'-hydroxy-3'-naphth-2-ylthiomethyl-4'-aza-5'-oxo-5'-(indol-4"-yl)pentyl]benzamide The titled compound was prepared and substantially in accordance with the procedure detailed in Example 61, using 100 mg (0.23 mmol) of the subtitled compound of Preparation 25E, 42 mg (0.26 mmol) of the titled compound of Preparation 32, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1% methanol in methylene chloride) to provide 43 mg of a white solid (m.p. 109°–110° C.).

Yield: 35%.

$^1$H NMR (CDCl$_3$): δ8.45 (br.s, 1H), 7.90 (s, 1H), 7.76 (m, 3H), 7.57–7.23 (m, 10H), 7.19–6.89 (m, 3H), 6.24 (d, J=6.2 Hz, 1H), 5.97 (s, 1H), 4.63 (m, 1H), 4.13 (m, 1H), 3.51 (m, 2H), 3.01 (m, 2H), 1.49 (s, 9H),

Analysis for $C_{34}H_{36}N_3O_3S$: Calcd: C, 72.18; H, 6.24; N. 7.43; Found: C, 72.31; H, 6.37; N, 7.22.

EXAMPLE 63

[2'R-(2'R*,3'S*)]-N-t-Butyl-2-(2'-hydroxy-3'-naphth-2-ylthiomethyl-4'-aza-5'-oxo-5'-(quinolin-5"-yl)pentyl]benzamide The titled compound was prepared substantially in accordance with the procedure detailed in Example 57, using 0.060 g (0.15 mmol) of the subtitled compound of Preparation 25E, 42 μL(0.38 mmol) of N-methylmorpholine, and 0.074 g (0.38 mmol) of the titled compound of Preparation 31 in 2 mL of tetrahydrofuran to provide 0.045 g of the white solid.

Yield: 54%.

$^1$H NMR (CDCl$_3$): δ8.85 (m, 1H), 8.75 (m, 1H), 8.75 (d, J=8.21 Hz, 1H), 8.07 (m, 2H), 7.95 (s, 1H), 7.76 (m, 3H), 7.64 (m, 2H), 7.54 (m, 2H), 7.44 (m, 2H), 7.38 (m, 3H), 7.25 (m, 1H), 4.88 (s, 2H), 4.45 (m, 1H), 4.05 (m, 1H), 3.69 (dd, J=14, 3.09 Hz, 1H) 3.23 (m, 1H), 3.05 (m, 2H), 1.32 (s, 9H).

IR (KBr): 3485, 3429, 3279, 3061, 2964, 1638, 1543, 1454, 1364, 1319, 1219, 1072, 806, 746 cm$^{-1}$.

HR MS for $C_{35}H_{36}N_3O_3S$ (MH$^+$): Calcd: 578.2477; Found: 578.2491.

Analysis for $C_{35}H_{35}N_3O_3S$·0.6H$_2$O: Calcd: C, 71.42; H. 6.20; N, 7.14; S, 5.45; Found: C, 71.44; H, 6.16; N, 7.19; S, 5.41.

EXAMPLE 64

[2'R-(2'R*,3'S*)]-N-t-Butyl-2-[2'-hydroxy-3'-naphth-2-ylthiomethyl-4'-aza-5'-oxo-5'-(1",2",3",4"-tetrahydroquinolin-5"-yl)pentyl]benzamide The titled compound was prepared substantially in accordance with the procedure detailed in Example 58, using 0.023 g (0.36 mmol) of sodium cyanoborohydride, 0.041 g (0.07 mmol) of the titled compound of Example 63, and 2 mL of acetic acid to provide 0.024 g of a white amorphous solid.

Yield: 60%.

$^1$H NMR (CDCl$_3$): δ7.88 (s, 1H), 7.75 (m, 3H), 7.42 (m, 6H), 6.79 (t, J=7.73 Hz, 1H), 6.54 (d, J=7.28 Hz, 1H), 6.44 (d, J=8.15 Hz, 2H), 6.10 (br. 1H), 5.91 (br.s, 1H), 4.45 (m, 1H), 4.05 (m, 1H), 3.48 (m, 2H), 3.24 (t, J=5.50 Hz, 2H), 2.89 (m, 4H) 1.85 (m, 2H), 1.46 (s, 9H).

IR (KBr): 3450, 2972, 1638, 1618, 1591, 1512, 1454, 1309, 1119, 1134, 1086, 814, 698, 621 cm$^{-1}$.

HR MS for $C_{35}H_{40}N_3O_3S$ (MH$^+$): Calcd: 582.2790; Found: 582.2792.

EXAMPLE 65

[2'R-(2'R*,3'S*)]-N-t-Butyl-2-[2'-hydroxy-3'-naphth-2-ylthiomethyl-4'-aza-5'-oxo-5'-(indolin-4"-yl)pentyl]benzamide The titled compound was prepared substantially in accordance with the procedure detailed in Example 61, using 100 mg (0.23 mmol) of the subtitled compound of Preparation 25E, 412 mg (0.26 mmol) of the titled compound of Preparation 32, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1.5% methanol in methylene chloride) to provide 12 mg of a white solid (m.p. 83°–84° C.).

Yield: 9%.

$^1$H NMR (CDCl$_3$): δ7.99 (s, 1H), 7.76 (m, 3H), 7.69–7.23 (m, 10H), 7.10 (d, J=8.8 Hz, 1H), 6.60 (d, J=8.9 Hz, 1H), 5.99 (d, J=6.2 Hz, 1H), 5.89 (s, 1H), 4.53 (m, 1H), 4.11 (m, 1H), 3.44 (m, 6H), 3.01 (m, 2H), 1.49 (s, 9H).

Analysis for $C_{34}H_{37}N_3O_3S$: Calcd: C, 71.92; H, 6.57; N, 7.40; Found: C, 72.21; H, 6.72; N, 7.26.

EXAMPLE 66

[2'R-(2'R*,3S*)]-N-t-Butyl-2-[2'-hydroxy-3'-naphth-2-ylthiomethyl-4'-aza-5'-oxo-5'-(quinolin-4"-yl)pentyl]benzamide The titled compound was prepared substantially in accordance with the procedure detailed in Example 61, using 100 mg (0.23 mmol) of the subtitled compound of Preparation 25E, 45 mg (0.26 mmol) of quinoline-4-carboxylic acid, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1.5% methanol in methylene chloride) to provide 42 mg of a white solid (m.p. 89°–92° C.).

Yield: 32%.

$^1$H NMR (CDCl$_3$): δ8.59 (s, 1H), 8.33 (d, J=7.9 Hz, 1H), 8.09 (d, J=8.4 Hz, 1H), 7.93 (s, 1H), 7.80–7.71 (m, 4H), 7.69–7.25 (m, 8H), 7.15 (s, 1H), 6.88 (d, J=8.4 Hz, 1H), 5.99 (s, 1H), 5.85 (s, 1H), 4.63 (m, 1H), 4.21 (m, 1H), 3.51 (d, 6.2 Hz, 2H), 3.02 (m, 2H), 1.39 (s, 9H).

Analysis for C$_{35}$H$_{35}$N$_3$ O$_3$S: Calcd: C, 72.76; H, 6.11; N, 7.27; Found: C, 72.91; H, 6.33; N, 7.36.

EXAMPLE 67

[2'R-(2'R*,3'S*)]-N-t-Butyl-2-[2'-hydroxy-3'-naphth-2-hiomethyl-4'-aza-5'-oxo-5'-(2"-methyl-3"-nitrophenyl)pentyl]benzamide The titled compound was prepared substantially in accordance with the Procedure detailed in Example 61, using 100 mg (0.23 mmol) of the subtitled compound of Preparation 25E, 47 mg (0.26 mmol) of 2-methyl-3-nitrobenzoic acid, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1% methanol in methylene chloride) to provide 100 mg of a white solid (m.p. 80°–81° C.).

Yield: 74%.

$^1$H NMR (CDCl$_3$): δ7.89 (s, 1H), 7.75 (m, 3H), 7.65–7.25 (m, 9H), 7.10 (d, J=7.9 Hz, 1H), 6.63 (d, J=8.9 Hz, 1H), 5.97 (d, J=6.0 Hz, 1H), 5.87 (s, 1H), 4.53 (m, 1H), 4.11 (m, 1H), 3.44 (m, J=6.3 Hz, 2H), 3.03 (dd, J=13.3, 10.2 Hz, 1H), 2.28 (dd, J=13.5, 2.8 Hz, 1H), 2.53 (s, 3H), 1.47 (s, 9H).

Analysis for C$_{33}$H$_{35}$N$_3$ O$_5$S: Calcd: C, 67.67; H, 6.02; N, 7.17; Found: C, 67.83; H, 5.93; N, 7.05.

EXAMPLE 68

[2'R-(2'R*,3'S*)]-N-t-Butyl-2-[2'-hydroxy-3'-naphth-2-ylthiomethyl-4'-aza-5'-oxo-5'-(3"-nitro-6"-methylphenyl)pentyl]benzamide The titled compound was prepared substantially in accordance with the procedure detailed in Example 61, using 100 mg (0.23 mmol) of the subtitled compound of Preparation 25E, 47 mg (0.26 mmol) of 2-methyl-5-nitrobenzoic acid, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1% methanol in methylene chloride) to provide 102 mg of a white solid (m.p. 85°–88° C.).

Yield: 75%.

$^1$H NMR (CDCl$_3$): δ8.17 (s, 1H), 8.07 (d, J=8.4 Hz, 1H), 7.78 (m, 2H), 7.59–7.22 (m, 10H), 6.71 (d, J=8.9 Hz, 1H), 6.03 (d, J=6.1 Hz, 1H), 5.9 (s, 1H), 4.52 (m, 1H), 4.13 (m, 1H), 3.45 (d, J=6.2 Hz, 2H), 3.03 (dd, J=13.3, 9.61 Hz, 1H), 2.9 (dd, J=13.3, 3.72 Hz, 1H), 2.55 (s, 3H), 1.43 (s, 9H).

Analysis for C$_{33}$H$_{35}$N$_3$O$_5$S: Calcd: C, 67.67; H, 6.02; N, 7.17; Found: C, 67.92; H, 6.22; N, 7.02.

EXAMPLE 69

[2'R(2'R*,3'S*)]-N-t-Butyl-2-[2'-hydroxy-3'-naphth-2-ylthiomethyl-4'-aza-5'-oxo-5'-(1"-N(methyl)indol-4"-yl)pentyl]benzamide The titled compound was prepared substantially in accordance with the procedure detailed in Example 61, using 100 mg (0.23 mmol) of the subtitled compound of Preparation 25E, 46 mg (0.26 mmol) of 1-N-methyl-4-carboxylic acid indoline, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 1% methanol in methylene chloride) to provide 42 mg of a white solid (m.p. 86°–89° C.).

Yield: 31%.

$^1$H NMR (CDCl$_3$): δ7.88 (s, 1H), 7.79–7.65 (m, 3H), 7.53–6.95 (m, 13H), 6.22 (d, J=6.3 Hz, 1H), 5.99 (s, 1H), 4.67 (m, 1H), 4.13 (m, 1H), 3.75 (s, 3H), 3.51 (m, 2H), 3.03 (m, 2H), 1.49 (s, 9H).

Analysis for C$_{35}$H$_{35}$N$_3$O$_3$S: Calcd: C, 72.51; H, 6.43; N, 7.25; Found: C, 72.83; H, 6.51; N, 7.15.

EXAMPLE 70

[2'R-(2'R*,3'S*)]-N-t-Butyl-2-[2'-hydroxy-3'-naphth-2-ylthiomethyl-4'-aza-5'-oxo-5'-(2"-methyl-3"-dihydroxyphenyl)pentyl]benzamide The titled compound was prepared substantially in accordance with the procedure detailed in Example 61, using 100 mg (0.23 mmol) of the subtitled compound of Preparation 25E, 44 mg (0.26 mmol) of the subtitled compound of Preparation 33C, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 2.5% methanol in methylene chloride) to provide 76 mg of a white solid (m.p. 121°–123° C.)

Yield: 58%.

$^1$H NMR (CDCl$_3$): δ7.89 (s, 1H), 7.75 (m, 2H), 7.55–7.22 (m, 10H), 6.85 (t, J=7.9 Hz, 1H), 6.72 (m, 2H), 6.61 (d, J=5.7 Hz, 1H), 6.50 (d, J=9.4 Hz, 1H), 6.13 (s, 1H), 5.92 (s, 1H), 4.51 (m, 1H), 4.09 (m, 1H), 3.51 (m, 2H), 3.12 (dd, J=13.1, 10 Hz, 1H), 2.87 (dd, J=13.1, 3.1 Hz, 1H), 2.13 (s, 3H), 1.46 (s, 9H).

Analysis for C$_{33}$H$_{36}$N$_2$O$_5$S: Calcd: C, 69.21; H, 6.34; N, 4.89; Found: C, 69.43; H, 6.72; N, 4.72.

EXAMPLE 71

[2'R-(2'R*,3'S*)]-N-t-Butyl-2-[2'-hydroxy-3'-naphth-2-ylthiomethyl-4'-aza-5'-oxo-5'-(2"-chloro-4"-aminophenyl)pentyl]benzamide The desired title compound was prepared substantially in accordance with the procedure detailed in Example 61, using 100 mg (0.23 mmol) of the subtitled compound of Preparation 25E, 45 mg (0.26 mmol) of 2-chloro-4-aminobenzoic acid, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 2% methanol in methylene chloride) to provide 92 mg of a white solid (m.p. 102°–104° C.).

Yield: 69%.

$^1$H NMR (CDCl$_3$): δ7.88 (s, 1H), 7.77 (m, 2H), 7.61–7.23 (m, 9H), 6.95 (t, J=7.7 Hz, 1H), 6.75 (m, 1H), 6.51 (d, J=7.8 Hz, 1H), 6.06 (d, J=6.1 Hz, 1H). 5.90 (s, 1H), 4.51 (m, 1H), 4.20 (s, 2H), 4.12 (m, 1H), 3.50 (m, 2H), 3.01 (m, 3H), 1.48 (s, 9H).

Analysis for C$_{32}$H$_{34}$ClN$_3$O$_3$S: Calcd: C, 66.71; H, 5.95; N, 7.29; Found: C, 66.92; H, 5.97; N, 7.16.

EXAMPLE 72

[2'R-(2'R*,3'S*)]-N-t-Butyl-2-[2'-hydroxy-3'-naphth-2-ylthiomethyl-4'-aza-5'-oxo-5'-(2"-methyl-5"-hydroxyphenyl)pentyl]benzamide The desired titled compound was prepared substantially in accordance with the procedure detailed in Example 61, using 100 mg (0.23 mmol) of the subtitled compound of Preparation 25E, 47 mg (0.26 mmol) of the subtitled compound of Preparation 29B, 32 mg (0.23 mmol) of HOBT, 40 mg (0.23 mmol) of EDC, and 0.16 mL (1.20 mmol) of triethylamine in 2.0 mL of dimethylformamide. The crude residue was purified using flash chromatography (eluent of 3% methanol in methylene chloride) to provide 86 mg of a white solid (m.p. 104°–106° C.).

Yield: 67%.

$^1$H NMR (CDCl$_3$): δ7.95 (s, 1H), 7.72 (m, 3H), 7.60–7.22 (m, 9H), 6.92 (t, J=7.5 Hz, 1H), 6.72 (m, 1H), 6.50 (d, J=7.6 Hz, 1H), 5.96 (s, 1H), 5.90 (s, 1H), 4.50 (m, 1H), 4.15 (m, 1H), 4.02 (m, 1H), 2.51 (m, 2H), 3.01 (m, 3H), 2.36 (s, 3H), 1.45 (s, 9H).

Analysis for C$_{33}$H$_{37}$N$_3$O$_3$S: Calcd: C, 71.32; H, 6.71; N, 7.56; Found: C, 71.56; H, 6.76; N, 7.52.

EXAMPLE 73

[2'R-(2'R*,3'S*)]-N-t-Butyl-2-[2'-hydroxy-3'-naphth-2-ylthiomethyl-4'-aza-5'-oxo-5'-(3''-hydroxy-4''-aminophenyl)pentyl]benzamide The desired titled compound was prepared substantially in accordance with the procedure detailed in Example 61, using 100 mg (0.23 mmol) of the subtitled compound of Preparation 25E, 40 mg (0.26 mmol) of 3-hydroxy-4-aminobenzoic acid, 32 mg (0.23 mmol) of HOBT, 45 mg (0.23 mmol) of EDC, and 0.16 mL (1.20 mmol) of triethylamine in 2.0 mL of dimethylformamide. The crude residue was purified using flash chromatography (eluent of 3% methanol in methylene chloride) to provide 43 mg of a white solid (m.p. 119°–122° C.).

Yield: 34%.

$^1$NMR (CDCl$_3$): δ7.91 (s, 1H), 7.75 (m, 2H), 7.60–7.20 (m, 10H), 5.96 (t, J=7.9 Hz, 1H), 6.75 (m, 1H), 6.55 (d, J=7.8 Hz, 1H), 6.1 (s, 1H), 5.95 (s, 1H), 4.51 (m, 1H), 4.23 (s, 2H), 4.12 (m, 1H). 3.52 (m, 2H), 3.00 (m, 3H), 1.48 (s, 9H).

Analysis for C$_{32}$H$_{35}$N$_3$O$_4$S: Calcd: C, 68.92; H, 6.33; N, 7.53; Found: C, 69.12; H, 6.57; N. 7.32.

Reaction Scheme III shows the structures of compounds in Examples 74 A through L below.

Reaction Scheme III

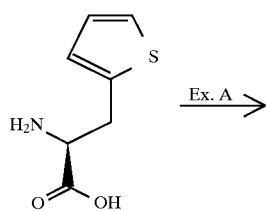

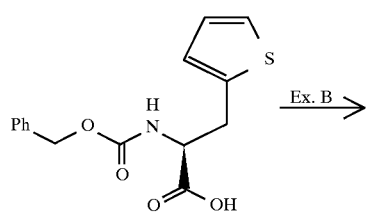

-continued
Reaction Scheme III

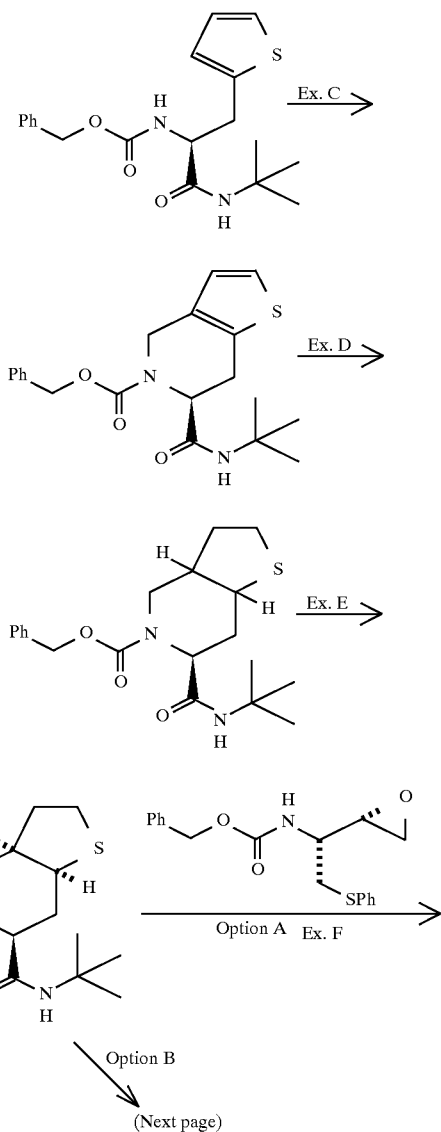

Option B (Next page)

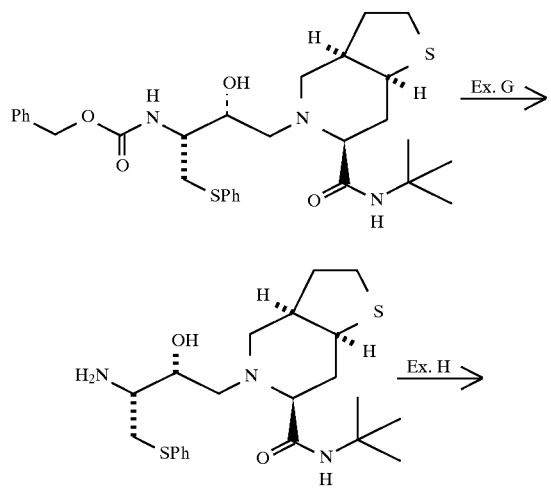

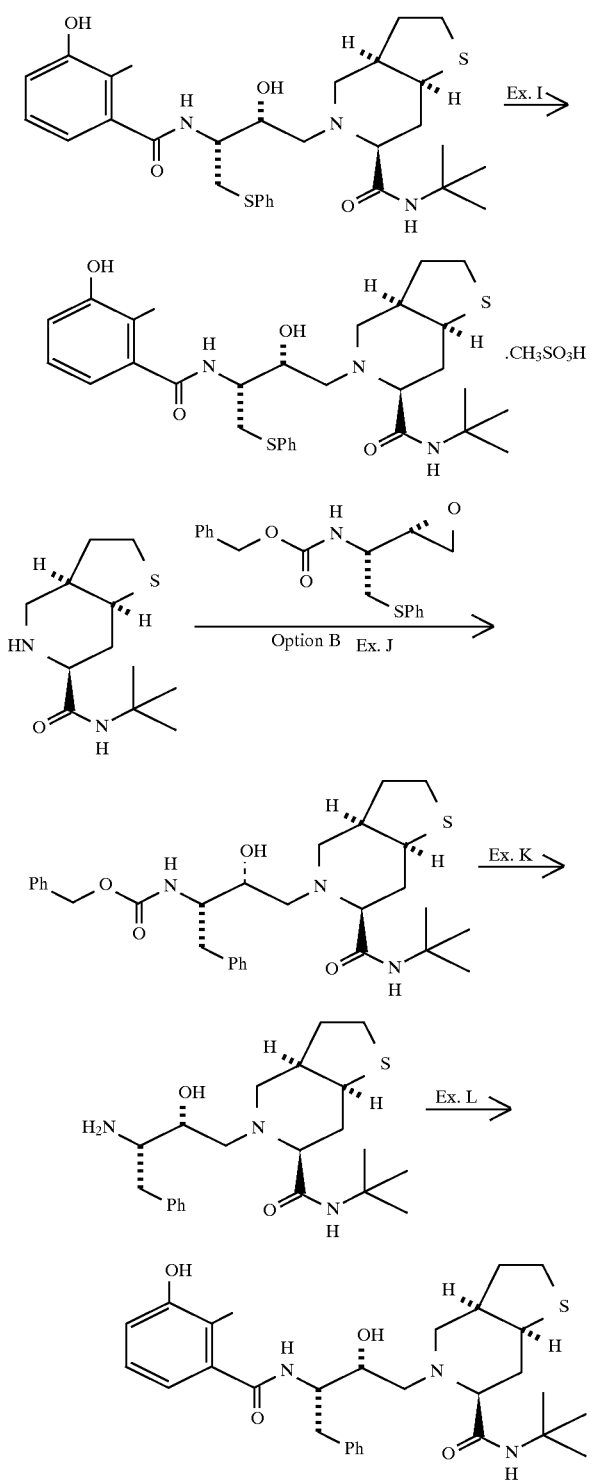

EXAMPLE 74

Example A

N-(Benzyloxycarbonyl)-3-(2-thienyl)-D,L-alanine

Into a 500 ml flask was placed 3.0 g of 3-(2-Thienyl)-D, L-alanine (optically active material in the L-form is available from Aldrich or SIGMA and could be used to obtain an optically active product) in 75 ml H₂O/60 ml dioxane, and 5.6 g K₂CO₃ was added, followed by 2.85 ml of carbobenzyloxy chloride. The mixture was stirred rapidly for 1 hour. TLC (21/7/7/9, EtOAc/AcOH/CH₃CN/H₂O) showed that the starting material was gone. A new higher Rf product was seen. The dioxane was concentrated off and the aqueous layer was washed with Et₂O (75 ml). The aqueous layer was mixed with CH₂Cl₂ (150 ml) and acidified to pH=2.0 with 5N HCl. The desired N-(Benzyloxycarbonyl)-3-(2-thienyl) -D,L-alanine was extracted with CH₂Cl₂. The organic layer was separated and dried with Na₂SO₄, filtered, and concentrated to give 5.05 g of desired N-(Benzyloxycarbonyl)-3-(2-thienyl)-D,L-alanine (98% yield).

¹H NMR (300 MHz, CDCl₃): δ7.37 (m, 5H); 7.18 (d, J=4Hz, 1H); 6.95 (m, 1H); 6.83 (m, 1H); 5.35 (d, J=8Hz, 1M); 5.15 (s, 2H); 4.7 (m, 1H); and 3.4 (m, 2H).

Example B

N-(Benzyloxycarbonyl)-3-(2-thienyl)-L-alanine tert-butyl amide

Into a 500 ml flask was placed 8.06 g of the subtitled compound of Example A, N-(Benzyloxycarbonyl)-3-(2-thienyl)-L-alanine, in 130 ml of THF. The compound was cooled to 0° C. N-Methylmorpholine (4.23 ml) was added, followed by isobutylchloroformate (4.04 ml ) over two minutes. The mixture was stirred for 15–20 minutes, and 3.74 ml of t-butylamine was added. The bath was removed, and the mixture was stirred at room temperature for two hours. The mixture was concentrated on rotovap, and the residue was taken up in ethyl acetate. The residue was washed successively with H₂O, HCl, and saturated NaHCO₃ solution. The organics were separated and dried with Na₂SO₄, filtered, and concentrated to an oil. The oil was dissolved in 100 ml hot hexane and cooled in a refrigerator overnight to give a solid. The hexane was decanted, followed by drying to yield a solid of 9.25 g N-(carbobenzyloxy)-3-(2-thienyl)-L-alanine-tert-butylamide (97% yield).

¹H NMR (300 MHz, CDCl₃): δ7.37 (s, 5H); 7.2 (d, J-4 Hz, 1H); 6.95 (dd, J=4Hz, 8 Hz, 1H); 6.87 (d, J=4Hz, 1H); 5.52 (m, 2H); 5.12 (s, 2H); 4.27 (m, 1H); 3.27 (m, 2H), and 1.23 (s, 9H).

Example C

N-t-butyl-5-benzyloxycarbonyl-(4,5,6,7)-tetrahydrothieno[3,2-c]pyridine-6S-N-t-butyl carboxamide Into a 50 ml flask was placed 500 mg of the subtitled compound of Example B, N-(Benzyloxycarbonyl)-3-(2-thienyl)-L-alanine tert-butyl amide, in 12 ml of 1,1, 2trichloroethane. 2 ml of TFA was added, followed by 2 ml dimethoxymethane. The mixture was heated to reflux, followed by TLC every five minutes. After 15 minutes, TLC showed that the starting material was gone. Mostly, the desired product was obtained, removed from heat, and poured into 30 ml of H₂O containing 3.5 g K₂CO₃ and 40 ml CH₂C₂. The desired product was transferred to a separatory funnel, and the organics were separated and dried with Na₂SO₄, filtered, and concentrated to oil. The product was purified by flash chromotography through 25 g (SiO₂) with 3% EtOAc/CH₂Cl₂. 357 mg of N-t-butyl-5-benzyloxycarbonyl-(4,5,6,7)-tetrahydrothieno[3,2-c] pyridine-6S-N-t-butyl carboxamide (69% yield) was obtained.

A period of fifteen minutes from time of reflux to removal of heating source and immediate work-up are very important to avoid side reactions.

$^1$H NMR (300 MHz, d$_6$ DMSO): δ7.35 (m, 7H); 6.83 (m, 1H); 5.15 (m, 2H); 4.98 (m, 1H); 4.35 (m, 2H); 3.10 (m, 2H); and 1.10 (s, 9H).

MS: m/e 372 (M+)

Example D

[6S-(6R*,3aS*,7aR*)]-N-(Benzyloxycarbonyl) octahydrothieno[3,2-c]pyridine-6-N-t-butyl carboxamide Into a high pressure hydrogenation vessel was placed the subtitled compound of Example C, N-t-butyl-5-benzyloxycarbonyl-(4,5,6,7)-tetrahydro-thieno[3,2-c] pyridine-6S-N-t-butyl carboxamide, (10.5 g) and 105 g of 5% Pd on carbon in 1100 ml of THF and 525 ml of ETOH. The mixture was placed under H$_2$ (3000 psi) at 80° C. for 24 hours. The reaction mixture was cooled and the catalyst was filtered and washed with 20% MeOH/CHCl$_3$. The organic filtrate was combined and concentrated to a crude oil. The oil was taken up in CH$_2$Cl$_2$ and flash chromatographed on 250 g of (SiO$_2$) eluted with 2% MeOH/Cl$_2$Cl$_2$. The desired cis isomer (major) came through contaminated with a small amount of a minor isomer. This mixture was recrystallized by dissolving in 1.5 ml of MeOH, adding 20 ml of Et$_2$O, followed by adding 120 ml of hexane, and the mixture was placed in a refrigerator overnight. The crystals obtained were filtered, washed with cold hexane and dried under vacuum to give 2.54 g of the cis isomer [6S-(6R*,3aS*,7aR*)]-N-(benzyloxycarbonyl)octahydrothieno[3,2-c] pyridine-6-N-t-butyl carboxamide (24% yield).

$^1$H NMR (300 MHz, CDCl$_3$): δ7.37 (s, 5H); 6.0 and 5.5 (br.s, 1H); 5.18 (br.s, 2H); 4.22 (m, 2H); 3.40 (m, 1H); 2.87 (m, 3H); 2.48 (m, 1H); 2.15 (m, 2H); 1.70 (m, 1H); and 1.15 (br.s, 9H).

MS: m/e 377 (M$^+$+1).

Example E

[6S-(6R*,3aS*,7aR*)]-Octahydrothieno [3,2-c] pyridine-6-N-t-butyl carboxamide

Into a 100 ml flask was placed 2.41 g of the subtitled compound of Example D, [6S-(6R*,3aS*,7aR*)]-N-(Benzyloxycarbonyl)-octahydrothieno[3,2-c]pyridine-6-N-t-butyl carboxamide, in 12 ml of 1:1 CH$_3$CN/CH$_2$Cl$_2$. The first portion of trimethylsilyl iodide (TMSI) (1.9 ml) was added and stirred for 10 minutes. A second portion of TMSI (0.94 ml) was added and stirred for 10 minutes. A third portion of TMSI (0.48 ml) was added and stirred for 30 minutes. The TLC (5% EtOAc/CH$_2$Cl$_2$) showed that the starting material was gone. The reaction mixture was diluted with 30 ml of diethylether and 40 ml of H$_2$O and 6 ml of 1N HCl. The ether layer was separated and washed with 15 ml of 0.1N HCl. The combined ether layers were discarded, and aqueous washes were combined. Saturated NaHCO$_3$ was added to adjust the pH of the aqueous layer to 8. The aqueous layer was extracted twice with 200 ml CH$_2$Cl$_2$ and the organic layers were combined and dried over Na$_2$SO$_4$. The solution was filtered and concentrated to give 1.3 g (84% yield) of desired [6S-(6R*,3aS*,7aR*)]-octahydrothieno[3,2-c]pyridine-6-N-t-butyl carboxamide.

$^1$H NMR (300 MHz, CDCl$_3$): δ6.43 (s, 1H); 3.22 (m, 2H); 2.95 (m, 4H); 2.17 (m, 3H); 2.0 (m, 1H); 1.55 (m, 2H); and 1.32 (s, 9H).

[α]$_D$ (EtOH)=−179.1° (at 25° C.).

Example F

[6S-(6R*,3aS*,7aR*,2'S*,3'S*)]-5-[2-Hydroxy-4-phenylthio-3-(benzoxycarbonyl)-aminobutyl]-octahydrothieno[3,2-c]pyridine-6-N-t-butyl carboxamide Into a 100 ml flask was placed 1.45 g of [1'R-(1'R*,1S*))-1-[(1'-N-(Benzyloxycarbonyl)amino-2'-(phenylthio)ethyl] oxirane (obtained following Preparation 8E ([1'R-(1'R*, 1S*)]-1-[(1'-N-(Benzyloxycarbonyl)amino-2'-(phenylthio) ethyl]oxirane may also be obtained as set forth in Example M below)) and 1.07 g of the subtitled compound of Example 74 E, [6S-(6R*,3aS*,7aR*)]-Octahydrothieno[3,2-c] pyridine-6-N-t-butyl carboxamide, in 30 ml of EtOH, and the mixture was heated to 65° C. for 60 hours. The reaction mixture was concentrated to a foam and purified on chromatotron (4000 micron plate), eluted with 1% MeOH/CH$_2$Cl$_2$. The desired fractions were concentrated to give 1.8 g of desired [6S-(6R*,3aS*,7aR*,2'S*,3'S*)]-5-(2-Hydroxy-4-phenylthio-3-(benzoxycarbonyl)-aminobutyl]-octahydrothieno[3,2-c]pyridine-6-N-t-butyl carboxamide. Some mixed fractions at the beginning were combined to give 326 mg of a mixture, which was again submitted to the same chromatographic conditions on a 2000 micron plate. An additional 228 mg of desired [6S-(6R*,3aS*,7aR*, 2'S*,3'S*)]-5-[2-Hydroxy-4-phenylthio-3-(benzoxycarbonyl)-aminobutyl]-octahydrothieno-[3,2-c] pyridine-6-N-t-butyl carboxamide was obtained. The total yield of [6S-(6R*,3aS*,7aR*,2'S*, 3'S*)]-5-[2-Hydroxy-4-phenylthio-3-(benzoxycarbonyl)-aminobutyl]-octahydrothieno[3,2-c]pyridine-6-N-t-butyl carboxamide obtained was (80.5% yield).

$^1$H NMR (300 MHz, CDCl$_3$): δ7.30 (m, 10H); 5.80 (m, 2H); 5.08 (AB, 2H); 3.95 (m, 2H); 3.42 (m, 2H); 3.17 (m, 3H); 2.90 (m, 2H); 2.67 (m, 1H); 2.58 (m, 1H); 2.48 (m, 1H); 2.35 (m, 2H); 1.98 (m, 4H); and 1.30 (s, 9H).

Example G

[6S-(6R*,3aS*,7aR*,2'S*,3'S*)]-5-(2-Hydroxy-4-phenylthio-3-aminobutyl]-octahydrothieno[3,2-c] pyridine-6-N-t-butyl carboxamide Into a 100 ml flask was placed 1.8 g of the subtitled compound of Example F. [6S-(6R*,3aS*,7aR*,2S*,3'S*)]-5-[2-Hydroxy-4-phenylthio-3-(benzoxycarbonyl)-aminobutyl]-octahydrothieno[3,2-c]pyridine-6-N-t-butyl carboxamide, in 10 ml each of CH$_2$Cl$_2$ and CH$_3$CN. A first portion of TMSI (1.14 ml) was added and stirred for 10 minutes. A second portion of TMSI (0.72 ml) was added and stirred for 10 minutes. A third portion of TMSI (0.24 ml) was added and stirred for 15 minutes. The reaction mixture was diluted with 40 ml of Et$_2$O and poured into 30 ml of 0.1N HCl and 60 ml of Et$_2$O. The Et$_2$O layer was separated and the organics were discarded. The aqueous layer was made basic with saturated NaHCO$_3$ solution and extracted with CH$_2$Cl$_2$ (2×100 ml). The organics were separated, dried with Na$_2$SO$_4$, filtered, and concentrated to afford 1.18 g of [6S-(6R*,3aS*,7aR*,2'S*,3S*)]-5-[2-Hydroxy-4-phenylthio-3-aminobutyl]-octahydrothieno[3,2-c]pyridine-6-N-t-butyl carboxamide (86% yield) as a white solid.

$^1$H NMR (300 MHz, CDCl$_3$): δ7.38 (m, 2H); 7.28 (m, 2H); 7.20 (m, 1H); 6.23 (s, 2H); 3.65 (s, 1H); 3.28 (m, 3H); 2.90 (m, 4H); 2.70 (m, 2H); 2.58 (m, 1H); 2.43 (m, 1H); 2.34 (m, 1H); 2.05 (m, 4H); 1.80 (m, 3H); and 1.32 (s, 9H).

IR (CHCl$_3$): 3430; 3005; 2973; 1670; 1514; 1456; 1366; and 1090 cm$^{-1}$.

MS: m/e 437 (M$^+$).

Example H

[6S-(6R*,3aS*,7aR*,2'S*,3'S*)]-2-(2'-Hydroxy-3'-phenylthiomethyl-4'-aza-5'-oxo-5'-(2"-methyl-3"-hydroxyphenyl)pentyl]-octahydrothieno-3,2-c]pyridine-6-N-t-butyl carboxamide Into a 25 ml flask was placed 40 mg of the subtitled compound of Example G, [6S-(6R*,3aS*,7aR*,2'S*,3S*)-5-[2-Hydroxy-4-phenylthio-3-aminobutyl]-octahydrothieno[3,2-c]pyridine-6-N-t-butyl carboxamide, 14 mg of 3-hydroxy-2-methyl benzoic acid, and 12.6 mg of HOBT in 2 ml of THF, and the reaction mixture was cooled to 10° C. DCC (18.7 mg) was added, and the mixture was warmed to room temperature and stirred for 85 hours. The reaction mixture was diluted with 2 ml of Et$_2$O and filtered through a cotton plug, the filtrate was concentrated, and the residue was eluted on chromatotron (2000 micron plate) with 3% MeOH/CHCl$_3$. The desired fractions were concentrated to give 44 mg of [6S-(6R*,3aS*,7aR*,2'S*,3'S*)]-2-[2'-Hydroxy-3'-phenylthiomethyl-4'-aza-5'-oxo-5'-(2"-methyl-3"-hydroxyphenyl)pentyl]-octahydrothieno[3,2-c]pyridine-6-N-t-butyl carboxamide (85% yield).

Example I

[6S-(6R*,3aS*,7aR*,2'S*,3'S*)]-2-(2'-Hydroxy-3'-phenylthiomethyl-4'-aza-5'-oxo-5'-(2"-methyl-3"-hydroxyphenyl)pentyl]-octahydrothieno[3,2-c]pyridine-6-N-t-butyl carboxamide methanesulfonic acid salt Into a 50 ml flask was placed 330 mg of the subtitled compound of Example H, [6S-(6R*,3aS*,7aR*,2'S*,3'S*)]-2-[2'-Hydroxy-3'-phenylthiomethyl-4'-aza-5'-oxo-5'-(2"-methyl- 3"-hydroxyphenyl)pentyl]-octahydrothieno[3,2-c]pyridine-6-N-t-butyl carboxamide, in CH$_2$Cl$_2$/CH$_3$CN (4 ml/2 ml), and 37.5 ml of MeSo$_3$H was added via a microliter-syringe. The mixture became cloudy. The reaction mixture was diluted with 1 ml of CH$_2$Cl$_2$, and Et$_2$O and hexane were added and concentrated. The residue was sonicated with hexane and concentrated two times to obtain 385 mg of desired [6S-(6R*,3aS*,7aR*,2'S*,3'S*)]-2-(2'-Hydroxy-3'-phenylthiomethyl-4'-aza-5'-oxo-5'-(2"-methyl-3"-hydroxyphenyl)pentyl]-octahydrothieno[3,2-c]pyridine-6-N-t-butyl carboxamide methanesulfonic acid salt (100% yield).

Example J

[6S-(6R*,3aS*,7aR*,2'S*,3'R*)]-5-(2-Hydroxy-4-phenyl-3-(benzoxycarbonyl)-aminobutyl]-octahydrothieno[3,2-c]pyridine-6-N-t-butyl carboxamide Into a 50 ml flask was placed 145 mg of [1'S-(1'R*,1R*)]-1-[(1'-N-(Benzyloxycarbonyl)amino-2'-(phenyl)ethyl]oxirane (obtainable as in Reaction Scheme A (steps 1 through 5) below, and 118 mg of the subtitled compound of Example E, [6S-(6R*,3aS*,7aR*)]-Octahydrothieno[3,2-c]pyridine-6-N-t-butyl carboxamide, as a mixture of enantiomers in 3 ml of EtOH. The mixture was heated to 65° C. and was maintained at this temperature for 20 hours. The reaction mixture was concentrated, and the crude residue was purified by chromatatron on a 2000 micron plate, eluted with 1% MeOH/CHCl$_3$ to afford 98 mg of [6S-(6R*,3aS*,7aR*,2'S*, 3'R*)]-5-[2-Hydroxy-4-phenyl-3 (benzoxycarbonyl)-aminobutyl]-octahydrothieno[3,2-c]pyridine-6-N-t-butyl carboxamide (37% yield) and 109 mg of a diasteromer of [6S-(6R*,3aS*,7aR*,2'S*,3'R*)]-5-[2-Hydroxy-4-phenyl-3-(benzoxycarbonyl)-aminobutyl]-octahydrothieno[3,2-c]pyridine-6-N-t-butyl carboxamide.

If substantially enantiomerically pure [6S-(6R*,3aS*,7aR*)]-Octahydrothieno(3,2-c]pyridine-6-N-t-butyl carboxamide is used instead of [6S-(6R*,3aS*,7aR*)]-Octahydrothieno[3,2-c]pyridine-6-N-t-butyl carboxamide as a mixture of enantiomers, a higher yield of [6S-(6R*, 3aS*,7aR*,2'S*,3'R*)]-5-[2-Hydroxy-4-phenyl-3-(benzoxycarbonyl)-aminobutyl]-octahydrothieno[3,2-c]pyridine-6-N-t-butyl carboxamide should result. (See, e.g., Example F above.)

Example K

[6S-(6R*,3aS*,7aR*,2'S*,3'R*)]-5-[2-Hydroxy-4-phenyl-3-aminobutyl]-octahydrothieno[3,2-c]pyridine-6-N-t-butyl carboxamide Into a 25 ml flask was placed 85 mg of the subtitled compound of Example J, [6S-(6R*,3aS*,7aR*,2'S*,3'R*)]-5-(2-Hydroxy-4-phenyl-3-(benzoxycarbonyl)-aminobutyl]-octahydrothieno[3,2-c]pyridine-6-N-t-butyl carboxamide, in CH$_3$CN/CH$_2$Cl$_2$. TMSI was added in portions of 56 microliters, 34 microliters and 11 microliters, respectively, every ten minutes and stirred for 1½ hours. The mixture was diluted with Et$_2$O (5 ml) and poured into 15 ml of 1N HCl and Et$_2$O (20 ml). The organics were separated and discarded. The aqueous layer was treated with 30 ml of saturated NaHCO$_3$ solution and extracted with CH$_2$Cl$_2$ (2×50 ml). The organics were dried with Na$_2$SO$_4$, filtered, and concentrated to an oil that crystallized to give 64 mg [6S-(6R*,3aS*,7aR*,2'S*,3'R*)]-5-[2-Hydroxy-4-phenyl-3-aminobutyl-octahydrothieno[3,2-c]pyridine-6-N-t-butyl carboxamide (100% yield).

$^1$H NMR (300 MHz, CDCl$_3$): δ7.28 (m, 5H); 6.38 (s, 1H); 3.75 (m, 1H); 3.32 (m, 2H); 3.12 (m, 1H); 2.93 (m, 2H); 2.78 (m, 2H); 2.58 (m, 3H); 2.38 (m, 1H); 2.12 (m, 5H); 1.83 (m, 2H); and 1.35 (s, 9H).

Example L

[6S-(6R*,3aS*,7aR*,2'S*,3'R*)]-2-[2'-Hydroxy-3'-phenylmethyl-4'-aza-5'-oxo-5'-(2"-methyl-3"-hydroxyphenyl)pentyl]-octahydrothieno[3,2-c]pyridine-6-N-t-butyl carboxamide Into a 25 ml flask was placed 64 mg of the subtitled compound of Example K, [6S-(6R*,3aS*,7aR*,2'S*,3'R*)]-5-[2-Hydroxy-4-phenyl-3-aminobutyl]-octahydrothieno[3,2-c]pyridine-6-N-t-butyl carboxamide, 24 mg of 3-hydroxy-2-methyl benzoic acid (obtained by the method disclosed in Preparation 23C), and 22 mg of HOBT.H$_2$O in 2 ml of THF, and the mixture was cooled to −10° C. DCC (32 mg) was added, and the mixture was warmed to room temperature and stirred for 60 hours. The reaction mixture was diluted with 2 ml of Et$_2$O, filtered through a cotton plug, and the filtrate was concentrated, and the residue was eluted on chromatotron (2000 micron plate) with 1.5% MeOH/CHCl$_3$ to 4% MeOH/CHCl$_3$ gradient. The desired fractions were concentrated to give 72 mg of [6S-(6R*,3aS*,7aR*,2'S*, 3'R*)]-2-[2'-Hydroxy-3'-phenylmethyl-4'-aza-5'-oxo-5'-(2"-methyl- 3"-hydroxyphenyl)pentyl]-octahydrothieno[3,2-c]pyridine-6-N-t-butyl carboxamide (85% yield).

EXAMPLE 75

[3S-(3R*,4aR*,8aR*,2'S*,3'S*)]-2-[2'-Hydroxy-3'-phenylthiomethyl-4'-aza-5'-oxo-5'-(2"-methyl-3"-hydroxyphenyl)pentyl]-decahydroisoquinoline-3-N-t-butyl carboxamide methanesulfonic acid salt This compound was prepared as in Example 23, with the exception that Preparation Steps 8A and 8D were changed as set forth on step (1) below, and the salt formation step (2) below was added.

(1)

To a 2 L flask was added Ph$_3$P (109.6 g) in 500 ml of CH$_2$Cl$_2$, and the mixture was cooled to −70° C. To the mixture was added a solution of diethylazidodicarboxylate (66 ml) in 60 ml of THF dropwise over 25 minutes. After 25 minutes, a solution of N-carbobenzyloxy-L-serine (100 g) in 400 ml of THF was added dropwise over 45 minutes and allowed to warm to room temperature in a water bath over two hours. 150 ml of THF was added to the mixture. In another flask, a solution of thiophenol (46 g) in 1 L of THF was cooled in an ice bath to 0° C. and treated portionwise with an NaH dispersion (10 g) to give a thick solution. After one hour, the crude lactone solution was added to the thiolate solution dropwise via an addition funnel over 30 minutes. After 12 hours, a white precipitate was filtered off, and the filter cake washed with THF. The solid was taken up in 0.4N NaHSO$_4$ and EtOAc, separated, and the organic layer was washed with brine, dried, and evaporated to afford 85 g of 2R-2-N-(benzyloxycarbonyl)amino-3-phenylthio propanoic acid as a viscous oil.

The original solid is believed to be the sodium salt of the desired product. Thus, the yield and ease of isolation may be improved by isolation of the sodium salt directly.

The crude chloroketone 3R-1-Chloro-2-oxo-3-N-(benzyloxycarbonyl)amino-4-phenylthio butane (16.87 g, 46.4 mmol) was added to 1 L absolute EtOH and 200 mL THF, and the solution was cooled in a CO$_2$-acetone bath (−78°T$_{int}$), and NaBH$_4$ (2.63 g, 69.5 mmol) in 200 ml absolute EtOH was added dropwise over 1 h (T$_{int}$<−75° C.). TLC analysis after the addition showed that the reaction was complete. The reaction was diluted with 300 mL ether and was quenched by the slow addition of 0.4N NaHSO$_3$ with stirring, which produced the evolution of gas. This mixture was concentrated under reduced pressure to remove most of the EtOH and additional water was added. The mixture was extracted with ether, and the combined organic layers were washed with saturated aqueous NaHCO$_3$ and brine, dried (Na$_2$SO$_4$), and concentrated to afford 15.7 g of an off white solid. This material was triturated with boiling hexane (300 mL), and the hexane was carefully decanted while hot. This was repeated 10 times (300 mL each) to provide 10.35 g of an off white solid (one pure isomer by TLC). The hexane filtrate was concentrated to give 6 g of white solid which was set aside. The triturated solid was heated with 50 mL CH$_2$Cl$_2$ and about 6 mL hexane and filtered hot. The clear solution was allowed to cool to 25° C. and was then placed in the freezer. The resulting solid was filtered and washed with hexanes to give 7.157 g of a white solid. The filtrate was combined with the hexane filtrate from above and with crude reaction product from two small scale experiments (500 mg starting ketone each), and the combined material was chromatographed on SiO$_2$ (2:1 hexanes-ether→1:1 hexanes-ether, loaded with CH$_2$Cl$_2$) to afford 2.62 g of additional product. A total of 10.31 g pure isomer of [2S-(2R*,3S*)]-1-Chloro-2-hydroxy-3-N-(benzyloxycarbonyl)amino-4-phenylthio butane (50% yield from acid) was obtained. alpha$_D$=−63.63° (c=1, MeOH).

(2)

Salt Formation (3S-(3R*,4aR*,8aR*,2'S*,3'S*)1-2-[2'-Hydroxy-3'-phenylthiomethyl-4'-aza-5'-oxo-5'-(2"-methyl-3"-hydroxyphenyl)pentyl]decahydroisoquinoline-3-N-t-butylcarboxamide (3.34 g) was dissolved in 30 ml of MeOH and 30 ml of CH$_2$Cl$_2$, and a solution of methanesulfonic acid (596 mg) in 10 ml of CH$_2$Cl$_2$ was added dropwise. After 10 minutes, the reaction mixture was concentrated to foam. The crude salt was taken up in 5 ml of THF and added slowly to a mixture of 175 ml of ethyl ether and 25 ml of hexanes with stirring until a fine suspension resulted. This was cooled in a freezer, filtered cold and washed several times with ethyl ether, followed by drying in a vacuum oven to afford 3.75 g (96%) of [3S-(3R*,4aR*,8aR*,2'S*,3'S*)]-2-[2'-Hydroxy-3'-phenylthiomethyl-4'-aza-5'-oxo-5'-[2"-methyl-3"-hydroxyphenyl)pentyl]-decahydroisoquinoline-3-N-t-butyl carboxamide methanesulfonic acid salt as a white powder.

EXAMPLE 76

3-(Bisbenzoxyphosphinyl)oxy-2-methyl Benzoic Acid

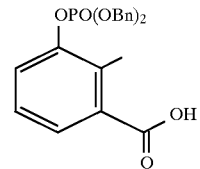

To a cooled (0° C.), stirred solution of 706 mg (4.67 mmol) of 3-hydroxy-2-methylbenzoic Acid in 30 mL of pyridine was added dropwise 10.3 mL (10.21 mmol) of a 1.0M solution of lithium hexamethyldisilazide over 5 minutes. After stirring for 5 minutes, 3.0 g (5.57 mmol) of tetrabenzylpyrophosphate was added in one portion, and the reaction mixture was warmed to room temperature over 30 minutes. The reaction mixture was concentrated, and the residue was partitioned between 2.5N HCL (200 mL) and a 50/50 mixture of ethyl acetate/hexane (200 mL). The layers were separated, and the aqueous layer was extracted twice with a 50/50 solution of ethyl acetate/hexane. The organic layers were combined, washed with brine and dried over sodium sulfate. Purification of the crude product by flash chromatography (gradient eluent of 50–70% ethyl acetate/hexane/2% Acetic acid) gave 910 mg of a light yellow oil, which is 3-(bisbenzoxyphosphinyl)oxy-2-methyl benzoic acid.

Yield: 47%

$^1$H NMR (CDCl$_3$): d 2.49 (s, 3H), 5.14 (d, J=8.60 Hz, 4H), 7.10–7.40 (m, 11H), 7.48 (d, J=8.09 Hz, 1H), 7.81 (d, J=7.80 Hz, 1H).

IR (CHCl3): 3700–2350 (br), 1700, 1457, 1382, 1273, 1240, 1179, 1082, 1034, 1023, 1001, 966, 881, 851 cm$^{-1}$.

MS (FD): m/e 413 (M$^+$, 100).

EXAMPLE 77

[3S-(3R*,4aR*,8aR*,2'S*,3'R*)]-2-[2'-Hydroxy-3'-phenylmethyl-4'-aza-5'-oxa-5'-(2"-methyl-3"-(bisbenzoxyphosphinyl)oxyphenyl)pentyl]decahydroisoquinoline-3-N-t-butyl carboxamide

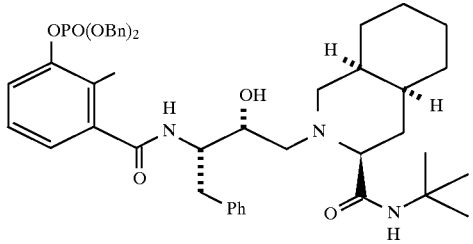

To a cooled (−10° C.) solution of 95 mg (0.23 mmol) of the subtitled compound of Example 76, 3-(Bisbenzoxyphosphinyl)oxy-2-methyl benzoic acid, 92 mg (0.23 mmol) of [3S-(3R*,4aR*,8aR*,2'S*,3'R*)]-2-[3'-Amino-2'-hydroxy-4'-phenyl]butyl decahydroisoquinoline-3-N-t-butyl carboxamide and 31 mg (0.23 mmol) of HOBt in 5 mL of anhydrous THF, was added 48 mg (0.23 mmol) of DCC in one portion. After stirring for 3 days at room temperature, the reaction mixture was diluted with ethyl acetate and filtered through a plug of cotton. The resulting filtrate was extracted twice with saturated sodium carbonate, washed with brine, and dried over sodium sulfate. Purification of the crude product by radial chromatography (2 mm plate; gradient eluent of 2.5–5% methanol/methylene chloride) gave 100 mg of a white foam, which is [3S-(3R*,4aR*,8aR*,2'S*,3'R*)]-2-[2'-Hydroxy-3'-phenylmethyl-4'-aza-5'-oxo-5'-(2"-methyl-3"-(Bisbenzoxyphosphinyl)oxyphenyl)pentyl]-decahydroisoquinoline-3-N-t-butyl carboxamide.

Yield: 52%

$^1$H NMR (CDCl$_3$): d 1.13 (s, 9H), 1.14–2.10 (m, 15H), 2.23–2.36 (m, 2H), 2.50–2.70 (m, 2H), 2.92–3.05 (m, 2H), 3.39–3.50 (m, 1H), 3.80–4.10 (m, 2H), 4.52–4.62 (m, 1H), 5.03–5.13 (m, 4H), 5.65 (s, 1H), 6.62 (d, J=8.51 Hz, 1H), 6.83 (d, J=7.60 Hz, 1H), 7.02 (t, J=8.10 Hz, 1H).

IR (CHCl3): 3690, 3600–3100 (br), 3009, 2929, 2866, 1672, 1603, 1513, 1456, 1368, 1277, 1239, 1182, 1037, 1023, 1001, 967, 880 cm$^{-1}$.

MS (FD): m/e 796 (M$^+$, 100).

Analysis for C$_{46}$H$_{58}$N$_3$O$_7$P$_1$: Calcd: C, 69.41; H, 7.34; N, 5.28. Found: C, 69.57; H, 7.33; N, 5.20.

EXAMPLE 78

[3S-(3R*,4aR*,8aR*,2'S*,3'R*)]-2-[2'-Hydroxy-3'-phenylmethyl-4'-aza-5'-oxa-5'-(2"-methyl-3"-Hydroxyphenyl)pentyl]decahydroisoquinoline-3-N-t-butyl carboxamide 3"-dihydrogen phosphate

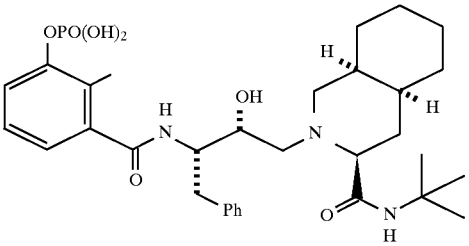

A mixture of 86 mg (0.108 mmol) of the subtitle compound of Example 77, [3S-(3R*,4aR*,8aR*,2'S*,3'R*)]-2-[2'-Hydroxy-3'-phenylmethyl-4'-aza-5'-oxo-5'-(2"-methyl-3"-(bisbenzoxyphosphinyl)oxyphenyl)pentyl]-decahydroisoquinoline-3-N-t-butyl carboxamide, and 23 mg of 10% Palladium on carbon in 16 mL of methanol was stirred under one atmosphere of hydrogen for 1 hour. The reaction mixture was filtered through celite and concentrated to give 61 mg of a white solid, which is [3S-(3R*,4aR*,8aR*,2'S*,3'R*)]-2-[2'-Hydroxy-3'-phenylmethyl-4'-aza-5'-oxo-5'-(2"-methyl-3"-hydroxyphenyl)pentyl]-decahydroisoquinoline-3-N-t-butyl carboxamide 3"-dihydrogen phosphate.

Yield: 96%

$^1$H NMR (Methanol-d$_4$): d 1.32 (s, 9H), 1.33–2.21 (m, 14H), 2.60–2.75 (m, 1H), 3.18–3.49 (m, 5H), 3.56–3.70 (m, 1H), 3.95–4.35 (m, 3H), 5.47 (s, 1H), 6.71 (d, J=7.26 Hz, 1H), 7.02 (t, J=8.24 Hz, 1H), 7.15–7.35 (m, 5H), 7.40 (d, J=8.18 Hz, 1H).

IR (KBr): 3800–2400 (br), 1673, 1545, 1456, 1395, 1368, 1222, 1185, 1077, 942, 857, 792 cm$^{-1}$.

MS (FAB): m/e 616.3 (M$^+$, 100).

EXAMPLE 79

[3S-(3R*,4aR*,8aR*,2'S*,3'S*)]-2-[2'-Hydroxy-3'-phenylthiomethyl-4'-aza-5'-oxa-5'-(2"-methyl-3"-(bisbenzoxyphosphinyl)oxyphenyl)pentyl]decahydroisoquinoline-3-N-t-butyl carboxamide

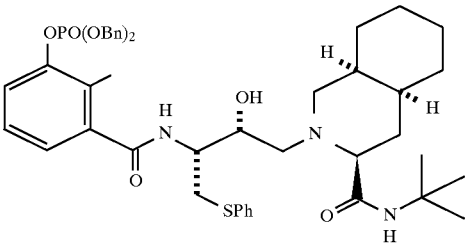

To a cooled (0° C.), stirred solution of 478 mg (1.16 mmol) of the subtitled compound of Example 76, 3-(bisbenzoxyphosphinyl)oxy-2-methyl benzoic acid, 500 mg (1.16 mmol) of (3S-(3R*,4aR*,8aR*,2'S*,3'S*)]-2-[3'-amino-2'-hydroxy-4'(phenyl)thio]butyl decahydroisoquinoline-3-N-t-butyl carboxamide, 352 mg (3.48 mmol) of triethyl amine, and 166 mg (1.23 mmol) of HOBt in 8 mL of anhydrous THF was added 254 mg (1.23 mmol) of DCC in one portion. After stirring overnight at room temperature, the reaction mixture was concentrated, the residue was taken up in ethyl acetate and filtered through a plug of cotton. The resulting filtrate was extracted twice with saturated sodium carbonate, washed with brine, and dried over sodium sulfate. Purification of the crude product by radial chromatography (6 mm plate; gradient eluent of 30% ethyl acetate/hexane) gave 644 mg of a white foam, which is [3S-(3R*,4aR*,8aR*,2'S*,3'S*)]-2-[2'-Hydroxy-3'-phenylthiomethyl-4'-aza-5'-oxo-5'-(2"-methyl- 3"- (Bisbenzoxyphosphinyl)oxyphenyl)pentyl]-decahydroisoquinoline-3-N-t-butyl carboxamide.

Yield: 67%

$^1$H NMR (CDCl$_3$): d 1.04 (s, 9H), 1.15–2.61 (m, 19H), 2.89–3.00 (m, 1H), 3.39–3.50 (m, 1H), 3.67 (s, 1H), 3.75–3.85 (m, 1H), 4.03–4.15 (m, 1H), 4.43–4.58 (m, 1H), 5.00–5.20 (m, 4H), 5.47 (s, 1H), 7.10–7.55 (m, 19H).

IR (CHCl$_3$): 3600–3150 (br), 3010, 2975, 2929, 2867, 1670, 1517, 1457, 1440, 1368, 1277, 1239, 1082, 1035, 1025, 1001, 968, 879 cm$^{-1}$.

MS (FAB): 828.4 (M$^+$, 100).

Analysis for C$_{46}$H$_{58}$N$_3$O$_7$S$_1$P$_1$: Calcd: C, 66.73; H, 7.06; N, 5.07; S, 3.87. Found: C, 66.56; H, 7.29; N, 4.82; S, 3.62.

EXAMPLE 80

[3S-(3R*,4aR*,8aR*,2'S*,3'S*)]-2-[2'-Hydroxy-3'-phenylthiomethyl-4'-aza-5'-oxa-5'-2"-methyl-3"-Hydroxyphenyl)pentyl]decahydroisoquinoline-3-N-t-butyl carboxamide 3"-Dihydrogen Phosphate Hydrochloride

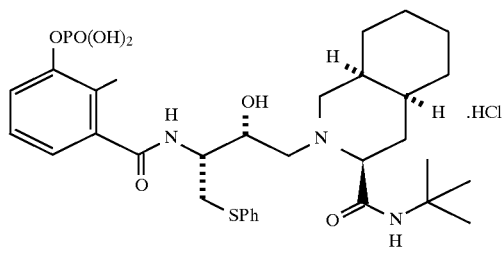

A mixture of 505 mg (0.61 mmol) of the subtitled compound of Example 79, [3S-(3R*,4aR*,8aR*,2'S*,3'S*)]-2-[2'-Hydroxy- 3'-phenylthiomethyl-4'-aza-5'-oxo-5'-(2"-methyl-3"-(Bisbenzoxyphosphinyl)oxyphenyl)pentyl]-decahydroisoquinoline-3-N-t-butyl carboxamide, and 500 mg of 10% Palladium on carbon in 20 mL of methanol was stirred under one atmosphere of hydrogen for 24 hours. The reaction mixture was filtered through celite and concentrated to give 380 mg of the crude product which was purified by HPLC (Waters Nova Pack C18 RCM Column (40×10 cm); Flow rate of 40 mL/minute; Eluent of 45% (1% HCl) water, 15% acetonitrile, 40% methanol), to give 230 mg of a white foam, which is [3S-(3R*,4aR*,8aR*,2'S*,3'S*)]-2-[2'-Hydroxy-3'-phenylthiomethyl-4'-aza-5'-oxo-5'-(2"-methyl-3"-hydroxyphenyl)pentyl]-decahydroisoquinoline-3--N-t-butyl carboxamide 3"-dihydrogen phosphate.

Yield: 58%

$^1$H NMR (Methanol-d$_4$) d 1.10–2.30 (m, 25H), 2.39 (s, 3H), 2.95–3.65 (m, 4H), 3.90–4.25 (m, 3H), 7.15–7.50 (m, 8H), 7.99 (s, 1H).

IR (KBr): 3700–2100 (br), 1674, 1547, 1458, 1440, 1395, 1368, 1241, 1182, 1074, 1025, 966, 867 cm$^{-1}$.

MS (FAB): m/e 648.3 (M$^+$+1, 100).

Analysis for C$_{32}$H$_{41}$N$_3$O$_9$S$_1$Cl$_1$P$_1$: Calcd: C, 53.37; H, 7.14; N, 5.83. Found: C, 53.44; H, 6.76; N, 5.84.

EXAMPLE 81

3-(Acetyl)hydroxy-2-methylbenzoic acid

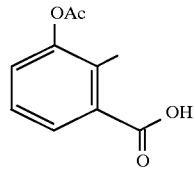

To a heterogeneous solution of 3.06 g (30 mmol) of acetic anhydride and 1.53 g (10 mmol) of 3-hydroxy-2-methylbenzoic acid was added one drop of concentrated sulfuric acid. The mixture was heated with a heat gun for 2 min. and then poured into 14 mL of cold water. The resulting precipitate was collected by vacuum filtration, washed twice with water and dried overnight in a vacuum oven. Recrystallization from 20% ethyl acetate/hexane (7 mL) gave 595 mg of a white solid, which is 3-(Acetyl)hydroxy-2-methyl benzoic acid.

Yield: 31%

IR (CHCl$_3$) 3700–2300 (br), 1765, 1698, 1460, 1404, 1372, 1299, 1273, 1172, 1081, 1041, 1012, 933, 913, 865, 823 cm$^1$.

MS (FD): m/e 194 (M$^+$, 100).

EXAMPLE 82

[3S-(3R*,4aR*,8aR*,2'S*,3'R*)]-2-[2'-Hydroxy-3'-phenylmethyl-4'-aza-5'-oxa-5'-(2"-methyl-3"-(acetyl)hydroxyphenyl)pentyl]decahydroisoquinoline-3-N-t-butyl carboxamide

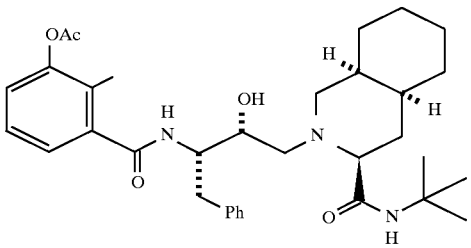

To a cooled (−10° C.) stirred solution of 34 mg (0.174 mmol) of the subtitled compound of Example 81, 3-(Acetyl)hydroxy-2-methyl benzoic acid, 70 mg (0.174 mmol) of [3S-(3R*,4aR*,8aR*,2'S*, 3'R*)]-2-[3'-Amino-2'-hydroxy-4'-phenyl)butyl decahydroisoquinoline-3-N-t-butyl carboxamide and 24 mg (0.174 mmol) of HOBt in 3 mL of anhydrous THF was added 36 mg (0.174 mmol) of DCC in one portion. After stirring for 2 days at room temperature, the reaction mixture was diluted with ethyl acetate and filtered through a plug of cotton. The resulting filtrate was extracted once with saturated sodium carbonate, once with brine, and dried over sodium sulfate. Purification of the crude product by radial chromatography (1 mm plate; gradient eluent of 0%–5% methanol/methylene chloride) gave 65 mg of a white foam, which is [3S-(3R*,4aR*,8aR*,2'S*, 3R*)]-2-[2'-Hydroxy-3'-phenylmethyl-4'-aza-5'-oxo-5'-(2"-methyl-3"-(acetyl)hydroxphenyl)pentyl)-decahydroisoquinoline-3-N-t-butyl carboxamide.

Yield: 65%

¹H NMR (CDCl₃): d 1.15 (s, 9H), 1.16–2.37 (m, 21H), 2.50–2.70 (m, 2H), 2.93–3.05 (m, 2H), 3.39–3.50 (m, 1H), 3.99–4.10 (m, 1H), 4.53–4.64 (m, 1H), 3.99–4.10 (m, 1H), 4.53–4.64 (m, 1H), 5.69 (s, 1H), 6.64 (d, J=8.45 Hz, 1H), 6.91 (d, J=7.47 Hz, 1H), 7.00 (d, J=7.57 Hz, 1H), 7.11 (t, J=7.75 Hz, 1H), 7.19–7.40 (m, 5H).

IR (CHCl₃): 3700–3100 (br), 3008, 2929, 2865, 1762, 1671, 1604, 1514, 1455, 1394, 1368, 1303, 1277, 1175, 1121, 1082, 1047, 910 cm⁻¹.

MS (FD): m/e 578 (M⁺, 100).

EXAMPLE 83

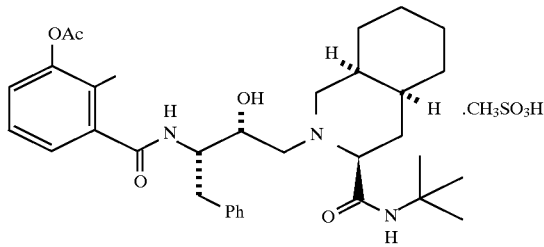

To a cold (0° C.) solution of 35 mg (0.061 mmol) of the subtitled compound of Example 82, (3S-(3R*,4aR*,8aR*,2'S*,3'R*)]-2-[2'-Hydroxy-3'-phenylmethyl-4'-aza-5'-oxo-5'-(2"-methyl-3"-(acetyl)hydroxyphenyl)pentyl]-decahydroisoquinoline-3-N-t-butyl carboxamide in 2 mL of anhydrous methylene chloride, was added dropwise 128 microliters (0.064 mmol) of a 0.5M solution of methane-sulfonic acid in methylene chloride. The resulting reaction was reduced to dryness under reduced pressure (0.2–0.1 Torr) to provide 40.5 mg (crude) of a light yellow foam, which is [3S-(3R*,4aR*,8aR*,2'S*,3'R*)]-2-[2'-Hydroxy-3'-phenylmethyl-4'-aza-5'-oxo-5'-(2"-methyl-3"-(acetyl)hydroxyphenyl)pentyl]-decahydroisoquinoline-3-N-t-butyl carboxamide methanesulfonic acid salt.

Yield: 98%

EXAMPLE 84

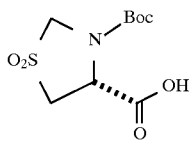

N-Boc-4-thio-L-proline (available from Sigma) (1.5 g) was dissolved in 3 ml of methanol and cooled to 0° C. in an ice bath. In a separate flask, 5.8 g of "OXONE" was dissolved in 5 ml of H₂O and added dropwise to the reaction mixture. After 30 minutes, the reaction mixture was allowed to warm to room temperature and stirred overnight, followed by dilution with CHCl₃/H₂O, separation, and extraction with CHCl₃ (3×100 ml). The organic layers were combined, dried over Na₂SO₄, and concentrated in vacuo to afford the compound of the formula shown above (700 mg, 41% yield) as a white solid.

EXAMPLE 85

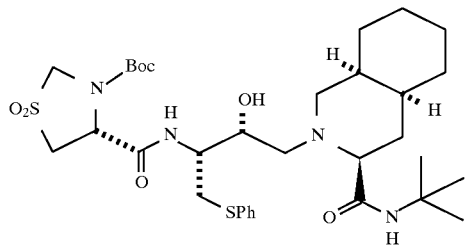

The compound of the formula shown in Example 84 and (3S-(3R*,4aR*,8aR*,2'S*,3'S*)]-2-[3'-amino-2'-hydroxy-4'-(phenyl)thio]butyl decahydroisoquinoline-3-N-t-butyl carboxamide were coupled together by a procedure similar to that shown in Example 79 above. The crude material was purified by flash chromatography (3% MeOH/CH₂Cl₂) to afford 40 mg (51% yield) of a compound of the formula shown above.

EXAMPLE 86

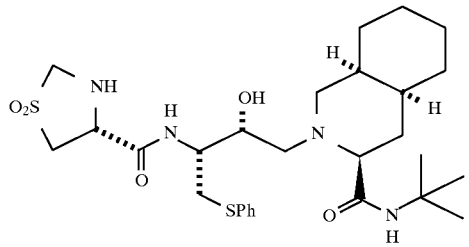

The compound of the formula shown in Example 85 (20 mg) was dissolved in 1 ml of CH₂Cl₂ and treated with 1 ml of trifluoroacetic acid. After 30 minutes at room temperature, the reaction product was concentrated in vacuo to give the compound of the formula shown above, which is [3S-(3R*,4aR*,8aR*,2'S*,3'S*,4"S)]-2-[2'-Hydroxy-3'-phenylthiomethyl-4"-aza-5'-oxo-5'(thiazolino-4"-yl-1", 1"-dioxide)pentyl]-decahydroisoquinoline-3-N-t-butyl carboxamide.

Pandex IC₅₀=244 ng/ml

EXAMPLE 87

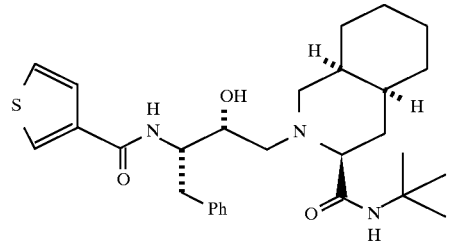

3-Carboxylic acid thiophene (available from Aldrich) and [3S-(3R*,4aR*,8aR*,2'S*,3'R*)]-2-[3'-Amino-2'-hydroxy-4'-phenyl]butyl decahydroisoquinoline-3-N-t-butyl carboxamide were coupled together by a procedure similar to Example 77 above. The crude material was purified by flash chromatography (2% MeOH/CH₂Cl₂) to afford 70 mg (63% yield) of the compound of the formula shown above, which is [3S-(3R*,4aR*,8aR*,2'S*,3'R*)]-2-[2'-Hydroxy-3'- phenylmethyl-4'-aza-5'-oxo-5'-(thieno-3"-yl)pentyl]-decahydroisoquinoline-3-N-t-butyl carboxamide.

Pandex $IC_{50}$=25% at 1,000 ng/ml

EXAMPLE 88

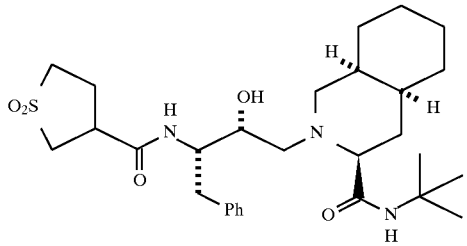

3-Carboxylic acid tetrahydrothiophene-1,1-dioxide and [3S-(3R*,4aR*,8aR*,2'S*,3'R*)]-2-[3'-Amino-2'-hydroxy-4'-phenyl]butyl decahydroisoquinoline-3-N-t-butyl carboxamide were coupled together by a procedure similar to that described in Example 77 above. The crude material was purified by flash chromatography (3% MeOH/CH$_2$Cl$_2$) to afford 50 mg (42% yield) of the compound of the formula shown above, [3S-(3R*,4aR*,8aR*,2'S*,3'R*)]-2-[2'-Hydroxy-3'-phenylmethyl-4'-aza-5'-oxo-5'-(tetrahydrothieno-3"-yl-1",1"-dioxide)pentyl]-decahydroisoquinoline-3-N-t-butyl carboxamide, as a mixture of diastereoisomers.

Pandex $IC_{50}$=28% at 20 ng/ml.

EXAMPLE 89

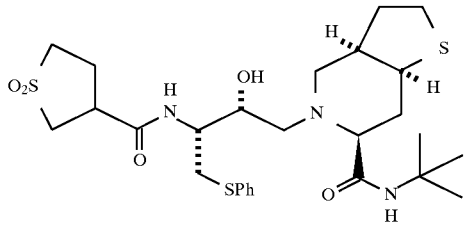

3-Carboxylic acid tetrahydrothiophene-1,1-dioxide and [6S-(6R*,3aS*,7aR*,2'S*,3'R*)]-5-[2-Hydroxy-4-phenyl-3-(benzoxycarbonyl)-aminobutyl)-octahydrothieno[3,2-c]pyridine-6-N-t-butyl carboxamide were coupled together by a procedure similar to that of Example 74H above. The crude material was purified by flash chromatography (3–4% MeOH/CH$_2$Cl$_2$) to afford 30 mg (57% yield) of [6S-(6R*,3aS*,7aR*,2'S*,3'S*)]-2-[2'-Hydroxy-3'-phenylthiomethyl-4'-aza-5'-oxo-5'-(tetrahydrothieno-3"-yl-1",1"-dioxide)pentyl]-octahydrothieno[3,2-c]pyridine-6-N-t-butyl carboxamide, as a mixture of diastereoisomers.

CEM $IC_{95}$=98 nM

Pandex $IC_{50}$=0.5 ng/ml (0.9)

EXAMPLE 90

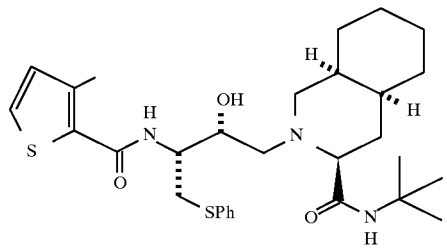

3-Methyl-2-carboxylic acid thiophene and (3S-(3R*,4aR*,8aR*,2'S*,3S*)]-2-[3'-amino-2'-hydroxy-4'(phenyl)thio]butyl decahydroisdquinoline-3-N-c-butyl carboxamide were coupled together by a procedure similar to that of Example 79 above, which afforded 39 mg (76% yield) of a compound of the above formula, which is [3S-(3R*,4aR*,8aR*,2'S*,3'S*)]-2-[2'-Hydroxy-3'-phenylthiomethyl-4'-aza-5'-oxo-5'-(3"-methyl-thieno-2"-yl)pentyl]-decahydroisoquinoline-3-N-t-butyl carboxamide.

EXAMPLE 91

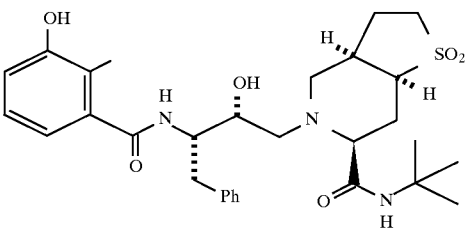

[6S-(6R*,3aS*,7aR*,2'S*,3'R*)]-2-[2'-Hydroxy-3'-phenylmethyl-4'-aza-5'-oxo-5'-(2"-methyl-3"-hydroxyphenyl)pentyl]-octahydrothieno[3,2-c]pyridine-6-N-t-butyl carboxamide (30.5 mg) was dissolved in 2 ml of MeOH. In another flask, "OXONE" (51 mg) was dissolved in 1 ml of water and added to the first flask. After 6 hours of stirring, another portion of "OXONE" (17 mg) was added, and the reaction mixture was stirred for 42 hours. The reaction mixture was diluted with CH$_2$Cl$_2$ and washed with water. The organic layer was dried with Na$_2$SO$_4$, filtered and concentrated. The crude residue was purified by radial chromatography (1000 micron plate; 3–9% MeOH/CH$_2$Cl$_2$) to afford 5 mg of [6S-(6R*,3aS*,7aR*,2'S*,3'R*)]-2-[2'-Hydroxy-3'-phenylthiomethyl-4'-aza-5'-oxo-5'-(2"-methyl-3"-hydroxyphenyl)pentyl]-octahydrothieno[3,2-c]pyridine-1,1-dioxide-6-N-t-butyl carboxamide.

EXAMPLE 92

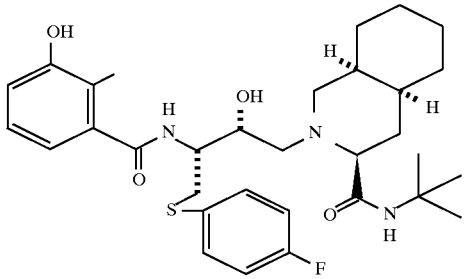

The compound shown above, [3S-(3R*,4aR*,8aR*,2'S*,3R*)]-2-[2'-Hydroxy-3'-(4'"-fluoro)phenylthiomethyl-4'- aza-5'-oxo-5'-(2"-methyl-3"-hydroxyphenyl)pentyl]-decahydroisoquinoline- 3-N-t-butyl carboxamide was prepared using analogous procedures as set forth in Example 23, with the exception that thiophenol was replaced by 4-fluorothiophenol in Preparation 8A.

The resulting product is used in an analogous manner as the product of Preparation 8A in the subsequent preparation protocol of Example 23.

EXAMPLE 93

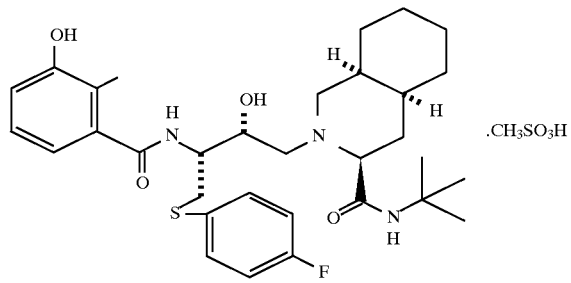

The compound shown above, [3S-(3R*,4aR*,8aR*,2'S*,3'R*)]-2-[2'-Hydroxy-3'-(4'"-fluoro)phenylthiomethyl-4'-aza-5'-oxo-5'-(2"-methyl-3"-hydroxyphenyl)pentyl]-decahydroisoquinoline-3-N-t-butyl carboxamide methanesulfonic acid salt was prepared by a method analogous to Example 75 (step 2) above.

As noted above, the compounds of the present invention are useful for inhibiting HIV protease, which is an enzyme associated with viral component production and assembly. An embodiment of the present invention is a method of treating HIV infection comprising administering to a host or patient, such as a primate, an effective amount of a compound of formula (1) or a pharmaceutically acceptable salt thereof. Another embodiment of the present invention is a method of treating AIDS comprising administering to a host or patient an effective amount of a compound of formula (1) or a pharmaceutically acceptable salt thereof. A further embodiment of the present invention is a method of inhibiting HIV protease comprising administering to an HIV infected cell or a host or patient, such as a primate, infected with HIV, an effective amount of a compound of formula (1) or a pharmaceutically acceptable salt thereof.

The term "effective amount" means an amount of a compound of formula (1) or its pharmaceutically acceptable salt that is effective to inhibit the HIV protease mediated viral component production and assembly. The specific dose of compound administered according to this invention to obtain therapeutic or inhibitory effects will, of course, be determined by the particular circumstances surrounding the case, including, for example, the compound administered, the route of administration, the condition being treated and the individual host or patient being treated. An exemplary daily dose (administered in single or divided doses) contains a dosage level of from about 0.01 mg/kg to about 50 mg/kg of body weight of a compound of this invention. Preferred daily doses generally are from about 0.05 mg/kg to about 20 mg/kg and, more preferably, from about 0.1 mg/kg to about 10 mg/kg.

The compounds of the invention may be administered by a variety of routes, including oral, rectal, transdermal, subcutaneous, intravenous, intramuscular and intranasal routes.

The compounds of the present invention are preferably formulated prior to administration. Therefore, another embodiment of the present invention is a pharmaceutical composition or formulation comprising an effective amount of a compound of formula (1) or a pharmaceutically acceptable salt thereof and a pharmaceutically acceptable carrier, such as a diluent or excipient therefor.

The active ingredient preferably comprises from 0.1% to 99.9% by weight of the formulation. By "pharmaceutically acceptable" it is meant that the carrier, such as the diluent or excipient, is compatible with the other ingredients of the formulation and not deleterious to the host or patient.

Pharmaceutical formulations may be prepared from the compounds of the invention by known procedures using known and readily available ingredients. In making the compositions of the present invention, the active ingredient will usually be admixed with a carrier, or diluted by a carrier, or enclosed within a carrier, which may be in the form of a capsule, sachet, paper or other suitable container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments (containing, for example, up to 10% by weight of the active compound), soft and hard gelatin capsules, suppositories, sterile injectable solutions, sterile packaged powders and the like.

Following formulation examples are illustrative only and not intended to limit the scope of the invention. The term "active ingredient" represents a compound of formula (1) or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|                         | Weight  |
| ----------------------- | ------- |
| Active ingredient       | 0.25    |
| Methanol                | 25.75   |
| Propellant 22           | 74.00   |
| (Chlorodifluoromethane) |         |
| Total                   | 100.00  |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|                                                | Quantity (mg/tablet) |
| ---------------------------------------------- | -------------------- |
| Active ingredient                              | 60                   |
| Starch                                         | 45                   |
| Microcrystalline cellulose                     | 35                   |
| Polyvinylpyrrolidone (as 10% solution in water)| 4                    |
| Sodium carboxymethyl starch                    | 4.5                  |
| Magnesium stearate                             | 0.5                  |
| Talc                                           | 1                    |
| Total                                          | 150                  |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which after mixing, are compressed on a tablet machine to yield tablets each weighing 150 mg.

Formulation 5

Capsules, each containing 80 mg of active ingredient, are made as follows:

|                            | Quantity (mg/capsule) |
| -------------------------- | --------------------- |
| Active ingredient          | 80 mg                 |
| Starch                     | 59 mg                 |
| Microcrystalline cellulose | 59 mg                 |
| Magnesium stearate         | 2 mg                  |
| Total                      | 200 mg                |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient               | 225 mg   |
| ------------------------------- | -------- |
| Saturated fatty acid glycerides | 2,000 mg |
| Total                           | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

Active ingredient 50 mg
Sodium carboxymethyl cellulose 50 mg
Syrup 1.25 ml
Benzoic acid solution 0.10 ml
Flavor q.v.
Color q.v.
Purified water to total 5 ml The active ingredient is passed through a No. 45 mesh U.S. sieve and mixed with the sodium carboxymethylcellulose and syrup to form a smooth paste. The benzoic acid solution, flavor and color are diluted with a portion of the water and added, with stirring. Sufficient water is then added to produce the required volume.

Formulation 8

An intravenous formulation is prepared as follows:

Active ingredient 100 mg
Isotonic saline 1,000 mL

The solution of the above ingredients generally is administered intravenously to a subject at a rate of 1 ml per minute.

ACTIVITY SCREENING

A number of tests were used to test the biological activity of HIV protease inhibitory compounds. For example, tests were used to analyze proteolytic inhibition rates and antiviral effects on HIV-infected cell lines. The procedures for these experiments are described below. The results from these assays are summarized in Table 1 below or are summarized in the examples above.

I. Primary Drug Screening of Anti-HIV Compounds at Southern Research Institute (SRI) (Results recorded in Table 1 are designated "SRI CEM (ng/ml)" or "SRI MT2 (ng/ml)")

A. Principle of MTT Assay:

SRI has an established program for the primary antiviral analysis of compounds in microtiter assays which measures the ability of a selected compound to inhibit HIV-induced cell killing. This assay involves the conversion of the tetrazolium dye MTT to a colored formazan product by mitochondrial enzymes in metabolically active cells. This assay system is used at SRI to screen over 30,000 compounds per year. Briefly, the assay involves the infection of CEM or MT2 cells in round bottom 96-well plates. The compound of interest is added just prior to infection. Following 6 days of incubation at 37° C. the plates are stained with MTT. The results of the assay are quantitated spectrophotometrically on a Molecular Devices Vmax plate reader. The data are analyzed by linear regression utilizing an in-house software program to calculate antiviral activity ($IC_{25}$, $IC_{50}$, $IC_{95}$) and toxicity ($TC_{25}$, $TC_{50}$, $TC_{95}$) as well as other values.

Primary antiviral assays are routinely performed in CEM or MT-2 cells. SRI has found that all active compounds have been identified in CEM cells, while experiments performed in the MT-2 cell line miss a small proportion of the active compounds.

B. Standard Screening Assays in CEM and MT-2 Cells

1. Compound dilution and delivery to the plates

Drugs are solubilized in the appropriate vehicle such as distilled water or DMSO if necessary. Latex gloves, lab coats and masks are used during all phases of the handling process to prevent exposure to potentially harmful agents. The drug is prepared at the appropriate concentration and stored at −20° C. until used by the screening laboratory. The first dilution of each compound is made in a dilution tube with medium to yield a concentration two-fold that of the highest test concentration. Sterile titer tubes are then used to make serial one half-log dilutions of each compound. Following drug dilution, the diluted compound is added to the appropriate well of a 96-well microtiter plate. Up to 12 dilutions can be assayed conveniently in triplicate on a single plate with all appropriate controls including cell control, virus control, toxicity control, drug color control, medium control and plastic (background) control. When testing includes only six dilutions, two drugs can be assayed on a single microtiter plate. The drugs are added to the plate in a final volume of 100 microliters.

2. Cells and virus

During the time the drug dilutions are prepared, cells are washed and counted. Viability is monitored by trypan blue dye exclusion and assays are not performed if the viability falls below 90%. Cells are maintained in an exponential growth phase and are split 1:2 on the day prior to assay to assure exponential growth rate.

For the primary screen, the cell lines utilized are CEM and MT-2. Unless otherwise indicated, the medium used is RPMI 1640 with 10% heat-inactivated fetal calf serum (FBS), glutamine and antibiotics.

Cells are propagated at 37° C. in an atmosphere of 5% $CO_2$ n air. The virus employed for this work is HIV-1 isolates IIIB and/or RF, which are prepared by an acute infection process.

Briefly, virus-infected cells are pelleted on a daily basis beginning at three days post-infection until the virus has killed all of the cells in the culture. Reverse transcriptase activity and p24 ELISA are used to identify pools with the greatest amount of virus.

These 24-hour harvests are pooled, filtered and frozen at −90° C. Prior to use in the assay, the infectious pool of virus is titered on all available cell lines in order to determine the amount of virus required in the antiviral assay.

In general, pools produced by the acute infection method require the addition of one microliter of infectious virus per well resulting in the screening of drugs at a multiplicity of infection of 0.01. In this manner, enough virus is prepared and frozen to complete over one thousand microtiter plates, allowing the testing of up to two thousand compounds from a single stock of infectious virus. The use of a single stock of virus for a long period of testing has very favorable effects on the repeatability of the assay systems.

Virus infection of the CEM and MT-2 cells for the antiviral assay is carried out in a bulk infection process. The appropriate number of cells required to complete the assay is mixed with infectious virus in a conical centrifuge tube in a small total volume of 1–2 milliliters.

Following a 4-hour incubation the infected cells are brought to the appropriate final concentration of $5\times10^4$ cells per milliliter with fresh tissue culture medium and 100 microliters are added to the appropriate experimental and virus control wells. Uninfected cells at the same concentration are plated for the toxicity controls and for the cell controls. Assays can also be performed using an in-well infection method. In this case, drug, cells and virus are added to the well individually. In each case the MOI is adjusted to give complete cell killing in the virus control wells by Day 6.

3. Evaluation of CPE-inhibition

Following the addition of cells and drugs to the microtiter plate, the plate is incubated for 6 days at 37° C. Experience has determined that incubation for longer periods of time (7–8 days) or the use of higher input cell numbers ($1\times10^4$) results in significant decreases in cell control viability and a narrowing in the differential in optical density between cell and virus controls upon staining with MTT.

The method of evaluating the antiviral assay involves the addition of 20 microliters of the tetrazolium salt MTT at 5 mg/ml to each well of the plate for 4–8 hours. After this incubation period, the cells are disrupted by the addition of 50 microliters of 20% SDS in 0.01N HCl.

The metabolic activity of the viable cells in the culture result in a colored reaction product which is measured spectropotometrically in a Molecular Devices Vmax plate reader at 570 nm. The optical density (O.D.) value is a function of the amount of formazan product which is proportional to the number of viable cells.

The plate reader is on-line to the screening laboratory microcomputer which evaluates the plate data and calculates plate data. The plate report provides a rundown of all pertinent information including the raw O.D. values, the calculated mean O.D.'s and the percent reduction in viral CPE as well as calculations including $TC_{50}$, $IC_{50}$ and antiviral and specificity indices. Finally, the results include a plot which visually depicts the effect of the compound on uninfected cells (toxicity) and the protective or nonprotective effect of the compound on the infected cells.

II. Whole Cell Screening of Anti-HIV Compounds at Eli Lilly (Results Recorded in Table 1 Are Designated "Whole Cell $IC_{50}$ nM" or "Whole Cell $IC_{90}$ nM"

A. Purpose and Materials

Purpose: To determine $IC_{50}$ and $CC_{50}$ for compounds:

Reagents and Materials

Media A

Media A[1% DMSO] (100 microliters DMSO+9.9 ml media A)

SN 123 used to infect cells (15 ml for 6 plates) (10 ml for 4 plates)

CEM cells @ [$1\times10^4$] cells/ml (4 plate=40 ml) (6 plate= 60 ml) DMSO (need 5 ml)

35B at [10 mM] (need 70 microliters of each)

A–D at [10 mM] in 100% DMSO 4 or 6 u-bottom 96-well plates 4 flat bottom 96-well plates for dilutions 8–10 boxes of sterile costar tips Approximately 10 reagent trays Costar 12-pette Relevant information 1000 cells/well=$1\times10^4$ cells/ml=1000 cells/100 microliters 200 microliters=total volume in a well Final concentration of DMSO=0.25%

Final dilution of Sn123=1:64

Serially diluted compounds 35B, A–D, 1:3

B. Procedure

1. Preparation and Plating of Cells, Media A and Media A (1% DMSO)

a. Number a 96-well tissue culture plate for each compound tested, one for a control plate, and one for the control compound.

| Plate # | Description |
|---|---|
| 1 | Controls Neg. and Pos. |
| 2 | 35B |
| 3 | A |
| 4 | B |
| 5 | C |
| 6 | D | b. Count cells on hemacytometer and resuspend them in 40 ml or 80 ml of Media A at a concentration of $[1\times10^4]$ cells/ml.
Counting Cells on a Hemacytomer
  Label two 1.8 ml nunc tubes 1 and 2.
  Put 0.5 ml of well mixed CEM cells (in growth phase) in tube 1.
  Put 50 micoliters PBS and 40 microliters of trypan blue into tube 2.
  Mix up the cells in tube 1 then remove 10 microliters of cells and put them into tube 2.
  Mix well in tube 2, then remove 10 microliters of the stained cells and put them on the hemacytometer.
  Count the number of cells in the center square of the hemacytometer with the microscope set on 10X.
  The concentration of the stock CEM's in cells/ml is as follows:
    Cells counted$\times 1\times 10^5$=Concentration of CEM's in [cells/ml].
  c. Add 200 microliters Media A to: A1 of places 2–6. These are Blanks. A4–H4 of plate 1. These are Blanks.
  d. Add 5 microliters Media A to all wells of Rows A–D of plates 2–6 except A1 (the top half of each plate).
  e. Add 50 microliters of Media A to wells A1–D3 of Plate 1 (the top half of the plate).
  f. Add 50 microliters Media A[1% DMSO] to all wells of Columns 1–3 of plate 1.
  g. Add 100 microliters of $[1\times10^4]$ cells/ml to all wells of Columns 1–3 of plate 1 and to all wells (except A1 which is the blank) of the other plates. This puts 1000 cells/well.
  h. Put plates in an incubator while doing drug dilutions.
2. Preparation Control and Test Drugs
  (a) Preparation of (35B, A–D) 1:3 serial dilutions in plate with 100% DMSO.
    (1) Put 60 microliters of DMSO into all wells of Columns 2–12, Rows A–E.
    (2) Put 70 microliters of 35B [10 mM] at 100% DMSO into well A1.
    (3) Put 70 microliters of A [10 mM] at 100% DMSO into well B1.
    (4) Put 70 microliters of B [10 mM] at 100% DMSO into well C1.
    (5) Put 70 microliters of C [10 mM] at 100% DMSO into well D1.
    (6) Put 70 microliters of D [10 mM] at 100% DMSO into well E1.
    (7) Serially dilute (35B, A–D) 1:3 down through Column 12 by transfering 30 microliters from Column 1 to Column 2, then from Column 2 to Column 3, etc., down through Column 12. Change tips before each dilution.
  (b) Preparation of 1:10 Dilution plate in Media A:
    (1) In rows A–E of another plate make a row for the first 1:10 dilution to correspond to each compound's 100% DMSO row.
      35B into Row A for the first 1:10 dilution.
      A into Row B for the first 1:10 dilution.
      B into Row C for the first 1:10 dilution.
      C into Row D for the first 1:10 dilution.
      D into Row E for the first 1:10 dilution.
    (2) Put 180 microliters of media A into all wells of rows A–E corresponding to the 100% DMSO rows. 2.5 ml needed per row.
    (3) Remove 20 microliters from all wells of each row of the 100% DMSO rows and transfer it to the corresponding 1:10 row.
  c. Preparation of 1:100 Dilution plate in Media A
    (1) Make a plate for every 3 compounds to be tested.
    (2) Put 225 microliters of media A into all wells of rows A, B, D, E, G, and H, leaving rows C and F empty. Use 20 ml of media A per plate.
    (3) Transfer 25 microliters of each compound from the row in the 1:10 dilution to the corresponding two rows on the 1:100 dilution plate changing tips before each transfer.

| Column No. | Drug Conc. [nM] | Drug Conc. [microliters] |
|---|---|---|
| 1 | 25000 | 25.00000 |
| 2 | 8333 | 8.33333 |
| 3 | 2778 | 2.77778 |
| 4 | 926 | 0.92593 |
| 5 | 309 | 0.30864 |
| 6 | 103 | 0.10288 |
| 7 | 34 | 0.03429 |
| 8 | 11 | 0.01143 |
| 9 | 3.81 | 0.00381 |
| 10 | 1.27 | 0.00127 |
| 11 | 0.42 | 0.00042 |
| 12 | 0.14 | 0.00014 |

3. Addition of Viral SN123 to Plates
  a. Thaw Sn123 in 37° C. water bath for approximately 10 minutes.
  b. Dilute Sn123 1:16 by adding 1 ml of Sn123 to 15 ml of media A.
  c. Add 50 microliters of Sn123 [1:16] to wells E1–H12 of plates 2–6 and to wells E1–H3 of plate 1.
4. Addition of Drugs to Plates
  a. Add 50 microliters of the control and test drugs from the rows in the 1:100 dilution plates to the appropriate rows in the final plates (changing tips before each transfer). One row in the 1:100 place will do 4 rows in the final place. Leave A1 blank.
  b. Incubate all plates 7 days at 37° C. 5% $CO_2$.
  c. Do Xtt protocol on day 7 as follows:
  d. Preparation of Xtt/PMS Solution: (4 plate=20 ml) (6 plate=30 ml)
    (1) Recipe for 2 mM PMS:
      15.3 mg PMS+0.5 ml PBS=PMS at [100 mM]100 microliters [100 mM] PMS+4.9 ml PBS=PMS at [2 mM]
    (2) Heat 500 ml of $H_2O$ in microwave for 5 minutes on high.
    (3) Put 20 or 30 ml of phenol red RPMI in a 50 ml centrifuge tube.
    (4) Put the RPMI in the beaker of hot water.
    (5) Add 20 or 30 mg of XTT to the warmed up RPMI. Final concentration of XTT=[1 mg/ml].
    (6) Wait for XTT to dissolve, then add 200 microliters of [2 mM] PMS per 10 ml of XTT solution.
  e. Addition of Xtt/PMS to Plate:
    (1) Add 50 microliters of XTT/PMS solution to all wells of all plates.

(2) Cover plates and incubate 4 hours at 37° C. at 5% $CO_2$.

(3) Remove plates from incubator and replace covers with plastic plate sealers.

(4) Mix contents of plates.

(5) Read plates at test wavelength 450 nM and reference wavelength 650 nM.

III. Fluorescence HIV-1 Protease Inhibitor Assay To Screen For Inhibition of HIV Protease (Results Recorded in Table 1 Are Designated "Pandex (ng/ml)")

As used herein, the abbreviations are defined as follows:
BSA-bovine serum albumin
BOC-t-butoxycarbonyl
BrZ-2-bromobenzyloxycarbonyl
2-ClZ-2-chlorobenzyloxycarbonyl
DCC-dicyclohexylcarbodiimide
DIEA-diisopropylethylamine
DTT-dithiothreitol
EDTA-ethylenediaminetetraacetic acid
FITC-fluorescein isothiocarbamyl
HERPES-4-(2-hydroxyethyl)-1-piperazine-ethanesulfonic acid
MES-4 morpholineethanesulfonic acid
PAM-phenylacetimidomethyl
TAPS-3-[tris(hydroxymethyl)methyl]amino-1-sulfonic acid
TRIS-tris(hydroxymethyl)aminomethane
TOS-p-toluenesulfonyl (tosyl)

A. Preparation of Protease and Gag Fractions

1. Culture of *E. coli* K12 L507/pHP10D

Lyophils of *E. coli* K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 ml LB medium (10 g Bacto-tryptone, 5 g Bacto-yeast extract, and 10 g aqueous sodium chloride per liter; the pH was adjusted to 7.5 and incubated at 32° C. overnight).

A small portion of the overnight culture was placed on LB-agar (LB medium with 15 g/L Sacto-agar) plates containing 12.5 micrograms/ml tetracycline in a manner so as to obtain a single colony isolate of *E. coli* K12 L507/pHP10D. The single colony obtained was inoculated into 10 ml of LB medium containing 12.5 micrograms/ml tetracycline and incubated overnight at 32° C. with vigorous shaking. The 10 ml overnight culture was inoculated into LB medium containing 12.5 micrograms/ml tetracycline and incubated at 32° C. with vigorous shaking until the culture reached mid-log phase.

2. Culture of *E. coli* K12 L507/pHGAG

Lyophils of *E. coli* K12 L507/pHGAG were obtained from the NRRL under the accession number NRRL B-18561 (deposited Nov. 14, 1989). A purified colony of *E. coli* K12 L507/pHGAG was isolated, and used as an inoculum for a culture which was grown to mid-log phase in substantial accordance with the teaching of Step A, above, for *E. Coli* K12 L507/pHP10D.

3. Preparation of Protease Fraction

A culture of *E. coli* K12 L507/pHP10D was grown to mid-log phase at 32° C. in LB media containing 12.5 micrograms/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 ml of 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000×g, the supernatant was diluted to a total volume of 60 ml with Buffer A and loaded onto a 2.0×19 cm QAE-Sepharose column (1 ml/min, 4° C.), that had been equilibrated in Buffer A. The column was washed isocratically for 180 min and then eluted with a gradient eluent of 0–1.0M aqueous sodium chloride in Buffer A over 120 min. Enzymatic activity was measured by HPLC using the synthetic peptide Ser-Gln-Asn-Tyr-Pro-Ile-Val as described in Margolin et al., *Biochem. Biophys. Res. Commun.*, 167, 554–560 (1990); the production of the p1 peptide (Ser-Gln-Asn-Tyr) was measured.

The active fractions were combined, adjusted to pH 1.2M in ammonium sulfate, and applied to a 2.0×18 cm hexyl agarose column that had been equilibrated in Buffer A containing 1.2M ammonium sulfate. The sample was loaded at a flow rate of 1 ml/min at 4° C., washed with the equilibration buffer for 240 min (1 ml/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 ml using an Amicon stirred cell with a YM-10 membrane and then applied to a MonoS cation exchange column (1.0×10 cm) that had been equilibrated in Buffer A. The sample was loaded at a flow rate of 1 ml/min at 25° C. After washing isocratically for 30 min, the protease was eluted using a linear gradient of 0–0.45M aqueous sodium chloride in Buffer A over 40 min. The column was washed isocratically in Buffer A containing 0.45M aqueous sodium chloride for 30 minutes.

The active fractions were combined and concentrated to 200 microliters using an Amicon stirred cell and a YM-10 membrane and then the protease was applied to a Superose 6 size exclusion column equilibrated in Buffer A containing 0.1M aqueous sodium chloride. The column was washed isocratically in this buffer at a flow rate of 0.5 ml/min, following which the HIV protease was eluted as a single peak.

QAE-Sepharose and hexyl agarose were purchased from Sigma Chemical Company. Superose 6 and MonoS were purchased from Pharmacia. Buffers and reagents were obtained from Sigma.

4. Preparation of Gag Fraction

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 ml lysis buffer containing 5 mg/ml lysozyme. Lysis buffer was comprised of 50 mM Tris-HCl (pH 7.8), 5 mM EDTA, 1 mM DTT, 100 mM NaCl, 1 microgram/ml E64 and 2 micrograms/ml aprotinin. The culture was incubated about 30 to 60 minutes at 4° C., then briefly sonicated in a Branson® Cell Disrupter at 60% power for three 20 second bursts with chilling between each burst. The culture was then centrifuged at 15,000×g. The supernatant, which contains the unprocessed gag protein, was partially purified by size exclusion chromatography on a Sephadex G-50 column and stored at −20° C. in 50% glycerol and lysis buffer.

B. Preparation of Substrate: $N^a$-Biotin-Gly-Ser-Gln-Asn-Tyr-Pro-Ile-Val-Gly-Lys($N^e$-FITC)-OH (a=Alpha, e=Epsilon)

1. Preparation of the amino-terminal biotinylated peptide

The protected peptide-resin $N^a$-Boc-Gly-Ser-Gln-Asn-Tyr(Brz)-Pro-Ile-Val-Gly-Lys(2-ClZ)-OCH$_2$-PAM-resin was synthesized on an Advanced Chemtech Model 200 peptide synthesizer at 1.5 mmol scale using the standard double-couple protocol. The amino terminal t-Boc group was removed with 50% trifluoroacetic acid in methylene chloride and the resulting resin neutralized with 5% diisopropylethylamine (DIEA) in methylene chloride. Then, 1.1 g (4.5 mmol) of biotin in 20 ml of dimethylsulfoxide was added to the peptide resin, followed by 4.5 mmol of dicyclohexylcarbodiimide (DCC) in 9 ml of methylene chloride. The resulting reaction mixture was diluted to 40 ml total volume using 11 ml of methylene chloride, and then allowed to react for approximately 5 hours. The reaction solution was concentrated, the resin washed sequentially with dimethylsulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (96%) yield.

2. Deprotection

The peptide was deprotected and cleaved from the resin using 50 ml of a hydrofluoric acid/m-cresol solution, 0° C., 1 hour. After removal of the hydrofluoric acid by vacuum distillation, the m-cresol was extracted from the reaction mixture using 100 ml of diethylether. The peptide was then solubilized in 50% aqueous acetic acid, frozen and lyophilized to provide 2.14 g.

3. Purification

The crude peptide, biotinylated at the amino terminal, was dissolved in 200 ml of a 5% acetonitrile in water solution containing 0.1% trifluoroacetic acid and then filtered through a 0.22 micron filter. The resulting solution was applied to a 2.2×25 cm reverse phase column of octadecylsilica (Vydac C-18) which had been equilibrated with the same buffer. The peptide was eluted using an 855 minute linear gradient of 7.5–25% acetonitrile, at 2 ml/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62% yield).

Amino acid analysis of the isolated biotinylated peptide gave the following ratios in agreement with theoretical: Asn 1.1; Ser 0.96; Gln 1.1; Pro 1.1; Gly 2.1; Val 0.80; Ile 0.78; Tyr 1.1; Lys 1.1. Fast-atom bombardment mass spectrometry gave a molecular ion mass peak of 1288, in agreement with theoretical.

4. Labeling

The purified biotinylated peptide was then labeled with a fluorescent marker at the C-terminal end for use in the Pandex assay. First, the biotinylate peptide (1.206 g, 0.936 mmol) was dissolved in 100 ml of 0.1M sodium borate, pH 9.5. Then, a solution of 3 g (7.7 mmol) of fluorescein isothiocyanate in 15 ml of dimethylsulfoxide was added to the reaction mixture in 10 equal portions over two hours. The resulting mixture was allowed to react for one hour after the final addition. The solution was adjusted to pH 3 using 5N hydrochloric acid, resulting in the formation of a precipitate which was removed by centrifugation.

The peptide solution was then adjusted to pH 7.8 using 5N sodium hydroxide and then diluted to 200 ml by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 ml/minute, with collection of fractions. Analytical HPLC was used to analyze the fractions. The fractions containing the desired product were then combined, frozen and lyophilized to provide 190.2 mg (12%).

Amino acid analysis of the purified peptide gave the following in agreement with theory: Asn 1.1; Ser 1.0; Gln 1.1; Pro 1.1; Gly 2.1; Val 0.8; Ile 0.8; Tyr 1.1; Lys 1.0. Fast-atom bombardment mass spectrometry gave a molecular ion mass peak of 1678, in agreement with theory.

5. Fluorescence HIV-1 Protease Inhibitor Assay

The following buffers and solutions are used in the Fluorescence HIV-1 Protease Inhibitor Assay:

MES-ALB Buffer:

0.05M 4-morpholine ethane sulfonic acid, pH 5.5

0.02M NaCl 0.002M EDTA 0.001M DTT 1.0 mg/ml BSA

TBSA Buffer:

0.02M TRIS 0.15M NaCl 1.0 mg/ml BSA

Avidin Coated

Beads Solution:

0.1% solution of Fluoricon Avidin Assay Particles (Avidin conjugated to solid polystyrene beads, 0.6–0.8 microns in diameter in TBSA Buffer Enzyme Solution:

27 IU/ml of purified HIV-1 protease in MES-ALB buffer (1 IU equals the amount of enzyme required to hydrolyze 1 micromole of substrate per minute at 37° C.)

To each well of a round bottom, 96-well plate is added 20 microliters of the Enzyme Solution followed by 10 microliters of the compound to be evaluated in a 20% aqueous dimethylsulfoxide solution. Purified HIV-1 protease was obtained as described above. The resulting solution is incubated for one hour at room temperature and then 20 microliters of a solution containing the substrate, prepared above, in MES-ALB buffer (1.5 microliters/ml) is added to each well. The solutions are then incubated for 16 hours at room temperature and then each well is diluted with 150 microliters of MES-ALB buffer.

To each well of a second round bottom, 96-well Pandex plate is added 25 microliters of the Avidin Coated Beads Solution. Then, to each well is added 25 microliters of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of the present invention are set forth below in Tables 1, 2, and 3. All values have been normalized to a positive control which is [1S-(1R*,4R*,5S*)]-N-(1-(2-amino-2-oxyethyl)-2-oxo-3-aza-4-phenylmethyl-5-hydroxy-6-(2-(1-t-butylamino-1-oxomethyl)phenyl)hexyl)-2-quinolinyl carboxamide.

Activity data for exemplary compounds emcompassed by the present invention is provided in Tables 1, 2, and 3 below and in the preceeding Examples. Results in Parentheses are for Example 1 of Published European Patent Application 0 526 009 A1=35B in same assay.

TABLE 1

Results in Parentheses are for Example 1 of Published European Patent Application 0 526 009 A1 - 35B in same assay

| Example | Whole cell $IC_{50}$ nM | Whole cell $IC_{90}$ nM | SRI CEM ng/ml | SRI MT2 ng/ml | Pandex ng/ml |
|---|---|---|---|---|---|
| 12 | 15 (69) | | 16.5 | 24.3 | 9.4[a] 11.4[b] |
| 28 | *35.7* (41.17) | *91.8* (76.45) | | | |
| 3 | 96.1 (70.0) | 286.3 (237.3) | 15.2 | 21.3 | 11.6[d] |
| 22 | 399.9 (74.8) | 798 (257.8) | 136 | 53 | 70[c] |
| 21 | 414.28 (41.17) | 886.16 (76.45) | 443 | 427 | 7.9[e] |
| 20 | 186.11 (43.96) | 671.15 (92.17) | 153 | 144 | 85[f] |
| 37 | | | | | 33[g] |

[a]35B 3.1 ng/ml; [b]35B 2.7 ng/ml; [c]35B 9.6 ng/ml;
[d]35B 0.48 ng/ml; [e]35 B 0.7 ng/ml; [f]35B 1.3 ng/ml;
[g]35B 1.2 ng/ml; **tested as the mesylate salt

| Example | Whole cell $IC_{50}$ nM | Whole cell $IC_{90}$ nM | SRI CEM ng/ml | SRI MT2 ng/ml | Pandex ng/ml |
|---|---|---|---|---|---|
| 25 | | | 211 | 169 | 2.0[b] 14.3[d] |
| 26 | 56 (70) | 165.7 (237.3) | 49.7 | 49.0 | 2.0[c] |

[b]35B 0.63 ng/ml; [d]35B 9.3 ng/ml; [3]35B 0.65 ng/ml

| Example | Whole cell $IC_{50}$ nM | Whole cell $IC_{90}$ nM | SRI CEM ng/ml | SRI MT2 ng/ml | Pandex ng/ml |
|---|---|---|---|---|---|
| 12 | 15 (69) | | 16.5 | 24.3 | 2.8[d] 11.4[b] |
| 23 | 2.39 (9.93) | 19.0 (53.5) | 8.62 | 6.27 | 0.2[c] 0.16[d] |
| 92 | 2.01 | 57.02 | | | <0.16[f] |
| 24 | 25 (19) | | 67 (74.8) | 41.4 46.4 | 2.8[e] 84%/20[d] |

[b]35B 2.7 ng/ml; [c] 35B 9.3 ng/ml; [d]35B 0.63 ng/ml;
[e]35B 0.48 ng/ml; [f]5B 1.24 ng/ml

| Example | Whole cell $IC_{50}$ nM | Whole cell $IC_{90}$ nM | SRI CEM ng/ml | SRI MT2 ng/ml | Pandex ng/ml |
|---|---|---|---|---|---|
| 29 | 1587.6 | 4455.7 | | | 2.0[a] |
| 23 | 2.39 (9.93) | 19.0 (53.5) | 8.62 | 6.27 | 0.2[b] 0.16[d] |
| 31 | 430.05 | 884.09 | | | 3.5[c] |
| 32 | 539.47 | 2307.2 | | | 1.5[c] |
| 38 | | | | | 35[e] |
| 39 | | | | | 8[f] |
| 90 | | | | | 27[g] |
| 30 | 366.63 | 735.75 | | | 5.0[a] |

[a]35B 1.2 ng/ml; [b]35B 2.7 ng/ml; [c]35B 2.9 ng/ml;
[d]35B 0.63 ng/ml; [e]35 B 2.3 ng/ml; [f]35B 1.5 ng/ml;
g) 35B 1.24 ng/ml

| Example | Whole cell[i] $IC_{90}$ nM | Whole cell[i] $IC_{50}$ nM | SRI CEM $IC_{50}$ ng/ml | SRI MT2 $IC_{50}$ ng/ml | Pandex ng/ml |
|---|---|---|---|---|---|
| 12 | 47.77 (??) 91.80* (76.45) | 15 (69) 35.71* (41.17) | 16.5 11.8 | 24.3 10.0 | 9.4[a] 11.4[b] |
| 3 | 73.15 (78.01) 286.3 (165.7) | 22.28 (31.33) 96.1 (70) | 15.2 11.3 | 21.3 21.5 | 11.6[d] |
| 11 | | 114 (9) | 420 338 | 649 387 | 13.7[b] |

[a]35B 3.1 ng/ml; [b]35B 2.7 ng/ml; [c]35B 0.38 ng/ml;
[d]35B 0.48 ng/ml; [e]35 B 1.5 ng/ml; [f]35B 1.5 ng/ml;
[g]35B 1.2 ng/ml; [h]35B 0.65 ng/ml; [i]Results in parentheses are for 35B in same assay; [k]35B 1.4 ng/ml; [l]35B 2.1 ng/ml
*Tested as mesylate salt

| Example | Whole cell[i] $IC_{90}$ nM | Whole cell[i] $IC_{50}$ nM | SRI CEM $IC_{50}$ ng/ml | SRI MT2 $IC_{50}$ ng/ml | Pandex ng/ml |
|---|---|---|---|---|---|
| 1 | | | 1000 1380 | 1310 1500 | 462[d] |
| 18 | | 738.75 (70.67) | 256 231 | 254 232 | 9.6[e] |
| 7 | | 323 (19) | 617 1330 | 2330 970 | 18.5[c] 22.1[d] |
| 14 | | | 2550 1240 | 1610 1290 | 48.7[d] |

[a]35B 3.1 ng/ml; [b]35B 2.7 ng/ml; [c]35B 0.38 ng/ml;
[d]35B 0.48 ng/ml; [e]35 B 1.5 ng/ml; [f]35B 1.5 ng/ml;
[g]35B 1.2 ng/ml; [h]35B 0.65 ng/ml; [i]Results in parentheses are for 35B in same assay; [k]35B 1.4 ng/ml; [l]35B 2.1 ng/ml
*Tested as mesylate salt

| Example | Whole cell $IC_{90}$ nM | Whole cell $IC_{50}$ nM | SRI CEM $IC_{50}$ ng/ml | SRI MT2 $IC_{50}$ ng/ml | Pandex ng/ml |
|---|---|---|---|---|---|
| 5 | | | 4970 4430 | 7800 5030 | 1000[c] |
| 17 | | | 2900 2500 | 8990 5390 | 346[b] |
| 9 | | | | | 52.7[a] |
| 8 | | | | | 5.80[a] |

[a]35B 3.1 ng/ml; [b]35B 2.7 ng/ml; [c]35B 0.38 ng/ml;
[d]35B 0.48 ng/ml; [e]35 B 1.5 ng/ml; [f]35B 1.5 ng/ml;
[g]35B 1.2 ng/ml; [h]35B 0.65 ng/ml; [i]Results in parentheses are for 35B in same assay; [k]35B 1.4 ng/ml; [l] 35B 2.1 ng/ml
*Tested as mesylate salt

| Example | Whole cell[i] $IC_{90}$ nM | Whole cell[i] $IC_{50}$ nM | SRI CEM $IC_{50}$ ng/ml | SRI MT2 $IC_{50}$ ng/ml | Pandex ng/ml |
|---|---|---|---|---|---|
| 16 | | | | | 125[c] |
| 15 | | | 1430 1590 | 1680 1470 | 181[d] |
| 36 | | | 2430 1730 | 1870 2300 | 93[e] |
| 82 | | | | | 158[f] |

[a]35B 3.1 ng/ml; [b]35B 2.7 ng/ml; [c]35B 0.38 ng/ml;
[d]35B 0.48 ng/ml; [e]35 B 1.5 ng/ml; [f]35B 1.5 ng/ml;
[g]35B 1.2 ng/ml; [h]35B 0.65 ng/ml; [i]Results in parentheses are for 35B in same assay; [k]35B 1.4 ng/ml; [l]35B 2.1 ng/ml
*Tested as mesylate salt

| Example | Whole cell[i] $IC_{90}$ nM | Whole cell[i] $IC_{50}$ nM | SRI CEM $IC_{50}$ ng/ml | SRI MT2 $IC_{50}$ ng/ml | Pandex ng/ml |
|---|---|---|---|---|---|
| 80 | 27.94 | 8.99 | | | 0.3% |

TABLE 1-continued

Results in Parentheses are for Example 1 of
Published European Patent Application 0 526 009 A1 - 35B
in same assay

|    |         |         |      |      | at $20^k$ $4^l$ |
|----|---------|---------|------|------|-----------------|
| 78 | 66.48   | 8.64    | 2040 | 1640 | $1993^g$        |
|    | (73.81) | (19.96) | 34.1 | 80.0 |                 |
|    |         |         | 45.8 | 80.0 |                 |
| 2  |         |         | 1380 | 1580 | $520^d$         |
|    |         |         | 1580 | 1630 |                 |

[a] 35B 3.1 ng/ml; [b] 35B 2.7 ng/ml; [c] 35B 0.38 ng/ml;
[d] 35B 0.48 ng/ml; [e] 35 B 1.5 ng/ml; [f] 35B 1.5 ng/ml;
[g] 35B 1.2 ng/ml; [h] 35B 0.65 ng/ml; [i] Results in parentheses are for 35B in same assay; [k] 35B 1.4 ng/ml; [l] 35B 2.1 ng/ml
*Tested as mesylate salt

| Example | Whole cell[i] $IC_{50}$ nM | Whole cell[i] $IC_{90}$ nM | SRI CEM $IC_{50}$ ng/ml | SRI MT2 $IC_{50}$ ng/ml | Pandex ng/ml |
|---------|------|------|-----|-----|-------|
| 19 | 16.10 | 41.96 | | | $0.42^a$ |
|    | (52.77) | (101.17) | | | |
| 33 | 39.54 | 200.15 | | | $2^b$ |
|    | (22.02) | (80.07) | | | |
| 34 | 149.05 | 564.04 | | | $54^b$ |
|    | (22.80) | (80.07) | | | |
| 35 | | | 501 | 519 | $73^c$ |
|    | | | 156 | 368 | |

[a] 35B 1.5 ng/ml; [b] 35B 1.2 ng/ml; [c] 35B 2.3 ng/ml;
[d] 35B 1.9 ng/ml; [e] Results in parentheses are for 35B in same assay
*Tested as the mesylate salt

TABLE 2

Example 74 I $IC_{50}$ = 0.3 nM (Pandex)
$IC_{50}$ = 4.06 nM (Whole Cell)
$IC_{90}$ = 9.74 nM (Whole Cell)

Example 75

$IC_{50}$ = 14.5 nM (Whole Cell)
$IC_{90}$ = 56.1 nM (Whole Cell)

TABLE 3

Inhibitory Activity

| Example No. | Fluorescence Assay $IC_{50}$ in ng/mL |
|-------------|---------------------------------------|
| Control | 1.0 |
| 1 | 962 |
| 2 | 1083 |
| 3 | 24.2 |
| 4 | 1425* |
| 5 | 2631* |
| 6 | 513* |
| 7 | 255* |
| 8 | 16.4 |
| 9 | 17 |
| 10 | N.T. |
| 11 | 5.1 |
| 12 | 8.3* |
| 13 | 346 |
| 14 | 101 |
| 15 | 377 |
| 16 | 329 |
| 17 | 269* |
| 18 | 67.2* |
| 19 | 0.32 |
| 20 | 6.5 |
| 21 | 9.4 |
| 22 | 0.73 |
| 23 | 0.25 |
| 24 | 5.8 |
| 25 | 3.2 |
| 26 | 3.1 |
| 27 | N.T. |
| 28 | N.T. |
| 29 | 1.7 |
| 30 | 4.2 |
| 31 | 1.2 |
| 32 | 0.52 |
| 33 | 1.7 |
| 34 | 4.5 |
| 35 | 31.7 |
| 36 | 62 |
| 37 | 27.5 |
| 38 | 15.2 |
| 39 | 5.3 |
| 40 | 10 |
| 41 | 6 |
| 42 | 106 |
| 43 | 540 |
| 44 | 70 |
| 45 | 133 |
| 46 | 63 |
| 47 | 91 |
| 48 | 177 |
| 49 | 86 |
| 50 | 120 |
| 51 | 500 |
| 52 | 281 |
| 53 | 55 |
| 54 | 77 |
| 55 | 112 |
| 56 | 94 |
| 57 | 800 |
| 58 | 180 |
| 59 | 350 |
| 60 | 400 |
| 61 | 1600 |
| 62 | 198 |
| 63 | 250 |
| 64 | 113 |
| 65 | 390 |
| 66 | 274 |
| 67 | 543.1 |
| 68 | 10000 |
| 69 | $IC_{35}(15000)$** |
| 70 | 105 |
| 71 | 180 |
| 72 | 630 |
| 73 | 1940 |

N.T. No tested.
*A calculated average.
**The concentration of the inhibitor was not increased above 15 µg/mL.

Exemplary structures of compounds encompassed by the present invention are shown in Table 4 below.

TABLE 4
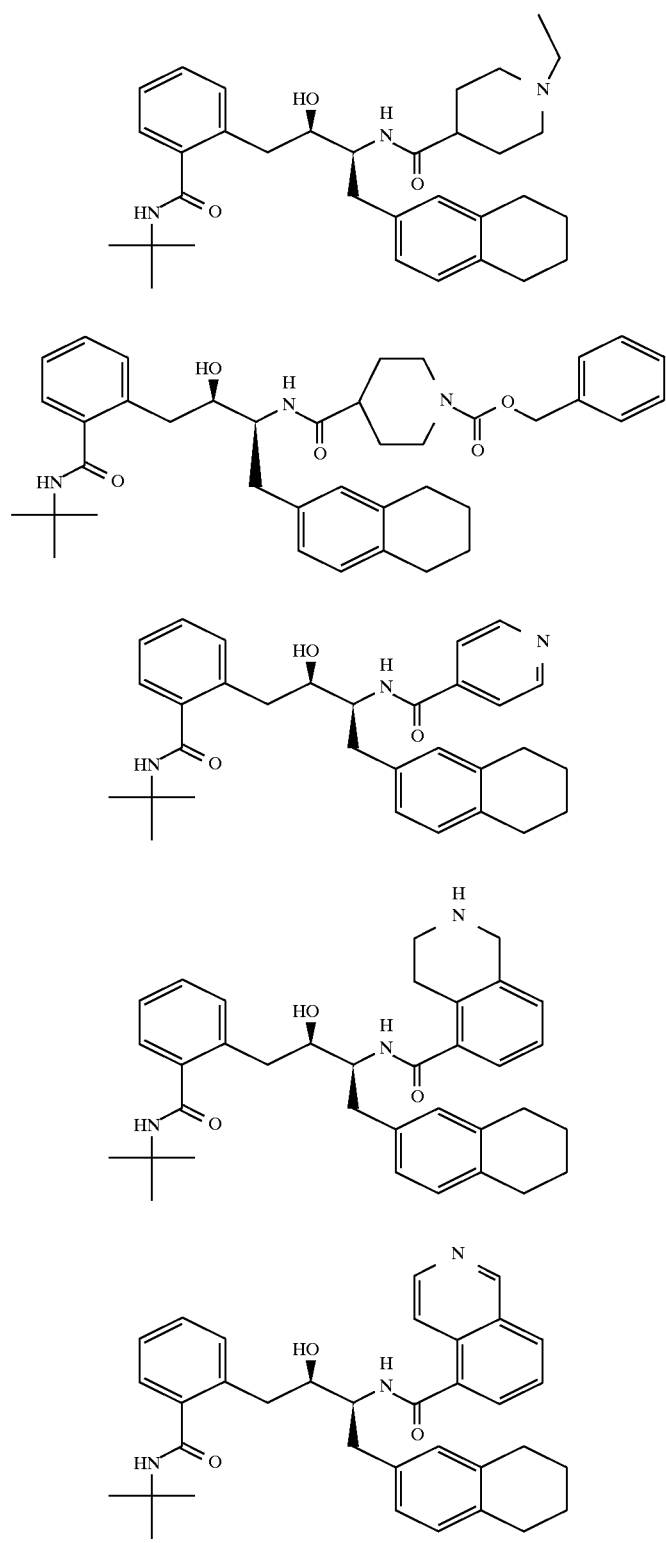

TABLE 4-continued
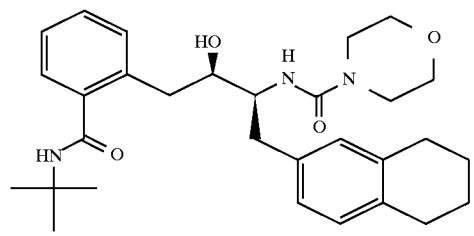
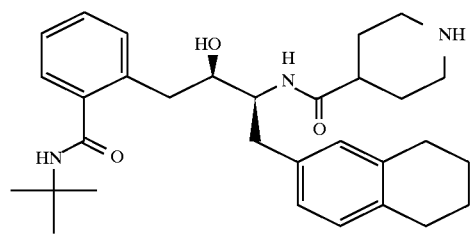
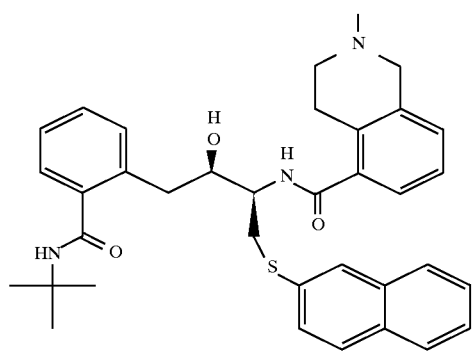
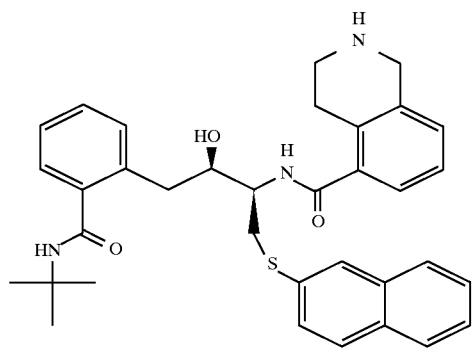
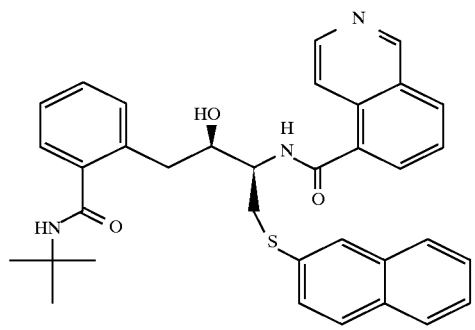

TABLE 4-continued
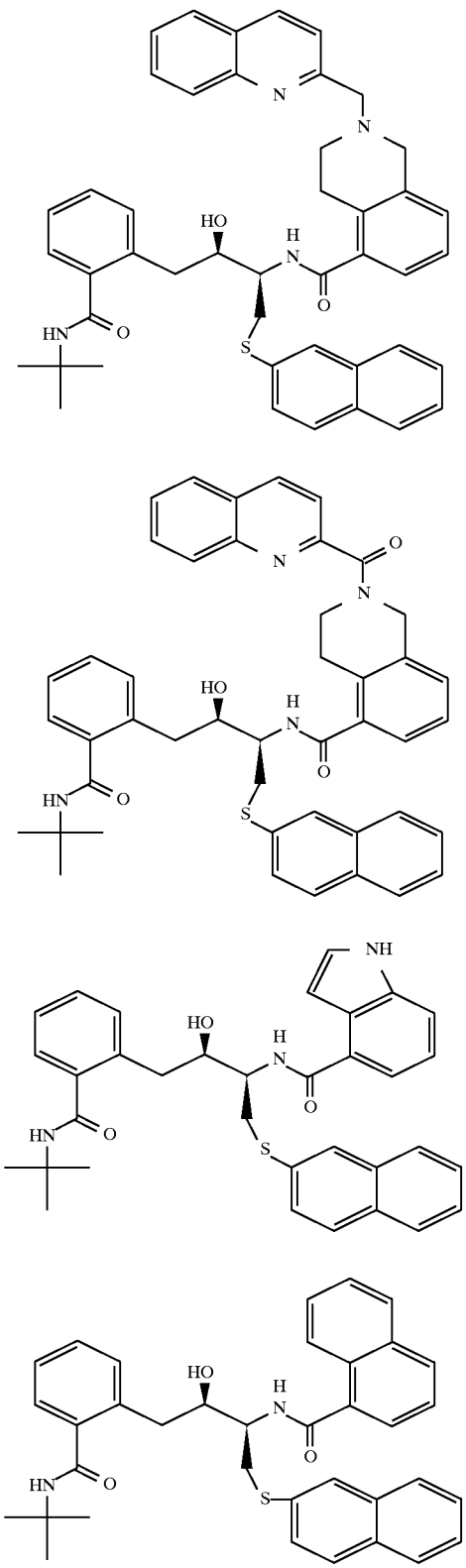

TABLE 4-continued
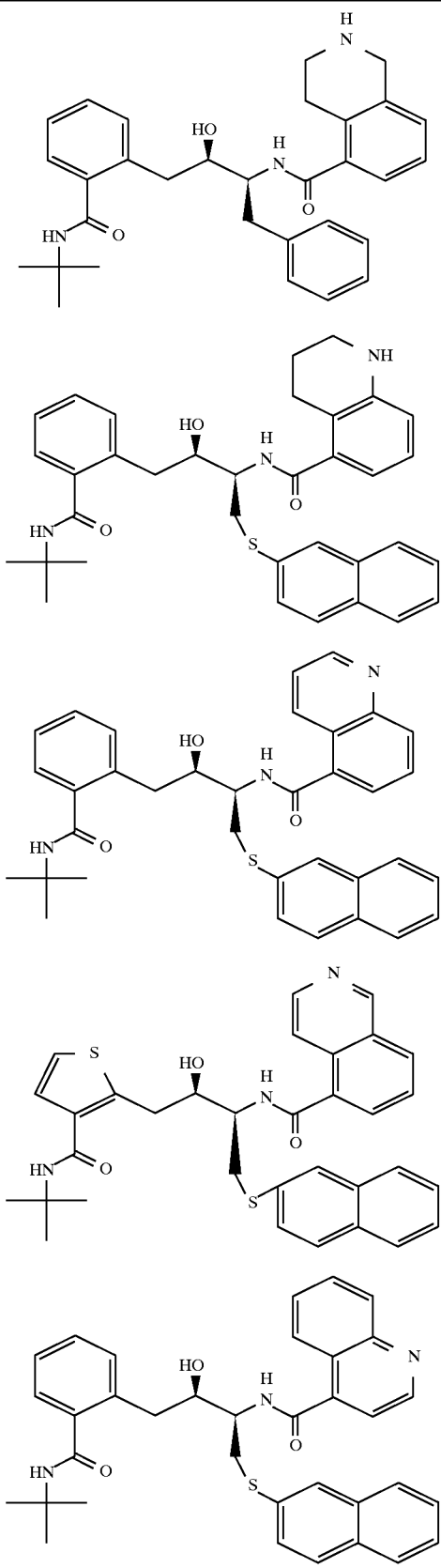

TABLE 4-continued
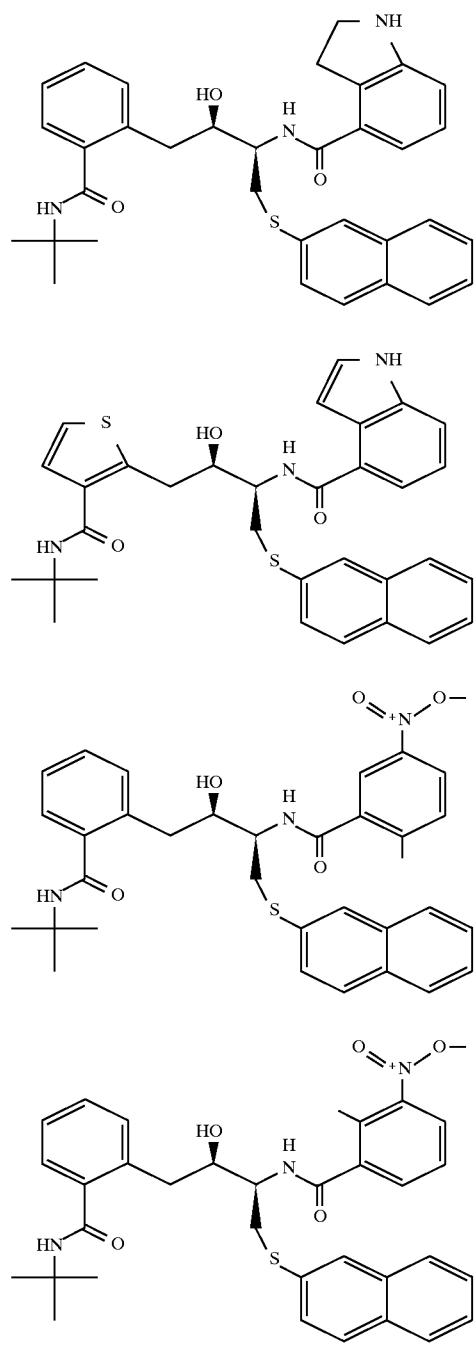

TABLE 4-continued
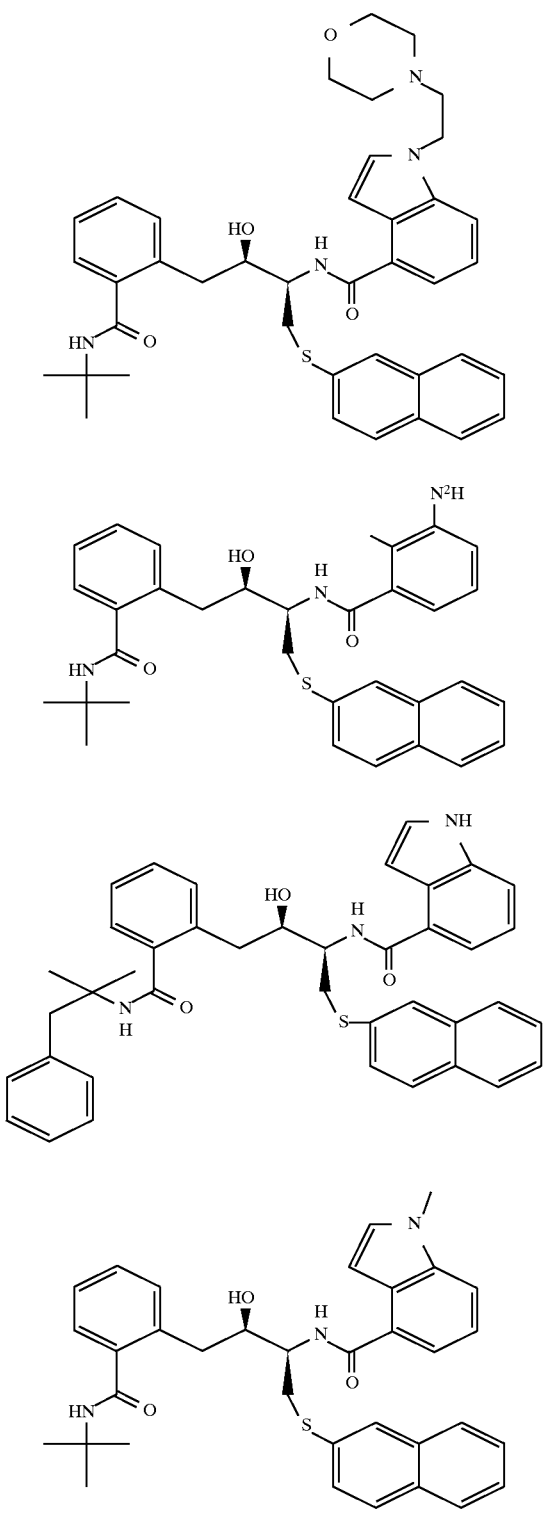

TABLE 4-continued
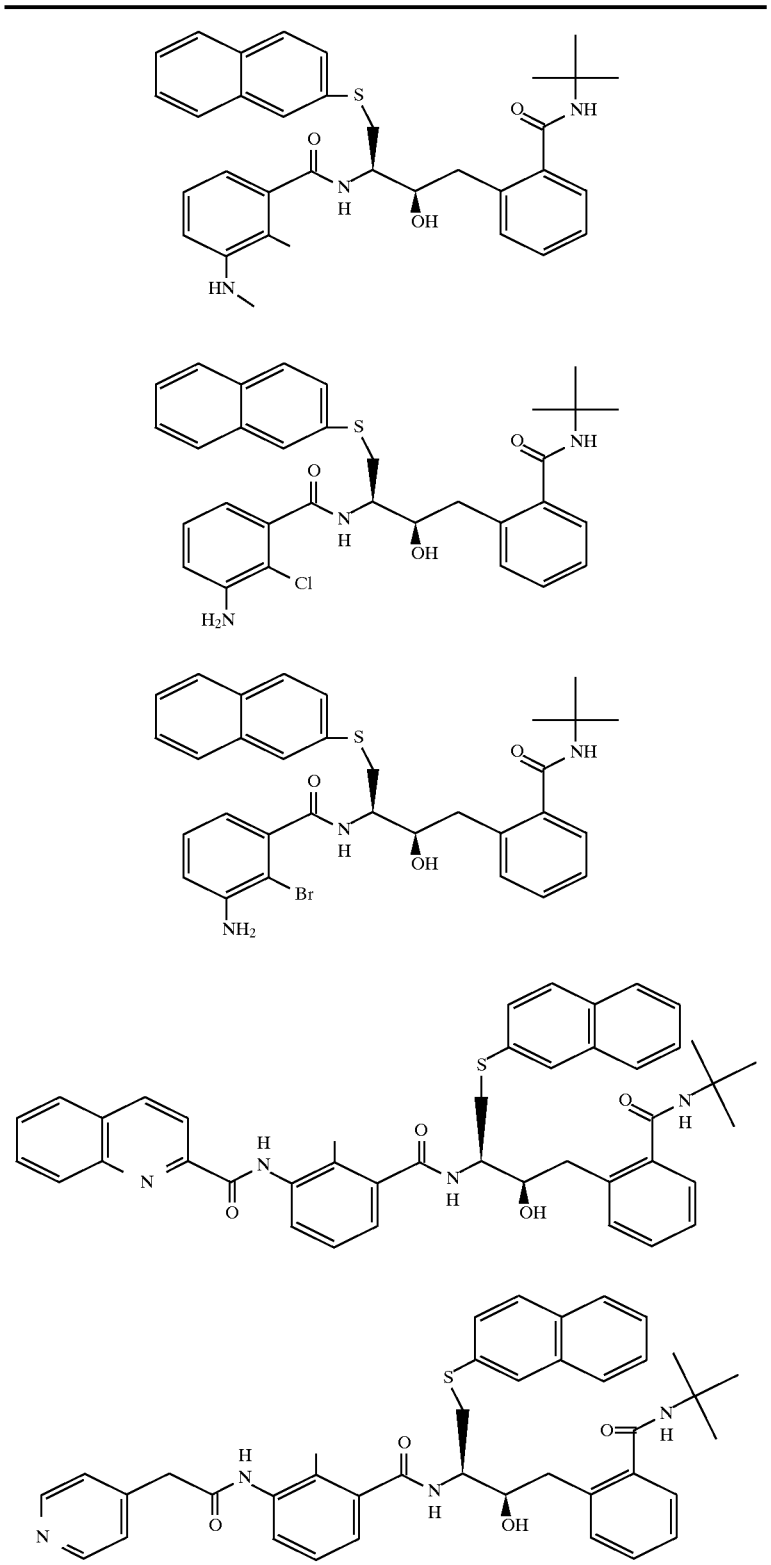

TABLE 4-continued
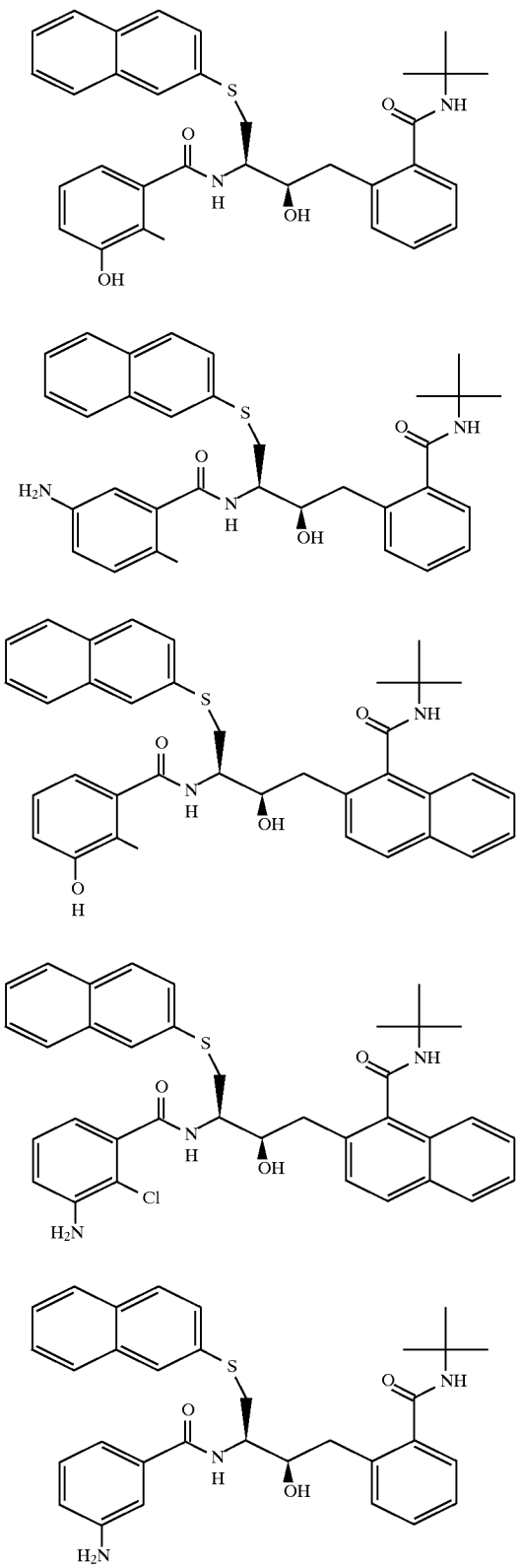

TABLE 4-continued
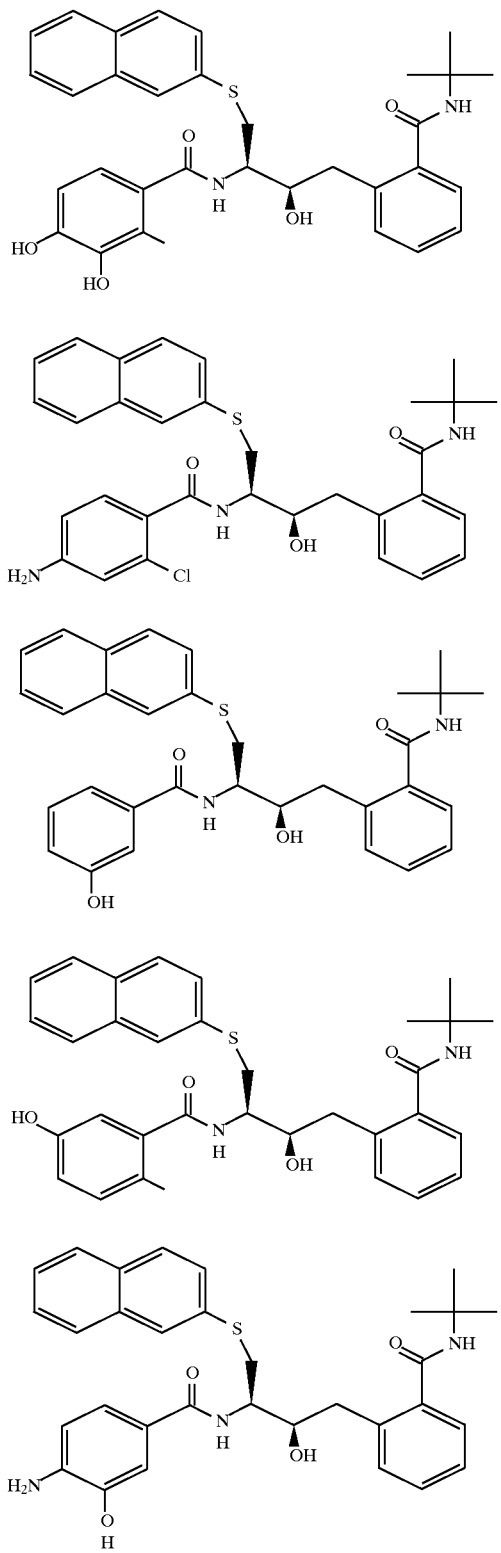

TABLE 4-continued
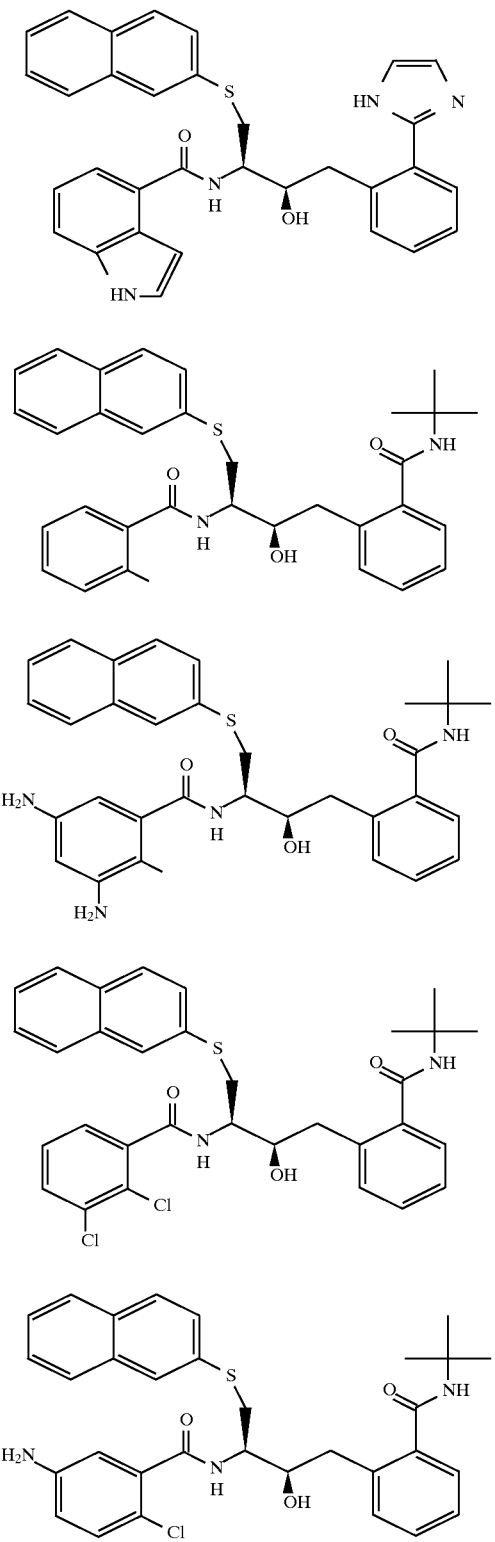

TABLE 4-continued

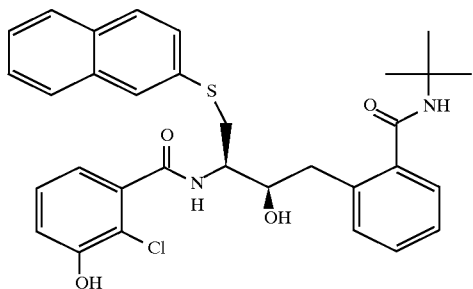

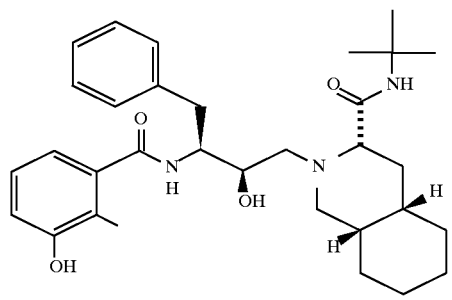

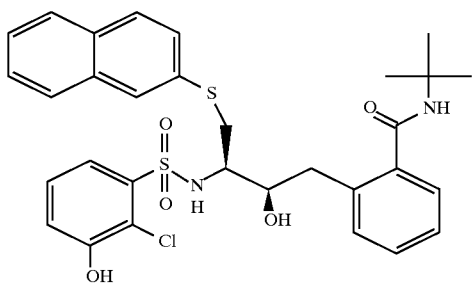

We claim:
1. A compound of the formula:

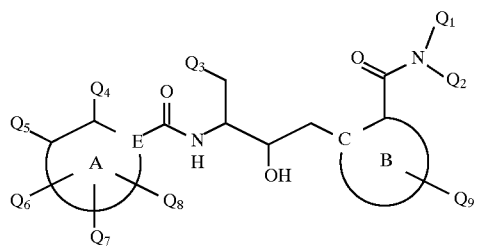

wherein:

$Q_1$ and $Q_2$ are each independently selected from hydrogen and substituted and unsubstituted alkyl and aryl;

$Q_3$ is selected from mercapto and substituted and unsubstituted alkoxyl, aryloxyl, thioether, amino, alkyl, cycloalkyl, saturated and partially saturated heterocycle, and aryl;

$Q_4$, $Q_5$, $Q_6$, $Q_7$, and $Q_8$ are each independently selected from hydrogen, hydroxyl, mercapto, nitro, halogen, —O—J, where J is a substituted or unsubstituted hydrolyzable group, and substituted and unsubstituted alkoxyl, aryloxyl, thioether, sulfinyl, sulfonyl, amino, alkyl, cycloalkyl, saturated and partially saturated heterocycle, aryl, and $L_6C(O)L_4$, where $L_6$ is a single bond, —O or —N, and further where $L_4$ is alkyl, hydroxyl, alkoxyl or hydrogen; and further wherein any one or more of $Q_4$, $Q_5$, $Q_6$, $Q_7$, and $Q_8$ may be a member of a spiro ring, and any two of $Q_4$, $Q_5$, $Q_6$, $Q_7$, and $Q_8$ may together be members of a ring;

E is carbon or nitrogen;

$Q_9$ is selected from hydrogen, halogen, hydroxyl, mercapto, and substituted and unsubstituted alkoxyl, aryloxyl, thioether, amino, alkyl, and aryl, where $Q_9$ may form part of a ring;

is a monocyclic or polycyclic carbocycle or heterocycle, which is optionally further substituted, and when

is heterocycle, each heterocyclic ring has one to three heteroatoms independently selected from nitrogen, oxygen, and sulfur; and

is a monocyclic or polycyclic carbocycle or heterocycle, which is optionally further substituted, and when

is heterocycle, each heterocyclic ring has from one to three heteroatoms independently selected from nitrogen, oxygen and sulfur, with the proviso that

is neither a 5- or 6-membered monocyclic ring, which is optionally further substituted, nor

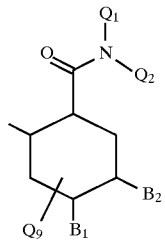

where $B_1$ and $B_2$ form part of a ring having from 3 to 10 members, which is optionally further substituted;

wherein at least one of

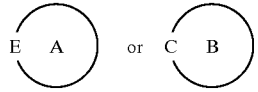

is a heterocycle; or a prodrug or pharmaceutically acceptable salt of said compound.

2. A compound, prodrug, or pharmaceutically acceptable salt according to claim 1, wherein E is carbon.

3. A compound, prodrug, or pharmaceutically acceptable salt according to claim 1, wherein $Q_3$ is substituted or unsubstituted aryl or thioether.

4. A compound, prodrug, or pharmaceutically acceptable salt according to claim 3, wherein E is carbon.

5. A compound, prodrug, or pharmaceutically acceptable salt according to claim 1, wherein $Q_1$ is hydrogen and $Q_2$ is substituted or unsubstituted alkyl.

6. A pharmaceutical composition comprising:

(a) an active ingredient that is:

(i) a compound of the formula:

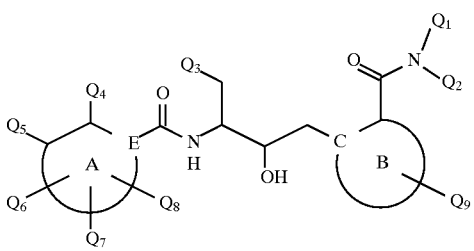

wherein:

$Q_1$ and $Q_2$ are each independently selected from hydrogen and substituted and unsubstituted alkyl and aryl;

$Q_3$ is selected from mercapto and substituted and unsubstituted alkoxyl, aryloxyl, thioether, amino, alkyl, cycloalkyl, saturated and partially saturated heterocycle, and aryl;

$Q_4$, $Q_5$, $Q_6$, $Q_7$, and $Q_8$ are each independently selected from hydrogen, hydroxyl, mercapto, nitro, halogen, —O—J, where J is a substituted or unsubstituted hydrolyzable group, and substituted and unsubstituted alkoxyl, aryloxyl, thioether, sulfinyl, sulfonyl, amino, alkyl, cycloalkyl, saturated and partially saturated heterocycle, aryl, and $L_6C(O)L_4$, where $L_6$ is a single bond, —O or —N, and further where $L_4$ is alkyl, hydroxyl, alkoxyl or hydrogen; and further wherein any one or more of $Q_4$, $Q_5$, $Q_6$, $Q_7$, and $Q_8$ may be a member of a spiro ring, and any two of $Q_4$, $Q_5$, $Q_6$, $Q_7$, and $Q_8$ may together be members of a ring;

E is carbon or nitrogen;

$Q_9$ is selected from hydrogen, halogen, hydroxyl, mercapto, and substituted and unsubstituted alkoxyl, aryloxyl, thioether, amino, alkyl, and aryl, where $Q_9$ may form part of a ring;

is a monocyclic or polycyclic carbocycle or heterocycle, which is optionally further substituted, and when

is heterocycle, each heterocyclic ring has one to three heteroatoms independently selected from nitrogen, oxygen, and sulfur; and

is a monocyclic or polycyclic carbocycle or heterocycle, which is optionally further substituted, and when

is heterocycle, each heterocyclic ring has from one to three heteroatoms independently selected from nitrogen, oxygen and sulfur, with the proviso that

is neither a 5- or 6-membered monocyclic ring, which is optionally further substituted, nor

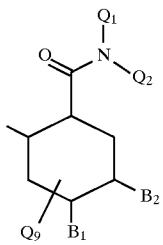

where $B_1$ and $B_2$ form part of a ring having from 3 to 10 members, which is optionally further substituted;
wherein at least one of

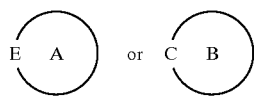

is a heterocycle; or
(ii) a prodrug or pharmaceutically acceptable salt of said compound; and
(b) a pharmaceutically acceptable carrier.

7. A pharmaceutical composition according to claim 6, wherein E is carbon.

8. A pharmaceutical composition according to claim 6, wherein $Q_3$ is substituted or unsubstituted aryl or thioether.

9. A pharmaceutical composition according to claim 8, wherein E is carbon.

10. A pharmaceutical composition according to claim 6, wherein $Q_1$ is hydrogen and $Q_2$ is substituted or unsubstituted alkyl.

11. A method of inhibiting HIV protease, comprising administering to a host an effective amount of:
a compound of the formula:

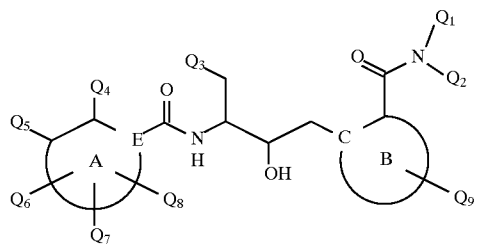

wherein:
$Q_1$ and $Q_2$ are each independently selected from hydrogen and substituted and unsubstituted alkyl and aryl;

$Q_3$ is selected from mercapto and substituted and unsubstituted alkoxyl, aryloxyl, thioether, amino, alkyl, cycloalkyl, saturated and partially saturated heterocycle, and aryl;

$Q_4$, $Q_5$, $Q_6$, $Q_7$, and $Q_8$ are each independently selected from hydrogen, hydroxyl, mercapto, nitro, halogen, —O—J, where J is a substituted or unsubstituted hydrolyzable group, and substituted and unsubstituted alkoxyl, aryloxyl, thioether, sulfinyl, sulfonyl, amino, alkyl, cycloalkyl, saturated and partially saturated heterocycle, aryl, and $L_6C(O)L_4$, where $L_6$ is a single bond, —O or —N, and further where $L_4$ is alkyl, hydroxyl, alkoxyl or hydrogen; and further wherein any one or more of $Q_4$, $Q_5$, $Q_6$, $Q_7$, and $Q_8$ may be a member of a spiro ring, and any two of $Q_4$, $Q_5$, $Q_6$, $Q_7$, and $Q_8$ may together be members of a ring;

E is carbon or nitrogen;

$Q_9$ is selected from hydrogen, halogen, hydroxyl, mercapto, and substituted and unsubstituted alkoxyl, aryloxyl, thioether, amino, alkyl, and aryl, where $Q_9$ may form part of a ring;

is a monocyclic or polycyclic carbocycle or heterocycle, which is optionally further substituted, and when

is heterocycle, each heterocyclic ring has one to three heteroatoms independently selected from nitrogen, oxygen, and sulfur; and

is a monocyclic or polycyclic carbocycle or heterocycle, which is optionally further substituted, and when

is heterocycle, each heterocyclic ring has from one to three heteroatoms independently selected from nitrogen, oxygen and sulfur, with the proviso that

is neither a 5- or 6-membered monocyclic ring, which is optionally further substituted, nor

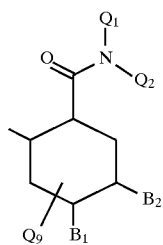

where $B_1$ and $B_2$ form part of a ring having from 3 to 10 members, which is optionally further substituted;

wherein at least one of

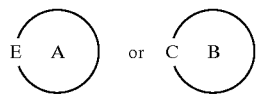

is a heterocycle;

or a prodrug or pharmaceutically acceptable salt of said compound.

12. A method according to claim 11, wherein E is carbon.

13. A method according to claim 11, wherein $Q_3$ is substituted or unsubstituted aryl or thioether.

14. A method according to claim 13, wherein E is carbon.

15. A method according to claim 11, wherein $Q_1$ is hydrogen and $Q_2$ is substituted or unsubstituted alkyl.

* * * * *

UNITED STATES PATENT AND TRADEMARK OFFICE
CERTIFICATE OF CORRECTION

PATENT NO.    : 5,824,688
DATED         : October 20, 1998
INVENTOR(S)   : Vicent J. Kalish et al.

It is certified that error appears in the above-identified patent and that said Letters Patent is hereby corrected as shown below:

Column 3,
Line 56 "or" should read -- of --.

Column 4,
Line 12, "13 O-J," should read -- -O-J, --; and
Lines 29-40,

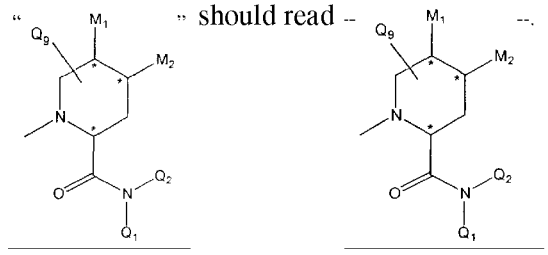

Column 6,
Lines 38-51,             should read

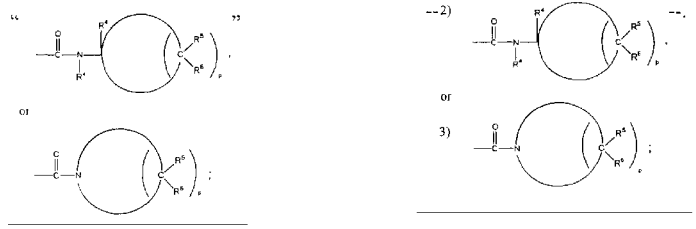

Column 8,
Lines 15-19,              should read

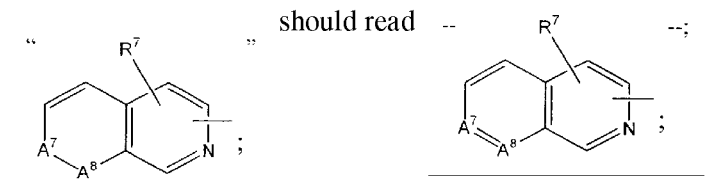

Line 25,, "or 4" should read -- or 4, --.

Column 10,
Line 46, "tetrahydrisoquinoliny]" should read -- tetrahydroisoquinolinyl --.

Column 13,
Line 8, "rings" should read -- ring --; and
Line 46, "stereisomers," should read -- stereoisomers, --.

UNITED STATES PATENT AND TRADEMARK OFFICE
CERTIFICATE OF CORRECTION

PATENT NO. : 5,824,688
DATED : October 20, 1998
INVENTOR(S) : Vicent J. Kalish et al.

It is certified that error appears in the above-identified patent and that said Letters Patent is hereby corrected as shown below:

Column 14,
Line 42, "–1 sulfonate," should read -- –1–sulfonate, --.

Column 15,
Line 28, "R is" should read -- $R^3$ is --.

Column 18,
Line 63. "–3–" should read -- –3'– --.

Column 19,
Line 14, "–4'aza" should read -- –4'–aza --; and
Line 34. "–4'aza" should read -- –4'–aza --.

Column 20,
Line 27, "–4'aza" should read -- –4'–aza --;
Line 53, "–3–naphth–2–yl" should read -- –3'–naphth–2– --; and
Line 62, "(2R*," should read -- (2'R*, --.

Column 22,
Line 57, "Procedures" should read -- procedures --.

Column 26,
Line 46, "–$CV^{6'}V^{6'}$13," should read -- or –$CV^{6'}V^{6'}$–; --.

Column 29,
Line 4, "Chemicai" should read -- Chemical --.

Column 31,
Line 39. "react on" should read -- reaction --.

Column 32,
Lines 58-65,

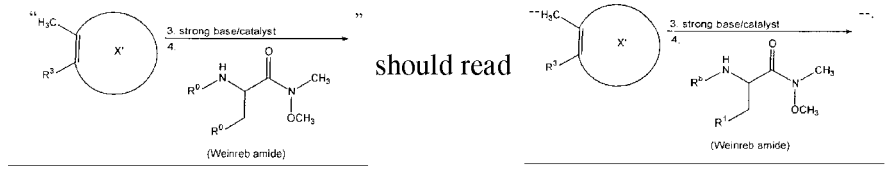

UNITED STATES PATENT AND TRADEMARK OFFICE
CERTIFICATE OF CORRECTION

PATENT NO. : 5,824,688
DATED : October 20, 1998
INVENTOR(S) : Vicent J. Kalish et al.

It is certified that error appears in the above-identified patent and that said Letters Patent is hereby corrected as shown below:

Column Lines 3-9, 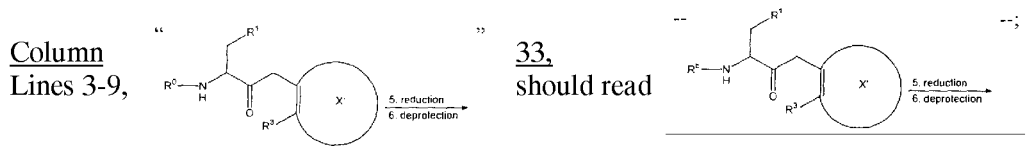 should read

Line 38, "1(B)" should read -- 1(B). --.

Column 34, Lines 1-11, 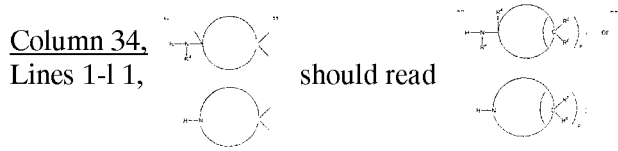 should read

Column 36, Lines 1-11, 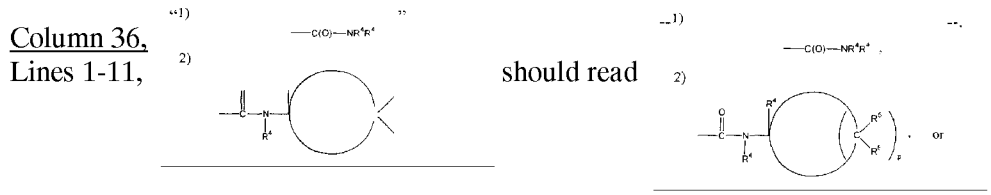 should read

Column 37,
Line 8, "broad doublet (br.s)," should read -- broad doublet (br.d), --; and
Line 59, "(br.s, 7H)," should read -- (br.s. 1H), --.

Column 39,
Line 36, "N." should read -- N, --.

Column 41,
Lines 20 and 61, "Asolution" should read -- A solution --.

Column 42,
Line 16, "3."should read -- B. --.

Column 43,
Line 59, "Potassium" should read -- potassium --.

UNITED STATES PATENT AND TRADEMARK OFFICE
CERTIFICATE OF CORRECTION

PATENT NO.     : 5,824,688
DATED          : October 20, 1998
INVENTOR(S)    : Vicent J. Kalish et al.

It is certified that error appears in the above-identified patent and that said Letters Patent is hereby corrected as shown below:

Column 45,
Line 6, "[2S–" should read -- A. [2S– --;
Line 28, "3.05 (m, 2H)," should read -- 5.05 (s, 2H),--: and
Line 38, "8.50-8460" should read -- 8.50-8.60 --.

Column 47,
Lines 27 and 47, "(benzyoxvcarbonyl)amino" should read -- (benzyloxycarbonyl)amino --.

Column 48,
Line 13, "j=6," should read -- J=6, --; and
Line 60, "31.5 g" should read -- 31.6 g --.

Column 49,
Line 31, "hydroxide" should read -- hydroxide. --.

Column 53,
Line 65, "1H NMR" should read -- $^1$H NMR --.

Column 54,
Line 19, "(m, 2H)" should read -- (m, 2H), --;
Line 40, "–Isopropyl)–" should read -- –Isopropyl– --;
Line 61, "(CHl3):" should read -- CHCl$_3$): --; and
Line 67, "Procedure" should read -- procedure --.

Column 56,
Line 31, "or an" should read -- of an --.

Column 58,
Line 8, "1039," should read -- 1038, --.

Column 59,
Line 22, "1H) 3.24" should read -- 1H), 3.24 --.

Column 60,
Line 6, "-34.68°" should read -- +34.68° --.

Column 61,
Line 15, "j=17" should read -- J=17 --;

UNITED STATES PATENT AND TRADEMARK OFFICE
CERTIFICATE OF CORRECTION

PATENT NO. : 5,824,688
DATED : October 20, 1998
INVENTOR(S) : Vicent J. Kalish et al.

It is certified that error appears in the above-identified patent and that said Letters Patent is hereby corrected as shown below:

Line 23, "(l3 mmol)-of" should read -- (l3 mmol) of --; and
Line 66, "124°" should read -- 124 --.

Column 62,
Line 8, "–4phenyl–" should read -- –4–phenvl– --;
Line 21, "(d, J=9" should read -- (s, J=9 --;
Line 41, "(CHCl₃)" should read -- (CHCl₃): --; and
Line 44, "5.92;" should read -- 6.92; --.

Column 63,
Line 25, "165°" should read -- 165 --;
Line 35, "2methyl–" should read -- 2–methvl– --;
Line 36, "142°" should read -- 142 --;
Line 48, "136°" should read -- 136 --;
Line 49, "$^1$NMR" should read -- $^1$H NMR--: and
Line 57, "5aminoisoquinoline" should read -- 5–aminoisoquinoline --.

Column 64,
Line 23, "270°" should read -- 270 --; and
Line 44, "142°" should read -- 142 --.

Column 65,
Line 13, "97°" should read -- 97 --;
Line 17, "8.58." should read -- 8.58; --;
Line 29, "69°" should read -- 69--:
Line 47, "l 79°" should read -- 179 --;
Line 63, "200°" should read -- 200 --; and
Line 65, "1H,)," should read --  1H), --.

Column 66,
Line 6, "3" hydroxyphenyl)" should read -- 3"–hydroxyphenyl) --;
Line 22, "[α]$_{D-90.80}$°" should read -- [α]$_D$-90.80° --; and
Line 56, "377 cm$^{-1}$." should read -- 877 cm$^{-1}$. --.

Column 68,
Line 2, "MeOH)" should read -- MeOH). --;
Line 5, "4.22-14.32" should read -- 4.22-4.32--: and
Line 49, "–4'–aza–5'–aza–5'–oxo–5'–" should read -- –4'–aza–5'–oxo–5'– --.

Column 69,

UNITED STATES PATENT AND TRADEMARK OFFICE
CERTIFICATE OF CORRECTION

PATENT NO.    : 5,824,688
DATED         : October 20, 1998
INVENTOR(S)   : Vicent J. Kalish et al.

It is certified that error appears in the above-identified patent and that said Letters Patent is hereby corrected as shown below:

Line 29, "7.34." should read -- 7.34; --.

Column 70,
Line 66, "1-5" should read -- 1-5% --.

Column 71,
Line 16, "–oxo–5'S–" should read -- –oxo–5'– --; and
Line 54, "1.16" should read -- δ 1.16-- and "(m, 12H)" should read -- (m, 12H), --.

Column 73,
Line 56, "of 30" should read -- of 3% --;
Line 60, "MeOH,)." should read -- MeOH). --; and
Line 65, "(br.s, 1H:)," should read -- (br.s, 1H), --.

Column 74,
Line 11, "–butyl–3"–" should read -- –butyl–3'''– --.

Column 76,
Line 1, "mmol" should read -- mmol) --;
Line 6, "place;" should read -- plate; --; and
Line 51, "–(2"–methyl–3"–" should read -- (2"–ethyl–3"– --.

Column 77,
Line 12, "163 mg" should read -- 136 mg --;
Line 16, "(t, J=7.87 Hz," should read -- 6.55 (t, J=7.87 Hz, --;
Line 37, "$^1$NMR"should read -- $^1$H NMR --;
Line 41, "7.51 (a," should read -- 7.51 (d, --;
Line 61, " 3-55" should read -- 3-5% --: and
Line 65, "(c=0.115)" should read -- (c=0.115). --.

Column 78,
Line 27, "7.89 (m, 2H.)," should read -- 7.89 (m, 2H), --.

Column 81,
Line 32, "4.34" should read -- 4.84 --;
Line 33. "5.74" should read -- 6.74 --;
Line 58, "47%" should read -- 47%. --; and
Line 63, "(m, 1H)" should read -- (m, 1H). --.

Column 82,

UNITED STATES PATENT AND TRADEMARK OFFICE
CERTIFICATE OF CORRECTION

PATENT NO. : 5,824,688
DATED : October 20, 1998
INVENTOR(S) : Vicent J. Kalish et al.

It is certified that error appears in the above-identified patent and that said Letters Patent is hereby corrected as shown below:

Line 19, "105°-106°" should read -- 105-106° --; and
Line 46, "111°-l 13°" should read -- 111-113° --.

Column 83,
Line 4, "107°-108°" should read -- 107-108° --;
Line 26, "110°-112°" should read -- 110-112° --; and
Line 50, "119°-120°C.)" should read -- 119-120°C.). --.

Column 84,
Line 8, "106°-107°" should read -- 106-107°-
Line 33, "115°-117°" should read -- 115-117° --;
Line 37, "6.10 (, 1H)." should read -- 6.10 (s, 1H),--: and
Line 58, "110°-112°" should read -- 110-112° --.

Column 85,
Line 14, "101°-102°" should read -- 101-102° --;
Line 37, "125°-128°" should read -- 125-128° --; and
Line 59, "85°-87°" should read -- 85-87° --.

Column 86,
Line 18, "125°-128°" should read -- 125-128° --;
Line 42, "116°-119°" should read -- 116-119° --;
Line 44, "74." should read -- 74%. --; and
Line 66, "109°-110°" should read -- 109-110° --.

Column 87,
Line 17, "HOST," should read -- HOBT, --;
Line 21, "104°-105°C.)" should read -- 104-105°C.). --;
Line 46, "109°-112°" should read -- 109-112° --; and
Line 52, "1H) 3.51" should read -- 1H), 3.51 --.

Column 88,
Line 10, "197°-199°" should read -- 197-199° --;
Line 28, "3"4"–" should read -- 3", 4"– --;
Line 41, "110°-113°" should read -- 110-113°--: and
Line 60, "–4"–aza–5"–" should read -- –4'–aza–5'– --.

Column 89,
Line 13, "HOST," should read -- HOBT, --;
Line 22, "92°-95°" should read -- 92-95° --;
Line 46, "109°-110°" should read -- 109-110° --;

UNITED STATES PATENT AND TRADEMARK OFFICE
CERTIFICATE OF CORRECTION

PATENT NO.    : 5,824,688
DATED         : October 20, 1998
INVENTOR(S)   : Vicent J. Kalish et al.

It is certified that error appears in the above-identified patent and that said Letters Patent is hereby corrected as shown below:

Line 51, "(s, 9H)," should read -- (s, 9H).--; and
Line 52, "N." should read -- N, --.

Column 90,
Line 6, "1H) 3.23" should read -- 1H), 3.23 --;
Line 11, "H." should read -- H, --;
Line 29, "(br. 1H)," should read -- (br.s, 1H), --;
Line 31, "(m, 4H)" should read -- (m, 4H), --;
Line 51, "83°-84°" should read -- 83-84° --; and
Line 62, ", 3S*)]–" should read -- , 3'S*)]– --.

Column 91,
Line 6, "89°-92°" should read -- 89-92° --;
Line 22, "Procedure" should read -- procedure --;
Line 29, "80°-81°" should read -- 80-81° --; and
Line 51, "85°-88°" should read -- 85-88° --.

Column 92,
Line 7, "86°-89°" should read -- 86-89° --;
Line 18, "–3"–" should read -- –3", 4"– --;
Line 29, "121°-123°C.)" should read -- 121-123°C.). --;
Line 52, "102°-104°" should read -- 102-104°--; and
Line 56, "1H). 5.90" should read -- 1H), 5.90 --.

Column 93,
Line 7, "104°-106°" should read -- 104-106° --;
Line 10, "δ 7.95" should read -- δ 7.85 --;
Line 34, "119°-122°" should read -- 119-122° --;
Line 37, "$^1$NMR" should read -- $^1$H NMR --;
Line 38, "5.96" should read -- 6.96 --; and
Line 40, "1H). 3.52" should read -- 1H), 3.52 --.

Column 95,
Lines 21-27, " 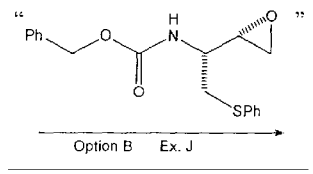 " should read -- 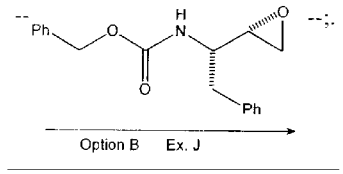 --;.

Column 96,

UNITED STATES PATENT AND TRADEMARK OFFICE
CERTIFICATE OF CORRECTION

PATENT NO.    : 5,824,688
DATED         : October 20, 1998
INVENTOR(S)   : Vicent J. Kalish et al.

It is certified that error appears in the above-identified patent and that said Letters Patent is hereby corrected as shown below:

Line 41, "J-4" should read -- J=4 --; and
Line 54, "2trichloroethane." should read -- 2-trichloroethane --.

Column 97,
Line 59, "CH$_2$Cl$_2$" should read -- CH$_2$Cl$_2$, --.

Column 98,
Line 10, ")–1–" should read -- ]–1– --;
Line 22, "–aminobuty" should read -- –aminobutyl]– --;
Line 23, "1 ]–" should be deleted;
Line 46, "F." should read -- F,--; and "2S*." should read -- 2'S*, --; and
Line 60, ",3S*" should read -- , 3'S* --.

Column 99,
Line 8, "–3.2–c]" should read -- [3,2–c]--:
Line 12, ", 3S*)–" should read -- , 3'S*)]---: and
Line 16. "10° C." should read -- -10° C. --.

Column 100,
Line 37, "aminobutyl–" should read -- aminobutyl]– --.

Column 101,
Line 67. "-63.63°" should read -- -63.6° --.

Column 103,
Line 6. "oxa" should read -- oxo --.

Column 104,
Lines 4 and 45, "oxa" should read -- oxo --.

Column 105,
Line 28, "oxa" should read -- oxo --; and
Line 61, "-d$_4$)" should read -- -d$_4$): --.

Column 106,
Line 35. "oxa" should read -- oxo--; and
Line 65, "3R*)]–" should read -- 3'R*)]– --.

Column 108,
Line 42. "–4"–aza–5'–oxo–5'" should read -- –4'–aza–5'–oxo–5'– --.

UNITED STATES PATENT AND TRADEMARK OFFICE
CERTIFICATE OF CORRECTION

PATENT NO.    : 5,824,688
DATED         : October 20, 1998
INVENTOR(S)   : Vicent J. Kalish et al.

It is certified that error appears in the above-identified patent and that said Letters Patent is hereby corrected as shown below:

Column 109,
Line 67, "(0.9)" should read -- (0.9). --.

Column 110,
Line 14, ", 3S*)]–" should read -- , 3'S*)]– --;
Line 15, "–3–N –c –" should read -- –3 –N –t – --; and
Line 67, " 3R*)]–" should read -- 3'R*)]– --.

Column 115,
Line 37, "n air." should read -- in air. --.

Column 116,
Line 56, "information" should read -- information: --; and
Line 66, "Preparation" should read -- Cell Preparation --.

Column 117,
Line 16, "Hemacytomer" should read -- Hemacytomer: --; and
Lines 32, 34 and 38, "Media" should read -- of Media --.

Column 118,
Line 11, "Media A" should read -- Media A: --;
Lines 50 and 51, "plate" should read -- plates --; and
Line 54, "[2 mM]" should read -- [2 mM]. --.

Column 119,
Line 21, "HERPES" should read -- HEPES --; and
Line 39, "Sacto-agar)" should read -- Bacto-agar) --.

Column 123,
Lines 60-62, "Whole     Whole " should read -- Whole      Whole  --.
              cell$^i$     cell$^i$                    cell$^i$    cell$^i$
              IC$_{90}$nM  IC$_{50}$nM                 CEM         CEM
                                                       IC$_{90}$nM IC$_{50}$nM Column 124,
Lines 18-20, 33-36, 47-50 and 62-65
"Whole        Whole " should read -- Whole      Whole  --; and
cell$^i$      cell$^i$                cell$^i$   cell$^i$
IC$_{90}$nM   IC$_{50}$nM             CEM        CEM

UNITED STATES PATENT AND TRADEMARK OFFICE
CERTIFICATE OF CORRECTION

PATENT NO. : 5,824,688
DATED : October 20, 1998
INVENTOR(S) : Vicent J. Kalish et al.

It is certified that error appears in the above-identified patent and that said Letters Patent is hereby corrected as shown below:

Line 25, "22.1 $^{d}$" should read -- 221 $^{d}$ --.     $IC_{90}nM$   $IC_{50}nM$ Column 125,
Line 11, "520$^{d}$" should read -- 521$^{d}$ --;
Lines 18-21, "Whole    Whole " should read -- Whole    Whole --.
           cell$^{i}$   cell$^{i}$                      cell$^{i}$   cell$^{i}$
           $IC_{90}nM$   $IC_{50}nM$                    CEM     CEM
                                                        $IC_{90}nM$   $IC_{50}nM$
Line 25, "54$^{b}$" should read -- 5.4$^{b}$ --.

Column
Table 4,         " 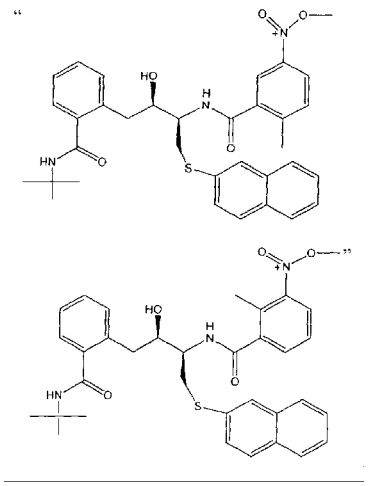      135,       -- 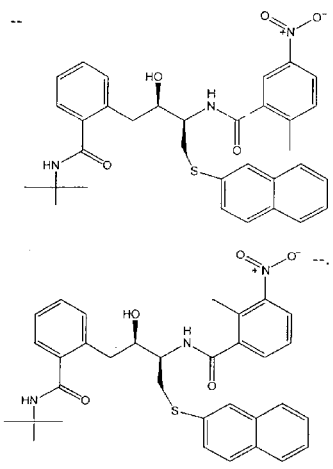
                                         should read Signed and Sealed this Thirty-first Day of August, 2004

JON W. DUDAS
Director of the United States Patent and Trademark Office